(12) United States Patent
Tachdjian et al.

(10) Patent No.: US 8,124,121 B2
(45) Date of Patent: Feb. 28, 2012

(54) FLAVORS, FLAVOR MODIFIERS, TASTANTS, TASTE ENHANCERS, UMAMI OR SWEET TASTANTS, AND/OR ENHANCERS AND USE THEREOF

(75) Inventors: Catherine Tachdjian, San Diego, CA (US); Andrew P. Patron, Encinitas, CA (US); Sara L. Adamski-Werner, San Diego, CA (US); Farid Bakir, San Diego, CA (US); Qing Chen, San Diego, CA (US); Vincent Darmohusodo, San Diego, CA (US); Stephen Terrence Hobson, San Diego, CA (US); Xiaodong Li, Oceanside, CA (US); Ming Qi, Shanghai (CN); Daniel H. Rogers, San Diego, CA (US); Marketa Rinnova, San Diego, CA (US); Guy Servant, San Diego, CA (US); Xiao-Qing Tang, San Diego, CA (US); Mark Zoller, La Jolla, CA (US); David Wallace, San Diego, CA (US); Amy Xing, San Diego, CA (US); Klaus Gubernator, Del Mar, CA (US)

(73) Assignee: Senomyx, Inc., San Diego, CA (US)

( * ) Notice: Subject to any disclaimer, the term of this patent is extended or adjusted under 35 U.S.C. 154(b) by 491 days.

(21) Appl. No.: 12/257,017

(22) Filed: Oct. 23, 2008
(Under 37 CFR 1.47)

(65) Prior Publication Data
US 2009/0111834 A1    Apr. 30, 2009

Related U.S. Application Data

(62) Division of application No. 10/913,303, filed on Aug. 6, 2004, now Pat. No. 7,476,399.

(60) Provisional application No. 60/494,071, filed on Aug. 6, 2003, provisional application No. 60/552,064, filed on Mar. 9, 2004.

(51) Int. Cl.
*A61K 47/00* (2006.01)
*A61K 31/4965* (2006.01)

(52) U.S. Cl. .................. 424/439; 514/255.05; 514/616; 514/357

(58) Field of Classification Search .................... 424/439
See application file for complete search history.

(56) References Cited

U.S. PATENT DOCUMENTS

| | | | |
|---|---|---|---|
| 3,294,544 A | 12/1966 | Stanko et al. | |
| 3,503,962 A | 3/1970 | Beregi et al. | |
| 3,535,335 A | 10/1970 | Beregi et al. | |
| 3,625,949 A | 12/1971 | Schorre et al. | |
| 4,034,109 A | 7/1977 | Rowsell et al. | |
| 4,091,018 A | 5/1978 | Asato | |
| 4,136,163 A | 1/1979 | Watson et al. | |
| 4,150,052 A | 4/1979 | Watson et al. | |
| 4,177,279 A | 12/1979 | Archibald et al. | |
| 4,332,724 A | 6/1982 | Bentley et al. | |
| 4,535,081 A | 8/1985 | Kadin | |
| 4,645,678 A | 2/1987 | Nofre et al. | |
| 4,810,715 A | 3/1989 | Schickaneder et al. | |
| 4,997,667 A | 3/1991 | Nofre et al. | |
| 5,176,928 A | 1/1993 | Shazer, Jr. et al. | |
| 5,709,048 A | 1/1998 | Holtz | |
| 5,877,218 A | 3/1999 | Herzig et al. | |
| 5,877,221 A | 3/1999 | Cohen et al. | |
| 5,880,159 A | 3/1999 | Herzig et al. | |
| 5,914,349 A | 6/1999 | Cohen et al. | |
| 5,994,408 A | 11/1999 | Cohen et al. | |
| 6,248,363 B1 * | 6/2001 | Patel et al. ..................... | 424/497 |
| 6,271,263 B1 | 8/2001 | Sklarz et al. | |
| 6,383,778 B1 | 5/2002 | Zuker et al. | |
| 6,417,370 B1 | 7/2002 | Lieb et al. | |
| 6,429,207 B1 | 8/2002 | Van Wagenen et al. | |
| 6,451,843 B1 | 9/2002 | Lieb et al. | |
| 6,462,148 B1 | 10/2002 | Suzuki et al. | |
| 6,528,685 B2 | 3/2003 | Cohen et al. | |
| 6,617,351 B1 | 9/2003 | Arnold et al. | |
| 6,818,747 B2 | 11/2004 | Yao et al. | |
| 7,476,399 B2 | 1/2009 | Tachdjian et al. | |
| 7,635,709 B2 * | 12/2009 | Korsten et al. ................ | 514/411 |
| 2002/0128433 A1 | 9/2002 | Yao et al. | |
| 2002/0132273 A1 | 9/2002 | Stryer et al. | |
| 2002/0143151 A1 | 10/2002 | Yao et al. | |

(Continued)

FOREIGN PATENT DOCUMENTS

CA          2406392 A1    11/2001
(Continued)

OTHER PUBLICATIONS

English Abstract of JP 2002-234898, Japan Patent Office Database.
English Abstract of JP 02-108697, Japan Patent Office Database.
English Abstract of JP 61-200951, Japan Patent Office Database.
English Abstract of JP 01-106853, Japan Patent Office Database.
Adler et al., "A Novel Family of Mammalian Taste Receptors," Cell, 100(6):693-702 (2000).
Ager et al., "Commercial, Synthetic Nonnutritive Sweeteners," Angew. Chem. Int. Ed., 37:1802-1817 (1998).
Ahn et al., "A General Diastereoselective Synthesis of Spiroacetals Related to Those in Ionophores via the Reaction of Lacones with Cerium(III) γ-Cerioalkoxide. MAD Reverses the Diastereoselectivity of the Addition of Methylmetallics to a β-Keto Ether[1,2]" J. Org. Chem., 59:3142-3150 (1994).

(Continued)

*Primary Examiner* — Gollamudi Kishore
*Assistant Examiner* — Snigdha Maewall
(74) *Attorney, Agent, or Firm* — Cooley LLP

(57) ABSTRACT

The present invention relates to the discovery that certain non-naturally occurring, non-peptide amide compounds and amide derivatives, such as oxalamides, ureas, and acrylamides, are useful flavor or taste modifiers, such as a flavoring or flavoring agents and flavor or taste enhancer, more particularly, savory (the "umami" taste of monosodium glutamate) or sweet taste modifiers, —savory or sweet flavoring agents and savory or sweet flavor enhancers, for food, beverages, and other comestible or orally administered medicinal products or compositions.

7 Claims, No Drawings

U.S. PATENT DOCUMENTS

| | | |
|---|---|---|
| 2002/0151052 A1 | 10/2002 | Chaudhari et al. |
| 2002/0160424 A1 | 10/2002 | Adler et al. |
| 2003/0008344 A1 | 1/2003 | Adler et al. |
| 2003/0054448 A1 | 3/2003 | Adler et al. |
| 2003/0089885 A1 | 5/2003 | Rogers et al. |
| 2003/0139470 A1 | 7/2003 | Ley et al. |
| 2003/0170608 A1 | 9/2003 | Pronin et al. |
| 2003/0207337 A1 | 11/2003 | Han et al. |
| 2003/0220479 A1 | 11/2003 | Li et al. |
| 2003/0228633 A1 | 12/2003 | Zoller et al. |
| 2003/0232407 A1 | 12/2003 | Zoller et al. |
| 2004/0072254 A1 | 4/2004 | Callamaras et al. |
| 2004/0132075 A1 | 7/2004 | Elliot et al. |
| 2004/0132134 A1 | 7/2004 | Adler et al. |
| 2004/0171042 A1 | 9/2004 | Adler et al. |
| 2004/0175792 A1 | 9/2004 | Zoller et al. |
| 2004/0175793 A1 | 9/2004 | Zoller et al. |
| 2004/0185469 A1 | 9/2004 | Zoller et al. |
| 2004/0191805 A1 | 9/2004 | Adler et al. |
| 2004/0191862 A1 | 9/2004 | Zoller et al. |
| 2004/0209286 A1 | 10/2004 | Adler et al. |
| 2004/0229239 A1 | 11/2004 | Adler et al. |
| 2005/0032158 A1 | 2/2005 | Adler et al. |
| 2005/0069944 A1 | 3/2005 | Adler |
| 2005/0084506 A1 | 4/2005 | Tachdjian et al. |
| 2005/0084932 A1 | 4/2005 | Zoller et al. |
| 2006/0045953 A1 | 3/2006 | Tachdjian et al. |

FOREIGN PATENT DOCUMENTS

| | | | |
|---|---|---|---|
| DE | 10109856 A1 | | 11/1957 |
| EP | 0 055 689 A1 | | 7/1982 |
| EP | 0 413 162 A2 | | 2/1991 |
| EP | 0 656 350 A1 | | 6/1995 |
| EP | 0 854 134 A1 | | 7/1998 |
| EP | 0 976 744 A1 | | 2/2000 |
| EP | 1 142 490 A1 | | 10/2001 |
| EP | 1 205 116 A2 | | 5/2002 |
| EP | 1 500 650 A1 | | 1/2005 |
| GB | 1 457 671 | | 12/1976 |
| GB | 1 489 359 | | 10/1977 |
| GB | 1 502 680 | | 3/1978 |
| JP | 50-64235 A | | 5/1975 |
| JP | 61-200951 | | 9/1986 |
| JP | 61-200951 A | | 9/1986 |
| JP | 01-106853 | | 4/1989 |
| JP | 1-106853 A | | 4/1989 |
| JP | 02-108697 | | 4/1990 |
| JP | 2-108697 A | | 4/1990 |
| JP | 4-8264 A | | 1/1992 |
| JP | 8-103243 A | | 4/1996 |
| JP | 2000-169438 A | | 6/2000 |
| JP | 2000-175650 A | | 6/2000 |
| JP | 2002-234898 | | 8/2002 |
| JP | 2002-234898 A | | 8/2002 |
| RU | 1811525 A3 | | 4/1993 |
| RU | 2162839 C2 | | 7/1996 |
| SU | 1750419 A3 | | 7/1992 |
| WO | WO 95/18617 A1 | | 7/1995 |
| WO | WO 96/21640 A1 | | 7/1996 |
| WO | WO 98/32733 A1 | | 7/1998 |
| WO | WO 99/07235 A1 | | 2/1999 |
| WO | WO 99/26927 A2 | | 6/1999 |
| WO | WO 00/06156 A1 | | 2/2000 |
| WO | WO 00/51970 A1 | | 9/2000 |
| WO | WO 00/63166 A1 | | 10/2000 |
| WO | WO 01/35768 A1 | | 5/2001 |
| WO | WO 01/77292 A2 | | 10/2001 |
| WO | WO 01/77676 A1 | | 10/2001 |
| WO | WO 01/79204 A1 | | 10/2001 |
| WO | WO 01/81311 A1 | | 11/2001 |
| WO | WO 01/97786 A2 | | 12/2001 |
| WO | WO 02/06254 A1 | | 1/2002 |
| WO | WO 02/036622 A2 | | 5/2002 |
| WO | WO 02/064139 A1 | | 8/2002 |
| WO | WO 02/064631 A2 | | 8/2002 |
| WO | WO 02/087361 A1 | | 11/2002 |
| WO | WO 03/001876 A2 | | 1/2003 |
| WO | WO 03/013517 A1 | | 2/2003 |
| WO | WO 03/037332 A1 | | 5/2003 |
| WO | WO 03/043444 A1 | | 5/2003 |
| WO | WO 03/070713 A1 | | 8/2003 |
| WO | WO 2004/000355 A1 | | 12/2003 |
| WO | WO 2004/011617 A2 | | 2/2004 |
| WO | WO 2004/026840 A1 | | 4/2004 |
| WO | WO 2004/080976 A1 | | 9/2004 |
| WO | WO 2004/081018 A1 | | 9/2004 |
| WO | WO 2004/089470 A2 | | 10/2004 |
| WO | WO 2004/092182 A1 | | 10/2004 |
| WO | WO 2004/113304 A1 | | 12/2004 |
| WO | WO 2005/015158 A2 | | 2/2005 |
| WO | WO 2005/041684 A2 | | 5/2005 |
| WO | WO 2006/084184 A2 | | 8/2006 |
| WO | WO 2006/084186 A2 | | 8/2006 |
| WO | WO 2006/084246 A2 | | 8/2006 |

OTHER PUBLICATIONS

Belitz et al., "Taste Properties of Amides," pp. 315-321, in Instrumental Analysis of Foods, vol. I, Academic Press, Inc. (1983).

Berge et al., "Pharmaceutical Salts,," J. Pharm. Sci., 66:1-19 (1977).

Biagi et al., "$N^6$-Cycloalkyl-2-phenyl-3-deaza-8-azaadenines: a new class of $A_1$ adenosine receptor ligands. A comparison with the corresponding adenines and 8-azaadenines," J. Med. Chem. 21(9):965-978 (1978).

Bors et al., "Antioxidant Mechanisms of Polyphenolic Caffeic Acid Oligomers, Constituents of Saliva officinalis," Bio. Res., 37:301-311 (2004).

Chandrashekar et al., "T2Rs Function as Bitter Taste Receptors," Cell, 100:703-711 (2000).

Clark et al., "Synthesis and Analgesic Activity of 1,3-Dihydro-3-(Substituted Phenyl)Imidazo[4,5-β]Pyridin-2-Ones and 3-(Substituted Phenyl)-1,2,3-Triazolo[4,5-β]Pyridines," Journal of Medicinal Chemistry, 21(9):965-978 (1978).

Crosignani et al., "Polymer-Supported Mukaiyama Reagent: A Useful Coupling Reagent for the Synthesis of Esters and Amides," Organic Letters, 6(24):4579-4582 (2004).

Date ct al., "Reactions of Lithiated ortho-Toluamides and Related Compounds with Vinysilanes: Synthesis of 1-Tetralones and 1-Naphtols," S. Chem. Pharm. Bull., 38(4):902-906 (1990).

Evangelista et al., "Synthesis and Anti-Ulcer Activity of Some New Compounds With Arylthiomethyl-Pyridine Structure," Farmaco Ed. Sci. Soc. Chim. Ital. 43(11):901-908 (1988).

Gawley et al., "(R,R)-1,3-Dibenzylisoindoline: A New C2-Symmetric Secondary Amine, by Stereoselective and Regioselective α,d-Dialkylation of Isoindoline, and an Improved Procedure for the Preparation of Isoindoline," J. Org. Chem., 53:5381-5383 (1988).

Higuchi et al., "4-Alkyl-and 3,4-Dialkyl-1,2,3,4-Tetrahydro-8-Pyridono[5,6-g]Quinolines: Potent, Nosteroidal Androgen Receptor Agonists," Bioorganic & Medicinal Chemistry Letters, 9:1335-1340 (1999).

Huang et al,, "2-{2-[3-(Pyridin-3-yloxy)phenyl]-2H-tetrazol-5-yl}pyridine: a highly potent, orally active, metabotropic glutamate subtype 5 (mGlu5) receptor antagonist," Bioorg. Med. Chem. Lett. 14(22):5473-5476 (2004).

Jasiczak et al., "Structure-Activity Relationship of Sweet Molecules: Phenylurea Derivatives," Polish J. Chem. 74;1259-1273 (2000).

Kinghorn et al., "Noncariogenic Intense Natural Sweeteners," Med. Res. Rev., 18(5):347-360 (1998).

Kinoshita et al., "Chalcogeno Morita-Baylis-Hillman Reaction of 2-(Methylchalcogeno)phenyl Vinyl Ketones with Aldehyds, Ketones, and α-Dicarbonyl Compounds," Eur. J. Org. Chem., 4852-4861 (2003).

Li et al., "Human Receptors for Sweet and Umami Taste," PNAS, 99(7):4692-4696 (2002).

Linton et al., "Acyl Dipeptides as Reversible Caspase Inhibitors. Part 1: Initial Lead Optimization," Bioorganic & Medicinal Chemistry Letters, 12:2969-2971 (2002).

Markus, "Culinary Applications of Flavor Enhancement in Product Development," Slide Presentation Annual Meeting of Institute of Food Technology, Las Vegas, Nevada, Jul. 12-16, 2004.

Matsunami et al., "A Family of Candidate Taste Receptors in Human and Mouse," Nature, 404:601-604 (2000).

McMurry, "Isoxazole Annelation Reaction: 1-Methyl-4,4a,5,6,7,8-Hexahydronaphthalen-2(3H)-One," Org. Syn. Coll., vol. 6, p. 781; vol. 53, p. 70, (1973).

Montmayeur et al., "A Candidate Taste Receptor Gene Near a Sweet Taste Locus," Nature Neuroscience, 4(5):492-498 (2001).

Morini et al., "From Small Sweeteners to Sweet Proteins: Anatomy of the Binding Sites of the Human T1R2.sub.—T1R3 Receptor," J. Med. Chem., 48(17):5520-5529 (Aug. 2005).

Musser et al., "Synthesis and Antiallergic Activities of 1,3-Oxazolo[4,5-h]quinolines," J. Med. Chem., 28:1255-1259 (1985).

Nelson et al., "Mammalian Sweet Taste Receptors," Cell, 106: 381-390 (2001).

Noyes et al., "Phthalimide," Organic Syntheses, Coll. vol. 1, p. 457; vol. 2, p. 75, 1941 and 1922.

Oshiro et al., "Novel Cerebroprotective Agents with Central Nervous System Stimulating Activity. 1. Synthesis and Pharmacology of 1-Amino 7-hydroxyindan Derivatives, " J. Med. Chem., 34:2004-2013 (1991).

Patonay et al., "Chemo- and Diastereoselectivity in the Dimethyldioxirane Oxidation of 2,3-Dihydro-4H-1-benzothiopyran-4-ones and 4H-1-Benzothiopyran-4-ones. Unusual Reactivity of 4H-1-Benzothiopyran-4-one 1-Oxides[1]," J. Org. Chem. 66:2275-2280 (2001).

Pernak et al., "Activity of New Quaternary Ammonium Compounds on Strains of Bacteria and Fungi. Part 5: Synthesis of 3-methyl-n-alkylthiomethylpyridine-, 1-methyl-3-n-alkylthiomethylimidazole- and 1-ethyl-3-n-alkylthiolimidazoline chlorides," Pharmazie 38(11):752-754 (1983).

Sarges et al., "5,8-Diubstituted 1-Aminotetralins. A Class of Compounds with a Novel Profile of Central Nervous System Activity," Journal of Medicinal Chemistry, 16(9):1003-1011 (1973).

Skupinska et al., "Concise Preparation of Amino-5,6,7,8-tetrahydroquinolines and Amino-5,6,7,8-tetrahydroisoquinolines via Catalytic Hydrogenation of Acetamidoquinolines and Acetamidoisoquinolines," J. Org. Chem., 67:7890-7893 (2002).

Skupinska et al., "Enzymatic Resolution of Bicyclic 1-Heteroarylamines using Candida antarcticai Lipase B," J. Org. Chem., 68(9):3546-3551 (2003).

Smith et al., "GRAS Flavoring Substances 21," Food Technology, 57(5):46-59 (2003).

Stalker et al., "Asymmetric Synthesis of Two New Conformationally Constrained Lysine Derivatives," Tetrahedron, 58:4837-4849 (2002).

Thate, "The Relationship Between Constitution and Taste Among Some Derivatives of Urea," Recueil Des Travaux Chimiques Des Pay-Bas et de La Belgique, 48:116-120 (1929).

Turnbull et al., "Disposition and Metabolism of 4-Methyl-2-(4-phenylbenzyl)-2-oxazoline-4-methanol in the Rat and Dog," Journal of Medicinal Chemistry, 17(1):45-48 (1974).

Thompson, "Examiner's first report on patent application No. 2004285410," 3 pages, Australia patent appl. No. 2004285410, IP Australia (Jul. 1, 2009).

Salas, Official action, 10 pages, Chile patent appl. No. 2015-2004 (Feb. 6, 2009) with redacted 6 pages translation provided by foreign associate.

Takiguchi, "Notice of Reasons for Rejection," 4 pages, Japan patent appl. No. 2006-522748, Japan Patent Office (Sep. 13, 2010) with 7 page translation.

Walsh, "Examination Report," 3 pages, New Zealand appl. No. 545746, Intellectual Property Office of New Zealand (Jun. 25, 2010).

"Written Opinion of the International Searching Authority," 5 pages, PCT appl. No. PCT/US04/25419, United States Patent and Trademark Office (Nov. 8, 2007).

"International Search Report," 8 pages, PCT appl. No. PCT/US04/25419, United States Patent and Trademark Office (Nov. 8, 2007).

Tallgreen, "International Search Report," 11 pages, PCT appl. No. PCT/US2006/004132, European Patent Office (Oct. 19, 2006).

Tallgreen, "Written Opinion of the International Searching Authority," 11 pages, PCT appl. No. PCT/US2006/004132, European Patent Office (Oct. 19, 2006).

\* cited by examiner

FLAVORS, FLAVOR MODIFIERS, TASTANTS, TASTE ENHANCERS, UMAMI OR SWEET TASTANTS, AND/OR ENHANCERS AND USE THEREOF

This application is a divisional of U.S. patent application Ser. No. 10/913,303, filed on Aug. 6, 2004 now U.S. Pat. No. 7,476,399 and published as U.S. Patent Application Publication No. 2005/0084506, which in turn claims the priority of U.S. provisional patent application Ser. No. 60/494,071 filed on Aug. 6, 2003, and also claims the priority of U.S. provisional patent application Ser. No. 60/552,064, filed Mar. 9, 2004, the entire disclosures of which are hereby incorporated herein by this reference.

FIELD OF THE INVENTION

The present invention relates to the discovery of flavor or taste modifiers, such as a flavoring or flavoring agents and flavor or taste enhancers, more particularly, savory ("umami") or sweet taste modifiers, —savory or sweet flavoring agents and savory or sweet flavor enhancers, for foods, beverages, and other comestible or orally administered medicinal products or compositions.

BACKGROUND OF THE INVENTION

For centuries, various natural and unnatural compositions and/or compounds have been added to comestible (edible) foods, beverages, and/or orally administered medicinal compositions to improve their taste. Although it has long been known that there are only a few basic types of "tastes," the biological and biochemical basis of taste perception was poorly understood, and most taste improving or taste modifying agents have been discovered largely by simple trial and error processes.

There has been significant recent progress in identifying useful natural flavoring agents, such as for example sweeteners such as sucrose, fructose, glucose, erythritol, isomalt, lactitol, mannitol, sorbitol, xylitol, certain known natural terpenoids, flavonoids, or protein sweeteners. See for example a recent article entitled "Noncariogenic Intense Natural Sweeteners" by Kinghorn et al. (Med Res Rev 18 (5) 347-360, 1998), which discussed recently discovered natural materials that are much more intensely sweet than common natural sweeteners such as sucrose, fructose, and the like. Similarly, there has been recent progress in identifying and commercializing new artificial sweeteners, such as aspartame, saccharin, acesulfame-K, cyclamate, sucralose, and alitame, etc., see a recent article by Ager, et al. (Angew Chem. Int. Ed. 1998, 37, 1802-1817). The entire disclosure of the two references identified above are hereby incorporated herein by reference, for the purpose of describing at least in part the knowledge of those of ordinary skill in the art regarding known sweetening agents.

However, there remains in the art a need for new and improved flavoring agents. For example, one of the five known basic tastes is the "savory" or "umami" flavor of monosodium glutamate ("MSG"). MSG is known to produce adverse reactions in some people, but very little progress has been made in identifying artificial substitutes for MSG. It is known that a few naturally occurring materials can increase or enhance the effectiveness of MSG as a savory flavoring agent, so that less MSG would be needed for a given flavoring application. For example the naturally occurring nucleotide compounds inosine monophosphate (IMP) or guanosine monophosphate (GMP) are known to have a multiplier effect on the savory taste of MSG, but IMP and GMP are very difficult and expensive to isolate and purify from natural sources, or synthesize, and hence have only limited practical application to most commercial needs in food or medicinal compositions. Less expensive compounds that would provide the flavor of MSG itself, or enhance the effectiveness of any MSG that is present could be of very high value. Similarly, discovery of compounds that are either new "High Intensity" sweeteners (i.e. they are many times sweeter than sucrose) would be of value, or any compounds that significantly increase the sweetness of known natural or artificial sweeteners, so that less of those caloric or non-caloric sweeteners would be required, would be of very high utility and value.

In recent years substantial progress has been made in biotechnology in general, and in better understanding the underlying biological and biochemical phenomena of taste perception. For example, taste receptor proteins have been recently identified in mammals which are involved in taste perception. Particularly, two different families of G protein coupled receptors believed to be involved in taste perception, T2R5 and T1R5, have been identified. (See, e.g., Nelson, et al., Cell (2001) 106(3):381-390; Adler, et al., Cell (2000) 100(6):693-702; Chandrashekar, et al., Cell (2000) 100:703-711; Matsunami, et al., Number (2000) 404:601-604; Li, et al., Proc. Natl. Acad. Sci. USA (2002) 99:4962-4966; Montmayeur, et al., Nature Neuroscience (2001) 4(S):492-498: U.S. Pat. No. 6,462,148; and PCT publications WO 02/06254, WO 00/63166 art, WO 02/064631, and WO 03/001876, and U.S. Patent publication US 2003-0232407 A1). The entire disclosures of the articles, patent applications, and issued patents cited immediately above are hereby incorporated herein by reference, for all purposes, including their disclosures of the identities and structures of T2R5 and T1R5 mammalian taste receptor proteins and methods for artificially expressing those receptors in cell lines and using the resulting cell lines for screening compounds as potential "savory" or "sweet" flavoring agents.

Whereas the T2R family includes a family of over 25 genes that are involved in bitter taste perception, the T1R5 only includes three members, T1R1, T1R2 and T1R3. (see Li, et al., Proc. Natl. Acad. Sci. USA (2002) 99:4962-4966.) Recently it was disclosed in WO 02/064631 and/or WO 03/001876 that certain T1R members, when co-expressed in suitable mammalian cell lines, assemble to form functional taste receptors. Particularly it was found that co-expression of T1R1 and T1R3 in a suitable host cell results in a functional T1R1/T1R3 savory ("umami") taste receptor that responds to savory taste stimuli, including monosodium glutamate. Similarly, it was found that co-expression of T1R2 and T1R3 in a suitable host cell results in a functional T1R2/T1R3 "sweet" taste receptor that responds to different taste stimuli including naturally occurring and artificial sweeteners. (See Li, et al. (Id.). The references cited above also disclosed assays and/or high throughput screens that measure T1R1/T1R3 or T1R2/T1R3 receptor activity by fluorometric imaging in the presence of the target compounds. We employed the above-described assays and/or high throughput screening methods to identify initial "lead" compounds that modulate the activity of T1R1/T1R3 "savory" taste receptors, or T1R2/T1R3 "sweet" taste receptors, then embarked on a long, complex and iterative process of investigation, evaluation, and optimization, so as to arrive at the various inventions described below.

SUMMARY OF THE INVENTION

The invention has many aspects, all of which relate in some fashion to certain non-naturally occurring amide compounds and/or amide derivative compounds having the generic structure shown below in Formula (I):

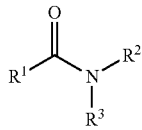

(I)

wherein $R^1$, $R^2$ and $R^3$ can be and are independently further defined in various ways, as is further detailed below. In all the embodiments of the amide compounds of Formula (I) the $R^1$ group is an organic residue comprising at least three carbon atoms, with a variety of alternative limits on the size and/or chemical characteristics of the $R^1$ group, as will be further described below. In many but not all embodiments, the amide compounds of Formula (I) are "primary" amides, i.e. one of $R^2$ and $R^3$ is an organic group comprising at least three carbon atoms, while the other of $R^2$ and $R^3$ is hydrogen.

The amide compounds of Formula (I) also comprise certain sub-classes of amide derivatives or classes of derivatives related to amides, such as for example ureas, urethanes, oxalamides, acrylamides, and the like, as will be further described below.

Many of the subgenuses and species of the "amide" compounds of Formula (I) are shown below to bind to and/or activate one or both of the T1R1/T1R3 "savory" ("umami") or T1R2/T1R3 sweet receptors in-vitro, at relatively low concentrations on the order of micromolar or lower concentrations. The amide compounds are also believed to similarly interact with savory or sweet flavor receptors of animals or humans in vivo, as has been confirmed by actual human taste tests of some of compounds of Formula (I).

Accordingly, many of the subgenuses and species of the "amide" compounds of Formula (I) further described hereinbelow can, at surprisingly low concentrations be used as savory or sweet flavoring agents, or savory or sweet agent enhancers. Accordingly, in some embodiments, the invention relates to methods for modulating the savory taste of a comestible or medicinal product comprising:
 a) providing at least one comestible or medicinal product, or a precursor thereof, and
 b) combining the comestible or medicinal product or precursor thereof with at least a savory flavor modulating amount, or a sweet flavor modulating amount, of at least one non-naturally occurring amide compound, or a comestibly acceptable salt thereof, so as to form a modified comestible or medicinal product;
wherein the amide compound has the formula:

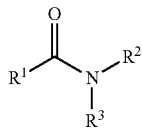

wherein $R^1$ comprises an organic or hydrocarbon residue having at least three carbon atoms and optionally one or more heteroatoms independently selected from oxygen, nitrogen, sulfur, halogens, or phosphorus; and
wherein optionally one of $R^2$ and $R^3$ is H, and wherein at least one of the other of $R^2$ and $R^3$ comprises an organic or hydrocarbon residue having at least three carbon atoms and optionally one or more heteroatoms independently selected from oxygen, nitrogen, sulfur, halogens, or phosphorus.

Additional optional limitations on the chemical and physical characteristics of the $R^1$, $R^2$, and $R^3$ groups will be described below. Some of the amide compounds of Formula (I) have been synthesized by methods known in the prior art for various purposes, but to the knowledge of the inventors it has not been previously recognized that such amides can be utilized at very low concentrations as savory or sweet flavoring agents, or savory or sweet taste enhancers. Moreover many of the amide compounds of Formula (I) disclosed herein are novel compounds that have not been previously synthesized at all, and are effective savory or sweet taste flavoring agents or taste enhancers.

The invention also relates to the comestible or medicinal products produced by the processes mentioned above, and to comestible or medicinal products or compositions, or their precursors that contain the amide compounds of Formula (I), which include but are not necessarily limited to food, drink, medicinal products and compositions intended for oral administration, and the precursors thereof.

In many embodiments, one or more of the amide compounds of Formula (I) further identified, described, and/or claimed herein, or a comestibly acceptable salt thereof, can be used in mixtures or in combination with other known savory or sweet compounds, or used as flavor enhancers in comestible food, beverage and medicinal compositions, for human or animal consumption.

In some embodiments, the amide compounds of Formula (I), while having little or perhaps even no sweet or savory flavor when tasted in isolation, can be employed at very low concentrations in order to very significantly enhance the effectiveness of other savory or sweet flavor agents in a comestible or medicinal composition, or a precursor thereof. The inventions described herein also relate to the flavor-modified comestible or medicinal products that contain flavor modulating amounts of one or more of the amide compounds disclosed herein.

Many of the amide compounds of Formula (I) and/or its various subgenuses of amide compounds, when used together with MSG or alone, increase or modulate a response in vitro, and savory taste perception in humans at surprisingly low concentrations. In some embodiments, the amide compounds of the invention are T1R1/T1R3 receptor agonists and accordingly can induce or enhance savory taste perception in humans. These compounds can enhance, potentiate, modulate or induce other natural and synthetic savory flavoring agents.

In related embodiments, many of the amide compounds within the scope of Formula (I) are T1R2/T1R3 receptor agonists and accordingly can induce sweet taste perception in humans at surprisingly low concentrations. These compounds can enhance, potentiate, modulate or induce other natural, semi-synthetic, or synthetic sweet flavoring agents, such as for example sucrose, fructose, glucose, erythritol, isomalt, lactitol, mannitol, sorbitol, xylitol, certain known natural terpenoids, flavonoids, or protein sweeteners, aspartame, saccharin, acesulfame-K, cyclamate, sucralose, and alitame, and the like, or a mixture thereof.

Unexpectedly, it has also been discovered that in many embodiments of the compounds of Formula (I) there are significant structural similarities and/or overlaps between the amide compounds that can produce or enhance the sweet and savory tastes of comestible or medicinal compositions, even though it is believed that the relevant biological taste receptor proteins are significantly different. Even more unexpectedly, it has been discovered that at least some of the amide compounds of Formula (I) disclosed herein can induce or enhance both the sweet and savory tastes of the comestible or medicinal products. Therefore in some aspects the invention is related to compounds of Formula (I) or its various subgenuses and species compounds that modulate (e.g., induce, enhance or potentiate) the flavor of known natural or synthetic sweetener agents.

In some embodiments, the invention relates to novel compounds, flavoring agents, flavor enhancers, flavor modifying compounds, and/or compositions containing the compounds of Formula (I), and its various subgenuses and species compounds.

In other embodiments, the invention is directed to compounds of Formula (I) or its various subgenuses and species compounds that modulate (e.g., induce, enhance or potentiate) the flavor of monosodium glutamate (MSG), or synthetic savory flavoring agents.

In some embodiments, the invention relates to comestible or medicinal compositions suitable for human or animal consumption, or precursors thereof, containing at least one compound of Formula (I), or a comestibly or pharmaceutically acceptable salt thereof. These compositions will preferably include comestible products such as foods or beverages, medicinal products or compositions intended for oral administration, and oral hygiene products, and additives which when added to these products modulate the flavor or taste thereof, particularly by enhancing (increasing) the savory and/or sweet taste thereof.

The present invention also relates to novel genuses and species of amide compounds within the scope of the compounds of Formula (I), and derivatives, flavoring agents, comestible or medicinal products or compositions, including savory or sweet flavoring agents and flavor enhancers containing the same.

The foregoing discussion merely summarizes certain aspects of the inventions and is not intended, nor should it be construed, as limiting the invention in any way.

DETAILED DESCRIPTION OF THE INVENTION

The present invention can be understood more readily by reference to the following detailed description of various embodiments of the invention and the Examples included therein and to the chemical drawings and Tables and their previous and following description. Before the present compounds, compositions, and/or methods are disclosed and described, it is to be understood that unless otherwise specifically indicated by the claims, the invention is not limited to specific foods or food preparation methods, specific comestibles or pharmaceutical carriers or formulations, or to particular modes of formulating the compounds of the invention into comestible or medicinal products or compositions intended for oral administration, because as one of ordinary skill in relevant arts is well aware, such things can of course, vary. It is also to be understood that the terminology used herein is for the purpose of describing particular embodiments only and is not intended to be limiting.

Definitions

As used herein, the term "medicinal product" includes both solids and liquid compositions which are ingestible non-toxic materials which have medicinal value or comprise medicinally active agents such as cough syrups, cough drops, aspirin and chewable medicinal tablets.

An oral hygiene product includes solids and liquids such as toothpaste or mouthwash.

A "comestibly, biologically or medicinally acceptable carrier or excipient" is a solid or liquid medium and/or composition that is used to prepare a desired dosage form of the inventive compound, in order to administer the inventive compound in a dispersed/diluted form, so that the biological effectiveness of the inventive compound is maximized. A comestibly, biologically or medicinally acceptable carrier includes many common food ingredients, such as water at neutral, acidic, or basic pH, fruit or vegetable juices, vinegar, marinades, beer, wine, natural water/fat emulsions such as milk or condensed milk, edible oils and shortenings, fatty acids, low molecular weight oligomers of propylene glycol, glyceryl esters of fatty acids, and dispersions or emulsions of such hydrophobic substances in aqueous media, salts such as sodium chloride, wheat flours, solvents such as ethanol, solid edible diluents such as vegetable powders or flours, or other liquid vehicles; dispersion or suspension aids; surface active agents; isotonic agents; thickening or emulsifying agents, preservatives; solid binders; lubricants and the like.

A "flavor" herein refers to the perception of taste and/or smell in a subject, which include sweet, sour, salty, bitter, umami, and others. The subject may be a human or an animal.

A "flavoring agent" herein refers to a compound or a biologically acceptable salt thereof that induces a flavor or taste in a animal or a human.

A "flavor modifier" herein refers to a compound or biologically acceptable salt thereof that modulates, including enhancing or potentiating, and inducing, the tastes and/or smell of a natural or synthetic flavoring agent in a animal or a human.

A "flavor enhancer" herein refers to a compound or biologically acceptable salt thereof that enhances the tastes or smell of a natural or synthetic flavoring agent.

"Savory flavor" herein refers to the savory "umami" taste typically induced by MSG (mono sodium glutamate) in a animal or a human.

"Savory flavoring agent," "savory compound" or "savory receptor activating compound" herein refers to a compound or biologically acceptable salt thereof that elicits a detectable savory flavor in a subject, e.g., MSG (mono sodium glutamate) or a compound that activates a T1R1/T1R3 receptor in vitro. The subject may be a human or an animal.

"Sweet flavoring agent," "sweet compound" or "sweet receptor activating compound" herein refers to a compound or biologically acceptable salt thereof that elicits a detectable sweet flavor in a subject, e.g, sucrose, fructose, glucose, and other known natural saccharide-based sweeteners, or known artificial sweeteners such as saccharine, cyclamate, aspartame, and the like as is further discussed herein, or a compound that activates a T1R2/T1R3 receptor in vitro. The subject may be a human or an animal.

A "savory flavor modifier" herein refers to a compound or biologically acceptable salt thereof that modulates, including enhancing or potentiating, inducing, and blocking, the savory taste of a natural or synthetic savory flavoring agents, e.g., monosodium glutamate (MSG) in a animal or a human.

A "sweet flavor modifier" herein refers to a compound or biologically acceptable salt thereof that modulates, including enhancing or potentiating, inducing, and blocking, the sweet taste of a natural or synthetic sweet flavoring agents, e.g., sucrose, fructose, glucose, and other known natural saccharide-based sweeteners, or known artificial sweeteners such as saccharine, cyclamate, aspartame, and the like, in a animal or a human.

A "savory flavor enhancer" herein refers to a compound or biologically acceptable salt thereof that enhances or potentiates the savory taste of a natural or synthetic savory flavoring agents, e.g., monosodium glutamate (MSG) in a animal or a human.

A "sweet flavor enhancer" herein refers to a compound or biologically acceptable salt thereof that enhances or potentiates the sweet taste of a natural or synthetic sweet flavoring agents, e.g., sucrose, fructose, glucose, and other known natural saccharide-based sweeteners, or known artificial sweeteners such as saccharine, cyclamate, aspartame, and the like as is further discussed herein in an animal or a human.

An "umami receptor activating compound" herein refers to a compound that activates an umami receptor, such as a T1R1/T1R3 receptor.

A "sweet receptor activating compound" herein refers to a compound that activates a sweet receptor, such as a T1R2/T1R3 receptor.

An "umami receptor modulating compound" herein refers to a compound that modulates (activates, enhances or blocks) an umami receptor.

A "sweet receptor modulating compound" herein refers to a compound that modulates (activates, enhances or blocks) a sweet receptor.

An "umami receptor enhancing compound" herein refers to a compound that enhances or potentiates the effect of a natural or synthetic umami receptor activating compound, e.g., monosodium glutamate (MSG).

A "sweet receptor enhancing compound" herein refers to a compound that enhances or potentiates the effect of a natural or synthetic sweet receptor activating compound, e.g., sucrose, fructose, glucose, and other known natural saccharide-based sweeteners, or known artificial sweeteners such as saccharine, cyclamate, aspartame, and the like as is further discussed herein.

A "savory flavoring agent amount" herein refers to an amount of a compound that is sufficient to induce savory taste in a comestible or medicinal product or composition, or a precursor thereof. A fairly broad range of a savory flavoring agent amount can be from about 0.001 ppm to 100 ppm, or a narrow range from about 0.1 ppm to about 10 ppm. Alternative ranges of savory flavoring agent amounts can be from about 0.01 ppm to about 30 ppm, from about 0.05 ppm to about 15 ppm, from about 0.1 ppm to about 5 ppm, or from about 0.1 ppm to about 3 ppm.

A "sweet flavoring agent amount" herein refers to an amount of a compound that is sufficient to induce sweet taste in a comestible or medicinal product or composition, or a precursor thereof. A fairly broad range of a sweet flavoring agent amount can be from about 0.001 ppm to 100 ppm, or a narrow range from about 0.1 ppm to about 10 ppm. Alternative ranges of sweet flavoring agent amounts can be from about 0.01 ppm to about 30 ppm, from about 0.05 ppm to about 15 ppm, from about 0.1 ppm to about 5 ppm, or from about 0.1 ppm to about 3 ppm.

A "savory flavor modulating amount" herein refers to an amount of a compound of Formula (I) that is sufficient to alter (either increase or decrease) savory taste in a comestible or medicinal product or composition, or a precursor thereof, sufficiently to be perceived by a human subject. A fairly broad range of a savory flavor modulating amount can be from about 0.001 ppm to 100 ppm, or a narrow range from about 0.1 ppm to about 10 ppm. Alternative ranges of savory flavor modulating amounts can be from about 0.01 ppm to about 30 ppm, from about 0.05 ppm to about 15 ppm, from about 0.1 ppm to about 5 ppm, or from about 0.1 ppm to about 3 ppm.

A "sweet flavor modulating amount" herein refers to an amount of a compound of Formula (I) that is sufficient to alter (either increase or decrease) sweet taste in a comestible or medicinal product or composition, or a precursor thereof, sufficiently to be perceived by a human subject. A fairly broad range of a sweet flavor modulating amount can be from about 0.001 ppm to 100 ppm, or a narrow range from about 0.1 ppm to about 10 ppm. Alternative ranges of sweet flavor modulating amounts can be from about 0.01 ppm to about 30 ppm, from about 0.05 ppm to about 15 ppm, from about 0.1 ppm to about 5 ppm, or from about 0.1 ppm to about 3 ppm.

A "savory flavor enhancing amount" herein refers to an amount of a compound that is sufficient to enhance the taste of a natural or synthetic flavoring agents, e.g., monosodium glutamate (MSG) in a comestible or medicinal product or composition. A fairly broad range of a savory flavor enhancing amount can be from about 0.001 ppm to 100 ppm, or a narrow range from about 0.1 ppm to about 10 ppm. Alternative ranges of savory flavor enhancing amounts can be from about 0.01 ppm to about 30 ppm, from about 0.05 ppm to about 15 ppm, from about 0.1 ppm to about 5 ppm, or from about 0.1 ppm to about 3 ppm.

A "sweet flavor enhancing amount" herein refers to an amount of a compound that is sufficient to enhance the taste of a natural or synthetic flavoring agents, e.g., sucrose, fructose, glucose, and other known natural saccharide-based sweeteners, or known artificial sweeteners such as saccharine, cyclamate, aspartame, and the like as is further discussed herein) in a comestible or medicinal product or composition. A fairly broad range of a sweet flavor enhancing amount can be from about 0.001 ppm to 100 ppm, or a narrow range from about 0.1 ppm to about 10 ppm. Alternative ranges of sweet flavor enhancing amounts can be from about 0.01 ppm to about 30 ppm, from about 0.05 ppm to about 15 ppm, from about 0.1 ppm to about 5 ppm, or from about 0.1 ppm to about 3 ppm.

An "umami receptor modulating amount" herein refers to an amount of a compound that is sufficient to modulate (activate, enhance or block) an umami receptor. A preferable range of an umami receptor modulating amount is 1 pM to 100 mM and most preferably 1 nM to 100 μM and most preferably mM to 30 μM. A fairly broad range of a umami flavor enhancing amount can be from about 0.001 ppm to 100 ppm, or a narrow range from about 0.1 ppm to about 10 ppm. Alternative ranges of umami flavor enhancing amounts can be from about 0.01 ppm to about 30 ppm, from about 0.05 ppm to about 15 ppm, from about 0.1 ppm to about 5 ppm, or from about 0.1 ppm to about 3 ppm.

A "T1R1/T1R3 receptor modulating or activating amount" is an amount of compound that is sufficient to modulate or activate a T1R1/T1R3 receptor. These amounts are preferably the same as the umami receptor modulating amounts.

An "umami receptor" is a taste receptor that can be modulated by a savory compound. Preferably an umami receptor is a G protein coupled receptor, and more preferably the umami receptor is a T1R1/T1R3 receptor.

Compounds of the invention modulate an umami receptor and preferably are agonists of the T1R1/T1R3 receptor. An agonist of this receptor has the effect of activating the G protein signaling cascade. In many cases, this agonist effect of the compound on the receptor also produces a perceived savory flavor in a taste test. It is desirable, therefore, that such inventive compounds serve as a replacement for MSG, which is not tolerated by some in, for example, comestible products.

In addition, this agonist effect also is responsible for the synergistic savory taste effect, which occurs when a compound of the invention is combined with another savory flavoring agent such as MSG. The nucleotides, IMP or GMP, are conventionally added to MSG, to intensify the savory flavor of MSG, so that relatively less MSG is needed to provide the same savory flavor in comparison to MSG alone. Therefore, it is desirable that combining compounds of the invention with another savory flavoring agent such as MSG advantageously eliminates the need to add expensive nucleotides, such as IMP, as a flavor enhancer, while concomitantly reducing or eliminating the amount of a savory compound such as MSG needed to provide the same savory flavor in comparison to the savory compound or MSG alone.

A "sweet receptor modulating amount" herein refers to an amount of a compound that is sufficient to modulate (activate, enhance or block) a sweet receptor. A preferable range of an sweet receptor modulating amount is 1 pM to 100 mM and most preferably 1 nM to 100 µM and most preferably 1 nM to 30 µM.

A "T1R2/T1R3 receptor modulating or activating amount" is an amount of compound that is sufficient to modulate or activate a T1R2/T1R3 receptor. These amounts are preferably the same as the sweet receptor modulating amounts.

A "sweet receptor" is a taste receptor that can be modulated by a sweet compound. Preferably an sweet receptor is a G protein coupled receptor, and more preferably the umami receptor is a T1R2/T1R3 receptor.

Many compounds of Formula (I) can modulate a sweet receptor and preferably are agonists of the T1R2/T1R3 receptor. An agonist of this receptor has the effect of activating the G protein signaling cascade. In many cases, this agonist effect of the compound on the receptor also produces a perceived sweet flavor in a taste test. It is desirable, therefore, that such inventive compounds serve as a replacement for sucrose, fructose, glucose, and other known natural saccharide-based sweeteners, or known artificial sweeteners such as saccharine, cyclamate, aspartame, and the like, or mixtures thereof as is further discussed herein.

A "synergistic effect" relates to the enhanced savory and/or sweet flavor of a combination of savory and/or or sweet compounds or receptor activating compounds, in comparison to the sum of the taste effects or flavor associated effects associated with each individual compound. In the case of savory enhancer compounds, a synergistic effect on the effectiveness of MSG may be indicated for a compound of Formula (I) having an EC50 ratio (defined hereinbelow) of 2.0 or more, or preferably 5.0 or more, or 10.0 or more, or 15.0 or more. An EC50 assay for sweet enhancement has not yet been developed, but in the case of both savory and sweet enhancer compounds, a synergistic effect can be confirmed by human taste tests, as described elsewhere herein.

When the compounds described here include one or more chiral centers, the stereochemistry of such chiral centers can independently be in the R or S configuration, or a mixture of the two. The chiral centers can be further designated as R or S or R,S or d,D, l/L or d,l, D,L. Correspondingly, the amide compounds of the invention, if they can be present in optically active form, can actually be present in the form of a racemic mixture of enantiomers, or in the form of either of the separate enantiomers in substantially isolated and purified form, or as a mixture comprising any relative proportions of the enantiomers.

Regarding the compounds described herein, the suffix "ene" added to any of the described terms means that the substituent is connected to two other parts in the compound. For example, "alkylene" is $(CH_2)_n$, "alkenylene" is such a moiety that contains a double bond and "alkynylene" is such a moiety that contains a triple bond.

As used herein, "hydrocarbon residue" refers to a chemical sub-group within a larger chemical compound which has only carbon and hydrogen atoms. The hydrocarbon residue may be aliphatic or aromatic, straight-chain, cyclic, branched, saturated or unsaturated. The hydrocarbon residue, when so stated however, may contain or be substituted with heteroatoms such as O, S or N, or the halogens (fluorine, chlorine, bromine, and iodine), or substituent groups containing heteroatoms (OH, $NH_2$, $NO_2$, $SO_3H$, and the like) over and above the carbon and hydrogen atoms of the substituent residue. Thus, when specifically noted as containing such heteroatoms, or designated as "substituted," the hydrocarbon residue may also contain carbonyl groups, amino groups, hydroxyl groups and the like, or contain heteroatoms inserted into the "backbone" of the hydrocarbon residue.

As used herein, "inorganic residue" refers to a residue that does not contain carbon, but contains at least some heteroatoms, including O, N, S, one or more halogens, or alkali metal or alkaline earth metal ions. Examples include, but are not limited to H, Na+, Ca++ and K+, halo, hydroxy, $NO_2$ or $NH_2$.

As used herein, the term "alkyl," "alkenyl" and "alkynyl" include straight- and branched-chain and cyclic monovalent substituents that respectively are saturated, unsaturated with at least one double bond, and unsaturated with at least one triple bond.

"Alkyl" refers to a hydrocarbon group that can be conceptually formed from an alkane by removing hydrogen from the structure of a hydrocarbon compound having straight or branched carbon chains, and replacing the hydrogen atom with another atom or substitutent group. In some embodiments of the invention, the alkyl groups are "C1 to C6 alkyl" such as methyl, ethyl, propyl, isopropyl, n-butyl, iso-butyl, sec-butyl, tert-butyl, amyl, tert-amyl, hexyl and the like. In some embodiments of the invention "C1 to C4 alkyl" groups (alternatively termed "lower alkyl" groups are methyl, ethyl, propyl, iso-butyl, sec-butyl t-butyl, and iso-propyl. Some of the preferred alkyl groups of the invention have three or more carbon atoms preferably 3 to 16 carbon atoms, 4 to 14 carbon atoms, or 6 to 12 carbon atoms.

Preferred alkenyl groups are "C2 to C7 alkenyl" such as vinyl, allyl, 2-butenyl, 3-butenyl, 2-pentenyl, 3-pentenyl, 4-pentenyl, 2-hexenyl, 3-hexenyl, 4-hexenyl, 5-hexenyl, 2-heptenyl, 3-heptenyl, 4-heptenyl, 5-heptenyl, 6-heptenyl, as well as dienes and trienes of straight and branched chains.

Preferred alkynyl groups are "C2 to C7 alkynyl" such as ethynyl, propynyl, 2-butynyl, 2-pentynyl, 3-pentynyl, 2-hexynyl, 3-hexynyl, 4-hexynyl, 2-heptynyl, 3-heptynyl, 4-heptynyl, 5-heptynyl as well as di- and tri-ynes of straight and branched chains including ene-ynes.

Hydrocarbon residues may be optionally substituted. Two of said optional substituents on adjacent positions can be joined to form a fused, optionally substituted aromatic or nonaromatic, saturated or unsaturated ring which contains 3-8 members. Optional substituents are generally hydrocarbon residues that may contain one or more heteroatoms or an inorganic residue such as H, $Na^+$, $Ca^{2+}$ or $K^+$.

The terms "substituted alkyl," "substituted alkenyl," "substituted alkynyl," and "substituted alkylene" denote that the alkyl, alkenyl, alkynyl and alkylene groups are substituted by one or more, and preferably one or two substituents, preferably halogen, hydroxy, C1 to C7 alkoxy, alkoxy-alkyl, oxo, C3 to C7 cycloalkyl, naphthyl, amino, (monosubstituted) amino, (disubstituted)amino, guanidino, heterocycle, substituted heterocycle, imidazolyl, indolyl, pyrrolidinyl, C1 to C7 acyl, C1 to C7 acyloxy, nitro, carboxy, carbamoyl, carboxamide, N—(C1 to C6 alkyl)carboxamide, N,N-di(C1 to C6 alkyl)carboxamide, cyano, methylsulfonylamino, thiol, C1 to C4 alkylthio or C1 to C4 alkylsulfonyl groups. The substituted alkyl groups may be substituted once or more, and preferably once or twice, with the same or with different substituents. In many embodiments of the invention, a preferred group of substituent groups include hydroxy, fluoro, chloro, $NH_2$, $NHCH_3$, $N(CH_3)_2$, $CO_2CH_3$, SEt, $SCH_3$, methyl, ethyl, isopropyl, vinyl, trifluoromethyl, methoxy, ethoxy, isopropoxy, and trifluoromethoxy groups. In many embodiments of the invention that comprise the above lists of substituent groups, an even more preferred group of substituent groups include hydroxy, SEt, $SCH_3$, methyl, ethyl, isopropyl, methoxy, and ethoxy groups.

Examples of the above substituted alkyl groups include the 2-oxo-prop-1-yl, 3-oxo-but-1-yl, cyanomethyl, nitromethyl, chloromethyl, hydroxymethyl, tetrahydropyranyloxymethyl, trityloxymethyl, propionyloxymethyl, aminomethyl, carboxymethyl, allyloxycarbonylmethyl, allyloxycarbonylaminomethyl, methoxymethyl, ethoxymethyl, t-butoxymethyl, acetoxymethyl, chloromethyl, trifluoromethyl, 6-hydroxyhexyl, 2,4-dichloro(n-butyl), 2-aminopropyl, 1-chloroethyl, 2-chloroethyl, 1-bromoethyl, 2-chloroethyl, 1-fluoroethyl, 2-fluoroethyl, 1-iodoethyl, 2-iodoethyl, 1-chloropropyl, 2-chloropropyl, 3-chloropropyl, 1-bromopropyl, 2-bromopropyl, 3-bromopropyl, 1-fluoropropyl, 2-fluoropropyl, 3-fluoropropyl, 2-aminoethyl, 1-aminoethyl, N-benzoyl-2-aminoethyl, N-acetyl-2-aminoethyl, N-benzoyl-1-aminoethyl, N-acetyl-1-aminoethyl and the like.

Examples of the above substituted alkenyl groups include styrenyl, 3-chloro-propen-1-yl, 3-chloro-buten-1-yl, 3-methoxy-propen-2-yl, 3-phenyl-buten-2-yl, 1-cyano-buten-3-yl and the like. The geometrical isomerism is not critical, and all geometrical isomers for a given substituted alkenyl can be used.

Examples of the above substituted alkynyl groups include phenylacetylen-1-yl, 1-phenyl-2-propyn-1-yl and the like.

The term "oxo" denotes a carbon atom bonded to two additional carbon atoms substituted with an oxygen atom doubly bonded to the carbon atom, thereby forming a ketone moiety.

"Alkoxy" refers to an OR group, wherein R is an alkyl or substituted alkyl. "Alkoxy-alkyl" refers to an alkyl group containing an alkoxy.

Preferred alkoxy groups are "C1 to C7 alkoxy" such as methoxy, ethoxy, n-propoxy, isopropoxy, n-butoxy, t-butoxy and like groups. The term "C1 to C7 substituted alkoxy" means the alkyl portion of the alkoxy can be substituted in the same manner as in relation to C1 to C6 substituted alkyl. Similarly, the term "C1 to C7 phenylalkoxy" as used herein means "C1 to C7 alkoxy" bonded to a phenyl radical.

"Acyloxy" refers to an OR group where R is an acyl group. Preferred acyloxy groups are "C1 to C7 acyloxy" such as formyloxy, acetoxy, propionyloxy, butyryloxy, pivaloyloxy, pentanoyloxy, hexanoyloxy, heptanoyloxy and the like.

As used herein, "acyl" encompasses the definitions of alkyl, alkenyl, alkynyl and the related hetero-forms which are coupled to an additional residue through a carbonyl group. Preferred acyl groups are "C1 to C7 acyl" such as formyl, acetyl, propionyl, butyryl, pentanoyl, pivaloyl, hexanoyl, heptanoyl, benzoyl and the like. More preferred acyl groups are acetyl and benzoyl.

The term "substituted acyl" denotes the acyl group substituted by one or more, and preferably one or two, halogen, hydroxy, oxo, alkyl, cycloalkyl, naphthyl, amino, (monosubstituted)amino, (disubstituted)amino, guanidino, heterocyclic ring, substituted heterocyclic ring, imidazolyl, indolyl, pyrrolidinyl, C1 to C7 alkoxy, alkoxy-alkyl, C1 to C7 acyl, C1 to C7 acyloxy, nitro, C1 to C6 alkyl ester, carboxy, alkoxycarbonyl, carbamoyl, carboxamide, N—(C1 to C6 alkyl)carboxamide, N,N-di(C1 to C6 alkyl)carboxamide, cyano, methylsulfonylamino, thiol, C1 to C4 alkylthio or C1 to C4 alkylsulfonyl groups. The substituted acyl groups may be substituted once or more, and preferably once or twice, with the same or with different substituents.

Examples of C1 to C7 substituted acyl groups include 4-phenylbutyroyl, 3-phenylbutyroyl, 3 phenylpropanoyl, 2-cyclohexanylacetyl, cyclohexanecarbonyl, 2-furanoyl and 3 dimethylaminobenzoyl.

Cycloalkyl residues are hydrocarbon groups within a molecule that comprise at least one ring having 3 to 8 carbon atoms linked into a ring. Examples of such cyclalkyl residues include cyclopropyl, cyclobutyl, cyclopentyl, cyclohexyl, cycloheptyl, cyclooctyl rings, and saturated bicyclic or fused polycyclic cycloalkanes such as decalin groups, norbornyl groups, and the like.

Preferred cycloalkyl groups include "C3 to C7 cycloalkyl" such as cyclopropyl, cyclobutyl, cyclopentyl, cyclohexyl or cycloheptyl rings. Similarly, the term "C5 to C7 cycloalkyl" includes the cyclopentyl, cyclohexyl or cycloheptyl rings.

"Substituted cycloalkyl" indicates the above cycloalkyl rings are substituted preferably by one or two halogen, hydroxy, C1 to C4 alkylthio, C1 to C4 alkylsulfoxide, C1 to C4 alkylsulfonyl, C1 to C4 substituted alkylthio, C1 to C4 substituted alkylsulfoxide, C1 to C4 substituted alkylsulfonyl, C1 to C6 alkyl, C1 to C7 alkoxy, C1 to C6 substituted alkyl, C1 to C7 alkoxy-alkyl, oxo (monosubstituted)amino, (disubstituted)amino, trifluoromethyl, carboxy, phenyl, substituted phenyl, phenylthio, phenylsulfoxide, phenylsulfonyl, amino. In many embodiments of substituted cycloalkyl groups, the substituted cycloalkyl group will have 1, 2, 3, or 4 substituent groups independently selected from hydroxy, fluoro, chloro, $NH_2$, $NHCH_3$, $N(CH_3)_2$, $CO_2CH_3$, SEt, $SCH_3$, methyl, ethyl, isopropyl, vinyl, trifluoromethyl, methoxy, ethoxy, isopropoxy, and trifluoromethoxy groups.

The term "cycloalkylene" means a cycloalkyl, as defined above, where the cycloalkyl radical is bonded at two positions connecting together two separate additional groups. Similarly, the term "substituted cycloalkylene" means a cycloalkylene where the cycloalkyl radical is bonded at two positions connecting together two separate additional groups and further bearing at least one additional substituent.

The term "cycloalkenyl" indicates preferably a 1,2, or 3-cyclopentenyl ring, a 1, 2, 3 or 4-cyclohexenyl ring or a 1, 2, 3, 4 or 5-cycloheptenyl ring, while the term "substituted cycloalkenyl" denotes the above cycloalkenyl rings substituted with a substituent, preferably by a C1 to C6 alkyl, halogen, hydroxy, C1 to C7 alkoxy, alkoxy-alkyl, trifluoromethyl, carboxy, alkoxycarbonyl oxo, (monosubstituted) amino, (disubstituted)amino, phenyl, substituted phenyl, amino, or protected amino.

The term "cycloalkenylene" is a cycloalkenyl ring, as defined above, where the cycloalkenyl radical is bonded at two positions connecting together two separate additional groups. Similarly, the term "substituted cycloalkenylene" means a cycloalkenylene further substituted preferably by halogen, hydroxy, C1 to C4 alkylthio, C1 to C4 alkylsulfoxide, C1 to C4 alkylsulfonyl, C1 to C4 substituted alkylthio, C1 to C4 substituted alkylsulfoxide, C1 to C4 substituted alkylsulfonyl, C1 to C6 alkyl, C1 to C7 alkoxy, C1 to C6 substituted alkyl, C1 to C7 alkoxy-alkyl, oxo, (monosubstituted) amino, (disubstituted)amino, trifluoromethyl, carboxy, alkoxycarbonyl, phenyl, substituted phenyl, phenylthio, phenylsulfoxide, phenylsulfonyl, amino, or substituted amino group.

The term "heterocycle" or "heterocyclic ring" denotes optionally substituted 3 to 8-membered rings having one or more carbon atoms connected in a ring that also have 1 to 5 heteroatoms, such as oxygen, sulfur and/or nitrogen inserted into the ring. These 3 to 8-membered rings may be saturated, unsaturated or partially unsaturated, but are preferably saturated. An "amino-substituted heterocyclic ring" means any one of the above-described heterocyclic rings is substituted with at least one amino group. Preferred heterocyclic rings include furanyl, thiofuranyl, piperidyl, pyridyl, morpholino, aziridinyl, piperidinyl, piperazinyl, tetrahydrofurano, pyrrolo, and tetrahydrothiophen-yl.

The term "substituted heterocycle" or "substituted heterocyclic ring" means the above-described heterocyclic ring is substituted with, for example, one or more, and preferably one or two, substituents which are the same or different which substituents preferably can be halogen, hydroxy, thio, alkylthio, cyano, nitro, C1 to C6 alkyl, C1 to C7 alkoxy, C1 to C7 substituted alkoxy, alkoxy-alkyl, C1 to C7 acyl, C1 to C7 acyloxy, carboxy, alkoxycarbonyl, carboxymethyl, hydroxymethyl, alkoxyalkyl amino, monosubstituted)amino, (disubstituted)amino carboxamide, N—(C1 to C6 alkyl)carboxamide, N,N-di(C1 to C6 alkyl)carboxamide, trifluoromethyl, N—((C1 to C6 alkyl)sulfonyl)amino, N-(phenylsulfonyl)amino groups, or substituted with a fused ring, such as benzo-ring. In many embodiments of substituted heterocyclic groups, the substituted cycloalkyl group will have 1, 2, 3, or 4 substituent groups independently selected from hydroxy, fluoro, chloro, $NH_2$, $NHCH_3$, $N(CH_3)_2$, $CO_2CH_3$, SEt, $SCH_3$, methyl, ethyl, isopropyl, vinyl, trifluoromethyl, methoxy, ethoxy, isopropoxy, and trifluoromethoxy groups.

An "aryl" groups refers to a monocyclic aromatic, linked bicyclic aromatic or fused bicyclic aromatic moiety comprising at least one six membered aromatic "benzene" ring, preferably comprising between 6 and 12 ring carbon atoms, such as phenyl, biphenyl or naphthyl groups, which may be optionally substituted with various organic and/or inorganic substituent groups, wherein the substituted aryl group and its substituents comprise between 6 and 18, or preferably 6 and 16 total carbon atoms. Preferred optional substituent groups include 1, 2, 3, or 4 substituent groups independently selected from hydroxy, fluoro, chloro, $NH_2$, $NHCH_3$, $N(CH_3)_2$, $CO_2CH_3$, SEt, $SCH_3$, methyl, ethyl, isopropyl, vinyl, trifluoromethyl, methoxy, ethoxy, isopropoxy, and trifluoromethoxy groups.

The term "heteroaryl" means a heterocyclic aryl derivative which preferably contains a five-membered or six-membered conjugated and aromatic ring system having from 1 to 4 heteroatoms, such as oxygen, sulfur and/or nitrogen, inserted into the unsaturated and conjugated heterocyclic ring. Heteroaryl groups include monocyclic heteroaromatic, linked bicyclic heteroaromatic or fused bicyclic heteroaromatic moieties. Examples of heteroaryls include pyridinyl, pyrimidinyl, and pyrazinyl, pyridazinyl, pyrrolyl, furanyl, thiofuranyl, oxazoloyl, isoxazolyl, phthalimido, thiazolyl, quinolinyl, isoquinolinyl, indolyl, or a furan or thiofuran directly bonded to a phenyl, pyridyl, or pyrrolyl ring and like unsaturated and conjugated heteroaromatic rings. Any monocyclic, linked bicyclic, or fused bicyclic heteroaryl ring system which has the characteristics of aromaticity in terms of electron distribution throughout the ring system is included in this definition. Typically, the heteroaromatic ring systems contain 3-12 ring carbon atoms and 1 to 5 ring heteroatoms independently selected from oxygen, nitrogen, and sulfur atoms.

The term "substituted heteroaryl" means the above-described heteroaryl is substituted with, for example, one or more, and preferably one or two, substituents which are the same or different which substituents preferably can be halogen, hydroxy, protected hydroxy, thio, alkylthio, cyano, nitro, C1 to C6 alkyl, C1 to C7 substituted alkyl, C1 to C7 alkoxy, C1 to C7 substituted alkoxy, alkoxy-alkyl, C1 to C7 acyl, C1 to C7 substituted acyl, C1 to C7 acyloxy, carboxy, alkoxycarbonyl, carboxymethyl, hydroxymethyl, amino, (monosubstituted)amino, (disubstituted)amino, carboxamide, N—(C1 to C6 alkyl)carboxamide, N,N-di(C1 to C6 alkyl)carboxamide, trifluoromethyl, N—((C1 to C6 alkyl)sulfonyl)amino or N-(phenylsulfonyl)amino groups. In many embodiments of substituted heteroaryl groups, the substituted cycloalkyl group will have 1, 2, 3, or 4 substituent groups independently selected from hydroxy, fluoro, chloro, $NH_2$, $NHCH_3$, $N(CH_3)_2$, $CO_2CH_3$, SEt, $SCH_3$, methyl, ethyl, isopropyl, vinyl, trifluoromethyl, methoxy, ethoxy, isopropoxy, and trifluoromethoxy groups.

Similarly, "arylalkyl" and "heteroarylalkyl" refer to aromatic and heteroaromatic systems which are coupled to another residue through a carbon chain, including substituted or unsubstituted, saturated or unsaturated, carbon chains, typically of 1-6C. These carbon chains may also include a carbonyl group, thus making them able to provide substituents as an acyl moiety. Preferably, arylalkyl or heteroarylalkyl is an alkyl group substituted at any position by an aryl group, substituted aryl, heteroaryl or substituted heteroaryl. Preferred groups also include benzyl, 2-phenylethyl, 3-phenylpropyl, 4-phenyl-n-butyl, 3-phenyl-n-amyl, 3-phenyl-2-butyl, 2-pyridinylmethyl, 2-(2-pyridinyl)ethyl, and the like.

The term "substituted arylalkyl" denotes an arylalkyl group substituted on the alkyl portion with one or more, and preferably one or two, groups preferably chosen from halogen, hydroxy, oxo, amino, (monosubstituted)amino, (disubstituted)amino, guanidino, heterocyclic ring, substituted heterocyclic ring, C1 to C6 alkyl, C1 to C6 substituted alkyl, C1 to C7 alkoxy, C1 to C7 substituted alkoxy, alkoxy-alkyl, C1 to C7 acyl, C1 to C7 substituted acyl, C1 to C7 acyloxy, nitro, carboxy, alkoxycarbonyl, carbamoyl, carboxamide, N—(C1 to C6 alkyl)carboxamide, N,N—(C1 to C6 dialkyl)carboxamide, cyano, N—(C1 to C6 alkylsulfonyl)amino, thiol, C1 to C4 alkylthio, C1 to C4 alkylsulfonyl groups; and/or the phenyl group may be substituted with one or more, and preferably one or two, substituents preferably chosen from halogen, hydroxy, protected hydroxy, thio, alkylthio, cyano, nitro, C1 to C6 alkyl, C1 to C6 substituted alkyl, C1 to C7 alkoxy, C1 to C7 substituted alkoxy, alkoxy-alkyl, C1 to C7 acyl, C1 to C7 substituted acyl, C1 to C7 acyloxy, carboxy, alkoxycarbonyl, carboxymethyl, hydroxymethyl, amino, (monosubstituted)amino, (disubstituted)amino, carboxamide, N—(C1 to C6 alkyl) carboxamide, N,N-di(C1 to C6 alkyl)carboxamide, trifluoromethyl, N—((C1 to C6 alkyl)sulfonyl)amino, N-(phenylsulfonyl)amino, cyclic C2 to C7 alkylene or a phenyl group, substituted or unsubstituted, for a resulting biphenyl group. The substituted alkyl or phenyl groups may be substituted with one or more, and preferably one or two, substituents which can be the same or different.

Examples of the term "substituted arylalkyl" include groups such as 2-phenyl-1-chloroethyl, 2-(4-methoxyphenyl)ethyl, 4-(2,6-dihydroxy phenyl)-n-hexyl, 2-(5-cyano-3-methoxyphenyl)-n-pentyl, 3-(2,6-dimethylphenyl)propyl, 4-chloro-3-aminobenzyl, 6-(4-methoxyphenyl)-3-carboxy-n-hexyl, 5-(4-aminomethylphenyl)-3-(aminomethyl)-n-pentyl, 5-phenyl-3-oxo-n-pent-1-yl and the like.

The term "arylalkylene" specifies an arylalkyl, as defined above, where the arylalkyl radical is bonded at two positions connecting together two separate additional groups. The definition includes groups of the formula: -phenyl-alkyl- and alkyl-phenyl-alkyl-. Substitutions on the phenyl ring can be 1,2, 1,3 or 1,4. The term "substituted arylalkylene" is an arylalkylene as defined above that is further substituted preferably by halogen, hydroxy, protected hydroxy, C1 to C4 alkylthio, C1 to C4 alkylsulfoxide, C1 to C4 alkylsulfonyl, C1 to C4 substituted alkylthio, C1 to C4 substituted alkylsulfoxide, C1 to C4 substituted alkylsulfonyl, C1 to C6 alkyl, C1 to C7 alkoxy, C1 to C6 substituted alkyl, C1 to C7 alkoxy-alkyl, oxo, (monosubstituted)amino, (disubstituted)amino, trifluoromethyl, carboxy, alkoxycarbonyl, phenyl, substituted phenyl, phenylthio, phenylsulfoxide, phenylsulfonyl, amino, or protected amino group on the phenyl ring or on the alkyl group.

The term "substituted phenyl" specifies a phenyl group substituted with one or more, and preferably one or two, moieties preferably chosen from the groups consisting of halogen, hydroxy, protected hydroxy, thio, alkylthio, cyano, nitro, C1 to C6 alkyl, C1 to C6 substituted alkyl, C1 to C7 alkoxy, C1 to C7 substituted alkoxy, alkoxy-alkyl, C1 to C7 acyl, C1 to C7 substituted acyl, C1 to C7 acyloxy, carboxy, alkoxycarbonyl, carboxymethyl, hydroxymethyl, amino, (monosubstituted)amino, (disubstituted)amino, carboxamide, N—(C1 to C6 alkyl)carboxamide, N,N-di(C1 to C6 alkyl)carboxamide, trifluoromethyl, N—((C1 to C6 alkyl)sulfonyl)amino, N-(phenylsulfonyl)amino or phenyl, wherein the phenyl is substituted or unsubstituted, such that, for example, a biphenyl results. In many embodiments of substituted phenyl groups, the substituted cycloalkyl group will have 1, 2, 3, or 4 substituent groups independently selected from hydroxy, fluoro, chloro, $NH_2$, $NHCH_3$, $N(CH_3)_2$, $CO_2CH_3$, SEt, $SCH_3$, methyl, ethyl, isopropyl, vinyl, trifluoromethyl, methoxy, ethoxy, isopropoxy, and trifluoromethoxy groups.

The term "phenoxy" denotes a phenyl bonded to an oxygen atom. The term "substituted phenoxy" specifies a phenoxy group substituted with one or more, and preferably one or two, moieties preferably chosen from the groups consisting of halogen, hydroxy, protected hydroxy, thio, alkylthio, cyano, nitro, C1 to C6 alkyl, C1 to C7 alkoxy, C1 to C7 substituted alkoxy, alkoxy-alkyl, C1 to C7 acyl, C1 to C7 acyloxy, carboxy, alkoxycarbonyl, carboxymethyl, hydroxymethyl, amino, (monosubstituted)amino, (disubstituted)amino, carboxamide, N—(C1 to C6 alkyl)carboxamide, N,N-di(C1 to C6 alkyl)carboxamide, trifluoromethyl, N—((C1 to C6 alkyl) sulfonyl)amino and N-phenylsulfonyl)amino.

The term "substituted phenylalkoxy" denotes a phenylalkoxy group wherein the alkyl portion is substituted with one or more, and preferably one or two, groups preferably selected from halogen, hydroxy, protected hydroxy, oxo, amino, (monosubstituted)amino, (disubstituted)amino, guanidino, heterocyclic ring, substituted heterocyclic ring, C1 to C7 alkoxy, alkoxy-alkyl, C1 to C7 acyl, C1 to C7 acyloxy, nitro, carboxy, alkoxycarbonyl, carbamoyl, carboxamide, N—(C1 to C6 alkyl)carboxamide, N,N—(C1 to C6 dialkyl)carboxamide, cyano, N—(C1 to C6 alkylsulfonyl) amino, thiol, C1 to C4 alkylthio, C1 to C4 alkylsulfonyl groups; and/or the phenyl group can be substituted with one or more, and preferably one or two, substituents preferably chosen from halogen, hydroxy, protected hydroxy, thio, alkylthio, cyano, nitro, C1 to C6 alkyl, C1 to C7 alkoxy, alkoxy-alkyl, C1 to C7 acyl, C1 to C7 acyloxy, carboxy, alkoxycarbonyl carboxymethyl, hydroxymethyl, amino, (monosubstituted)amino, (disubstituted)amino, carboxamide, N—(C1 to C6 alkyl) carboxamide, N,N-di(C1 to C6 alkyl)carboxamide, trifluoromethyl, N((C1 to C6 alkyl)sulfonyl)amino, N-(phenylsulfonyl)amino or a phenyl group, substituted or unsubstituted, for a resulting biphenyl group. The substituted alkyl or phenyl groups may be substituted with one or more, and preferably one or two, substituents which can be the same or different.

The term "substituted naphthyl" specifies a naphthyl group substituted with one or more, and preferably one or two, moieties either on the same ring or on different rings chosen from the groups consisting of halogen, hydroxy, protected hydroxy, thio, alkylthio, cyano, nitro, C1 to C6 alkyl, C1 to C7 alkoxy, alkoxy-alkyl, C1 to C7 acyl, C1 to C7 acyloxy, carboxy, alkoxycarbonyl, carboxymethyl, hydroxymethyl, amino, (monosubstituted)amino, (disubstituted)amino, carboxamide, N—(C1 to C6 alkyl)carboxamide, N,N-di(C1 to C6 alkyl)carboxamide, trifluoromethyl, N—((C1 to C6 alkyl) sulfonyl)amino or N (phenylsulfonyl)amino.

The terms "halo" and "halogen" refer to the fluoro, chloro, bromo or iodo atoms. There can be one or more halogen, which are the same or different. Preferred halogens are chloro and fluoro. Although many of the compounds of the invention having halogen atoms as substituents are very effective in binding to the relevant taste receptors, such halogenated organic compounds can often have undesirable toxicological properties when administered to an animal in vivo. Therefore, in many embodiments of the compounds of Formula (I), if a halogen atom (including a fluoro or chloro atom) is listed as a possible substitutent atom, an alternative preferred group of substitutents would NOT include the halogen, fluorine, or chlorine groups.

The term "(monosubstituted)amino" refers to an amino group with one substituent preferably chosen from the group consisting of phenyl, substituted phenyl, C1 to C6 alkyl, C1 to C6 substituted alkyl, C1 to C7 acyl, C1 to C7 substituted acyl, C2 to C7 alkenyl, C2 to C7 substituted alkenyl, C2 to C7 alkynyl, C2 to C7 substituted alkynyl, C7 to C12 phenylalkyl, C7 to C12 substituted phenylalkyl and heterocyclic ring. The (monosubstituted)amino can additionally have an amino-protecting group as encompassed by the term "protected (monosubstituted)amino."

The term "(disubstituted)amino" refers to an amino group substituted preferably with two substituents chosen from the group consisting of phenyl, substituted phenyl, C1 to C6 alkyl, C1 to C6 substituted alkyl, C1 to C7 acyl, C2 to C7 alkenyl, C2 to C7 alkynyl, C7 to C12 phenylalkyl, and C7 to C12 substituted phenylalkyl. The two substituents can be the same or different.

The term "amino-protecting group" as used herein refers to substituents of the amino group commonly employed to block or protect the amino functionality while reacting other functional groups of the molecule. The term "protected (monosubstituted)amino" means there is an amino-protecting group on the monosubstituted amino nitrogen atom. In addition, the term "protected carboxamide" means there is an amino-protecting group on the carboxamide nitrogen. Similarly, the term "protected N—(C1 to C6 alkyl)carboxamide" means there is an amino-protecting group on the carboxamide nitrogen.

The term "alkylthio" refers to sulfide groups such as methylthio, ethylthio, n-propylthio, isopropylthio, n-butylthio, t-butylthio and like groups.

The term "alkylsulfoxide" indicates sulfoxide groups such as methylsulfoxide, ethylsulfoxide, n-propylsulfoxide, isopropylsulfoxide, n-butylsulfoxide, sec-butylsulfoxide and the like.

The term "alkylsulfonyl" encompasses groups such as methylsulfonyl, ethylsulfonyl, n-propylsulfonyl, isopropylsulfonyl, n-butylsulfonyl, t-butylsulfonyl and the like.

The terms "substituted alkylthio," "substituted alkylsulfoxide," and "substituted alkylsulfonyl," denote the alkyl portion of these groups may be substituted as described above in relation to "substituted alkyl."

The terms "phenylthio," "phenylsulfoxide," and "phenylsulfonyl" specify a thiol, a sulfoxide, or sulfone, respectively, containing a phenyl group. The terms "substituted phenylthio," "substituted phenylsulfoxide," and "substituted phenylsulfonyl" means that the phenyl of these groups can be substituted as described above in relation to "substituted phenyl."

The term "alkoxycarbonyl" means an "alkoxy" group attached to a carbonyl group. The term "substituted alkoxycarbonyl" denotes a substituted alkoxy bonded to the carbonyl group, which alkoxy may be substituted as described above in relation to substituted alkyl.

The term "phenylene" means a phenyl group where the phenyl radical is bonded at two positions connecting together two separate additional groups. Examples of "phenylene" includes 1,2-phenylene, 1,3-phenylene, and 1,4-phenylene.

The term "substituted alkylene" means an alkyl group where the alkyl radical is bonded at two positions connecting together two separate additional groups and further bearing an additional substituent. Examples of "substituted alkylene" includes aminomethylene, 1-(amino)-1,2-ethyl, 2-(amino)-1,2-ethyl, 1-(acetamido)-1,2-ethyl, 2-(acetamido)-1,2-ethyl, 2-hydroxy-1,1-ethyl, 1-(amino)-1,3-propyl.

The term "substituted phenylene" means a phenyl group where the phenyl radical is bonded at two positions connecting together two separate additional groups, wherein the phenyl is substituted as described above in relation to "substituted phenyl."

The terms "cyclic alkylene," "substituted cyclic alkylene," "cyclic heteroalkylene," and "substituted cyclic heteroalkylene," defines such a cyclic group bonded ("fused") to the phenyl radical resulting in a bicyclic ring system. The cyclic group may be saturated or contain one or two double bonds. Furthermore, the cyclic group may have one or two methylene or methine groups replaced by one or two oxygen, nitrogen or sulfur atoms which are the cyclic heteroalkylene.

The cyclic alkylene or heteroalkylene group may be substituted once or twice by the same or different substituents preferably selected from the group consisting of the following moieties: hydroxy, protected hydroxy, carboxy, protected carboxy, oxo, protected oxo, C1 to C4 acyloxy, formyl, C1 to C7 acyl, C1 to C6 alkyl, C1 to C7 alkoxy, C1 to C4 alkylthio, C1 to C4 alkylsulfoxide, C1 to C4 alkylsulfonyl, halo, amino, protected amino, (monosubstituted)amino, protected (monosubstituted)amino, (disubstituted)amino, hydroxymethyl or a protected hydroxymethyl.

The cyclic alkylene or heteroalkylene group fused onto the benzene radical can contain two to ten ring members, but it preferably contains three to six members. Examples of such saturated cyclic groups are when the resultant bicyclic ring system is 2,3-dihydro-indanyl and a tetralin ring. When the cyclic groups are unsaturated, examples occur when the resultant bicyclic ring system is a naphthyl ring or indolyl. Examples of fused cyclic groups which each contain one nitrogen atom and one or more double bond, preferably one or two double bonds, are when the benzene radical is fused to a pyridino, pyrano, pyrrolo, pyridinyl, dihydropyrrolo, or dihydropyridinyl ring. Examples of fused cyclic groups which each contain one oxygen atom and one or two double bonds are when the benzene radical ring is fused to a furo, pyrano, dihydrofurano, or dihydropyrano ring. Examples of fused cyclic groups which each have one sulfur atom and contain one or two double bonds are when the benzene radical is fused to a thieno, thiopyrano, dihydrothieno or dihydrothiopyrano ring. Examples of cyclic groups which contain two heteroatoms selected from sulfur and nitrogen and one or two double bonds are when the benzene radical ring is fused to a thiazolo, isothiazolo, dihydrothiazolo or dihydroisothiazolo ring. Examples of cyclic groups which contain two heteroatoms selected from oxygen and nitrogen and one or two double bonds are when the benzene ring is fused to an oxazolo, isoxazolo, dihydrooxazolo or dihydroisoxazolo ring. Examples of cyclic groups which contain two nitrogen heteroatoms and one or two double bonds occur when the benzene ring is fused to a pyrazolo, imidazolo, dihydropyrazolo or dihydroimidazolo ring or pyrazinyl.

The term "carbamoyl" means a —NCO— group where the radical is bonded at two positions connecting two separate additional groups.

One or more of the compounds of the invention, may be present as a salt. The term "salt" encompasses those salts that form with the carboxylate anions and amine nitrogens and include salts formed with the organic and inorganic anions and cations discussed below. Furthermore, the term includes salts that form by standard acid-base reactions with basic groups (such as amino groups) and organic or inorganic acids. Such acids include hydrochloric, hydrofluoric, trifluoroacetic, sulfuric, phosphoric, acetic, succinic, citric, lactic, maleic, fumaric, palmitic, cholic, pamoic, mucic, D-glutamic, D-camphoric, glutaric, phthalic, tartaric, lauric, stearic, salicyclic, methanesulfonic, benzenesulfonic, sorbic, picric, benzoic, cinnamic, and like acids.

The term "organic or inorganic cation" refers to counter-ions for the carboxylate anion of a carboxylate salt. The counter-ions are chosen from the alkali and alkaline earth metals, (such as lithium, sodium, potassium, barium, aluminum and calcium); ammonium and mono-, di- and tri-alkyl amines such as trimethylamine, cyclohexylamine; and the organic cations, such as dibenzylammonium, benzylammonium, 2-hydroxyethylammonium, bis(2-hydroxyethyl)ammonium, phenylethylbenzylammonium, dibenzylethylenediammonium, and like cations. See, for example, "Pharmaceutical Salts," Berge, et al., *J. Pharm. Sci.* (1977) 66:1-19, which is incorporated herein by reference. Other cations encompassed by the above term include the protonated form of procaine, quinine and N-methylglucosamine, and the protonated forms of basic amino acids such as glycine, ornithine, histidine, phenylglycine, lysine and arginine. Furthermore, any zwitterionic form of the instant compounds formed by a carboxylic acid and an amino group is referred to by this term. For example, a cation for a carboxylate anion will exist when R2 or R3 is substituted with a (quaternary ammonium)methyl group. A preferred cation for the carboxylate anion is the sodium cation.

The compounds of the invention can also exist as solvates and hydrates. Thus, these compounds may crystallize with, for example, waters of hydration, or one, a number of, or any fraction thereof of molecules of the mother liquor solvent. The solvates and hydrates of such compounds are included within the scope of this invention.

The term "amino acid" includes any one of the twenty naturally-occurring amino acids or the D-form of any one of the naturally-occurring amino acids. In addition, the term "amino acid" also includes other non-naturally occurring amino acids besides the D-amino acids, which are functional equivalents of the naturally-occurring amino acids. Such non-naturally-occurring amino acids include, for example, norleucine ("Nle"), norvaline ("Nva"), L- or D-naphthalanine, ornithine ("Orn"), homoarginine (homoArg) and others well known in the peptide art, such as those described in M. Bodanzsky, "Principles of Peptide Synthesis," 1st and 2nd revised ed., Springer-Verlag, New York, N.Y., 1984 and 1993, and Stewart and Young, "Solid Phase Peptide Synthesis," 2nd ed., Pierce Chemical Co., Rockford, Ill., 1984, both of which are incorporated herein by reference. Amino acids and amino acid analogs can be purchased commercially (Sigma Chemical Co.; Advanced Chemtech) or synthesized using methods known in the art.

"Amino acid side chain" refers to any side chain from the above-described "amino acids."

"Substituted" herein refers to a substituted moiety, such as a hydrocarbon, e.g., substituted alkyl or benzyl wherein at least one element or radical, e.g., hydrogen, is replaced by another, e.g., a hydrogen is replaced by a halogen as in chlorobenzyl. A residue of a chemical species, as used in the specification and concluding claims, refers to a structural fragment, or a moiety that is the resulting product of the chemical species in a particular reaction scheme or subsequent formulation or chemical product, regardless of whether the structural fragment or moiety is actually obtained from the chemical species. Thus, an ethylene glycol residue in a polyester refers to one or more —OCH$_2$CH$_2$O— repeat units in the polyester, regardless of whether ethylene glycol is used to prepare the polyester. Similarly, a 2,4-thiazolidinedione residue in a chemical compound refers to one or more -2,4-thiazolidinedione moieties of the compound, regardless of whether the residue was obtained by reacting 2,4-thiazolidinedione to obtain the compound.

The term "organic residue" defines a carbon containing residue, i.e. a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic resides can preferably comprise 1 to 18 carbon atoms, 1 to 15, carbon atoms, 1 to 12 carbon atoms, 1 to 8 carbon atoms, or 1 to 4 carbon atoms.

By the term "effective amount" of a compound as provided herein is meant a sufficient amount of the compound to provide the desired regulation of a desired function, such as gene expression, protein function, or a disease condition. As will be pointed out below, the exact amount required will vary from subject to subject, depending on the species, age, general condition of the subject, specific identity and formulation of the drug, etc. Thus, it is not possible to specify an exact "effective amount." However, an appropriate effective amount can be determined by one of ordinary skill in the art using only routine experimentation.

It must be noted that, as used in the specification and the appended claims, the singular forms "a," "an" and "the" include plural referents unless the context clearly dictates otherwise. Thus, for example, reference to "an aromatic compound" includes mixtures of aromatic compounds.

Often, ranges are expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not. For example, the phrase "optionally substituted lower alkyl" means that the lower alkyl group may or may not be substituted and that the description includes both unsubstituted lower alkyl and lower alkyls where there is substitution.

The Amide Compounds of the Invention

The compounds of the invention are all organic (carbon containing) compounds that all have at least one "amide" group therein, have the following general structure, which will be hereinafter referred to as the amide compounds having Formula (I) shown below:

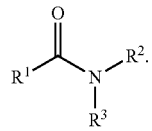

(I)

The amide compounds of Formula (I) do not include any amide compounds that are known to naturally occur in biological systems or foods, such as peptides, proteins, nucleic acids, glycopeptides or glycoproteins, or the like. The amide compounds of Formula (I) of the invention are man-made and artificial synthetic amide compounds, although the Applicants do not exclude the possibility that compounds of Formula (I) could conceivably be purposely prepared, either in their specified form or in the form of a peptide or protein-modified "prodrug" form by human beings utilizing one or more of the methods of modern biotechnology.

For the various embodiments of the compounds of Formula (I), the $R^1$, $R^2$ and $R^3$ groups can be and are independently further defined in various ways, as will now be further detailed, so as to form and/or include a substantial number of subgenuses and/or species of compounds of Formula (I). It is hereby specifically contemplated that any of subgenuses and/or species of compounds of Formula (I) described below can, either in their specified form or as a comestibly acceptable salt, be combined in an effective amount with a comestible or medicinal product or precursor thereof by the processes and/or methods described elsewhere herein, or by any such other processes as would be apparent to those of ordinary skill in preparing comestible or medicinal products or precursor thereof, to form a savory or sweet flavor modified comestible or medicinal product, or a precursor thereof.

In some embodiments of the compounds of Formula (I), $R^1$ is a hydrocarbon residue that may contain one or more heteroatoms or an inorganic residue, and $R^2$ and $R^3$ are each independently H or a hydrocarbon residue that may contain one or more heteroatoms; more preferably, $R^1$, $R^2$ and $R^3$ are independently selected from the group consisting of arylalkenyl, heteroarylalkenyl, arylalkyl, heteroarylalkyl, alkyl, alkoxy-alkyl, alkenyl, cycloalkyl, cycloalkenyl, aryl, heteroaryl, —$R^4$OH, —$R^4$CN, —$R^4$CO$_2$H, —$R^4$CO$_2$R$^5$, —$R^4$COR$^5$, —$R^4$CONR$^5$R$^6$, —$R^4$NR$^5$R$^6$, —$R^4$N(R$^5$)COR$^6$, —$R^4$SR$^5$, —$R^4$SOR$^5$, —$R^4$SO$_2$R$^5$, —$R^4$SO$_2$NR$^5$R$^6$ and —$R^4$N(R$^5$)SO$_2$R$^6$, or optionally substituted groups thereof and preferably one of $R^2$ or $R^3$ is H; wherein each $R^4$ is independently a hydrocarbon residue that may contain one or more heteroatoms, preferably independently selected from small (C1-C6) alkylene or (C1-C6) alkoxyalkylene; and wherein each $R^5$ and $R^6$ are independently H or a hydrocarbon residue that may contain one or more heteroatoms, preferably independently selected from small (C1-C6) alkyl or (C1-C6) alkoxyalkyl.

In many embodiments of the compounds of Formula (I), $R^1$ comprises an organic or hydrocarbon-based residue having at least three carbon atoms and optionally one to 20, 15, 10, 8, 7, 6, or 5 heteroatoms independently selected from oxygen, nitrogen, sulfur, halogens, or phosphorus.

In many embodiments of the compounds of Formula (I), one of $R^2$ and $R^3$ is optionally H, and one or both of $R^2$ and $R^3$ comprises an organic or hydrocarbon-based residue having at least three carbon atoms and optionally one to ten heteroatoms independently selected from oxygen, nitrogen, sulfur, halogens, or phosphorus.

The compounds of Formula (I) are relatively "small molecules" as compared to many biological molecules, and can often have a variety of limitations on their overall absolute physical size, molecular weight, and physical characteristics, so that they can be at least somewhat soluble in aqueous media, and are of appropriate size to effectively bind to the relevant heterodimeric T1R1/T1R3 or T1R2/T1R3 taste receptors, which share a common T1R3 protein subunit.

While not wishing to be bound by any theory, it is believed that MSG binds to the T1R1 subunit of T1R1/T1R3 "savory" taste receptors, and several known sweeteners bind to the T1R2 subunit of T1R2/T1R3 sweet receptors. Accordingly, our unexpected and surprising discovery that the amide compounds of Formula (I) can share many overlapping physical and chemical features, and can sometimes bind to either one or both of the savory and sweet receptors, is perhaps in retrospect reasonable and/or rational from a chemical/biochemical/biological point of view.

As an example of the overlapping physical and chemical properties and/or physical/chemical limitations on the savory and/or sweet amides of Formula (I), in most embodiments of the compounds of Formula (I), the molecular weight of the compounds of Formula (I) should be less than about 800 grams per mole, or in further related embodiments less than or equal to about 700 grams per mole, 600 grams per mole, 500 grams per ole, 450 grams per mole, 400 grams per mole, 350 grams per mole, or 300 grams per mole.

Similarly, the compounds of Formula (I) can have preferred ranges of molecular weight, such as for example from about 175 to about 500 grams per mole, from about 200 to about 450 grams per mole, from about 225 to about 400 grams per mole, from about 250 to about 350 grams per mole.

In a related series of embodiments, $R^1$ has between 3 and 16 carbon atoms or 4 and 14 carbon atoms or 5 and 12 carbon atoms, and 0, 1, 2, 3, 4, or 5 heteroatoms selected from oxygen, nitrogen, sulfur, fluorine, or chlorine, and/or at least one of $R^2$ or $R^3$ has been 3 and 16 carbon atoms and 0, 1, 2, 3, 4, or 5 heteroatoms independently selected from oxygen, nitrogen, sulfur, fluorine, or chlorine; or preferably at least one of $R^2$ or $R^3$ has between 4 and 14 carbon atoms and 0, 1, 2, 3, 4, or 5 heteroatoms independently selected from oxygen, nitrogen, sulfur, fluorine; or even more preferably, at least one of $R^2$ or $R^3$ has between 5 and 12 carbon atoms and 0, 1, 2, or 3 heteroatoms independently selected from oxygen, nitrogen, and sulfur.

In addition to the above described general physical and chemical characteristics and/or limitations, which can be shared by the various subgenuses of the sweet and savory compounds of Formula (I), the compounds of Formula (I) can also share more specifically definable chemical structural features or chemical groups or residues, as is further described below.

For example, in some embodiments, $R^1$, $R^2$, and $R^3$ can be independently selected from the group consisting of an arylalkenyl, heteroarylalkenyl, arylalkyl, heteroarylalkyl, alkyl, alkoxy-alkyl, alkenyl, cycloalkyl, cycloalkenyl, aryl, heteroaryl, $-R^4OH$, $-R^4OR^5$, $-R^4CN$, $-R^4CO_2H$, $-R^4CO_2R^5$, $-R^4COR^5$, $-R^4SR^5$, and $-R^4SO_2R^5$, and optionally substituted derivative thereof comprising 1, 2, 3, or 4 carbonyl, amino groups, hydroxyl, or halogen groups, and wherein $R^4$ and $R^5$ are $C_1$-$C_6$ hydrocarbon residues.

In further related embodiments of the amide compounds of Formula (I), $R^1$, $R^2$ and $R^3$ can be independently selected from the group consisting of an arylalkenyl, heteroarylalkenyl, arylalkyl, heteroarylalkyl, alkyl, alkoxy-alkyl, alkenyl, cycloalkyl, cycloalkenyl, heterocycle, aryl and heteroaryl groups, and optionally substituted derivatives thereof comprising 1, 2, 3 or 4 carbonyl, amino groups, hydroxyl, or chlorine, or fluorine groups. In both of the embodiments just mentioned, an alternative and preferred set of optional substituent groups would be substituents independently selected from hydroxy, fluoro, chloro, $NH_2$, $NHCH_3$, $N(CH_3)_2$, $CO_2CH_3$, SEt, $SCH_3$, methyl, ethyl, isopropyl, vinyl, trifluoromethyl, methoxy, ethoxy, isopropoxy, and trifluoromethoxy substituent groups.

In many embodiments of the compounds of Formula (I), one of $R^2$ and $R^3$ is hydrogen and the other $R^2$ or $R^3$ group is an organic residue or group. For example, in many embodiments of the compounds of Formula (I), at least one or $R^2$ and $R^3$ is a branched or cyclic organic residue having a carbon atom directly bonded to both (a) the amide nitrogen atom and (b) two additional carbon atoms from other organic residues, which are branched or cyclic organic residues comprising additional hydrogen atoms and up to 10 optional additional carbon atoms, and optionally from zero to five heteroatoms independently selected from oxygen, nitrogen, sulfur, fluorine, and chlorine. Such branched $R^2$ and $R^3$ groups include organic radicals having the formula:

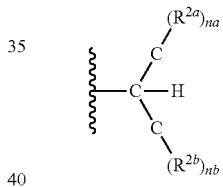

wherein na and nb are independently selected from 1, 2, and 3, and each $R^{2a}$ or $R^{2b}$ substituent residue is independently selected from hydrogen, a halogen, a hydroxy, or a carbon-containing residue optionally having from zero to five heteroatoms independently selected from oxygen, nitrogen, sulfur, and a halogen. In some such embodiments, the $R^{2a}$ or $R^{2b}$ are independent substituent groups, but in other embodiments one or more of the $R^{2a}$ or $R^{2b}$ radicals can be bonded together to form ring structures.

In some such embodiments of the compounds of Formula (I), at least one of the $R^2$ and $R^3$ is a branched alkyl radical having 5 to 12 carbon atoms, or at least one of $R^2$ and $R^3$ is a cycloalkyl or cycloalkenyl ring comprising 5 to 12 ring carbon atoms. In such embodiments of $R^2$ and $R^3$ the branched alkyl radical or the cycloalkyl or cycloalkenyl ring can be optionally substituted with 1, 2, 3, or 4 substituent groups independently selected from hydroxy, fluoro, chloro, $NH_2$, $NHCH_3$, $N(CH_3)_2$, $CO_2CH_3$, SEt, $SCH_3$, methyl, ethyl, isopropyl, vinyl, trifluoromethyl, methoxy, ethoxy, isopropoxy, and trifluoromethoxy.

In other embodiments of the amide compounds of Formula (I), at least one of the $R^2$ and $R^3$ is a "benzylic" radical having the structure

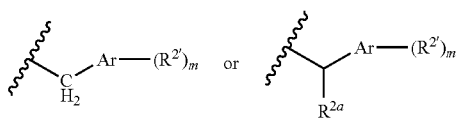

wherein Ar is an aromatic or heteraromatic ring such as phenyl, pyridyl, furanyl, thiofuranyl, pyrrolyl, or similar aromatic ring systems, m is 0, 1, 2, or 3, and each $R^{2'}$ is independently selected from hydroxy, fluoro, chloro, $NH_2$, $NHCH_3$, $N(CH_3)_2$, $CO_2CH_3$, SEt, $SCH_3$, methyl, ethyl, isopropyl, vinyl, trifluoromethyl, methoxy, ethoxy, isopropoxy, and trifluoromethoxy, and each $R^{2a}$ substituent group can be independently selected from the group consisting of an alkyl, alkoxy-alkyl, alkenyl, cycloalkenyl, cycloalkyl, —$R^4OH$, —$R^4OR^5$, —$R^4CN$, —$R^4CO_2H$, —$R^4CO_2R^5$, —$R^4COR^5$, —$R^4SR^5$, and —$R^4SO_2R^5$ group.

In many embodiments of the compounds of Formula (I), at least one of $R^2$ or $R^3$ is a $C_3$-$C_{10}$ branched alkyl. These $C_3$-$C_{10}$ branched alkyls have been found to be highly effective $R^2$ groups for both savory and sweet amide compounds In further embodiments the $C_3$-$C_{10}$ branched alkyl may optionally substituted with one or two substituents independently selected from a hydroxy, fluoro, chloro, $NH_2$, $NHCH_3$, $N(CH_3)_2$, $CO_2CH_3$, $SCH_3$, SEt, methyl, ethyl, isopropyl, vinyl, trifluoromethyl, methoxy, ethoxy, isopropoxy, and trifluoromethoxy group.

In further embodiments of the compounds of Formula (I), at least one of $R^2$ or $R^3$ is an α-substituted carboxylic acid or α-substituted carboxylic acid lower alkyl ester. Preferably, at least one of $R^2$ or $R^3$ is an α-substituted carboxylic acid lower alkyl (especially methyl) ester. In some such preferred embodiments, the α-substituted carboxylic acid or α-substituted carboxylic acid ester residue corresponds to that of a naturally occurring and optically active α-amino acid or an ester thereof, or its opposite enantiomer.

In many embodiments of the compounds of Formula (I), at least one of $R^2$ or $R^3$ is a 5 or 6 membered aryl or heteroaryl ring, optionally substituted with 1, 2, 3 or 4 substituent groups selected from the group consisting of alkyl, alkoxyl, alkoxy-alkyl, OH, CN, $CO_2H$, CHO, $COR^6$, $CO_2R^6$, $SR^6$, halogen, alkenyl, cycloalkyl, cycloalkenyl, aryl, and heteroaryl: and $R^6$ is $C_1$-$C_6$ alkyl. Preferably the aryl or heteroaryl ring is substituted with 1, 2, 3 or 4 substituent groups selected from the group consisting of hydroxy, fluoro, chloro, $NH_2$, $NHCH_3$, $N(CH_3)_2$, $CO_2CH_3$, $SCH_3$, SEt, methyl, ethyl, isopropyl, vinyl, trifluoromethyl, methoxy, ethoxy, isopropoxy, and trifluoromethoxy groups.

In some embodiments of the compounds of Formula (I), at least one of $R^2$ or $R^3$ is a phenyl, pyridyl, furanyl, thiofuranyl, or pyrrolyl ring optionally substituted with one or two substituents independently selected from hydroxy, fluoro, chloro, $NH_2$, $NHCH_3$, $N(CH_3)_2$, $CO_2CH_3$, $SCH_3$, SEt, methyl, ethyl, isopropyl, vinyl, trifluoromethyl, methoxy, ethoxy, isopropoxy, and trifluoromethoxy.

In many embodiments of the compounds of Formula (I), at least one of $R^2$ or $R^3$ is a cycloalkyl, cycloalkenyl, or saturated heterocyclic ring having 3 to 10 ring carbon atoms, optionally substituted with 1, 2, or 3 substituents independently selected from the group consisting of $NH_2$, $NHCH_3$, $N(CH_3)_2$, $CO_2CH_3$, SEt, $SCH_3$, $C_1$-$C_4$ alkyl, $C_1$-$C_4$ haloalkyl, $C_1$-$C_4$ alkoxy, $C_1$-$C_4$ haloalkoxy, hydroxy, and halogen. In some further embodiments, at least one of $R^2$ or $R^3$ is a cyclopentyl, cyclohexyl, cycloheptyl, cyclooctyl ring, or piperidyl ring optionally substituted with 1, 2, or 3 substituents independently selected from the group consisting of hydroxy, fluoro, chloro, $NH_2$, $NHCH_3$, $N(CH_3)_2$, $CO_2CH_3$, SEt, $SCH_3$, methyl, ethyl, isopropyl, vinyl, trifluoromethyl, methoxy, ethoxy, isopropoxy, and trifluoromethoxy. In some preferred embodiments, at least one of $R^2$ or $R^3$ is a cyclohexyl, optionally substituted with 1, 2, or 3 methyl groups. Examples of such methyl substituted cyclohexyl rings have the formula

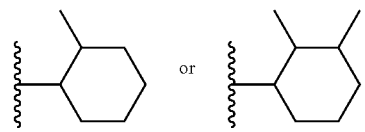

In many embodiments of the compounds of Formula (I), especially compounds having activity for sweet receptors, at least one of $R^2$ or $R^3$ is a 1-(1,2,3,4) tetrahydronapthalene ring or an 2,3-dihydro-1H-indene ring having the formula:

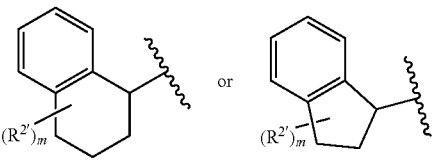

wherein m is 0, 1, 2, or 3, and each $R^{2'}$ can be bonded to either the aromatic or non-aromatic ring and is independently selected from hydroxy, fluoro, chloro, $NH_2$, $NHCH_3$, $N(CH_3)_2$, $CO_2CH_3$, $SCH_3$, SEt, methyl, ethyl, isopropyl, vinyl, trifluoromethyl, methoxy, ethoxy, isopropoxy, and trifluoromethoxy. It is to be understood that optical and/or diastereomeric isomerism can occur on the cyclohexyl or cyclopentyl rings of these substituent, and differing optical and/or diastereomers can often have at least somewhat differing biological activities.

In some embodiments at least one of $R^2$ or $R^3$ is a 1-(1,2,3,4) tetrahydronapthalene ring with certain preferred substitution patterns. In particular, at least one of $R^2$ or $R^3$ may have the formula:

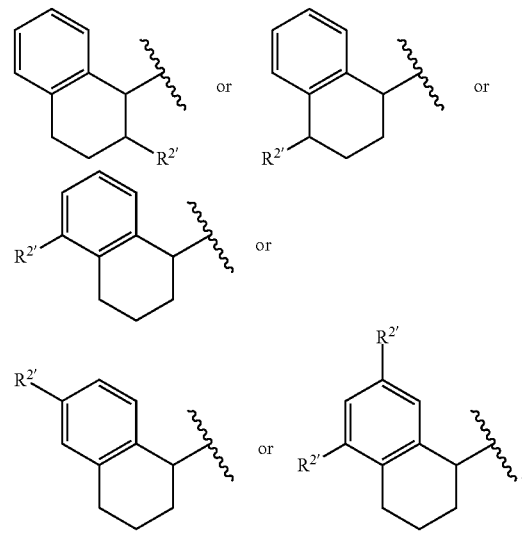

wherein each $R^{2'}$ are independently selected from the group consisting of hydrogen, hydroxy, fluoro, chloro, $NH_2$, $NHCH_3$, $N(CH_3)_2$, $COOCH_3$, $SCH_3$, SEt, methyl, ethyl, isopropyl, vinyl, trifluoromethyl, methoxy, ethoxy, isopropoxy, and trifluoromethoxy groups. Similarly, in some preferred embodiments, at least one of $R^2$ or $R^3$ may have the formula:

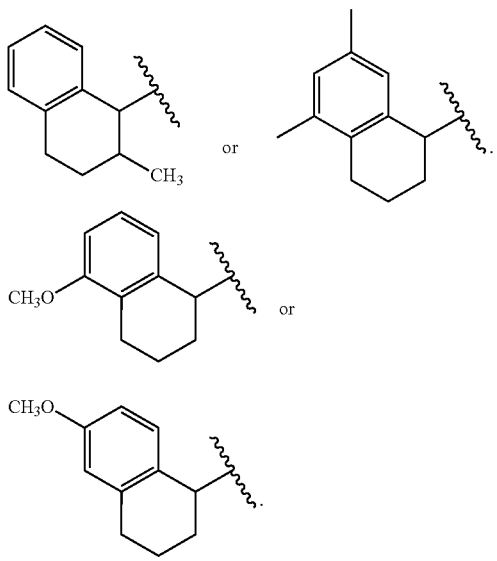

In some embodiments at least one of $R^2$ or $R^3$ is an unsubstituted 1-(1,2,3,4) tetrahydronapthalene ring in racemic or optically active form, as shown below:

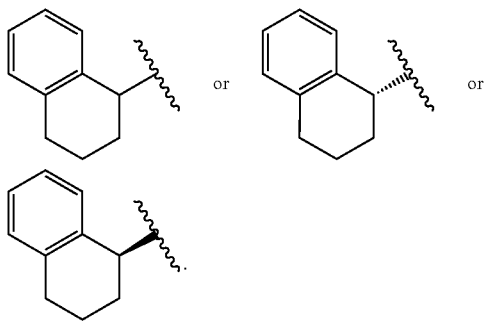

Aromatic or Heteroaromatic Compounds

In many preferred embodiments of the amide compounds of Formula (I) having one or both of savory and sweet receptor agonist activity, there is a preferred subgenus of amide compounds having the following formula (II):

(II)
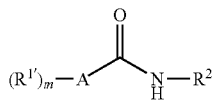

wherein A comprises a 5 or 6 membered aryl or heteroaryl ring; m is 0, 1, 2, 3 or 4; each $R^1$ is independently selected from alkyl, alkoxy, alkoxy-alkyl, hydroxyalkyl, OH, CN, $CO_2H$, $CO_2R^6$, CHO, $COR^6$, $SR^6$, halogen, alkenyl, cycloalkyl, cycloalkenyl, heterocycle, aryl, and heteroaryl; and $R^6$ is $C_1$-$C_6$ alkyl, and $R^2$ can be any of the embodiments contemplated herein above, or the like.

In some embodiments, the A group of Formula (II) comprises an aryl ring, i.e. it contains at least one six-membered aromatic benzene ring. The aryls include at least benzene and napthalene rings, which may not, but in many embodiments are further substituted with at least 1, 2, or 3 $R^{1'}$ substituent groups independently selected from the group consisting of hydroxy, fluoro, chloro, $NH_2$, $NHCH_3$, $N(CH_3)_2$, $COOCH_3$, $SCH_3$, SEt, methyl, ethyl, isopropyl, vinyl, trifluoromethyl, methoxy, ethoxy, isopropoxy, and trifluoromethoxy groups.

In some preferred embodiments, one or two of the $R^{1'}$ substituent groups are bonded together to form a saturated alkylenedioxy ring on an phenyl ring, as exemplified by the following preferred structures (II a) and (IIb);

(IIa)
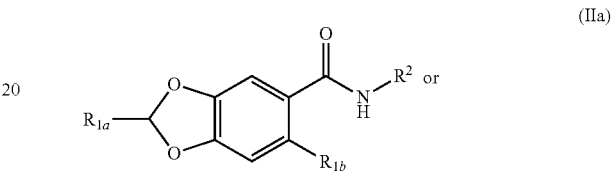

(IIb)
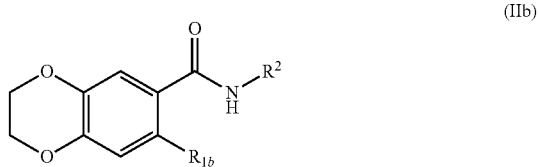

wherein $R_{1a}$ and $R_{1b}$ are independently hydrogen or a lower alkyl, or alternatively $R_{1a}$ and $R_{1b}$ are independently hydrogen or methyl, or alternatively both $R_{1a}$ and $R_{1b}$ are hydrogen.

In many embodiments of the amide compounds of Formula (II), A is heteroaryl ring, and typically a monocyclic or fused bicyclic heteroaryl ring. The fused bicyclic heteraryls are typified by the following benzofurans (Formula IIc) and benzothiofurans (Formula (IId):

(IIc)
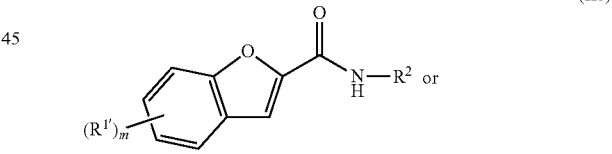

(IId)
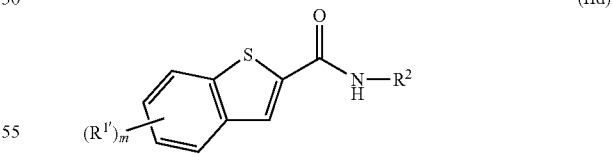

wherein m is 0, 1, 2, or 3 and each $R^{1'}$ can be bonded to either the phenyl or heteroaryl rings and each $R^{1'}$ is independently selected from, hydroxy, fluoro, chloro, $NH_2$, $NHCH_3$, $N(CH_3)_2$, $CO_2CH_3$, $SCH_3$, SEt, methyl, ethyl, isopropyl, vinyl, trifluoromethyl, methoxy, ethoxy, isopropoxy, and trifluoromethoxy.

Additional examples of fused bicyclic heteroaryls as A groups are typified by the following benzoxazole compounds (Formula IIe) and (Formula IIf):

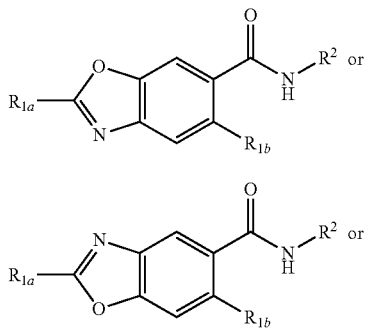

(IIe)

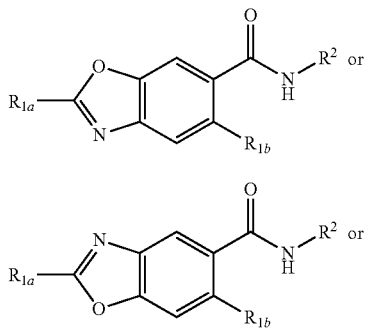

(IIf)

wherein $R_{1a}$ or $R_{1b}$ is independently hydrogen or a lower alkyl.

In many embodiments of the amide compounds of Formula (II), A is a monocyclic heteroaryl ring. The monocyclic heteroaryls that can be used as an A group in Formula (II) are typified by the following structures:

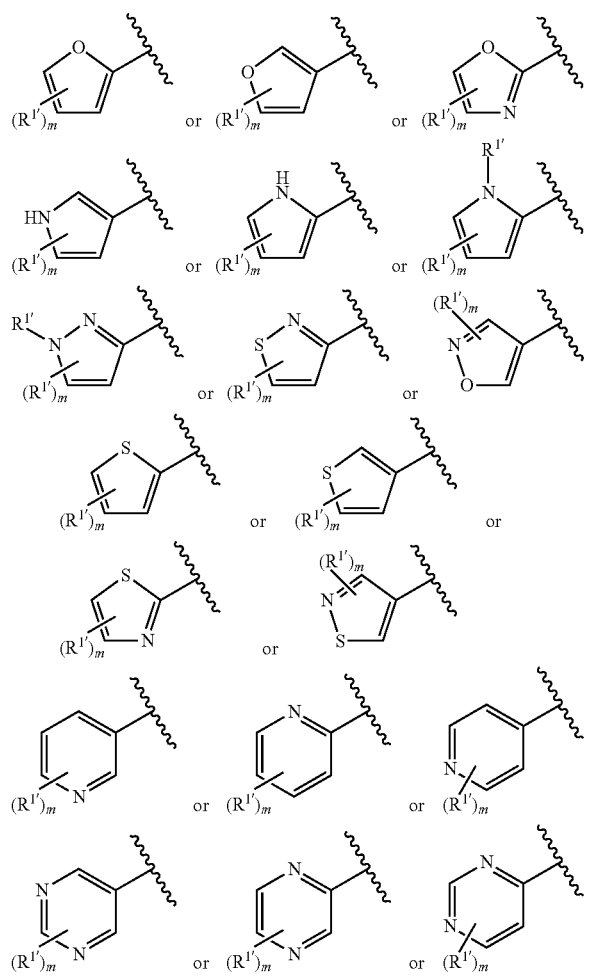

wherein m is 0, 1, 2, or 3, and each $R^{1'}$ is independently selected from, hydroxy, fluoro, chloro, $NH_2$, $NHCH_3$, $N(CH_3)_2$, $CO_2CH_3$, $SCH_3$, SEt, methyl, ethyl, isopropyl, vinyl, trifluoromethyl, methoxy, ethoxy, isopropoxy, and trifluoromethoxy.

In some preferred embodiments of the compounds of Formula (II), A is a substituted furan, thiofuran, or oxazole ring, so as to form compounds having Formulas (IIg), (IIh) and (IIi):

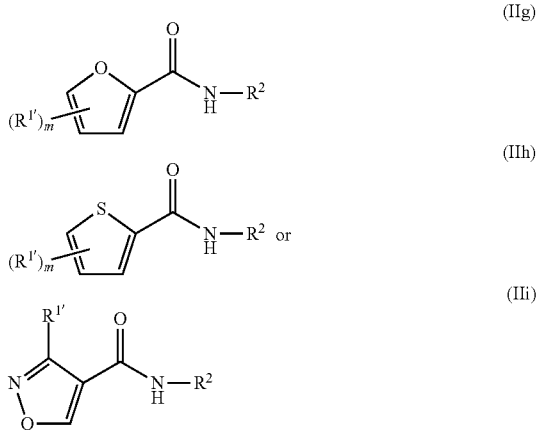

wherein m is 0, 1, 2, or 3 and each $R^{1'}$ is independently selected from hydroxy, fluoro, chloro, $NH_2$, $NHCH_3$, $N(CH_3)_2$, $CO_2CH_3$, $SCH_3$, SEt, methyl, ethyl, isopropyl, vinyl, trifluoromethyl, methoxy, ethoxy, isopropoxy, and trifluoromethoxy. In some of these embodiments, m is 1 or 2.

In many embodiments of the compounds of the various subgenuses of Formula (II) described immediately above, at least one of $R^2$ or $R^3$ can be a $C_3$-$C_{10}$ branched alkyl; an α-substituted carboxylic acid or an α-substituted carboxylic acid lower alkyl ester; a 5 or 6 membered aryl or heteroaryl ring, optionally substituted with 1, 2, 3 or 4 substituent groups selected from the group consisting of hydroxy, fluoro, chloro, $NH_2$, $NHCH_3$, $N(CH_3)_2$, $CO_2CH_3$, $SCH_3$, SEt, methyl, ethyl, isopropyl, vinyl, trifluoromethyl, methoxy; ethoxy, isopropoxy, and trifluoromethoxy groups; a cyclohexyl, optionally substituted with 1, 2, or 3 methyl groups; or a 1-(1,2,3,4) tetrahydronapthalene ring or an 2,3-dihydro-1H-indene ring having the formula:

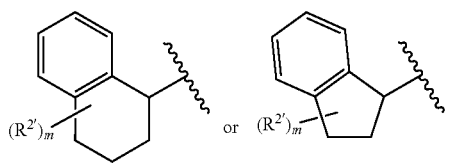

wherein m is 0, 1, 2, or 3, and each $R^{2'}$ can be bonded to either the aromatic or non-aromatic ring and is independently selected from hydroxy, fluoro, chloro, $NH_2$, $NHCH_3$, $N(CH_3)_2$, $CO_2CH_3$, $SCH_3$, SEt, methyl, ethyl, isopropyl, vinyl, trifluoromethyl, methoxy, ethoxy, isopropoxy, and trifluoromethoxy; as were described hereinabove with respect to the general amide compounds of Formula (I).

The subgenuses of aromatic or heteroaromatic amide compounds of Formula (II) described immediately above contain many excellent agonists of T1R1/T1R3 savory ("umami") taste receptors, and/or T1R2/T1R3 sweet taste receptors, at very low concentrations of the amide compound on the order of micromolar concentrations or less, and can induce a noticeable sensation of a savory umami flavor in humans, and/or can serve as enhancers of the savory umami flavor of MSG, or significantly enhance the effectiveness of a variety of known sweeteners, especially saccharide based sweeteners.

Accordingly, many of the aromatic or heteroaromatic amide compounds of Formula (II) can be utilized as savory or sweet flavoring agents or savory or sweet flavor enhancers when contacted with a wide variety of comestible products and/or compositions, or their precursors, as is described elsewhere herein.

In another subgenus of the compounds of Formula (I), the amide compound has Formula (III):

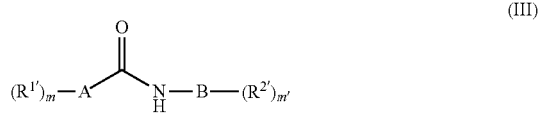

(III)

wherein A comprises a 5 or 6 membered aryl or heteroaryl ring; m is 0, 1, 2, 3 or 4; each $R^{1'}$ is independently selected from alkyl, alkoxyl, alkoxy-alkyl, hydroxyalkyl, OH, CN, $CO_2H$, CHO, $COR^6$, $CO_2R^6$, SH, $SR^6$, halogen, alkenyl, cycloalkyl, cycloalkenyl, aryl, and heteroaryl and $R^6$ is $C_1$-$C_6$ alkyl; B is a 5 or 6 membered aryl or heteroaryl ring; mg is 0, 1, 2, 3 or 4; $R^{2'}$ is selected from the group consisting of alkyl, alkoxyl, alkoxy-alkyl, OH, CN, $CO_2H$, CHO, $COR^6$, $CO_2R^6$, $SR^6$, halogen, alkenyl, cycloalkyl, cycloalkenyl, aryl, and heteroaryl: and $R^6$ is $C_1$-$C_6$ alkyl.

In the compounds of Formula (III), the optional $R^{1'}$ and $R^{2'}$ substituent groups can also be independently selected from hydroxy, fluoro, chloro, $NH_2$, $NHCH_3$, $N(CH_3)_2$, $CO_2CH_3$, $SCH_3$, SEt, methyl, ethyl, isopropyl, vinyl, trifluoromethyl, methoxy, ethoxy, isopropoxy, and trifluoromethoxy groups.

In the compounds of Formula (III), both the A and B rings comprise a five or six membered aryl or heteroaryl ring. For the A ring, any of the various embodiments of the A rings recited above for the compounds of Formula (II), including phenyl and the monocyclic and bicyclic heteroaryls can be suitable. In some bicyclic embodiments, the A ring of the compounds of Formula (III) have the following structures:

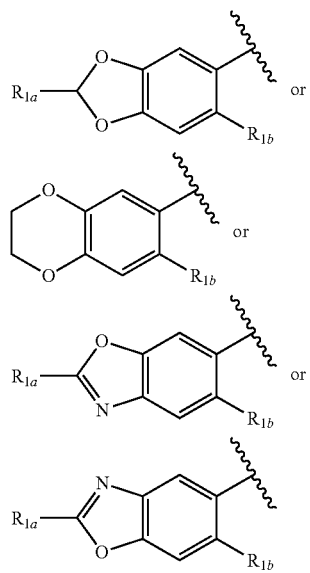

wherein $R_{1a}$ and $R_{1b}$ are independently hydrogen or a lower alkyl.

In the compounds of Formula (III), the B rings are typically an optionally substituted monocyclic five or six membered aryl or heteroaryl ring, such as a phenyl, pyridyl, furanyl, thiofuranyl, pyrrolyl, and like monocycles. In some embodiments compounds of Formula (III) wherein B is phenyl, i.e. wherein the amide compound is readily derived from an substituted aniline precursor, can in many cases be previously known chemical compounds, but we believe it has been previously unknown that such compounds can be used as very effective umami flavorant compounds, at less than micromolar concentrations or less, see for example compound A1 in Table 1 below.

Urea Compounds

In another subgenus of the amide compounds of Formula (I), the amide compound is a urea compound having the Formula (IV):

(IV)

wherein $R^7$, $R^8$ and $R^9$ are each a hydrocarbon residue that may contain one or more heteroatoms or an inorganic residue, and preferably is independently selected from arylalkenyl, heteroarylalkenyl, arylalkyl, heteroarylalkyl, alkyl, alkoxy-alkyl, alkenyl, cycloalkyl, cycloalkenyl, aryl and heteroaryl groups, each of which may be optionally substituted, or one of $R^7$ or $R^8$ can be and often is H.

In some embodiments of the urea compounds of Formula (IV), $R^7$ and $R^9$ together form a heterocyclic or heteroaryl ring having 5, 6, or 7 ring atoms that may be optionally substituted with 1, 2, or 3 substituents independently selected from hydroxy, fluoro, chloro, $NH_2$, $NHCH_3$, $N(CH_3)_2$, $COOCH_3$, $SCH_3$, SEt, methyl, ethyl, isopropyl, vinyl, trifluoromethyl, methoxy, ethoxy, isopropoxy, and trifluoromethoxy groups. Examples of such urea compound can have the Formulas (IVa) and (IVb):

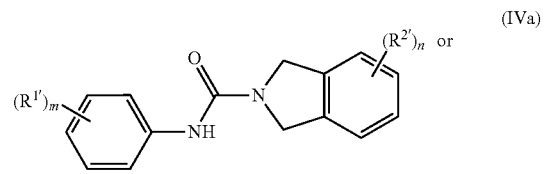

(IVa)

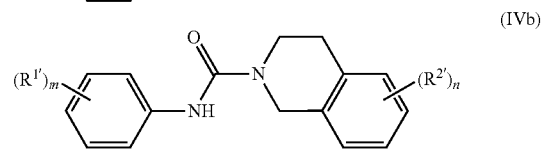

(IVb)

wherein m and n are independently 0, 1, 2, or 3, and each $R^1$ and $R^{2'}$ is independently selected from fluoro, chloro, $NH_2$, $NHCH_3$, $N(CH_3)_2$, $CO_2CH_3$, SEt, $SCH_3$, methyl, ethyl, isopropyl, vinyl, trifluoromethyl, methoxy, ethoxy, isopropoxy, and trifluoromethoxy. In such embodiments, n is preferably 0.

In additional embodiments of the urea compounds of Formula (IV), $R^9$ and one of $R^7$ and $R^9$ are independently selected from arylalkenyls, heteroarylalkenyls, arylalkyls, heteroarylalkyls, alkyls, alkoxy-alkyls, alkenyls, cycloalkyls, cycloalkenyls, aryls and heteroaryls, each of which carbon containing groups may be optionally substituted with 1, 2, or 3 substituents independently selected from hydrogen, hydroxy, fluoro, chloro, $NH_2$, $NHCH_3$, $N(CH_3)_2$, $COOCH_3$, $SCH_3$, SEt, methyl, ethyl, isopropyl, vinyl, trifluoromethyl, methoxy, ethoxy, isopropoxy, and trifluoromethoxy groups.

In additional embodiments of the urea compounds of Formula (IV), $R^9$ and one of $R^7$ and $R^8$ are independently selected from arylalkyl, heteroarylalkyl, alkyl, cycloalkyl, aryl, heterocycle, and heteroaryl, each of which may optionally comprise one to five heteroatoms independently selected from oxygen, nitrogen, sulfur, chlorine, and fluorine.

In additional embodiments of the urea compounds of Formula (IV), $R^9$ and one of $R^7$ and $R^8$ are independently selected from alkyl, phenyl, cyclohexyl, or pyridyl, each of which may optionally comprise one to four substituents independently selected from hydroxy, fluoro, chloro, $NH_2$, $NHCH_3$, $N(CH_3)_2$, $CO_2CH_3$, SEt, $SCH_3$, methyl, ethyl, isopropyl, vinyl, trifluoromethyl, methoxy, ethoxy, isopropoxy, and trifluoromethoxy.

In additional embodiments of the urea compounds of Formula (IV), at least one of $R^7$ and $R^8$ has one of the heteroaromatic formulas:

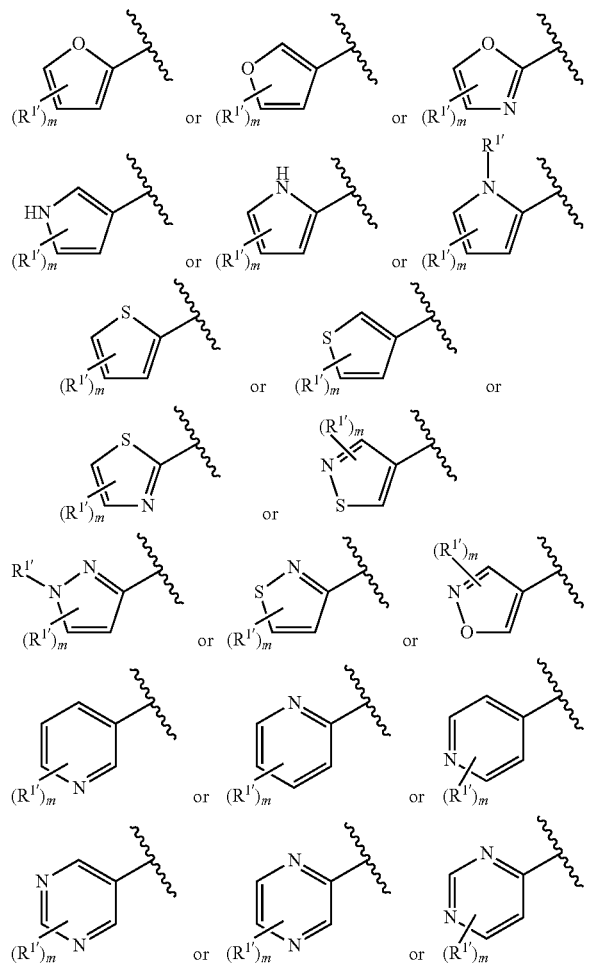

wherein m is 0, 1, 2, or 3, and each $R^{1'}$ independently selected from hydrogen, hydroxy, fluoro, chloro, $NH_2$, $NHCH_3$, $N(CH_3)_2$, $COOCH_3$, $SCH_3$, SEt, methyl, ethyl, isopropyl, vinyl, trifluoromethyl, methoxy, ethoxy, isopropoxy, and trifluoromethoxy groups. In such embodiments, $R^9$ is preferably a $C_3$-$C_{10}$ branched alkyl, arylalkyl, or a cycloalkyl that can be optionally substituted with 1, 2, or 3 substituents independently selected from hydrogen, hydroxy, fluoro, chloro, $NH_2$, $NHCH_3$, $N(CH_3)_2$, $COOCH_3$, $SCH_3$, SEt, methyl, ethyl, isopropyl, vinyl, trifluoromethyl, methoxy, ethoxy, isopropoxy, and trifluoromethoxy groups.

In additional embodiments of the urea compounds of Formula (IV), at least one of $R^7$ and $R^8$ is a phenyl ring optionally substituted with 1, 2, or 3 substituents independently selected from hydrogen, hydroxy, fluoro, chloro, $NH_2$, $NHCH_3$, $N(CH_3)_2$, $COOCH_3$, $SCH_3$, SEt, methyl, ethyl, isopropyl, vinyl, trifluoromethyl, methoxy, ethoxy, isopropoxy, and trifluoromethoxy groups. In such embodiments, $R^9$ is preferably a $C_3$-$C_{10}$ branched alkyl, arylalkyl, or a cycloalkyl that can be optionally substituted with 1, 2, or 3 substituents independently selected from hydrogen, hydroxy, fluoro, chloro, $NH_2$, $NHCH_3$, $N(CH_3)_2$, $COOCH_3$, $SCH_3$, SEt, methyl, ethyl, isopropyl, vinyl, trifluoromethyl, methoxy, ethoxy, isopropoxy, and trifluoromethoxy groups.

In additional embodiments of the urea compounds of Formula (IV), $R^9$ is a $C_3$-$C_{10}$ branched alkyl. In additional embodiments of the urea compounds of Formula (IV), $R^9$ has the structure

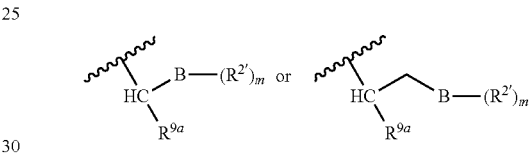

wherein B is a phenyl, pyridyl, furanyl, thiofuranyl, pyrrole, cyclopentyl, cyclohexyl, or piperidyl ring, m is 0, 1, 2, or 3, and each $R^2$ is independently selected from hydrogen, hydroxy, fluoro, chloro, $NH_2$, $NHCH_3$, $N(CH_3)_2$, $COOCH_3$, $SCH_3$, SEt, methyl, ethyl, isopropyl, vinyl, trifluoromethyl, methoxy, ethoxy, isopropoxy, and trifluoromethoxy groups, and $R^{9a}$ is a selected from the group consisting of an alkyl, alkoxy-alkyl, alkenyl, cycloalkenyl, cycloalkyl, $-R^4OH$, $-R^4OR^5$ $-R^4CN$, $-R^4CO_2H$, $-R^4CO_2R^5$, $-R^4COR^5$, $-R^4SR^5$, and $-R^4SO_2R^5$ comprising 1 to 12 carbon atoms, or preferably Oxalamide Compounds In another subgenus of the amide compounds of Formula (I), the amide compound is an oxalamide compound having Formula (V):

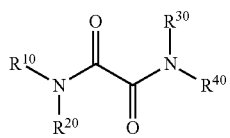

wherein $R^{10}$ and $R^{30}$ are each independently selected a hydrocarbon residue that may contain one or more heteroatoms, or preferably, $R^{10}$ and $R^{30}$ are independently selected from the group consisting of arylalkyl, heteroarylalkyl, heterocyclealkyl, or optionally substituted groups thereof, and $R^{20}$ and $R^{40}$ are each independently H or a hydrocarbon residue that may contain one or more heteroatoms; preferably $R^{20}$, and $R^{40}$ are H or $C_1$-$C_3$ alkyl, or optionally substituted groups thereof. More preferably $R^{20}$ and $R^{40}$ are H. Moreover, there can be 0, 1, 2, 3, or 4 optional substituent groups for $R^{10}$ and $R^{30}$ independently selected from hydroxy, fluoro, chloro, $NH_2$, $NHCH_3$, $N(CH_3)_2$, $CO_2CH_3$, $SCH_3$, SEt, methyl, ethyl, isopropyl, vinyl, trifluoromethyl, methoxy, ethoxy, isopropoxy, and trifluoromethoxy groups.

In preferred embodiment of the oxalamide compounds of Formula (V), $R^{10}$ and $R^{30}$ are independently selected hydrocarbon residues having at least three carbon atoms and optionally one to ten heteroatoms independently selected from oxygen, nitrogen, sulfur, halogens, or phosphorus, and wherein $R^{20}$ and $R^{40}$ are independently selected from hydrogen and a hydrocarbon residue having at least three carbon atoms and optionally one to ten heteroatoms independently selected from oxygen, nitrogen, sulfur, halogens, or phosphorus.

In many preferred embodiment of the oxalamide compounds of Formula (V), $R^{20}$ and $R^{40}$ are hydrogen. In such embodiments, $R^{10}$ and $R^{30}$ can be independently selected from the group consisting of arylalkyls, heteroarylalkyls, cycloalkyl-alkyls, and heterocycle-alkyls comprising five to 15 carbon atoms, wherein each of $R^{10}$ and $R^{30}$ can optionally comprise one to one to four substituents independently selected from hydrogen, hydroxy, fluoro, chloro, $NH_2$, $NHCH_3$, $N(CH_3)_2$, $CO_2CH_3$, SEt, $SCH_3$, methyl, ethyl, isopropyl, vinyl, trifluoromethyl, methoxy, ethoxy, isopropoxy, and trifluoromethoxy groups.

In many embodiments of the oxalamide compounds of Formula (V), the oxalamide compound has the Formula (Va):

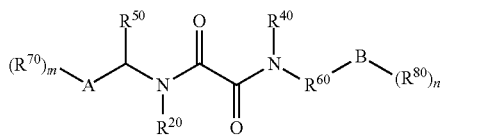

(Va)

wherein A and B are independently an aryl, heteroaryl, cycloalkyl, or a heterocycle comprising 5 to 12 ring atoms; m and n are independently 0, 1, 2, 3 or 4-8; $R^{20}$ and $R^{40}$ are hydrogen, $R^{50}$ is hydrogen or an alkyl or substituted alkyl residue comprising one to four carbon atoms; $R^{60}$ is absent or a $C_1$-$C_5$ alkylene or a $C_1$-$C_5$ substituted alkylene; $R^{70}$ and $R^{80}$ are independently selected from the group consisting of hydrogen, alkyl, alkoxyl, alkoxy-alkyl, OH, $SR^9$, halogen, CN, $NO_2$, $CO_2R^9$, $COR^9$, $CONR^9R^{10}$, $NR^9R^{10}$, $NR^9COR^{10}$, $SOR^9$, $SO_2R^9$, $SO_2NR^9R^{10}$, $NR^9SO_2R^{10}$, alkenyl, cycloalkyl, cycloalkenyl, aryl, heteroaryl, and heterocycle; $R^9$ and $R^{10}$ are independently selected from H, $C_1$-$C_6$ alkyl, $C_3$-$C_6$ cycloalkyl, and $C_1$-$C_6$ alkenyl.

In preferred embodiments of the oxalamide compounds of Formula (Va), $R^{60}$ is a —$CH_2CH_2$ group, A and B are independently selected from phenyl, pyridyl, furanyl, thiofuranyl and pyrrolyl rings and $R^{70}$ and $R^{80}$ are independently selected from hydroxy, fluoro, chloro, $NH_2$, $NHCH_3$, $N(CH_3)_2$, $CO_2CH_3$, SEt, $SCH_3$, methyl, ethyl, isopropyl, vinyl, trifluoromethyl, methoxy, ethoxy, isopropoxy, and trifluoromethoxy groups.

In some embodiments of the oxalamide compounds of Formula (Va), A and B are independently a phenyl, pyridyl, furanyl, benzofuranyl, pyrrole, benzothiophene, piperidyl, cyclopentyl, cyclohexyl, or cycloheptyl ring; m and n are independently 0, 1, 2, or 3; $R^{20}$ and $R^{40}$ are hydrogen; $R^{50}$ is hydrogen or methyl; $R^{60}$ is a $C_1$-$C_5$ or preferably $C_2$ alkylene; $R^{70}$ and $R^{80}$ are independently selected from hydrogen, hydroxy, fluoro, chloro, $NH_2$, $NHCH_3$, $N(CH_3)_2$, $CO_2CH_3$, SEt, $SCH_3$, methyl, ethyl, isopropyl, vinyl, trifluoromethyl, methoxy, ethoxy, isopropoxy, and trifluoromethoxy groups.

In many embodiments of the oxalamide compounds of Formula (V), the oxalamide compound has the Formula (Vb):

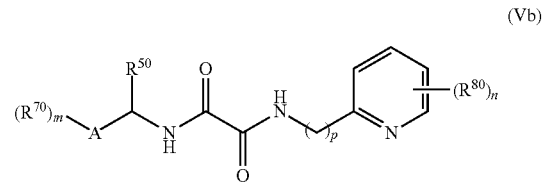

(Vb)

wherein A is a phenyl, pyridyl, furanyl, pyrrole, piperidyl, cyclopentyl, cyclohexyl, or cycloheptyl ring; m and n are independently 0, 1, 2, or 3; $R^{50}$ is hydrogen or methyl; P is 1 or 2; and $R^{70}$ and $R^{80}$ are independently selected from the group consisting of hydrogen, hydroxy, fluoro, chloro, $NH_2$, $NHCH_3$, $N(CH_3)_2$, $COOCH_3$, $SCH_3$, SEt, methyl, ethyl, isopropyl, vinyl, trifluoromethyl, methoxy, ethoxy, isopropoxy, and trifluoromethoxy, or two of $R^{70}$ together form a methylenedioxy ring. In some embodiments of the oxalamide compounds of Formula (Vb), the pyridyl-$R^{80}$ radical has the structure:

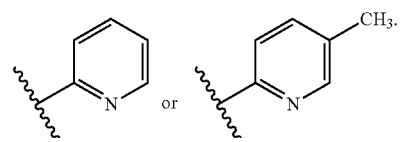

In certain preferred embodiments of the amide compounds of Formula (V), the oxalamide compound has the Formula (Vc):

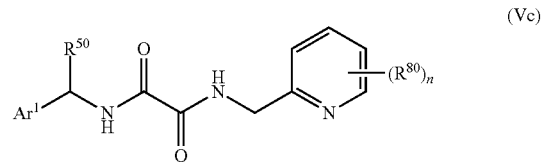

(Vc)

wherein $Ar^1$ is a substituted aryl or heteroaryl ring comprising five to 12 carbon atoms; $R^{50}$ is hydrogen or methyl; n is 0, 1, 2, or 3; each $R^{80}$ is independently selected from the group consisting of hydroxy, fluoro, chloro, $NH_2$, $NHCH_3$, $N(CH_3)_2$, $CO_2CH_3$, SEt, $SCH_3$, methyl, ethyl, isopropyl, vinyl, trifluoromethyl, methoxy, ethoxy, isopropoxy, and trifluoromethoxy groups. In some embodiments of the oxalamide compounds of Formula (Vc), $Ar^1$ is a 2-, 3-, or 4-monosubstituted phenyl, 2,4-, 2,3-, 2,5, 2,6, 3,5-, or 3,6- disubstituted phenyl, 3-alkyl-4-substituted phenyl, a trisubstituted phenyl wherein the substituent groups are independently selected from the group consisting of hydrogen, hydroxy, fluoro, chloro, $NH_2$, $NHCH_3$, $N(CH_3)_2$, $CO_2CH_3$, SEt, $SCH_3$, methyl, ethyl, isopropyl, vinyl, trifluoromethyl, methoxy, ethoxy, isopropoxy, and trifluoromethoxy, or two adjacent substituents together form a methylenedioxy ring on the phenyl ring. In some embodiments of the oxalamide compounds of Formula (Vc), $Ar^1$ is a substituted heteroaryl ring comprising 5 to 12 carbon atoms and wherein the substituent groups are independently selected from the group consisting of hydrogen, hydroxy, fluoro, chloro, $NH_2$, $NHCH_3$, $N(CH_3)_2$, $CO_2CH_3$, SEt, $SCH_3$, methyl, ethyl, isopropyl, vinyl, trifluoromethyl, methoxy, ethoxy, isopropoxy, and trifluoromethoxy.

In certain preferred embodiments of the amide compounds of Formula (V), the oxalamide compound has the Formula (Vd):

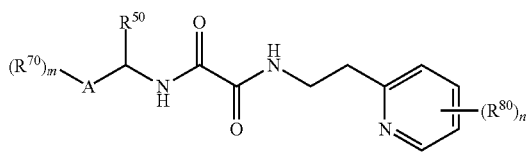

(Vd)

wherein A is a substituted aryl or heteroaryl ring comprising five to 12 carbon atoms; $R^{50}$ is hydrogen or methyl; n is 0, 1, 2, or 3; each $R^{80}$ is independently selected from the group consisting of hydrogen, hydroxy, fluoro, chloro, $NH_2$, $NHCH_3$, $N(CH_3)_2$, $COOCH_3$, $SCH_3$, SEt, methyl, ethyl, isopropyl, vinyl, trifluoromethyl, methoxy, ethoxy, isopropoxy, and trifluoromethoxy. Preferably, A is a phenyl, pyridyl, furanyl, pyrrole, piperidyl, cyclopentyl, cyclohexyl, or cycloheptyl ring optionally substituted with 1, 3, or 3 substituent groups independently selected from the group consisting of hydrogen, hydroxy, fluoro, chloro, $NH_2$, $NHCH_3$, $N(CH_3)_2$, $COOCH_3$, $SCH_3$, SEt, methyl, ethyl, isopropyl, vinyl, trifluoromethyl, methoxy, ethoxy, isopropoxy, and trifluoromethoxy groups.

In certain preferred embodiments of the amide compounds of Formula (V), the oxalamide compound has the Formula (Ve):

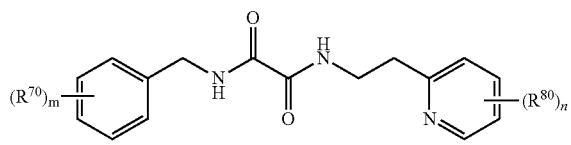

(Ve)

wherein m and n are independently 0, 1, 2, or 3; $R^{70}$ and $R^{80}$ are independently selected from the group consisting of hydrogen, alkyl, alkoxyl, alkoxy-alkyl, OH, $SR^9$, halogen, CN, $NO_2$, $CO_2R^9$, $COR^9$, $CONR^9R^{10}$, $NR^9R^{10}$, $NR^9COR^{10}$, $SOR^9$, $SO_2R^9$, $SO_2NR^9R^{10}$, $NR^9SO_2R^{10}$, alkenyl, cycloalkyl, cycloalkenyl, aryl, heteroaryl, and heterocycle; and $R^9$ and $R^{10}$ are independently selected from H, $C_1$-$C_6$ alkyl, $C_3$-$C_6$ cycloalkyl, and $C_1$-$C_6$ alkenyl groups. Preferably, $R^{70}$ and $R^{80}$ are independently selected from the group consisting of hydrogen, hydroxy, fluoro, chloro, $NH_2$, $NHCH_3$, $N(CH_3)_2$, $COOCH_3$, $SCH_3$, SEt, methyl, ethyl, isopropyl, vinyl, trifluoromethyl, methoxy, ethoxy, isopropoxy, and trifluoromethoxy groups. Preferably, the pyridyl-$R^{80}$ radical of the oxalamide compound of Formula (Ve) has the structure:

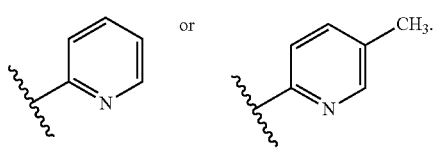

As can be noted by inspection of the Examples attached hereinbelow, oxalamide compounds of Formulas (Va)-(Ve) are excellent agonists of T1R1/T1R3 savory ("umami") taste receptors at very low concentrations on the order of micromolar concentrations or less, induce a noticeable sensation of a savory umami flavor in humans, and/or can serve as enhancers of the savory umami flavor of MSG. Accordingly, oxalamide compounds of Formulas (Vc), (Vd) and (Ve) can be utilized as savory flavoring agents or savory flavor enhancers when contacted with a wide variety of comestible products and/or compositions, or their precursors, as is described elsewhere herein.

Acrylamide Compounds

In another subgenus of the amide compounds of Formula (I), the amide compound is an acrylamide compound having Formula (VI):

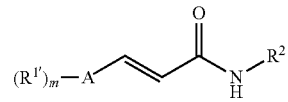

(VI)

wherein A is a 5 or 6 membered aryl or heteroaryl ring; m is 0, 1, 2, 3 or 4; each $R^{1'}$ is independently selected from alkyl, alkoxyl, alkoxy-alkyl, OH, CN, $CO_2H$, $CO_2R^6$, CHO, $COR^6$, $SR^6$, halogen, alkenyl, cycloalkyl, cycloalkenyl, aryl, and heteroaryl, and $R^2$ can be any of the various embodiments of $R^2$ described hereinabove with respect to the amides of Formula (I).

In some of the acrylamide compounds of Formula (VI), A is a phenyl ring and m is 1, 2, 3 or 4, or preferably m is 1 or 2, and $R^{1'}$ can be independently selected from hydrogen, hydroxy, fluoro, chloro, $NH_2$, $NHCH_3$, $N(CH_3)_2$, $CO_2CH_3$, SEt, $SCH_3$, methyl, ethyl, isopropyl, vinyl, trifluoromethyl, methoxy, ethoxy, isopropoxy, and trifluoromethoxy groups. In some of the acrylamide compounds of Formula (VI), $R^2$ is a $C_3$-$C_{10}$ alkyl, or an α-substituted carboxylic acid lower alkyl ester.

Comestibly or Pharmaceutically Acceptable Compounds

Many of the amide compounds of Formula (I) or its various enumerated subgenuses comprise acidic or basic groups, so that depending on the acidic or basic character ("pH") of the comestible or medicinal compositions in which they are formulated, they may be present as salts, which are preferably comestibly acceptable (i.e. designated as generally recognized as safe, or GRAS) or pharmaceutically acceptable salts (many of which have been recognized by the Federal Food and Drug Administration).

The amide compounds of Formula (I) having acidic groups, such as carboxylic acids, will tend (at near neutral physiological pH) to be present in solution in the form of anionic carboxylates, and therefore will in preferred embodiments have an associate comestibly and/or pharmaceutically acceptable cation, many of which are known to those of ordinary skill in the art. Such comestibly and/or pharmaceutically acceptable cations include alkali metal cations (lithium, sodium, and potassium cations), alkaline earth metal cations (magnesium, calcium, and the like), or ammonium $(NH_4)^+$ or organically substituted ammonium cations such as $(R-NH_3)^+$ cations.

The amide compounds of Formula (I) having basic substituent groups, such as amino or nitrogen containing heterocyclic groups, will tend (at near neutral physiological pH, or at the acidic pH common in many foods) to be present in solution in the form of cationic ammonium groups, and therefore will in preferred embodiments have an associate comestibly and/or pharmaceutically acceptable anion, many of which are known to those of ordinary skill in the art. Such comestibly and/or pharmaceutically acceptable anionic groups include the anionic form of a variety of carboxylic acids (acetates, citrates, tartrates, anionic salts of fatty acids, etc.), halides (especially fluorides or chlorides), nitrates, and the like.

The amide compounds of Formula (I) and its various sub-genuses should preferably be comestibly acceptable, i.e. deemed suitable for consumption in food or drink, and should also be pharmaceutically acceptable. The typical method of demonstrating that a flavorant compound is comestibly acceptable is to have the compound tested and/or evaluated by an Expert Panel of the Flavor and Extract Manufacturers Association and declared as to be "Generally Recognized As Safe" ("GRAS"). The FEMA/GRAS evaluation process for flavorant compounds is complex but well known to those of ordinary skill in the food product preparation arts, as is discussed by Smith et al. in an article entitled "GRAS Flavoring Substances 21," Food Technology, 57(5), pgs 46-59, May 2003, the entire contents of which are hereby incorporated herein by reference.

When being evaluated in the FEMA/GRAS process, a new flavorant compound is typically tested for any adverse toxic effects on laboratory rats when fed to such rats for at least about 90 days at a concentration 100-fold, or 1000-fold, or even higher concentrations than the proposed maximum allowable concentration of the compound in a particular category of food products being considered for approval. For example, such testing of the amide compounds of the invention might involve combining the amide compound with rat chow and feeding it to laboratory rats such as Crl:CD(SD)IGS BR rats, at a concentration of about 100 milligrams/Kilogram body weight/day for 90 days, and then sacrificing and evaluating the rats by various medical testing procedures to show that the amide compound of Formula (I) causes no adverse toxic effects on the rats.

The Compounds of the Invention as Savory or Sweet Taste Enhancers

The amide compounds of Formula (I) and its various compound sub-genuses and species, as described above are intended to be savory or sweet taste flavorant compounds or flavor modifiers for comestible or medicinal products. As is apparent from the teachings and Examples herein, many compounds of Formula (I) are agonists of an hT1R1/hT1R3 "savory" receptor, or an hT1R2/hT1R3 sweet receptor, at least at relatively high amide compound concentrations, and accordingly many of the amide compounds of Formula (I) can have at least some utility as savory or sweet flavorants or flavor enhancers, at least at relatively high concentrations.

Nevertheless, it is preferable to use as little of such artificial flavorants as possible, so as to minimize both cost and any undesirable health side effects of administration of the compounds of Formula (I) at high concentration levels. Accordingly, it is desirable to test the compounds of Formula (I) for their effectiveness as taste receptor agonists at lower concentration levels, so as to identify the best and most effective amide compounds within the compounds of Formula (I). As was disclosed in WO 03/001876, and U.S. Patent publication US 2003-0232407 A1, and as described hereinbelow, laboratory procedures now exist for measuring the agonist activities of compounds for an hT1R1/hT1R3 "savory" and hT1R2/hT1R3 sweet receptors. Such measurement methods typically measure an "$EC_{50}$", i.e. the concentration at which the compound causes 50% activation of the relevant receptor.

Preferably, the amide compounds of Formula (I) that are savory flavor modifiers have an $EC_{50}$ for the hT1R1/hT1R3 receptor of less than about 10 μM. More preferably, such amide compounds have an $EC_{50}$ for the hT1R1/hT1R3 receptor of less than about 5 μM, 3 μM, 2 μM, 1 μM, or 0.5 μM.

Preferably, the amide compounds of Formula (I) that are sweet flavor modifiers or sweet flavor enhancers have an $EC_{50}$ for the hT1R2/hT1R3 receptor of less than about 10 μM. More preferably, such amide compounds have an $EC_{50}$ for the hT1R2/hT1R3 receptor of less than about 5 μM, 3 μM, 2 μM, 1 μM, or 0.5 μM.

In some embodiments, the amide compounds of Formula (I) are savory flavor modulators or enhancers of the agonist activity of monosodium glutamate for an hT1R1/hT1R3 receptor. Hereinbelow is described an assay procedure for so-called $EC_{50}$ ratios, i.e. for dissolving a compound of Formula (I) in water containing MSG, and measuring the degree to which the amide compound lowers the amount of MSG required to activate 50% of the available hT1R1/hT1R3 receptors. Preferably, the amide compounds of Formula (I), when dissolved in a water solution comprising about 1 μM of the amide compound will decrease the observed $EC_{50}$ of monosodium glutamate for an hT1R1/hT1R3 receptor expressed in an HEK293-Gα15 cell line by at least 50%, i.e. the amide compound will have an EC50 ratio of at least 2.0, or preferably 3.0, 5.0, or 7.0.

Although no specific $EC_{50}$ ratio assays for sweet enhancers have yet been developed, it is believed the amide compounds of Formula (I), and more specifically many of the amides of Formula (II) can modulate the binding of a known sweetener such as for example sucrose, fructose, glucose, erythritol, isomalt, lactitol, mannitol, sorbitol, xylitol, a known natural terpenoid, flavonoid, or protein sweetener, aspartame, saccharin, acesulfame-K, a cyclamate, sucralose, alitame or erythritol to an hT1R2/hT1R3 receptor. Appropriate assays for such sweet enhancement properties can be readily developed by one of ordinary skill in the arts by using appropriate cell lines expressing hT1R2/hT1R$^3$ receptors.

The above identified assays are useful in identifying the most potent of the amide compounds of Formula (I) for savory and/or sweet taste modifier or enhancer properties, and the results of such assays are believed to correlate well with actual savory or sweet taste perception in animals and humans, but ultimately the results of the assays can be confirmed, at least for the most potent of the compounds of Formula (I), by human taste testing. Such human taste testing experiments can be well quantified and controlled by tasting the candidate compounds in aqueous solutions, as compared to control aqueous solution, or alternatively by tasting the amides of the inventions in actual food compositions.

Accordingly, in order to identify the more potent of the savory taste modifiers or agents, a water solution comprising a savory flavor modifying amount of the amide compound should have a savory taste as judged by the majority of a panel of at least eight human taste testers.

Correspondingly, in order to identify the more potent of the savory taste enhancers, a water solution, comprising a savory flavor modifying amount of an amide compound of Formula (I) and 12 mM monosodium glutamate, would have an increased savory taste as compared to a control water solution comprising 12 mM monosodium glutamate, as determined by the majority of a panel of at least eight human taste testers. Preferably, in order to identify the more potent of the savory taste enhancers, a water solution comprising a savory flavor modifying amount (preferably about 30, 10, 5, or 2 ppm) of the amide compound of Formula (I) and 12 mM monosodium glutamate will have an increased savory taste as compared to a control water solution comprising 12 mM monosodium glutamate and 100 μM inosine monophosphate, as determined by the majority of a panel of at least eight human taste testers.

Similar human taste testing procedures can be used to identify which of the compounds of Formula (I) are the more effective sweet taste agents or sweet taste enhancing agents. Preferred sweet taste modifiers of Formula (I) can be identified when a modified comestible or medicinal product has a sweeter taste than a control comestible or medicinal product that does not comprise the amide compound, as judged by the majority of a panel of at least eight human taste testers.

Preferred sweet taste enhancers of Formula (I) can be identified when a water solution comprising a sweet tasting amount of a known sweetener selected from the group consisting of sucrose, fructose, glucose, erythritol, isomalt, lactitol, mannitol, sorbitol, xylitol, a known natural terpenoid, flavonoid, or protein sweetener, aspartame, saccharin, acesulfame-K, cyclamate, sucralose, and alitame, and a sweet flavor modifying amount of the amide compound (preferably about 30, 10, 5, or 2 ppm) has a sweeter taste than a control water solution comprising the sweet tasting amount of the known sweetener, as judged by the majority of a panel of at least eight human taste testers. In such taste test experiments, sucrose would preferably be present at a concentration of about 6 grams/100 milliliters, a 50:50 mixture of glucose and fructose would preferably be present at a concentration of about 6 grams/100 milliliters, aspartame would preferably be present at a concentration of about 1.6 mM, acesulfame-K would preferably be present at a concentration of about 1.5 mM, cyclamate would preferably be present at a concentration of about 10 mM, sucralose would preferably be present at a concentration of about 0.4 mM, or alitame would preferably be present at a concentration of about 0.2 mM.

Using the Compounds of Formula (I) to Prepare Comestible Compositions

Flavors, flavor modifiers, flavoring agents, flavor enhancers, savory ("umami") flavoring agents and/or flavor enhancers, according to the invention have application in foods, beverages and medicinal compositions wherein savory or sweet compounds are conventionally utilized. These compositions include compositions for human and animal consumption. This includes foods for consumption by agricultural animals, pets and zoo animals.

Those of ordinary skill in the art of preparing and selling comestible compositions (i.e edible foods or beverages, or precursors or flavor modifiers thereof) are well aware of a large variety of classes, subclasses and species of the comestible compositions, and utilize well-known and recognized terms of art to refer to those comestible compositions while endeavoring to prepare and sell various of those compositions. Such a list of terms of art is enumerated below, and it is specifically contemplated hereby that the various subgenuses and species of the compounds of Formula (I) could be used to modify or enhance the savory and/or sweet flavors of the following list comestible compositions, either singly or in all reasonable combinations or mixtures thereof:

One or more confectioneries, chocolate confectionery, tablets, countlines, bagged selflines/softlines, boxed assortments, standard boxed assortments, twist wrapped miniatures, seasonal chocolate, chocolate with toys, alfajores, other chocolate confectionery, mints, standard mints, power mints, boiled sweets, pastilles, gums, jellies and chews, toffees, caramels and nougat, medicated confectionery, lollipops, liquorice, other sugar confectionery, gum, chewing gum, sugarised gum, sugar-free gum, functional gum, bubble gum, bread, packaged/industrial bread, unpackaged/artisanal bread, pastries, cakes, packaged/industrial cakes, unpackaged/artisanal cakes, cookies, chocolate coated biscuits, sandwich biscuits, filled biscuits, savoury biscuits and crackers, bread substitutes, breakfast cereals, rte cereals, family breakfast cereals, flakes, muesli, other rte cereals, children's breakfast cereals, hot cereals, ice cream, impulse ice cream, single portion dairy ice cream, single portion water ice cream, multi-pack dairy ice cream, multi-pack water ice cream, take-home ice cream, take-home dairy ice cream, ice cream desserts, bulk ice cream, take-home water ice cream, frozen yoghurt, artisanal ice cream, dairy products, milk, fresh/pasteurised milk, full fat fresh/pasteurised milk, semi skimmed fresh/pasteurised milk, long-life/uht milk, full fat long life/uht milk, semi skimmed long life/uht milk, fat-free long life/uht milk, goat milk, condensed/evaporated milk, plain condensed/evaporated milk, flavoured, functional and other condensed milk, flavoured milk drinks, dairy only flavoured milk drinks, flavoured milk drinks with fruit juice, soy milk, sour milk drinks, fermented dairy drinks, coffee whiteners, powder milk, flavoured powder milk drinks, cream, cheese, processed cheese, spreadable processed cheese, unspreadable processed cheese, unprocessed cheese, spreadable unprocessed cheese, hard cheese, packaged hard cheese, unpackaged hard cheese, yoghurt, plain/natural yoghurt, flavoured yoghurt, fruited yoghurt, probiotic yoghurt, drinking yoghurt, regular drinking yoghurt, probiotic drinking yoghurt, chilled and shelf-stable desserts, dairy-based desserts, soy-based desserts, chilled snacks, fromage frais and quark, plain fromage frais and quark, flavoured fromage frais and quark, savoury fromage frais and quark, sweet and savoury snacks, fruit snacks, chips/crisps, extruded snacks, tortilla/corn chips, popcorn, pretzels, nuts, other sweet and savoury snacks, snack bars, granola bars, breakfast bars, energy bars, fruit bars, other snack bars, meal replacement products, slimming products, convalescence drinks, ready meals, canned ready meals, frozen ready meals, dried ready meals, chilled ready meals, dinner mixes, frozen pizza, chilled pizza, soup, canned soup, dehydrated soup, instant soup, chilled soup, uht soup, frozen soup, pasta, canned pasta, dried pasta, chilled/fresh pasta, noodles, plain noodles, instant noodles, cups/bowl instant noodles, pouch instant noodles, chilled noodles, snack noodles, canned food, canned meat and meat products, canned fish/seafood, canned vegetables, canned tomatoes, canned beans, canned fruit, canned ready meals, canned soup, canned pasta, other canned foods, frozen food, frozen processed red meat, frozen processed poultry, frozen processed fish/seafood, frozen processed vegetables, frozen meat substitutes, frozen potatoes, oven baked potato chips, other oven baked potato products, non-oven frozen potatoes, frozen bakery products, frozen desserts, frozen ready meals, frozen pizza, frozen soup, frozen noodles, other frozen food, dried food, dessert mixes, dried ready meals, dehydrated soup, instant soup, dried pasta, plain noodles, instant noodles, cups/bowl instant noodles, pouch instant noodles, chilled food, chilled processed meats, chilled fish/seafood products, chilled processed fish, chilled coated fish, chilled smoked fish, chilled lunch kit, chilled ready meals, chilled pizza, chilled soup, chilled/fresh pasta, chilled noodles, oils and fats, olive oil, vegetable and seed oil, cooking fats, butter, margarine, spreadable oils and fats, functional spreadable oils and fats, sauces, dressings and condiments, tomato pastes and purees, bouillon/stock cubes, stock cubes, gravy granules, liquid stocks and fonds, herbs and spices, fermented sauces, soy based sauces, pasta sauces, wet sauces, dry sauces/powder mixes, ketchup, mayonnaise, regular mayonnaise, mustard, salad dressings, regular salad dressings, low fat salad dressings, vinaigrettes, dips, pickled products, other sauces, dressings and condiments, baby food, milk formula, standard milk formula, follow-on milk formula, toddler milk formula, hypoallergenic milk formula, prepared baby food, dried baby food, other baby food, spreads, jams and preserves, honey, chocolate spreads, nut-based spreads, and yeast-based spreads.

Preferably, the compounds of Formula (I) can be used to modify or enhance the savory or sweet flavor of one or more of the following sub-genuses of comestible compositions: confectioneries, bakery products, ice creams, dairy products, sweet and savory snacks, snack bars, meal replacement products, ready meals, soups, pastas, noodles, canned foods, frozen foods, dried foods, chilled foods, oils and fats, baby foods, or spreads, or a mixture thereof.

In general an ingestible composition will be produced that contains a sufficient amount of at least one compound within the scope of Formula (I) or its various subgenuses described hereinabove to produce a composition having the desired flavor or taste characteristics such as "savory" or "sweet" taste characteristics.

Typically at least a savory flavor modulating amount, a sweet flavor modulating amount, a savory flavoring agent amount, or a sweet flavoring agent amount, of one or more of the compounds of Formula (I) will be added to the comestible or medicinal product, so that the savory or sweet flavor modified comestible or medicinal product has an increased savory and/or sweet taste as compared to the comestible or medicinal product prepared without the amide compound, as judged by human beings or animals in general, or in the case of formulations testing, as judged by a majority of a panel of at least eight human taste testers, via procedures described elsewhere herein.

The concentration of savory or sweet flavoring agent needed to modulate or improve the flavor of the comestible or medicinal product or composition will of course vary dependent on many variables, including the specific type of ingestible composition, what savory compounds are present and the concentrations thereof, and the effect of the particular compound on such savory compounds. As noted, a significant application of the compounds of Formula (I) is for modulating (inducing, enhancing or inhibiting) the savory or sweet tastes or other taste properties of other natural or synthetic savory tastants. A broad but also low range of concentrations of the amide compounds of Formula (I) would typically be required, i.e. from about 0.001 ppm to 100 ppm, or narrower alternative ranges from about 0.1 ppm to about 10 ppm, from about 0.01 ppm to about 30 ppm, from about 0.05 ppm to about 15 ppm, from about 0.1 ppm to about 5 ppm, or from about 0.1 ppm to about 3 ppm.

Examples of foods and beverages wherein compounds according to the invention may be incorporated included by way of example the Wet Soup Category, the Dehydrated and Culinary Food Category, the Beverage Category, the Frozen Food Category, the Snack Food Category, and seasonings or seasoning blends.

"Wet Soup Category" means wet/liquid soups regardless of concentration or container, including frozen Soups. For the purpose of this definition soup(s) means a food prepared from meat, poultry, fish, vegetables, grains, fruit and other ingredients, cooked in a liquid which may include visible pieces of some or all of these ingredients. It may be clear (as a broth) or thick (as a chowder), smooth, pureed or chunky, ready-to-serve, semi-condensed or condensed and may be served hot or cold, as a first course or as the main course of a meal or as a between meal snack (sipped like a beverage). Soup may be used as an ingredient for preparing other meal components and may range from broths (consomme) to sauces (cream or cheese-based soups).

"Dehydrated and Culinary Food Category" means: (i) Cooking aid products such as: powders, granules, pastes, concentrated liquid products, including concentrated bouillon, bouillon and bouillon like products in pressed cubes, tablets or powder or granulated form, which are sold separately as a finished product or as an ingredient within a product, sauces and recipe mixes (regardless of technology); (ii) Meal solutions products such as: dehydrated and freeze dried soups, including dehydrated soup mixes, dehydrated instant soups, dehydrated ready-to-cook soups, dehydrated or ambient preparations of ready-made dishes, meals and single serve entrees including pasta, potato and rice dishes; and (iii) Meal embellishment products such as: condiments, marinades, salad dressings, salad toppings, dips, breading, batter mixes, shelf stable spreads, barbecue sauces, liquid recipe mixes, concentrates, sauces or sauce mixes, including recipe mixes for salad, sold as a finished product or as an ingredient within a product, whether dehydrated, liquid or frozen.

"Beverage Category" means beverages, beverage mixes and concentrates, including but not limited to, alcoholic and non-alcoholic ready to drink and dry powdered beverages.

Other examples of foods and beverages wherein compounds according to the invention may be incorporated included by way of example carbonated and non-carbonated beverages, e.g., sodas, fruit or vegetable juices, alcoholic and non-alcoholic beverages, confectionery products, e.g., cakes, cookies, pies, candies, chewing gums, gelatins, ice creams, sorbets, puddings, jams, jellies, salad dressings, and other condiments, cereal, and other breakfast foods, canned fruits and fruit sauces and the like.

Additionally, the subject compounds can be used in flavor preparations to be added to foods and beverages. In preferred instances the composition will comprise another flavor or taste modifier such as a savory tastant.

Accordingly, in some embodiments, the inventions relate to methods for modulating the savory or sweet taste of a comestible or medicinal product comprising:

a) providing at least one comestible or medicinal product, or a precursor thereof, and b) combining the comestible or medicinal product or precursor thereof with at least a savory flavor modulating amount or a sweet flavor modulating amount of at least one non-naturally occurring amide compound, or a comestibly acceptable salt thereof, so as to form a modified comestible or medicinal product;

wherein the amide compound has the formula:

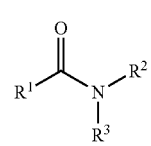

(I)

wherein the amide compound is an amide of Formula (I), or any of its various subgenuses or species compounds described herein, wherein $R^1$, $R^2$, and $R^3$ can be defined in the many ways also described hereinabove.

The invention also relates to the modified comestible or medicinal products produced by such processes, and similar processes for producing comestible or medicinal products well known to those of ordinary skill in the art.

The amide compounds of Formula (I) and its various subgenuses can be combined with or applied to the comestible or medicinal products or precursor thereof in any of innumerable ways known to cooks the world over, or producers of comestible or medicinal products. For example, the amide compounds of Formula (I) could be dissolved in or dispersed in or one one of many comestibly acceptable liquids, solids, or other carriers, such as water at neutral, acidic, or basic pH, fruit or vegetable juices, vinegar, marinades, beer, wine, natural water/fat emulsions such as milk or condensed milk, edible oils and shortenings, fatty acids, certain low molecular weight oligomers of propylene glycol, glyceryl esters of fatty acids, and dispersions or emulsions of such hydrophobic substances in aqueous media, salts such as sodium chloride, vegetable flours, solvents such as ethanol, solid edible diluents such as vegetable powders or flours, and the like, and then combined with precursors of the comestible or medicinal products, or applied directly to the comestible or medicinal products.

Making the Amide Compounds of Formula (I)

The starting materials used in preparing the compounds of the invention, i.e. the various structural subclasses and species of the amide compounds of Formula (I) and their synthetic precursors, especially the organic carboxylic acids and benzoic acids, isocyanates, and the various amines, anilines, amino acids, etc, were often known compounds, or made by known methods of the literature, or are commercially available from various sources well known to those of ordinary skill in the art, such as for example, Sigma-Aldrich Corporation of St. Louis Mo. USA and their subsidiaries Fluka and Riedel-de Haën, at their various other worldwide offices, and other well know suppliers such as Fisher Scientific, TCI America of Philadelphia Pa., ChemDiv of San Diego Calif., Chembridge of San Diego Calif., Asinex of Moscow Russia, SPECS/BIOSPECS of the Netherlands, Maybridge of Cornwall England, Acros, TimTec of Russia, Comgenex of South San Francisco Calif. and ASDI Biosciences of Newark Deleware.

It will be apparent to the skilled artisan that methods for preparing precursors and functionality related to the compounds claimed herein are generally described in the literature. The skilled artisan given the literature and this disclosure is well equipped to prepare any of the necessary starting materials and/or claimed compounds. In some of the Examples cited below, starting materials were not readily available, and therefore were synthesized, and the synthesis of the starting materials is therefore exemplified.

It is recognized that the skilled artisan in the art of organic chemistry can readily carry out manipulations without further direction, that is, it is well within the scope and practice of the skilled artisan to carry out these manipulations. These include reduction of carbonyl compounds to their corresponding alcohols, oxidations, acylations, aromatic substitutions, both electrophilic and nucleophilic, etherifications, esterification, saponification, nitrations, hydrogenations, reductive amination and the like. These manipulations are discussed in standard texts such as March's *Advanced Organic Chemistry* (3d Edition, 1985, Wiley-Interscience, New York), Feiser and Feiser's *Reagents for Organic Synthesis*, Carey and Sundberg, *Advanced Organic Chemistry* and the like, the entire disclosures of which are hereby incorporated by reference in their entirieties for their teachings regarding methods for synthesizing organic compounds.

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene and P. Wuts, *Protecting Groups in Organic Synthesis*, 3rd Ed., John Wiley & Sons (1999).

The following abbreviations have the indicated meanings:
$CH_3CN$=Acetonitrile
$CHCl_3$=Chloroform
DIC=N,N'-Diisopropylcarbodiimide
DIPEA=Diisopropylethylamine
DMAP=4-(dimethylamino)-pyridine
DMF=N,N-dimethylformamide
EDCI=1-(3-Dimethylaminopropyl)-3-ethylcarbodiimide hydrochloride
DCM=Dichloromethane
ESIMS=electron spray mass spectrometry
$Et_3N$=triethylamine
EtOAc=ethyl acetate
EtOH=Ethyl Alcohol
Fmoc=N-(9-fluorenylmethoxycarbonyl-
HCl=Hydrochloric acid
$H_2SO_4$=Sulfuric acid
HOBt=1-Hydroxybenzotriazole
MeOH=Methyl Alcohol
$MgSO_4$=magnesium sulfate
$NaHCO_3$=sodium bicarbonate
NaOH=Sodium Hydroxide
$Na_2SO_4$=Sodium Sulfate
Ph=phenyl
r.t.=room temperature
SPOS=solid phase organic synthesis
THF=tetrahydrofuran
TLC=thin layer chromatography
Alkyl Group Abbreviations
Me=methyl
Et=ethyl
n-Pr=normal propyl
i-Pr=isopropyl
n-Bu=normal butyl
i-Bu=isobutyl
t-Bu=tertiary butyl
s-Bu=secondary butyl
n-Pen=normal pentyl
i-Pen=isopentyl
n-Hex=normal hexyl
i-Hex=isohexyl
Polymer Supported Reagent Abbreviations
PS-Trisamine=Tris-(2-aminoethyl)amine polystyrene
PS-Chloroacetyl=
PS-NCO=methylisocyanate polystyrene
PS-benzadehyde=
PS-TsNHNH$_2$=toluensulfonylhydrazone polystyrene The following example schemes are provided for the guidance of the reader, and represent preferred methods for making the compounds exemplified herein. These methods are not limiting, and it will be apparent that other routes may be employed to prepare these compounds. Such methods specifically include solid phase based chemistries, including combinatorial chemistry. The skilled artisan is thoroughly equipped to prepare the necessary and/or claimed compounds by those methods given the literature and this disclosure.

Scheme 1a

As shown in Scheme 1a, amide derivatives (I) are prepared from the coupling of acid derivatives (II) with amines (III) in the presence of a coupling reagent such as 1-ethyl-3-(3-dimethylaminopropyl)-carbodiimide hydrochloride and a base. In Method A, a polymer supported (PS) carbodiimide is used. Method B uses a non-polymer supported carbodiimide.

Scheme 1b - Alternative Method for Preparing Amides

X = halide

As shown in Scheme 1b, amide derivatives (I) are alternatively prepared from the coupling of acid halides, esters, or anhydrides (IV) with amines (III) in the presence of a base.

Scheme 1c—Synthesis of Amides Via Combinatorial Arrays

The following procedure was used and can be used to synthesize amides in combinatorial array.

Use acetonitrile as system solvent.
Weigh amines into 8 mL vials.
Using Tecan, dissolve amines to 100 mM in DCM/CH$_3$CN (1:2, from trough).
Weigh acid into 8 mL vials.
Using Tecan, dissolve acids to 110 mM in DCM/CH$_3$CN (1:2, from trough).
Preload 1.2 mL Greiner plate with 30 mg PS-carbodiimide resin using Peli 1400 Case Titer plate II. Use acetonitrile as the system solvent for synthesis.
Add 200 mL (20 mmol, 1 equiv.) of amine to each well of the synthesis plates.
Add 200 mL (22 mmol, 1.1 equiv.) of acid to each well of the synthesis plates.
Add 110 mL (22 mmol, 1.1 equiv.) of HOBt (0.20 M in DMF) to each well of the synthesis plates by 8-channel pipette.
Seal plates with cap mat and shake (normal speed) at room temperature overnight.
Load 20 mg/well PS-Trisamine resin into the synthesis plates using Titer plate loader thin-I. Adjust resin amount based on its loading.
Add 200 mL of DCM/CH$_3$CN to plate.
Foil seal plates and shake (fast speed) at room temperature overnight.
Use methanol as system solvent for transfer to storage plate.
Transfer 150 mL to the storage plate then wash 2 times with 150 mL of methanol '(shake slowly for 5 min.). Perform transfers from Top in each well. (Needle height –2)
Dry plates in Genevac.
Make up analytical plates (2.5 mM theoretical) and submit for analysis.
Dilution plates made up based on analytical results.

Scheme 1c. Preparation of Oxalamides

As a general procedure, one amine is allowed to react with ethyl oxalyl chloride in the presence of tertiary amine in organic solvent, such as dioxane, acetonitrile, tetrahydrofuran, tetrahydropyran, and dimethylformamide, at room temperature for 0.5-2 hours. Then the second amine is added and the suspension is heated at 80° C. using oil bath overnight or at 160° C. in a microwave reactor for 5 minutes. The reaction mixture can be subject to preparative HPLC, or an aqueous work-up and the crude product can typically be readily purified by recrystallization, flash column chromatography, or other methods well known to those of ordinary skill in the art to afford the pure oxalamide. Yields reported below were not optimized.

Scheme 1d. Preparation of Ureas

Scheme 2

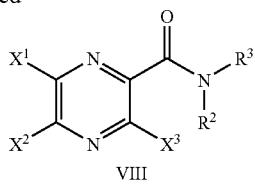

VIII $X^1$, $X^2$ and $X^3$ are each independently alkyl or alkoxy

Scheme 2 describes a method for preparation of pyrazines derivatives (VIII). For instance, reaction of substituted or unsubstituted 2,3-diaminopropionic acids (V) with 2,3-diones (VI) under heating conditions in the presence of base yields, after acidification, the substituted pyrazine-2-carboxylic acid (VII). The acid is condensed with various amines (III) to produce the desired amide (XIII) using the conditions shown in Scheme 1a.

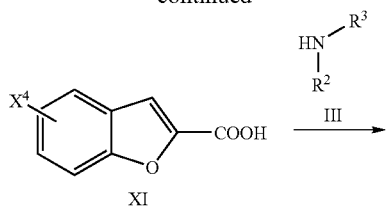

$X^4$ is alkyl, halide, alkoxy or thioalkyl.

Scheme 3 describes a method for preparation of benzofuran derivatives (XII). For instance, reaction of 2-hydroxybenzaldehydes (IX) with 2-bromo-malonic acid diethyl ester (X) under heating conditions in the presence of base yields substituted benzofuran-2-carboxylic acid (XI). The acid is condensed with various amines (III) to produce the desired amide (XII) using the conditions shown in Scheme 1a.

Scheme 3

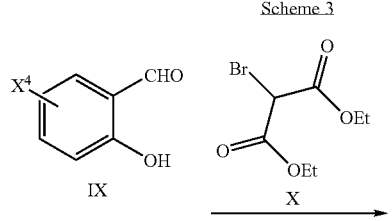

Scheme 4

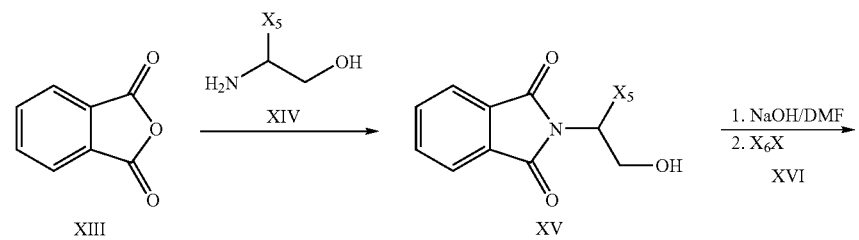

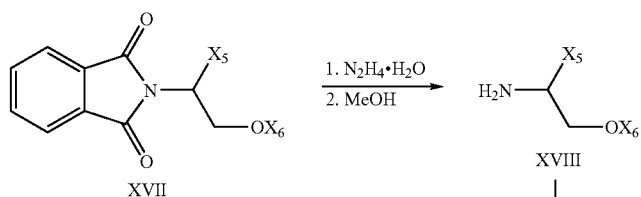

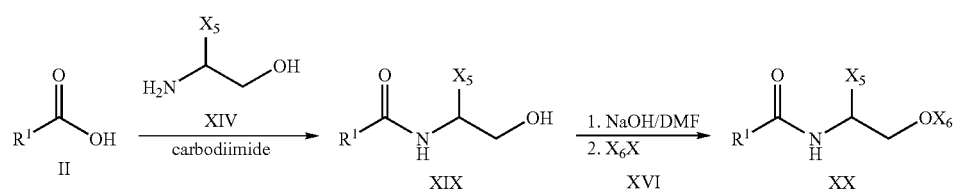

$X_5$ is H, alkyl, aryl, aryl-alkyl, heteroaryl-alkyl
$X_6$ is alkyl, alkoxyalkyl, arylalkyl, heteroarylalkyl
X is halide.

Scheme 4 describes methods of preparation of an alkoxyalkyl amide (XX). In one method phthalic anhydride (XIII) is heated with amino alcohol (XIV) to give the alcohol (XV) which is then reacted with alkyl halide (XVI) in presence of a base to produce the alkoxy (XVII). Treatment of the phtalimide (XVII) with hydrazine produce the desired amine (XVIII) that is further condensed with the acid (II) as described in scheme 1a to provide the alkoxyalkylamide (XX). Alternatively acid (II) is condensed with the amino alcohol (XIV) using the method describe in scheme 1a to provide the alcohol (XIX) that is further alkylated to give (XX).

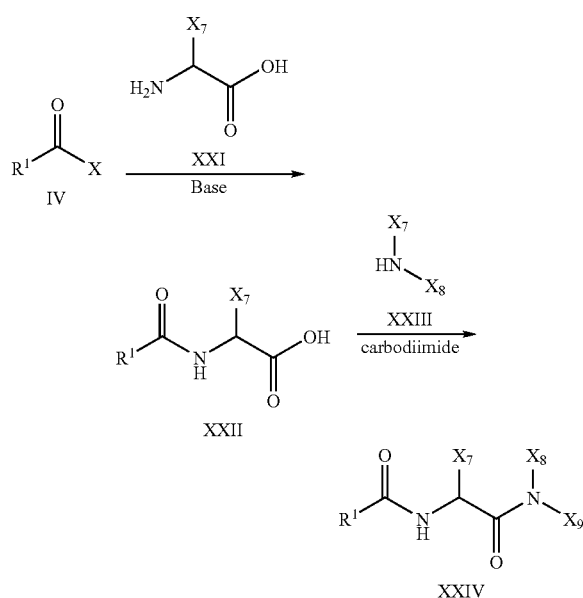

X is halide
$X_7$ is H, alkyl, alkoxyalkyl, aryl, aryl-alkyl, heteroaryl-alkyl
$X_8$ and $X_9$ are each independently H, alkyl, alkoxyalkyl, arylalkyl and heteroarylalkyl.

Scheme 5 describes a methods for the preparation of amido-amide (XXIV). Alkyl halide (IV) is treated with amino acid (XXI) as described in scheme 1b to give the corresponding acid (XXII) that is further condensed with amine (XXIII) as described in scheme 1a to provide the amido amide derivative (XXIV).

Scheme 6 describes a methods for the preparation of benzooxazole (XXVIII). Amino phenol (XXV) can be condensed with a variety of reagents to form the benzoxazole (XXVI) having a wide variety of substituent $X_9$ using a method described in the literature (see e.g., *J. Med. Chem.* 28 (1985) 1255) and/or by the method cited in Examples 39 to 47. The benzooxazole intermediate (XXVI) is then condensed with amine (V) using the method described in scheme 1a to give the amide (XXVII). Alternatively the amide (XXVII) is prepared by first condensing the amino phenol (XXV) with the amine (V) to give the aminophenol intermediate (XXVIII) that is further converted to the benzoxazole (XXVII) using the various method described above.

Measuring the Biological Activity of the Compounds of The Invention

Cell based technologies and assays, such as those disclosed in WO 02/064631, and WO 03/001876, and U.S. Patent Publication US 2003-0232407 A1 were used both to initially screen a wide variety of classes of compounds for agonist or antagonist activity for T1R1/T1R3 "savory" taste receptors, or T1R2/T1R3 "sweet" taste receptors that had been expressed in appropriate cell lines. Once initial "hits" were obtained for amide compounds in such cell lines, the same assays and also certain cell and/or receptor-based assays were used as analytical tools to measure the ability of the compounds of Formula (I) to enhance the savory taste of MSG or the sweet taste of known sweeteners such as sucrose, fructose, and were used to provide empirical data to guide an interactive process of synthesizing and testing structural variants of the amide compounds, in combination with occasional human taste testing of high interest compounds, so as to design, test, and identify species and genuses of compounds with increased and optimized levels of desirable biological activities.

Many embodiments of the inventions relate to the identification of specific compounds and classes of the amide compounds of Formula (I) that modulate (increase or decrease) the activity of the T1R1/T1R3 (preferably hT1R1/hT1R3) savory taste receptor (umami receptor), alone or in combination with another compound that activates hT1R1/hT1R3, e.g., MSG. Particularly, in many embodiments the invention relate to the amides of Formula (I) that modulate the activity of hT1R1/hT1R3 (human umami receptor) in vitro and/or in vivo. In another aspect, the invention relates to compounds that modulate the human perception of savory (umami) taste,

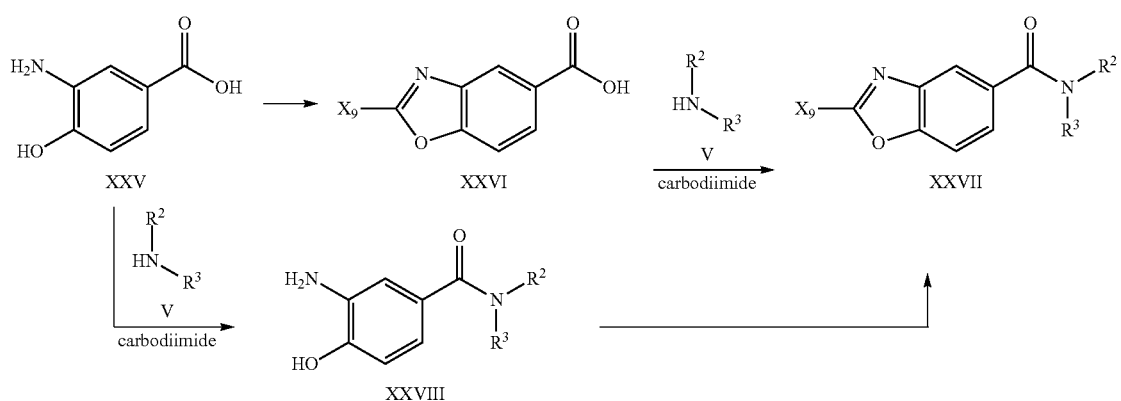

alone or in combination with another compound or flavorant, when added to a comestible or medicinal product or composition.

Many embodiments of the inventions relate to the identification of classes and/or species of the amide compounds of Formula (I) that modulate (increase or decrease) the activity of the T1R2/T1R3 (preferably hT1R2/hT1R3) sweet taste receptor (alone or in combination with another compound that activates hT1R2/hT1R3, or otherwise induces a sweet taste, e.g., sucrose, glucose, fructose, and the like. Particularly, the invention relates to the amides of Formula (I) that modulate the activity of hT1R2/hT1R3 (human sweet receptor) in vitro and/or in vivo. In another aspect, the invention relates to compounds that modulate the human perception of sweet taste, alone or in combination with another compound or flavorant composition, when added to a comestible or medicinal product or composition.

In some embodiments of the invention, it has been very unexpectedly discovered that at least some of the amide compounds of Formula (I) can modulate the human perception of both umami and sweet taste, alone or in combination with another compound or flavorant composition, when added to a comestible or medicinal product or composition.

In Vitro hT1R1/hT1R3 Umami Taste Receptor Activation Assay

In order to identify new savory flavoring agents and enhancers, including compounds with savory agonist and enhancer activities (dual activity), the compounds of Formula (I) were screened in primary assays and secondary assays including compound dose response and enhancement assay. In a primary assay for potential ability to modulate umami taste, amide compounds of Formula (I) that can be either savory flavoring agents in their own right or flavor enhancers of MSG are identified and scores of their activities are given as percentage of the maximum MSG intensity (%). In compound dose response, an $EC_{50}$ is calculated to reflect the potency of the compound as a savory agonist or enhancer.

An HEK293 cell line derivative (See e.g., Chandrashekar, et al., Cell (2000) 100: 703-711) which stably expresses Gα15 and hT1R1/hT1R3 under an inducible promoter (see WO 03/001876 A2) was used to identify compounds with savory tasting properties.

Compounds covered in this document were initially selected based on their activity on the hT1R1/hT1R3-HEK293-Gα15 cell line. Activity was determined using an automated fluorometric imaging assay on a FLIPR instrument (Fluorometric Intensity Plate Reader, Molecular Devices, Sunnyvale, Calif.) (designated FLIPR assay). Cells from one clone (designated clone I-17) were seeded into 384-well plates (at approximately 48,000 cells per well) in a medium containing Dulbecco's modified Eagle's medium (DMEM) supplemented with GlutaMAX (Invitrogen, Carlsbad, Calif.), 10% dialyzed fetal bovine serum (Invitrogen, Carlsbad, Calif.), 100 Units/ml Penicillin G, 100 µg/ml Streptomycin (Invitrogen, Carlsbad, Calif.) and 60 µM mifepristone (to induce expression of hT1R1/hT1R3, (see WO 03/001876 A2). I-17 cells were grown for 48 hours at 37° C. I-17 cells were then loaded with the calcium dye Fluo-3AM (Molecular Probes, Eugene, Oreg.), 4 µM in a phosphate buffered saline (D-PBS) (Invitrogen, Carlsbad, Calif.), for 1.5 hours at room temperature. After replacement with 25 µl D-PBS, stimulation was performed in the FLIPR instrument and at room temperature by the addition of 25 µL D-PBS supplemented with different stimuli at concentrations corresponding to twice the desired final level. Receptor activity was quantified by determining the maximal fluorescence increases (using a 480 nm excitation and 535 nm emission) after normalization to basal fluorescence intensity measured before stimulation.

For dose-responses analysis, stimuli were presented in duplicates at 10 different concentrations ranging from 1.5 nM to 30 µM. Activities were normalized to the response obtained with 60 mM monosodium glutamate, a concentration that elicits maximum receptor response. $EC_{50}$s (concentration of compound that causes 50% activation of receptor) were determined using a non-linear regression algorithm, where the Hill slope, bottom asymptotes and top asymptotes were allow to vary. Identical results were obtained when analyzing the dose-response data using commercially available software for non-linear regression analysis such as GraphPad PRISM (San Diego, Calif.).

In order to determine the dependency of hT1R1/hT1R3 for the cell response to different stimuli, selected compounds were subjected to a similar analysis on I-17 cells that had not been induced for receptor expression with mifepristone (designated as un-induced I-17 cells). The un-induced I-17 cells do not show any functional response in the FLIPR assay to monosodium glutamate or other savory-tasting substances. Compounds were presented to un-induced umami cells at 10 µM—or three times the maximum stimulation used in the dose-response analysis. Compounds covered in this document do not show any functional response when using un-induced umami cells in the FLIPR assay.

In some aspects of the present invention, an $EC_{50}$ of lower than about 10 mM is indicative of compounds that induce T1R1/T1R3 activity and is considered a savory agonist. Preferably a savory agonist will have $EC_{50}$ values of less than about 1 mM; and more preferably will have $EC_{50}$ values of less than about 20 µM, 15 µM, 10 µM, 5 µM, 3 µM, 2 µM, 1 µM, 0.8 µM or 0.5 µM.

In umami taste enhancement activity assay experiments, which produce an "$EC_{50}$ ratio" measurement of how effectively the amide compounds of the invention enhance the savory flavorant (typically MSG) already in a test solution. A series of measurements of the dose response is run in solutions comprising MSG alone, then a second dose response is run with MSG in combination with predetermined amounts of a candidate compound of Formula (I) at the same time.

In this assay, increasing concentrations of monosodium glutamate (ranging from 12 µM to 81 mM) were presented, in duplicates, in the presence or absence of a fixed concentration of the test compound. Typical compound concentrations tested were 30 µM, 10 µM, 3 µM, 1 µM, 0.3 µM, 0.1 µM and 0.03 µM. The relative efficacy of compounds of Formula (I) at enhancing the receptor was determined by calculating the magnitude of a shift in the $EC_{50}$ for monosodium glutamate. Enhancement was defined as a ratio ($EC_{50}R$) corresponding to the $EC_{50}$ of monosodium glutamate, determined in the absence of the test compound, divided by the $EC_{50}$ of monosodium glutamate, determined in the presence of the test compound. Compounds exhibiting $EC_{50}R>2.0$ were considered enhancers.

Stated alternatively, "$EC_{50}$ ratio" as compared to MSG is calculated based on the following definitions:

$EC_{50}$ Ratio vs. MSG=$EC_{50}$ (MSG)/$EC_{50}$(MSG+[Compound])

wherein "[compound]" refers to the concentration of the compound of Formula (I) used to elicit (or enhance or potentiate) the MSG dose response.

It should be noted that the $EC_{50}$ ratio measured can depend somewhat on the concentration of the compound itself. Preferred savory enhancers would have a high $EC_{50}$ Ratio vs.

MSG at a low concentration of the compound used. Preferably the $EC_{50}$ ratio experiments to measure umami enhancement are run at a concentration of a compound of Formula (I) between about 10 μM to about 0.1 μM, or preferably at 1.0 μM or 3.0 μM.

An $EC_{50}$ ratio of greater than 1 is indicative of a compound that modulates (potentiates) hT1R1/hT1R3 activity and is a savory enhancer. More preferably, the savory taste enhancer compounds of Formula (I) will have $EC_{50}$ ratio values of at least 1.2, 1.5, 2.0, 3.0, 4.0, 5.0, 8.0, or 10.0, or even higher.

In one aspect, the extent of savory modulation of a particular compound is assessed based on its effect on MSG activation of T1R1/T1R3 in vitro. It is anticipated that similar assays can be designed using other compounds known to activate the T1R1/T1R3 receptor.

Specific compounds and generic classes of compounds that been shown to modulate hT1R1/hT1R3 based on their $EC_{50}$ ratios evaluated according to the above formula are identified in the detailed description of the invention, the examples, and the claims.

The procedures used for human taste testing of the umami/savory compounds of Formula (I) are reported hereinbelow. Comparable $EC_{50}$ assays for activity of the compounds of Formula (I) for sweet receptor agonism and/or sweet taste perception in humans are also reported hereinbelow.

In Vitro hT1R2/hT1R3 Sweet Taste Receptor Activation Assay:

An HEK293 cell line derivative (Chandrashekar, J., Mueller, K. L., Hoon, M. A., Adler, E., Feng, L., Guo, W., Zuker, C. S., Ryba, N. J., *Cell* 2000, 100, 703-711.) that stably expresses Gα15 and hT1R2/hT1R3 (Li, X., Staszewski, L., Xu, H., Durick, K., Zoller, M., Adler, E. *Proc Natl Acad Sci USA* 2002, 99, 4692-4696.) see also World Patent # WO 03/001876 A2) was used to identify compounds with sweet taste enhancing properties.

Compounds covered in this document were initially selected based on their activity on the hT1R2/hT1R3-HEK293-Gα15 cell line (Li, et al. vide supra). Activity was determined using an automated fluorometric imaging assay on a FLIPR instrument (Fluorometric Intensity Plate Reader, Molecular Devices, Sunnyvale, Calif.) (designated FLIPR assay). Cells from one clone (designated S-9 cells) were seeded into 384-well plates (at approximately 50,000 cells per well) in a medium containing DMEM Low Glucose (Invitrogen, Carlsbad, Calif.), 10% dialyzed fetal bovine serum (Invitrogen, Carlsbad, Calif.), 100 Units/ml Penicillin G, and 100 μg/ml Streptomycin (Invitrogen, Carlsbad, Calif.) (Li, et al. vide supra) see also World Patent #WO 03/001876 A2). S-9 cells were grown for 24 hours at 37° C. S-9 cells were then loaded with the calcium dye Fluo-3AM (Molecular Probes, Eugene, Oreg.), 4 μM in a phosphate buffered saline (D-PBS) (Invitrogen, Carlsbad, Calif.), for 1 hour at room temperature. After replacement with 25 μl D-PBS, stimulation was performed in the FLIPR instrument and at room temperature by the addition of 25 μl D-PBS supplemented with different stimuli at concentrations corresponding to twice the desired final level. Receptor activity was quantified by determining the maximal fluorescence increases (using a 480 nm excitation and 535 nm emission) after normalization to basal fluorescence intensity measured before stimulation.

For dose-responses analysis, stimuli were presented in duplicates at 10 different concentrations ranging from 60 nM to 30 μM. Activities were normalized to the response obtained with 400 mM D-fructose, a concentration that elicits maximum receptor response. EC50s were determined using a non-linear regression algorithm (using a Senomyx, Inc. software), where the Hill slope, bottom asymptotes and top asymptotes were allow to vary. Identical results were obtained when analyzing the dose-response data using commercially available software for non-linear regression analysis such as GraphPad PRISM (San Diego, Calif.).

In order to determine the dependency of hT1R2/hT1R3 for the cell response to different stimuli, selected compounds were subjected to a similar analysis on HEK293-Gα15 cells (not expressing the human sweet receptor). The HEK293-Gα15 cells do not show any functional response in the FLIPR assay to D-Fructose or any other known sweeteners. Similarly, compounds covered in this document do not induce any functional response when using HEK293-Gα15 cells in the FLIPR assay.

EXAMPLES

The following examples are given to illustrate a variety of exemplary embodiments of the invention and are not intended to be limiting in any manner.

For the purpose of this document, the compounds individually disclosed in the following Examples 1-174 and corresponding Tables A-E can be referred in shorthand by the number of the example. For example, as shown immediately bellow, Example 1 discloses a synthesis of a particular compound (N-(heptan-4-yl)benzo[d][1,3]dioxole-5-carboxamide), and the results of experimental assays of its biological effectiveness, which compound is and can be referred to herein in shorthand form as Compound 1. Similarly, the first compound illustrated in Table A can be referred to elsewhere herein as Compound A1.

Example 1

N-(heptan-4-yl)benzo[d][1,3]dioxole-5-carboxamide

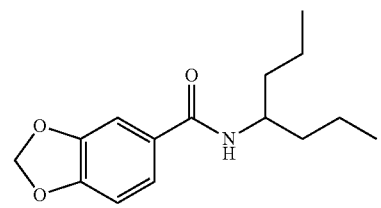

To a solution of heptan-4-amine (8.06 mL, 54 mmol) in triethylamine (15.3 mL, 108 mmol) and dichloromethane (135 mL), was added, dropwise at 0° C., a solution of benzo [1,3]dioxole-5-carbonyl chloride (10 g, 54 mmol) dissolved in dichloromethane (135 mL). The reaction mixture was stirred for 1 h. Solvent was removed under reduced pressure and the residue was dissolved in EtOAc. The organic layer was washed successively with 1 N aq. HCl, 1 N aq. NaOH, water, brine, dried (MgSO$_4$) and concentrated. The residue was recrystallized in EtOAc and Hexanes to afford 6.9 g of N-(heptan-4-yl)benzo[d][1,3]dioxole-5-carboxamide (48.3%) as a white solid. $^1$H NMR (500 MHz, CDCl$_3$): δ 0.92 (t, 6H), 1.38 (m, 6H), 1.53 (m, 2H), 4.11 (m, 1H), 5.63 (m, 1H), 6.01 (s, 2H), 7.98 (d, 1H), 7.27 (s, d, 2H). MS (M+H, 264).

The compound had $EC_{50}$ for activation of a hT1R1/hT1R3 umami receptor expressed in an HEK293 cell line of 0.2 μM, and when present at 0.03 μM enhanced the effectiveness of monosodium glutamate with an $EC_{50}$ ratio of 6.92.

Example 2

N-(2-methylheptan-4-yl)benzo[d][1,3]-dioxole-5-carboxamide

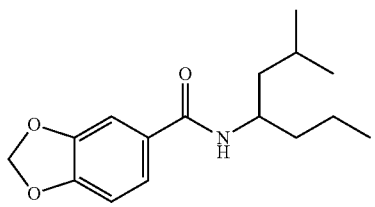

Prepared in a similar manner to example 1 using benzo[d][1,3]dioxole-5-carbonyl chloride and 2-methylheptan-4-amine (example 2a). $^1$H NMR (500 MHz, $CDCl_3$): δ 0.93 (m, 9H); 1.38 (m, 5H); 1.53 (m, 1H); 1.66 (m, 1H); 4.21 (m, 1H); 5.61 (d, 1H); 6.01 (s, 2H); 6.82 (d, 1H); 7.26 (m, 2H). MS (278, M+H)

a. Preparation of 2-methylheptan-4-amine:

To a solution of 2-methylheptan-4-one (4.24 g, 33.07 mmol), in methanol (60 mL), were added ammonium acetate (25.50 g, 330.71 mmol) and sodium cyanoborohydride (2.08 g, 33.07 mmol). The reaction mixture was stirred at room temperature for about 24 hours. The solvent was removed under reduced pressure and the residue was diluted with water and basified with 15% NaOH aqueous and extracted with ether. The extract was washed with brine, dried over anhydrous magnesium sulfate, filtered and evaporated to give 3.3 g of 2-methylheptan-4-amine (77%). MS (M+H, 130).

The compound had $EC_{50}$ for activation of a hT1R1/hT1R3 umami receptor expressed in an HEK293 cell line of 0.22 μM.

Example 3

N-(2-methylhexan-3-yl)benzo[d][1,3]dioxole-5-carboxamide

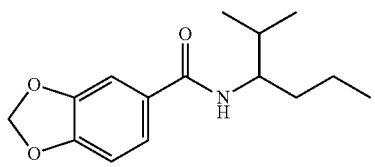

Prepared in a similar manner to example 1 using benzo[d][1,3]dioxole-5-carbonyl chloride and 2-methylhexan-3-amine (example 3a). $^1$H NMR (500 MHz, $CDCl_3$): δ 0.93 (m, 9H); 1.37 (m, 3H); 1.56 (m, 1H); 1.83 (m, 1H); 4.01 (m, 1H); 5.67 (d, 1H); 6.02 (s, 2H); 6.82 (d, 1H); 7.28 (m, 2H). MS (M+H, 264).

a. 2-methylhexan-3-amine was prepared using the same procedure described in example 2a starting from 2-methylhexan-3-one. Yield: 40%. $^1$H NMR (500 MHz, $CDCl_3$): δ 0.86 (d, 3H); 0.91 (m, 6H); 1.20-1.29 (m, 2H); 1.38-1.47 (m, 2H); 1.47 (s, 2H); 1.58 (m, 1H); 2.51 (m, 1H). MS (M+H, 116).

The compound had $EC_{50}$ for activation of a hT1R1/hT1R3 umami receptor expressed in an HEK293 cell line of 0.61 μM.

Example 4

N-(2,3-dimethylcyclohexyl)benzo[d][1,3]dioxole-5-carboxamide

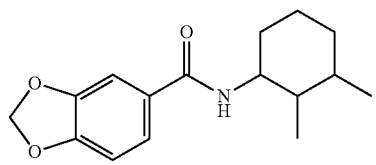

2,3-dimethylcyclohexanamine (20 μmol) and benzo[d][1,3]dioxole-5-carboxylic acid (1.1 eq) were each dissolved in acetonitrile/dichloromethane (200 μL, 2:1). PS-Carbodiimide resin (2 eq) was loaded into a 1.2 mL 96 well Greiner plate, followed by the addition of amine and acid solutions. Hydroxybenzotriazole (1.1 eq) was dissolved in DMF (100 mL) and was added into the reaction well. The reaction was shaken overnight at room temperature. Once the reaction was completed, PS-Trisamine resin (1.5 eq) was added into the reaction mixture and the solution was allowed to shake overnight at room temperature. Acetonitrile (200 mL) was added into the reaction well, and the top clear solution was transferred into a new plate. The solution was evaporated to give N-(2,3-dimethylcyclohexyl)benzo[d][1,3]dioxole-5-carboxamide. MS (M+H, 276.20).

The compound had $EC_{50}$ for activation of a hT1R1/hT1R3 umami receptor expressed in an HEK293 cell line of 0.45 μM, and when present at 1 μM enhanced the effectiveness of monosodium glutamate with an $EC_{50}$ ratio of 8.4.

Example 5

N-(5-methylhexan-3-yl)benzo[d][1,3]dioxole-5-carboxamide

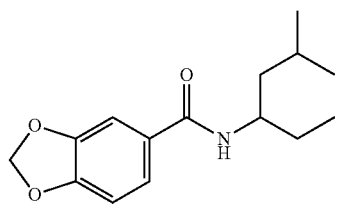

Prepared in a similar manner to example 1 using benzo[d][1,3]dioxole-5-carbonyl chloride and 5-methylhexan-3-amine (example 5a). Yield: 48%. $^1$H NMR (500 MHz, $CDCl_3$): δ 0.94 (m, 9H); 1.37 (t, 3H); 1.45 (m, 1H); 1.64 (m, 2H); 4.13 (m, 1H); 5.61 (d, 1H); 6.01 (s, 2H); 6.82 (d, 1H); 7.27 (m, 2H). MS (M+H, 264).

a. 2-methylhexan-3-amine was prepared using the same procedure described in example 2a starting from 5-methylhexan-3-one. Yield: 54%. MS (M+H, 116).

The compound had $EC_{50}$ for activation of a hT1R1/hT1R3 umami receptor expressed in an HEK293 cell line of 0.57 μM.

Example 6

(R)-methyl 2-(benzo[d][1,3]dioxole-6-carboxamido)-4-methylpentanoate

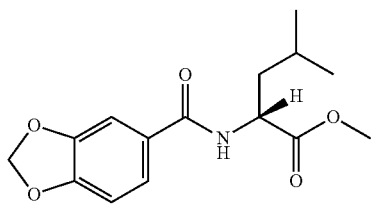

Prepared in a similar manner to example 1 using benzo[d][1,3]dioxole-5-carbonyl chloride and D-leucine methyl ester hydrochloride. Yield: 83%. $^1$H NMR (500 MHz, CDCl$_3$): δ 0.98 (m, 6H); 1.63-1.67 (m, 1H); 1.71-1.76 (m, 2H); 3.76 (s, 3H); 4.83 (m, 1H); 6.03 (s, 2H); 6.38 (d, 1H); 6.83 (d, 1H); 7.32 (s, 1H); 7.33 (d, 1H). MS (M+H, 294). m.p: 89-90° C.

The compound had EC$_{50}$ for activation of a hT1R1/hT1R3 umami receptor expressed in an HEK293 cell line of 0.34 μM, and when present at 0.1 μM enhanced the effectiveness of monosodium glutamate with an EC$_{50}$ ratio of 4.9.

Example 7

N-(1,2,3,4-tetrahydronaphthalen-1-yl)benzo[d][1,3]dioxole-5-carboxamide

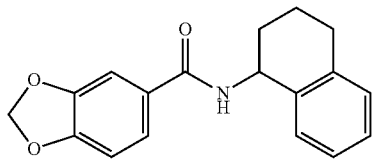

Prepared in a similar manner to example 4 using benzo[d][1,3]dioxole-5-carboxylic acid and 1,2,3,4-tetrahydronaphthalen-1-amine. MS (M+H, 296.6).

The compound had EC$_{50}$ for activation of a hT1R1/hT1R3 umami receptor expressed in an HEK293 cell line of 0.71 μM, and when present at 0.3 μM enhanced the effectiveness of monosodium glutamate with an EC$_{50}$ ratio of 7.8.

Example 8

(R)—N-(1-hydroxy-4-methylpentan-2-yl)benzo[d][1,3]dioxole-5-carboxamide

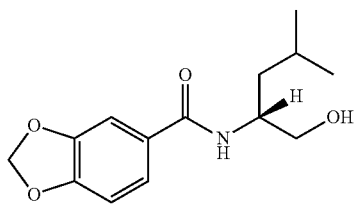

Prepared in a similar manner to example 4 using benzo[d][1,3]dioxole-5-carboxylic acid and (R)-aminoleucinol. MS (M+H, 266.1)

The compound had an EC$_{50}$ for activation of a hT1R1/hT1R3 umami receptor expressed in an HEK293 cell line of 9 μM, and when present at 3 μM enhanced the effectiveness of monosodium glutamate with an EC$_{50}$ ratio of 2.

Example 9

(R)—N-(1-methoxy-4-methylpentan-2-yl)benzo[d][1,3]dioxole-5-benzo[d][1,3]dioxole-5-carboxylic Acid

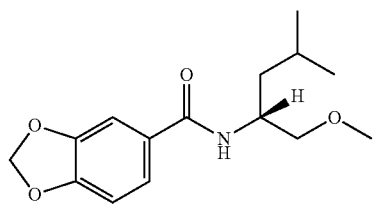

Prepared in a similar manner to example 4 using (R)-1-methoxy-4-methyl and pentan-2-amine (example 9a). Yield: 55%. $^1$H NMR (500 MHz, CDCl$_3$): δ 0.95 (m, 6H); 1.43 (m, 1H); 1.55 (m, 1H); 1.65 (m, 1H); 3.36 (s, 3H); 3.46 (m, 2H); 4.33 (m, 1H); 6.01 (s, 2H); 6.13 (d, 1H); 6.82 (d, 1H); 7.28 (m, 2H). MS (M+H, 280).

a. (R)-1-methoxy-4-methylpentan-2-amine

To a solution of (R)-2-(1-methoxy-4-methylpentan-2-yl)isoindoline-1,3-dione (example 9b) (3.87 g, 14.84 mmol) in methanol (30 mL), was added hydrazine hydrate (0.866 ml, 17.81 mmol) and the reaction mixture was warmed up to 45° C. for about 3 hours. The mixture was acidified with 2N HCl and stirred at 45° C. for 30 min. The solution was cooled to room temperature, filtered and evaporated. The residue was taken up with 2N NaOH and extracted with ether, dried over MgSO4, filtered and evaporated to give 1.51 g of (R)-1-methoxy-4-methylpentan-2-amine. Yield 77%. $^1$H NMR (500 MHz, CDCl$_3$): δ 0.91 (m, 6H); 1.17 (m, 2H); 1.58 (s, 2H); 1.71 (m, 1H); 3.02 (m, 1H); 3.10 (m, 1H); 3.32 (m, 1H); 3.35 (s, 3H).

b. (R)-2-(1-methoxy-4-methylpentan-2-yl)isoindoline-1,3-dione (R)-2-(1-hydroxy-4-methylpentan-2-yl)isoindoline-1,3-dione (example 9c) (5.88 g, 23.87 mmol) was dissolved in dry THF (25 mL) and hexamethyl-phosphoramide (30 mL) and the solution cooled to 0° C. Sodium hydride (60% in mineral oil, 1.15 g, 28.65 mmol) was added and after 10 minutes iodomethane (7.43 ml, 119.35 mmol) was added dropwise and the solution was warmed up slowly to room temperature and stirred over night. The reaction mixture was poured into ice/water, extracted with EtOAC, washed with brine, dried over MgSO$_4$, filtered and evaporated. The residue was purified on silica gel (20% EtOAC in hexane) to give 3.92 g of (R)-2-(1-methoxy-4-methylpentan-2-yl)isoindoine-1,3-dione (63%).

c. (R)-2-(1-hydroxy-4-methylpentan-2-yl)isoindoline-1,3-dione

Phthalic anhydride (10.30 g, 69.55 mmol) and D-Leucinol (8.15 g, 69.55 mmol) were mixed in THF (100 mL), the reaction mixture was heated at 85° C. and refluxed for 18 hours. After cooling to room temperature, water was added and the solution was extracted with EtOAC, the extracts were washed with 1 N HCl, water, aq. NaHCO₃, water and brine, dried over MgSO₄, filtered and evaporated to give 8.1 g of (R)-2-(1-hydroxy-4-methylpentan-2-yl)isoindoline-1,3-dione (47%). ¹H NMR (500 MHz, CDCl₃): δ 0.94 (m, 6H); 1.54 (m, 2H); 1.99 (m, 1H); 3.86 (m, 1H); 4.04 (m, 1H); 4.47 (m, 1H); 7.72 (m, 2H); 7.83 (m, 2H).

The compound had an $EC_{50}$ for activation of a hT1R1/hT1R3 umami receptor expressed in an HEK293 cell line of 3.5 μM.

Example 10

(R)-methyl 2-(benzo[d][1,3]dioxole-6-carboxamido)-3-methylbutanoate

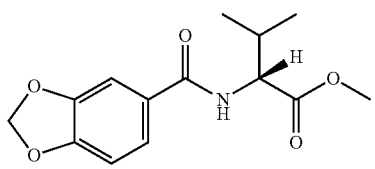

Prepared in a similar manner to example 4 using benzo[d][1,3]dioxole-5-carboxylic acid and (R)-methyl 2-amino-3-methylbutanoate. Yield: 50%. MS (M+H, 280.1).

The compound had an $EC_{50}$ for activation of a hT1R1/hT1R3 umami receptor expressed in an HEK293 cell line of 1.16 μM.

Example 11

2-(benzo[d][1,3]dioxole-6-carboxamido)-4-methylpentyl Dihydrogen Phosphate

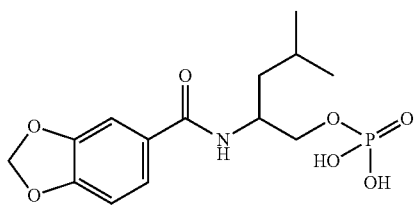

N-(1-hydroxy-4-methylpentan-2-yl)benzo[d][1,3]dioxole-5-carboxamide (example 11a) (0.57 mmol, 151 mg) was dissolved in anhydrous acetonitrile (2 ml) and 1 ml of 0.45 M solution of tetrazole in acetonitrile was added under nitrogen and stirred for 5 min. Then 0.627 (1.1 eq, 207 μl) of dibenzyl diisopropyl phosphoroamidite was added drop wise under nitrogen. The mixture was stirred for 1 h. The solvent was evaporated and a crude intermediate was dissolved in DCM and washed twice with 2% potassium carbonate and brine and dried with sodium sulphate. The material was dried down and oxidized with 5 ml of tert.butylhydroperoxide (4 M solution in nonane) for 30 min. The solvent was evaporated and the dibenzylester intermediate was purified (preparative TLC). The benzyl groups were hydrolyzed using trifluoroacetic acid (3 ml of a mixture of 95% TFA and 5% water, 1.5 h, rt). The final product was dried down providing 69 mg (35%) of pure material. ¹H NMR (500 MHz, CDCl₃): δ 0.88-0.90 (t, 6H), 1.23-1.27 (m, 2H), 1.36-1.37 (m, 1H), 1.53-1.62 (m, 2H), 3.93 (s, 1H), 3.98 (s, 1H), 4.32 (s, 1H), 5.90 (s, 2H), 6.66-6.67 (d, 1H), 6.98-6.99 (b, 2H), 7.14 (s, 2H); ³¹P: δ 0.51 (s). MS (M+H, 346.0).

a. N-(1-hydroxy-4-methylpentan-2-yl)benzo[d][1,3]dioxole-5-carboxamide was prepared in a similar manner to example 4 from piperonylic acid and 2-amino-4-methylpentan-1-ol.

The compound had an $EC_{50}$ for activation of a hT1R1/hT1R3 umami receptor expressed in an HEK293 cell line of 10.9 μM.

Example 12

N-(hexan-3-yl)-4-methoxy-3-methylbenzamide

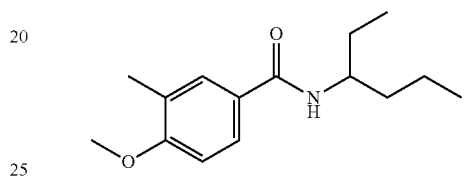

Prepared in a similar manner to example 4 using 4-methoxy-3-methylbenzoic acid and hexan-3-amine (example 28a). ¹H NMR (500 MHz, CDCl₃): δ 0.94 (m, 6H); 1.41 (m, 4H); 1.46 (m, 1H); 1.64 (m, 1H); 2.24 (s, 3H); 3.87 (s, 3H); 4.08 (m, 1H); 5.69 (d, 1H); 6.83 (d, 1H); 7.54 (s, 1H); 7.62 (d, 1H). MS (M+H, 250).

The compound had an $EC_{50}$ for activation of a hT1R1/hT1R3 umami receptor expressed in an HEK293 cell line of 0.12 μM.

Example 13

(R)—N-(1-(dimethylamino)-4-methyl-1-oxopentan-2-yl)benzo[d][1,3]dioxole-5-carboxamide

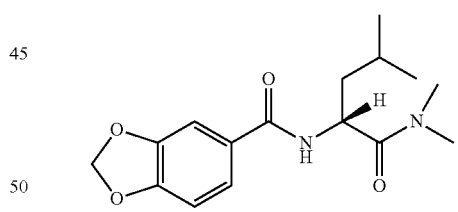

(R)-2-(benzo[d][1,3]dioxole-6-carboxamido)-4-methylpentanoic acid (example 13a) (52 mg, 0.19 mmol) in DMF (4 mL) and dimethyl amine (2M in Methanol, 36 μL, 2 eq) were condensed in presence of HOBt (26 mg, 1 eq) and of 1-ethyl-3-(3-dimethylaminopropyl)-carbodiimide hydrochloride (44 mg, 1.2 eq) at room temperature overnight. The reaction mixture was evaporated and the residue was dissolved in ethylacetate and washed successively with saturated NaHCO₃ and water, dried over MgSO₄ filtered and evaporated to give 48.6 mg of the product (84%). The material was further purified using RPHPLC. ¹H NMR (500 MHz, CDCl₃): δ 0.93-0.94 (d, 3H), 1.03-1.05 (d, 3H), 1.48-1.52 (m, 1H), 1.59-1.63 (m, 1H), 2.98 (s, 3H), 3.14 (s, 3H), 5.17-5.21 (m, 1H), 6.01 (s, 2H), 6.80-6.82 (d, 1H), 6.89-6.91 (d, 1H), 7.29-3.30 (d, 1H), 7.33-7.35 (dd, 1H). MS (M+H, 307.2).

a. (R)-2-(benzo[d][1,3]dioxole-6-carboxamido)-4-methylpentanoic Acid

Prepared in a similar manner to example 1 using benzo[d][1,3]dioxole-5-carbonyl chloride and D-Leucine. Yield: 55%. MS (M+H, 280.2).

The compound had an $EC_{50}$ for activation of a hT1R1/hT1R3 umami receptor expressed in an HEK293 cell line of 1.06 μM.

Example 14

2-(benzo[d][1,3]dioxole-6-carboxamido)pentyl Acetate

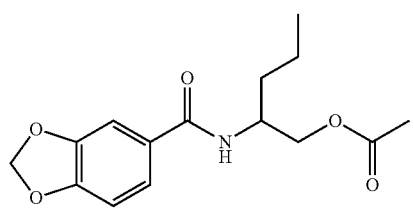

To a solution of N-(1-hydroxypentan-2-yl)benzo[d][1,3]dioxole-5-carboxamide (example 14a) (59.8 mg, 0.238 mmol) in dichloromethane (5 mL) was added triethylamine (166 mL, 1.19 mmol). Acetyl anhydride (112.5 mL, 1.19 mmol) was slowly added and the mixture was stirred under argon at ambient temperature overnight. The solution was washed successively with a saturated solution of sodium bicarbonate, water and brine. The organic layer was dried over anhydrous sodium sulfate. Filtration followed by solvent removal under reduced pressure afforded 50.8 mg of 2-(benzo[d][1,3]dioxole-6-carboxamido)pentyl acetate (73%). $^1$H NMR (CDCl$_3$): δ0.95 (t, 3H, J=7.2 Hz), 1.43 (m, 2H), 1.57 (m, 2H), 2.1 (s, 3H), 4.11 (dd, 1H, J=3.5 Hz, J=11.5 Hz), 4.27 (dd, 1H, J=3.5 Hz, J=11.4 Hz), 4.29 (m, 1H), 6.02 (s, 2H), 6.1 (m, 1H), 6.82 (d, 1H, J=8.4 Hz), 7.27 (m, 2H). MS (M+H, 294).

a. N-(1-hydroxypentan-2-yl)benzo[d][1,3]dioxole-5-carboxamide was prepared in a similar manner to example 4 using benzo[d][1,3]dioxole-5-carboxylic acid and 2-aminopentan-1-ol. Yield: 76%. MS (M+H, 252).

The compound had an $EC_{50}$ for activation of a hT1R1/hT1R3 umami receptor expressed in an HEK293 cell line of 11.9 μM, and when present at 3 μM enhanced the effectiveness of monosodium glutamate with an $EC_{50}$ ratio of 4.1.

Example 15

(R)—N-(4-methyl-1-oxo-1-(2-(pyridin-3-yl)ethylamino)pentan-2-yl)benzo[d][1,3]dioxole-5-carboxamide

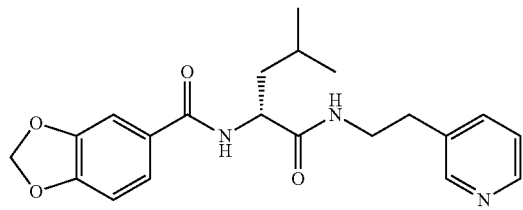

Prepared in a similar manner to example 13 using 2-(3-pyridyl)ethylamine and (R)-2-(benzo[d][1,3]dioxole-6-carboxamido)-4-methylpentanoic acid (example 13a). (MS M+384.2).

The compound had an $EC_{50}$ for activation of a hT1R1/hT1R3 umami receptor expressed in an HEK293 cell line of 1.7 μM.

Example 16

N—((R)-1-(2-(hydroxymethyl)pyrrolidin-1-yl)-4-methyl-1-oxopentan-2-yl)benzo[d][1,3]-dioxole-5-carboxamide

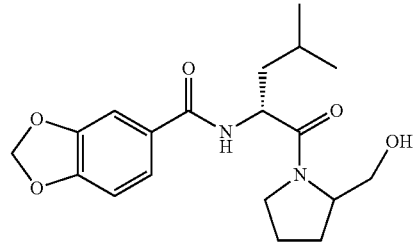

Prepared in a similar manner to example 13 using R/S propinol and (R)-2-(benzo[d][1,3]dioxole-6-carboxamido)-4-methylpentanoic acid (example 13a). (MS M+363.2).

The compound had an $EC_{50}$ for activation of a hT1R1/hT1R3 umami receptor expressed in an HEK293 cell line of 3 μM.

Example 17

N-(heptan-4-yl)-6-methylbenzo[d][1,3]dioxole-5-carboxamide

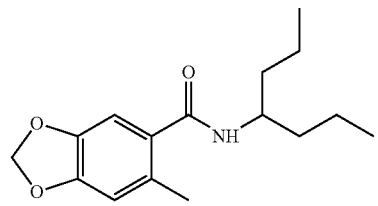

Prepared in a similar manner to example 4 using 6-methylbenzo[d][1,3]dioxole-5-carboxylic acid and heptan-4-amine. MS (M+H, 278.67).

The compound had an $EC_{50}$ for activation of a hT1R1/hT1R3 umami receptor expressed in an HEK293 cell line of 0.11 μM.

Example 18

N-(heptan-4-yl)-2-methylbenzo[d][1,3]dioxole-5-carboxamide

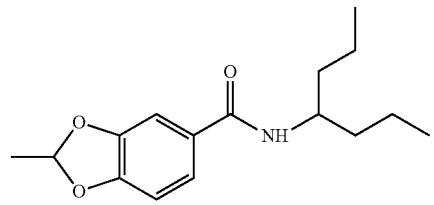

N-(heptan-4-yl)-3,4-dihydroxybenzamide (example 18a) (0.5 mmol) was dissolved in toluene (1.6 mL). P-Toluenesulfonic acid monohydrate (0.3 eq) was added to the reaction, followed by addition of acetaldehyde (2 eq). The reaction was performed using microwave (180 C, 300 W) and ran for 10 minutes. The solvent was evaporated. The residue was dissolved in methanol (1 mL) and purified by HPLC. Yield 20%, MS (M+H 278.10).

a. N-(heptan-4-yl)-3,4-dihydroxybenzamide was prepared in a similar manner to example 4 using 3,4-dihydroxybenzoic acid and heptan-4-amine. Yield: 25%. MS (M+H, 252.1).

The compound had an $EC_{50}$ for activation of a hT1R1/hT1R3 umami receptor expressed in an HEK293 cell line of 0.1 μM, and when present at 0.03 μM enhanced the effectiveness of monosodium glutamate with an $EC_{50}$ ratio of 3.68.

Example 19

Ethyl 2-(5-(heptan-4-ylcarbamoyl)benzo[d][1,3]dioxol-2-yl)acetate

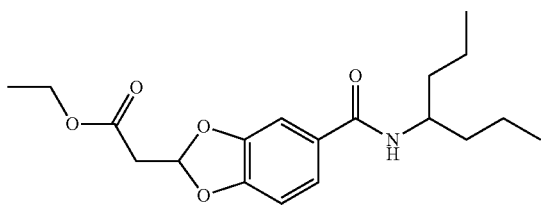

N-(heptan-4-yl)-3,4-dihydroxybenzamide (example 18a) (0.29 mmol, 75 mg) was dissolved in dry acetone with 6 eq excess (242 mg) of potassium carbonate then 1.2 eq excess (36 μl) of propynoic acid ethyl ester was added and a mixture was refluxed for 24 h. The solvent was evaporated and a solid was dissolved in dichloromethane and extracted with 10% $NaHCO_3$ and water. The crude product was purified by chromatography on silica gel to give 72 mg of desired product (71%). $^1$H NMR (500 MHz, $CDCl_3$): δ 0.91-0.94 (t, 6H), 1.23-1.30 (m, 4H), 1.37-1.41 (4H), 2.97-2.98 (d, 2H), 3.70-3.74 (dd, 2H), 4.12-4.17 (m, 1H), 4.2-4.24 (m, 3H), 5.61-5.64 (d, 1H), 6.58-6.60 (t, 1H), 6.79-6.81 (d, 1H), 7.23 (s, 1H), 7.60-7.85 (b, 1H). MS (M+H, 350.1).

The compound had an $EC_{50}$ for activation of a hT1R1/hT1R3 umami receptor expressed in an HEK293 cell line of 14 μM, and when present at 3 μM enhanced the effectiveness of monosodium glutamate with an $EC_{50}$ ratio of 2.5.

Example 20

N-(heptan-4-yl)-2,2-dimethylbenzo[d][1,3]dioxole-5-carboxamide

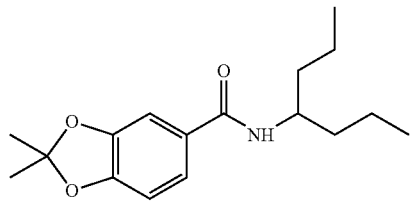

Prepared in a similar manner to example 4 using sodium 2,2-dimethylbenzo[d][1,3]dioxole-5-carboxylate and 4-heptylamine (example 20a). Yield 30%. $^1$H NMR: δ 0.92 (t, 6H, J=7.2 Hz), 1.42 (m, 6H), 1.53 (m, 2H), 1.68 (s, 6H), 4.12 (m, 1H), 5.61 (d, 1H, J=8.9 Hz), 6.72 (d, 1H, J=8 Hz), 7.16 (d, 1H, J=1.5 Hz), 7.22 (dd, 1H, J=1.5 Hz, J=17 Hz). MS (M+H, 292).

a. Sodium 2,2-dimethylbenzo[d][1,3]dioxole-5-carboxylate and 4-heptylamine

Ethyl 2,2-dimethylbenzo[d][1,3]dioxole-5-carboxylate (example 20b) (461 mg, 2.08 mmol) was stirred in dioxane (16 mL) and 1.0N aqueous NaOH (4.16 mL) for 20 hours at room temperature. The solvent was removed under reduced pressure to afford the desired product (449 mg). (M–H, 193).

b. Ethyl 2,2-dimethylbenzo[d][1,3]dioxole-5-carboxylate

Ethyl 3,4-dihydroxybenzoate (910.9 mg, 5 mmol) was combined with 2,2-dimethoxypropane (1.23 mL, 10 mmol) and a catalytic amount of p-toluene sulfonic acid in toluene. The mixture was heated to reflux using a Dean-Stark trap for 20 hours. After solvent removal under reduced pressure, the crude was dissolved in ethyl acetate and washed successively with a saturated aqueous solution of sodium bicarbonate, water, and brine. The organic layer was dried over anhydrous sodium sulfate. Purification by chromatography on silica gel using a gradient hexane:ethyl acetate, 90:10 to 75:25, afforded a white powder (539.1 mg, 49%). $^1$H NMR ($CDCl_3$): δ 1.36 (t, 3H, J=7.2 Hz), 1.69 (s, 6H), 4.32 (q, 2H, J=7.1 Hz, J=14.2 Hz), 6.74 (d, 1H, d, J=8.2 Hz), 7.38 (d, 1 h, J=1.7 Hz), 7.61 (dd, 1H, J=1.8 Hz, J=8.3 Hz).

The compound had an $EC_{50}$ for activation of a hT1R1/hT1R3 umami receptor expressed in an HEK293 cell line of 2.7 μM.

Example 21

N-(heptan-4-yl)-2-isopropylbenzo[d][1,3]dioxole-5-carboxamide

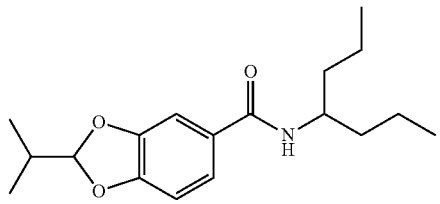

Prepared in a similar manner to example 4 using 2-isopropylbenzo[d][1,3]dioxole-5-carboxylic acid (example 21a) and 4-hepthylamine. Yield: 34%. $^1$H NMR ($CDCl_3$): δ 0.92 (t, 6H, J=7.2 Hz), 1.04 (d, 6H, J=6.9 Hz), 1.40 (m, 6H), 1.43 (m, 2H), 2.15 (m, 1H), 4.11 (m, 1H), 5.62 (d, 1H, J=8.9 Hz), 5.96 (d, 1H, J=4.4 Hz), 6.75 (d, 1H, J=8.0 Hz), 7.19 (d, 1H, J=1.8 Hz), 7.22 (d, 1H, J=1.9 Hz), 7.23 (d, 1H, J=1.6 Hz). MS (M+H, 291).

a. 2-isopropylbenzo[d][1,3]dioxole-5-carboxylic acid: 3,4-dihydrobenzoic acid (154.12 mg, 1 mmol) and isobutyraldehyde (182 μL, 2 mmoles) were combined in toluene (3 mL) and a catalytic amounts of p-toluene sulfonic acid was added. The mixture was subjected to the microwave for 10 minutes at 180° C. with a power set at 275. The solution was filtered and evaporated to afford 100 mg of the desired product (48%). MS (M–H, 207).

The compound had an $EC_{50}$ for activation of a hT1R1/hT1R3 umami receptor expressed in an HEK293 cell line of 11.5 μM, and when present at 3 μM enhanced the effectiveness of monosodium glutamate with an $EC_{50}$ ratio of 2.2.

Example 22

2,2-difluoro-N-(heptan-4-yl)benzo[d][1,3]dioxole-5-carboxamide

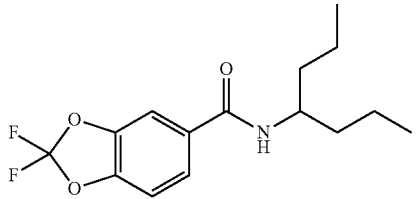

Prepared in a similar manner to example 4 using 2,2-difluorobenzo[d][1,3]dioxole-5-carboxylic acid and 4-hepthylamine. (M+H, 300.2).

The compound had an $EC_{50}$ for activation of a hT1R1/hT1R3 umami receptor expressed in an HEK293 cell line of 1.51 μM, and when present at 1 μM enhanced the effectiveness of monosodium glutamate with an $EC_{50}$ ratio of 2.87.

Example 23

2,3-Dihydro-benzo[1,4]dioxine-6-carboxylic Acid (1-propyl-butyl)-amide

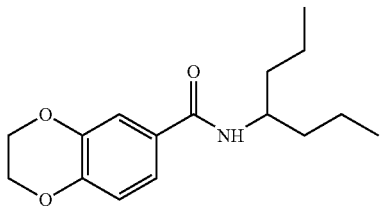

Prepared in a similar manner to example 4 using 2,3-Dihydro-benzo[1,4]dioxine-6-carboxylic acid and heptan-4-amine. MS (M+H, 278.2).

The compound had an $EC_{50}$ for activation of a hT1R1/hT1R3 umami receptor expressed in an HEK293 cell line of 0.49 μM.

Example 24

N-(heptan-4-yl)-3,4-dihydro-2H-benzo[b][1,4]dioxepine-7-carboxamide

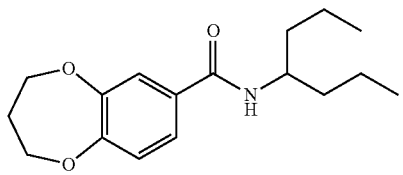

Prepared in a similar manner to example 4 using 2,3-Dihydro-benzo[1,4]dioxine-6-carboxylic acid and heptan-4-amine. MS (M+H, 292.2).

The compound had an $EC_{50}$ for activation of a hT1R1/hT1R3 umami receptor expressed in an HEK293 cell line of 6.4 μM.

Example 25

Benzofuran-2-carboxylic(1-propylbutyl)amide

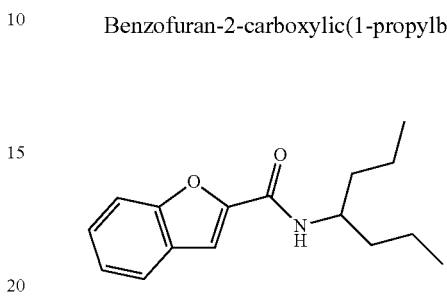

Prepared in a similar manner to example 1 using benzofuran-2-carbonyl chloride and heptan-4-amine. Yield: 73%. $^1$H NMR (500 MHz, CDCl$_3$): δ 0.93 (t, 6H, J=7.2 Hz), 1.41 (m, 8H), 3.01 (s, 3H), 4.18 (m, 1H), 6.29 (d, 1H, J=9.94 Hz), 7.20 (d, 1H, J=8.62 Hz), 7.37 (m, 2H), 7.44 (s, 1H). MS (M+H, 260)

The compound had an $EC_{50}$ for activation of a hT1R1/hT1R3 umami receptor expressed in an HEK293 cell line of 0.88 μM, and when present at 0.3 μM enhanced the effectiveness of monosodium glutamate with an $EC_{50}$ ratio of 2.6.

Example 26

N-(heptan-4-yl)-5-methylbenzofuran-2-carboxamide

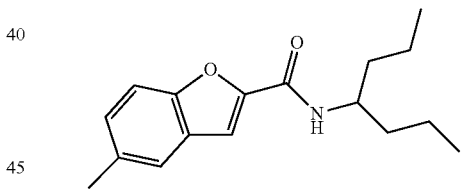

Prepared in a similar manner to example 4 using 5-methylbenzofuran-2-carboxylic acid (example 26a) and heptan-4-amine. Yield: 46%. $^1$H NMR (500 MHz, CDCl$_3$): δ 0.94 (t, 6H, J=7.2 Hz), 1.41 (m, 10H), 2.44 (s, 1H), 4.18 (m, 1H), 6.29 (d, 1H, J=8.6 Hz), 7.21 (d, 1H, J=8.4 Hz), 7.37 (m, 2H), 7.44 (s, 1H). MS (M+H, 274)

a. 5-methylbenzofuran-2-carboxylic acid: 2-Hydroxy-5-methylbenzaldehyde (544.2 mg, 4 mmol) was combined with diethylbromomalonate (1 mL, 6 mmol) and potassium carbonate (1.1 g, 8 mmol) in methyl ethyl ketone (5 mL) and the mixture was heated to reflux overnight. The solvent was removed by rotary evaporation to afford a crude oil. The oil was then taken in a 10% solution of potassium hydroxide in ethanol (10 mL) and heated to reflux for 45 minutes. The solvent was removed under reduced pressure and the residue was then treated with a 2.0 N solution of $H_2SO_4$. The free acid was then extracted with copious amounts of ethyl acetate. The organic layer was dried over anhydrous sodium sulfate. Ethyl acetate removal afforded 566 mg of 5-Methyl-2-carboxybenzofuran (80%) as of a yellowish powder. $^1$H NMR (500 MHz, CD$_3$OD): δ2.44 (s, 3H), 7.30 (d, 1H, J=8.7 Hz), 7.45 (d, 1H, J=8.5 Hz), 7.51 (d, 2H, J=7.5 Hz).

The compound had an EC$_{50}$ for activation of a hT1R1/hT1R3 umami receptor expressed in an HEK293 cell line of 0.94 μM.

Example 27

(R)-methyl 4-methyl-2-(5-methylbenzofuran-2-carboxamido)pentanoate

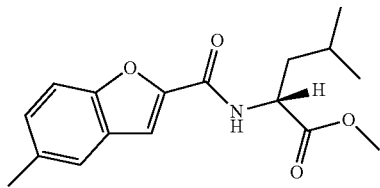

Prepared in a similar manner to example 4 using 5-methylbenzofuran-2-carboxylic acid (example 26a) and D-leucine methyl ester. $^1$H NMR (500 MHz, CDCl$_3$): δ0.98 (d, 3H, J=6.26 Hz), 1.00 (d, 3H, J=6.17 Hz), 1.56 (s, 3H), 1.76 (m, 3H), 2.48 (s, 3H), 3.78 (s, 3H), 4.86 (m, 1H), 6.95 (m, 1H), 7.23 (dd, 1H, J=8.54 Hz, J=1.55 Hz), 7.40 (m, 2H). 7.44 (dd, 1H, J=1.72, J=0.9 Hz). MS 304 (M+H, 304)

The compound had an EC$_{50}$ for activation of a hT1R1/hT1R3 umami receptor expressed in an HEK293 cell line of 0.11 μM.

Example 28

N-(hexan-3-yl)-5-methylbenzofuran-2-carboxamide

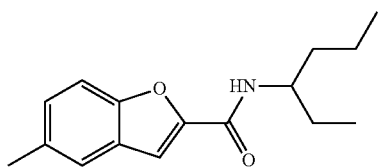

Prepared in a similar manner to example 4 using 5-methylbenzofuran-2-carboxylic (example 26a) and hexan-3-amine (example 28a) Yield: 49%. $^1$H NMR (500 MHz, CDCl$_3$): δ0.94 (m, 6H), 1.40-1.68 (m, 6H), 2.36 (s, 3H), 4.07 (m, 1H), 5.74 (d, 1H, J=8.97 Hz), 7.16 (d, 1H, J=7.80 Hz), 7.31 (dd, 1H, J=1.73 Hz, J=1.73 Hz), 7.66 (d, 1H, J=1.72 Hz). MS (M+H, 260).

a. Hexan-3-amine was prepared using the same procedure described in example 2a starting from hexan-3-one. Yield: 58%. $^1$H NMR (500 MHz, CDCl$_3$): δ 0.94 (m, 6H); 1.36-1.58 (m, 6H); 2.83 (m, 1H); 3.12 (s, 2H). MS: (102, M+H).

The compound had an EC$_{50}$ for activation of a hT1R1/hT1R3 umami receptor expressed in an HEK293 cell line of 0.74 μM.

Example 29

N-(hexan-3-yl)-5-methoxybenzofuran-2-carboxamide

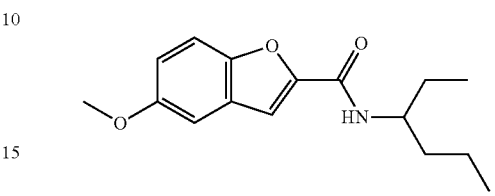

Prepared in a similar manner to example 4 using 5-methoxybenzofuran-2-carboxylic acid and hexan-3-amine (example 28a). Yield: 32%. $^1$H NMR (500 MHz, CDCl$_3$): δ 0.96 (m, 6H); 1.40-1.67 (m, 6H); 3.85 (s, 3H); 4.09 (m, 1H); 6.28 (d, 1H); 7.01 (dd, 1H); 7.08 (d, 1H); 7.38 (m, 2H). MS (276, M+H).

The compound had an EC$_{50}$ for activation of a hT1R1/hT1R3 umami receptor expressed in an HEK293 cell line of 0.4 μM.

Example 30

(R)-methyl 3-cyclohexyl-2-(5-methoxybenzofuran-2-carboxamido) Propanoate

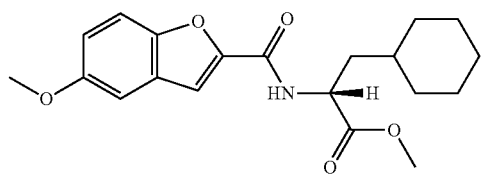

Prepared in a similar manner to example 4 using 5-methoxybenzofuran-2-carboxylic acid and (R)-methyl 2-amino-3-cyclohexylpropanoate. Yield: 45%. MS (M+H, 260.3).

The compound had an EC$_{50}$ for activation of a hT1R1/hT1R3 umami receptor expressed in an HEK293 cell line of 1.14 μM.

Example 31

5-methoxy-N-(5-methylhexan-3-yl)benzofuran-2-carboxamide

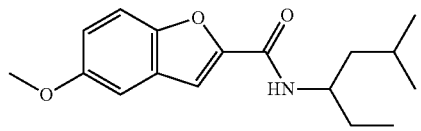

Prepared in a similar manner to example 4 using 5-methoxybenzofuran-2-carboxylic acid and 5-methylhexan-3-amine (example 5a). Yield: 67%. $^1$H NMR (500 MHz, CDCl$_3$): δ 0.96 (m, 9H); 1.39-1.52 (m, 3H); 1.66 (m, 2H);

3.85 (s, 3H); 4.17 (m, 1H); 6.24 (d, 1H); 7.01 (dd, 1H); 7.08 (d, 1H); 7.38 (m, 2H). MS (290, M+H).

The compound had an EC$_{50}$ for activation of a hT1R1/hT1R3 umami receptor expressed in an HEK293 cell line of 1.04 μM.

Example 32

Preparation of (R)-methyl 4-chloro-2-(5-methylbenzofuran-2-carboxamido)pentanoate

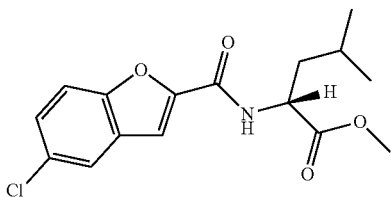

Prepared in a similar manner to example 4 using 5-chlorobenzofuran-2-carboxylic acid and D-leucine methyl ester. MS (M+H, 324).

The compound had an EC$_{50}$ for activation of a hT1R1/hT1R3 umami receptor expressed in an HEK293 cell line of 0.82 μM.

Example 33

(R)-methyl 4-methyl-2-(3-methylbenzofuran-2-carboxamido)pentanoate

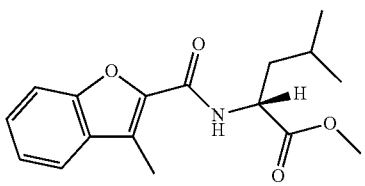

Prepared in a similar manner to example 4 using 3-methylbenzofuran-2-carboxylic acid and D-leucine methyl ester. MS (M+H, 304).

The compound had an EC$_{50}$ for activation of a hT1R1/hT1R3 umami receptor expressed in an HEK293 cell line of 1.18 μM.

Example 34

N-(heptan-4-yl)benzo[b]thiophene-2-carboxamide

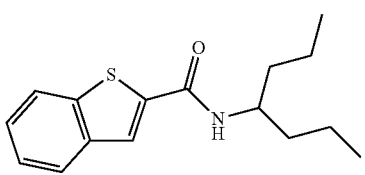

Prepared in a similar manner to example 4 using benzo[b]thiophene-2-carboxylic acid and 4-hepthylamine. MS (M+H, 276).

The compound had an EC$_{50}$ for activation of a hT1R1/hT1R3 umami receptor expressed in an HEK293 cell line of 0.21 μM.

Example 35

N-(heptan-4-yl)-1H-indole-2-carboxamide

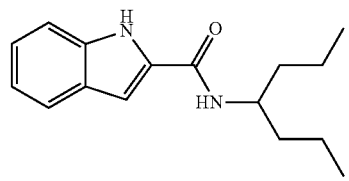

Prepared in a similar manner to example 4 using 1H-indole-2-carboxylic acid and 4-hepthylamine. MS (M+H, 259).

The compound had an EC$_{50}$ for activation of a hT1R1/hT1R3 umami receptor expressed in an HEK293 cell line of 6.8 μM.

Example 36

(R)-methyl 4-methyl-2-(5-methyl-1H-indole-2-carboxamido)pentanoate

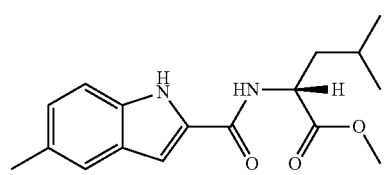

Prepared in a similar manner to example 4 using 5-Methyl-1H-indole-2-carboxylic acid and D-leucine methyl ester. Yield: 50%. $^1$H NMR (500 MHz, CDCl$_3$): δ0.98 (d, 3H, J=6.3 Hz), 1.00 (d, 3H, J=6.1 Hz), 2.44 (s, 3H), 3.784 (s, 3H), 4.87 (m, 1H), 6.56 (d, 1H, J=8.39 Hz), 6.85 (dd, 1H, J=1.94 Hz, J=0.68 Hz), 7.12 (dd, 1H, J=8.46 Hz, J=1.55 Hz), 7.31 (d, 1H, J=8.45 Hz), 7.42 (s, 1H). MS (MH+, 303).

The compound had an EC$_{50}$ for activation of a hT1R1/hT1R3 umami receptor expressed in an HEK293 cell line of 6.6 μM.

Example 37

N-(heptan-4-yl)-1-methyl-1H-indole-2-carboxamide

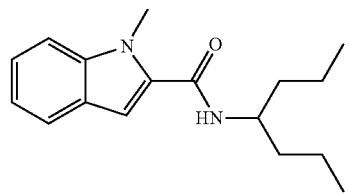

Prepared in a similar manner to example 4 using 1-methyl-1H-indole-2-carboxylic acid and 4-hepthylamine. Yield 45%. $^1$H NMR (500 MHz, CDCl$_3$): δ 0.95 (t, 6H, J=7.2 Hz), 1.46

(m, 4H), 1.57 (m, 4H), 4.05 (s, 3H), 4.15 (m, 1H), 5.85 (d, 1H), 6.80 (s, 1H), 7.14 (t, 1H, J=7.4 Hz), 7.31 (t, 1H, J=7.5 Hz), 7.38 (d, 1H, J=8.4 Hz), 7.62 (d, 1H, J=8 Hz). MS (M+H, 273).

The compound had an $EC_{50}$ for activation of a hT1R1/hT1R3 umami receptor expressed in an HEK293 cell line of 1.79 μM.

Example 38

N-(heptan-4-yl)-1H-benzo[d]imidazole-5-carboxamide

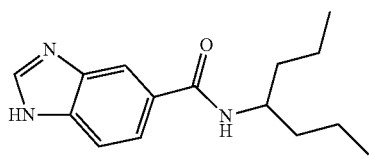

Prepared in a similar manner to example 4 using 1H-benzo[d]imidazole-5-carboxylic acid and 4-hepthylamine. Yield: 80%. $^1$H NMR (500 MHz, CDCl$_3$): δ 0.94 (t, 6H, J=7.2 Hz), 1.42 (m, 6H), 1.57 (m, 2H), 4.21 (m, 1H), 6.18 (m, 1H), 7.64 (m, 2H), 8.16 (m, 1H), 8.28 (s, 1H). MS (M+H, 260).

The compound had an $EC_{50}$ for activation of a hT1R1/hT1R3 umami receptor expressed in an HEK293 cell line of 18.6 μM.

Example 39

Benzooxazole-5-carboxylic Acid (1-propylbutyl)amide

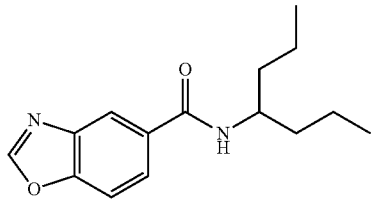

Prepared in a similar manner to example 4 using benzooxazol-5-carboxylic acid (Example 39a) and 4-heptylamine. $^1$H NMR (500 MHz, CDCl$_3$): δ 8.16 (d, J=5.4 Hz, 1H), 7.89 (d, J=8.6 Hz, 1H), 7.64 (d, J=8.6 Hz, 1H), 5.82 (d, J=8.6 Hz, 1H) 4.10-4.22 (m, 1H), 1.58-1.62 (m, 4H), 1.40-1.49 (m, 4H), 0.95 (t, J=7.2 Hz, 6H); ESIMS: 261 (M+H).

a. benzooxazol-5-carboxylic acid: A mixture of 3-amino-4-hydroxybenzoic acid (500 mg, 3.26 mmol) and trimethyl orthoformate (5 mL) was heated at 65° C. for 2 h under argon. The reaction mixture was cooled to room temperature, filtered and washed with hexanes. The filtrate was concentrated in vacuo to afford the product as a white solid (78 mg, 15%): $^1$H NMR (500 MHz, CDCl$_3$): δ 8.57 (d, J=1.5 Hz, 1H), 8.20 (dd, J=8.4, 1.8 Hz, 1H), 8.20 (s, 1H), 7.67 (d, J=9.0 Hz, 1H). MS (M+H, 164).

The compound had an $EC_{50}$ for activation of a hT1R1/hT1R3 umami receptor expressed in an HEK293 cell line of 1.91 μM.

Example 40

2-Methyl-benzooxazole-5-carboxylic Acid (1-propyl-butyl)-amide

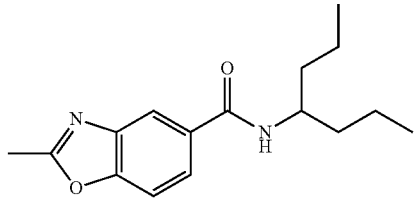

Prepared in a similar manner to example 4 starting from 2-methyl benzooxazol-5-carboxylic acid (example 40) and 4-heptylamine. $^1$H NMR (500 MHz, CDCl$_3$) δ 8.00 (d, J=1.6 Hz, 1H), 7.77 (d, J=8.5, 1.6 Hz, 1H), 7.50 (d, J=8.5 Hz, 1H), 5.79 (d, J=8.9 Hz, 1H for NH) 4.10-4.22 (m, 1H), 2.66 (s, 3H), 1.58-1.65 (m, 4H), 1.38-1.55 (m, 4H), 0.94 (t, J=7.2 Hz, 6H); MS (APCI, M+1): 275.2.

a. 2-methyl benzooxazol-5-carboxylic acid: A mixture of 3-amino-4-hydroxybenzoic acid (1.5 g, 9.79 mmol) and trimethyl orthoacetate (15 mL, large excess) was heated at 65° C. for 5 hrs under argon. The reaction mixture was cooled to room temperature, filtered, washed with hexanes. The filtrate was concentrated in vacuo to afford the product as a yellow solid (1.4 g, 80%): $^1$H NMR (500 MHz, CD$_3$OD) δ 8.26 (d, J=1.7 Hz, 1H), 8.07 (dd, J=8.5, 1.6 Hz, 1H), 7.67 (d, J=8.2 Hz, 1H), 2.67 (s, 1H); MS (APCI, M+1): 178.10.

The compound had an $EC_{50}$ for activation of a hT1R1/hT1R3 umami receptor expressed in an HEK293 cell line of 0.33 μM.

Example 41

2-Ethyl-benzooxazole-5-carboxylic Acid (1-propyl-butyl)-amide

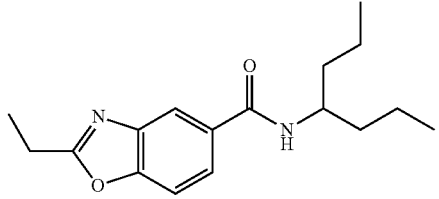

A mixture of 3-amino-4-hydroxy-N-(1-propylbutyl)benzamide (example 41a) and trimethyl orthopropyrate was heated at 65° C. for 5 hr under N$_2$. The reaction mixture was cooled to room temperature and concentrated in vacuo. The resulting residue was purified on silica gel via Preparative-TLC (3% MeOH in CH$_2$Cl$_2$) to afford the product as a white solid (42 mg, 73%): mp 107-108° C.; MS (APCI, M+1): 289.10.

a. 3-amino-4-hydroxy-N-(1-propylbutyl)benzamide was prepared in a similar manner to example 4 using 3-Amino-4-hydroxybenzoic acid and 4-heptylamine. Yield 57%. $^1$H NMR (500 MHz, CDCl$_3$): δ 0.93 (t, 6H); 1.26-1.51 (m, 8H); 4.09 (m, 1H); 6.74 (m, 1H); 7.05 (s, 1H); 7.43 (m, 2H); 7.77 (m, 2H). MS: (251, M+H).

Example 42

2-Methoxy-benzooxazole-5-carboxylic Acid (1-propyl-butyl)-amide

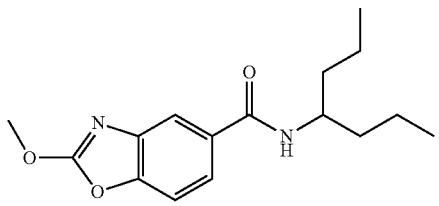

Prepared in a similar manner to example 41 using 3-amino-4-hydroxy-N-(1-propylbutyl)benzamide (example 4aa) and tetramethylorthocarbonate. Yield: 60%. mp 137-138° C.; MS (M+H, 291.10).

The compound had an EC$_{50}$ for activation of a hT1R1/hT1R3 umami receptor expressed in an HEK293 cell line of 0.69 μM.

Example 43

2-Ethoxy-benzooxazole-5-carboxylic Acid (1-propyl-butyl)-amide

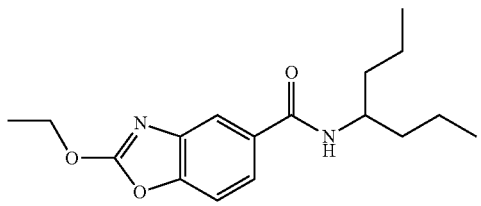

Prepared in a similar manner to example 41 using 3-amino-4-hydroxy-N-(1-propylbutyl)benzamide (example 41a) and tetraethoxymethane: mp 128-129° C.; MS (M+H, 305.1).

The compound had an EC$_{50}$ for activation of a hT1R1/hT1R3 umami receptor expressed in an HEK293 cell line of 5 μM.

Example 44

N-(heptan-4-yl)-2-(methylthio)benzo[d]oxazole-5-carboxamide

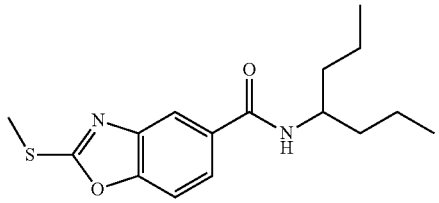

To a solution of N-(Heptan-4-yl)-2-(mercapto)benzo[d]oxazole-5-carboxamide (example 44a) (50 mg, 0.17 mmol) in DMF (3 mL) at 0° C. was added K$_2$CO$_3$ (29 mg, 0.17 mmol) and MeI (29 mg, 0.20). The resulting reaction mixture was heated at 80° C. overnight. The solvent was removed under reduced pressure. The residue was diluted with dichloromethane and washed with water, dried (Na$_2$SO$_4$), filtered, concentrated in vacuo, purified via PTLC (15% EtOAc in hexanes) to afford the product as a white solid (50 mg, 96%): mp 113-114° C.; $^1$H NMR (500 MHz, CDCl$_3$) δ 7.94 (d, J=1.8 Hz, 1H), 7.73 (dd, J=8.5, 1.6 Hz, 1H), 7.46 (d, J=8.4 Hz, 1H), 5.76 (d, J=8.4 Hz, 1H), 4.15-4.25 (m, 1H), 2.77 (s, 3H), 1.58-1.65 (m, 2H), 1.1.38-1.55 (m, 6H), 0.94 (t, J=7.2 Hz, 6H); MS (APCI, M+): 307.2.

a. N-(Heptan-4-yl)-2-(mercapto)benzo[d]oxazole-5-carboxamide: To a solution 3-amino-4-hydroxy-N-(1-propylbutyl)benzamide (example 41a) (250 mg, 1.0 mmol) in EtOH was added KSCSOEt (160 mg, 1.0 mmol). The resulting reaction mixture was heated at 80° C. overnight. The solvent was removed under reduced pressure. And the residue was taken up in water. The resulting mixture was acidified with HOAc to pH ~5 and then filtered. The residue was washed with water to afford the product as a white solid (160 mg, 55%). MS (M+H, 293.1).

The compound had an EC$_{50}$ for activation of a hT1R1/hT1R3 umami receptor expressed in an HEK293 cell line of 3.1 μM.

Example 45

Chloromethyl benzooxazol-5-carboxylic Acid (1-propyl-butyl)amide

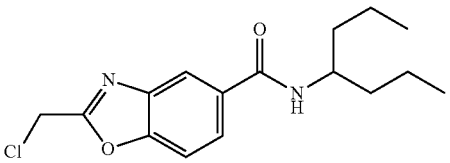

Prepared in a similar manner to example 41 using 3-amino-4-hydroxy-N-(1-propylbutyl)benzamide (example 41a) and trimethyl chloro-orthoacetate. Yield: 65%. mp 108.5-109° C. MS (M+H, 309.05).

The compound had an EC$_{50}$ for activation of a hT1R1/hT1R3 umami receptor expressed in an HEK293 cell line of 0.23 μM.

Example 46

2-Methyl-benzooxazole-6-carboxylic Acid (1-propyl-butyl)-amide

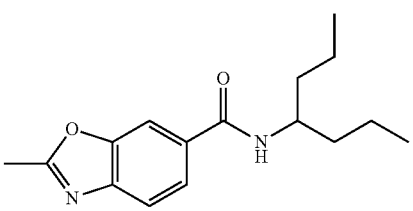

Prepared in a similar manner to example 4 using 2-methyl benzooxazol-6-carboxylic acid (example 46a) and 4-heptylamine Yield 50%: $^1$H NMR (500 MHz, CD$_3$OD) δ 8.19 (d, J=1.4 Hz, 1H), 8.05 (dd, J=8.3, 1.5 Hz, 1H), 7.63 (d, J=8.2 Hz, 1H), 2.68 (s, 1H); MS (M+1, 178.10).

a. 2-methyl benzooxazol-6-carboxylic acid was prepared in a similar manner to example 40a from 4-amino-3-hydroxy-benzoic acid (50%): $^1$H NMR (500 MHz, CD$_3$OD) δ 8.19 (d, J=1.4 Hz, 1H), 8.05 (dd, J=8.3, 1.5 Hz, 1H), 7.63 (d, J=8.2 Hz, 1H), 2.68 (s, 1H); MS (M+H, 178.10).

The compound had an $EC_{50}$ for activation of a hT1R1/hT1R3 umami receptor expressed in an HEK293 cell line of 2.1 μM.

Example 47

2-Chloromethyl-benzooxazole-6-carboxylic Acid (1-propyl-butyl)-amide

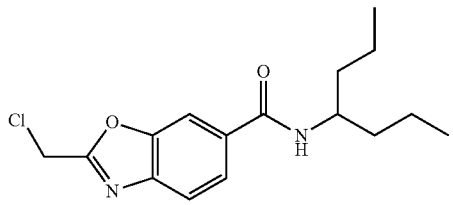

Prepared in a similar manner to example 41 using 3-amino-4-hydroxy-N-(1-propylbutyl)benzamide (example 47a) and trimethyl chloro-orthoacetate. The product was obtained as a white solid (45 mg, 73%): mp 137.0-137.5° C.; MS (M+H, 309.05.

a. 3-amino-4-hydroxy-N-(1-propylbutyl)benzamide was prepared in a similar manner to example 41a from 4-amino-3-hydroxybenzoic acid. Yield: 50%. $^1$H NMR (500 MHz, CDCl$_3$): δ 0.91 (t, 6H); 1.41 (m, 6H); 1.54 (m, 2H); 4.13 (m, 1H); 5.81 (d, 1H); 6.63 (d, 1H), 6.95 (d, 1H); 7.82 (s, 1H). MS: (251, M+H)

The compound had an $EC_{50}$ for activation of a hT1R1/hT1R3 umami receptor expressed in an HEK293 cell line of 0.45 μM.

Example 48

4-methyl-3-methylsulfanyl-N-(1-propylbutyl)benzamide

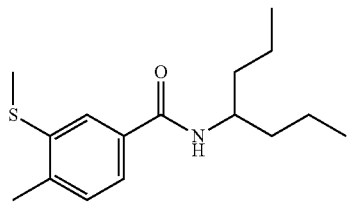

Prepared in a similar manner as example 4 using 4-methyl-3-(methylthio)benzoic acid (example 48a) and 4-heptylamine. Yield: 50%. $^1$H NMR (500 MHz, CDCl$_3$): δ 0.93 (t, 6H, J=7.2 Hz), 1.40-1.41 (m, 8H), 2.35 (s, 3H), 2.51 (s, 1H), 4.15 (m, 1H), 5.75 (d, 1H, J=8.5 Hz), 7.15 (d, 1H, J=7.8 Hz), 7.31 (d, 1H, J=7.8 Hz), 7.65 (d, 1H, J=1.5 Hz). MS (M+H, 280).

a. 4-methyl-3-(methylthio)benzoic acid: 3-Amino-4-methylbenzoic acid was suspended in ice-water (55 mL), and concentrated HCl (8.56 mL) was slowly added. An aqueous solution of sodium nitrite (2.4 g in 5.5 mL) was added to the suspension over a period of 15 minutes and the mixture was stirred for another 15 minutes. Then, an aqueous solution of sodium acetate (9.31 g in 18 mL) was added dropwise. The reaction was allowed to proceed for 45 min. A heavy orange precipitate was obtained. The precipitate was filtered off and washed with small portions of ice-cold water. The solid was combined with a solution of potassium xanthogenate (11.93 g) and potassium carbonate (8.22 g) in 250 mL of water. The reaction vessel was placed in a preheated oil bath at 70° C. and the mixture was stirred for 25 minutes. The reddish solution was taken out of the bath and stirred for 15 minutes or until the temperature reached 30° C. Sodium hydroxide (0.782 g) was added and stirred to dissolution. Dimethylsulfate (5.70 mL) was added. The mixture was stirred for 1 hour at room temperature then briefly refluxed. Solvent removal under reduced pressure yielded an orange solid. The solid was treated with a 2.0 N solution of H$_2$SO$_4$ and extracted with EtOAc. The extracts were washed with water then dried over anhydrous MgSO$_4$. The solvent was removed under reduced pressure to give a reddish crude solid. The solid was adsorbed on silica gel and purified by column chromatography (gradient 5 to 50% ethyl acetate in hexane) to give 4-methyl-3-(methylthio) benzoic acid as a pale yellow powder (2 g). $^1$H NMR (500 MHz, CDCl$_3$): δ 2.39 (s, 3H), 2.54 (s, 3H), 7.24 (d, 1H, J=7.8 Hz), 7.79 (d, 1H, J=7.8 Hz), 7.86 (d, 1H, J=1.5 Hz).

The compound had an $EC_{50}$ for activation of a hT1R1/hT1R3 umami receptor expressed in an HEK293 cell line of 0.21 μM.

Example 49

(R)-methyl 4-methyl-2-(4-methyl-3-(methylthio) benzamido)pentanoate

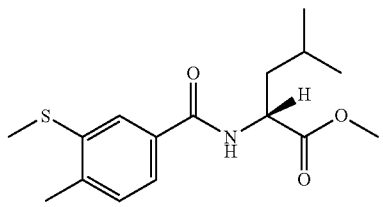

Prepared in a similar manner to example 4 using 3-methyl-4-(methylthio)benzoic acid (example 48a) and D Leucine methyl ester. Yield: 45%. $^1$H NMR (500 MHz, CDCl$_3$): δ 0.97 (d, 3H, J=6.36 Hz), 0.99 (d, 3H, J=6.1 Hz), 1.64-1.77 (m, 2H), 2.36 (s, 3H), 2.51 (s, 3H), 3.77 (s, 3H), 4.85 (m, 1H), 6.50 (d, 1H, J=8.10 Hz), 7.18 (d, 1H, J=7.83 Hz), 7.38 (dd, 1H, J=7.77 Hz, J=1.78 Hz), 7.65 (d, 1H, J=1.65 Hz). MS (M+H, 310).

The compound had an $EC_{50}$ for activation of a hT1R1/hT1R3 umami receptor expressed in an HEK293 cell line of 0.1 μM.

Example 50

(R)-methyl 4-methyl-2-(4-(methylthio)benzamido) pentanoate

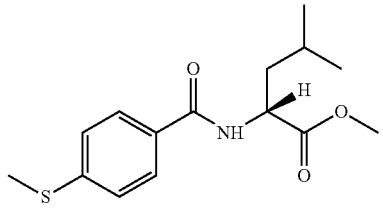

Prepared in a similar manner to example 4 using 4-(methylthio)benzoic acid and D Leucine methyl ester. MS (M+H, 296).

The compound had an $EC_{50}$ for activation of a hT1R1/hT1R3 umami receptor expressed in an HEK293 cell line of 0.16 µM.

Example 51

N-(heptan-4-yl)-3-methyl-4-(methylthio)benzamide

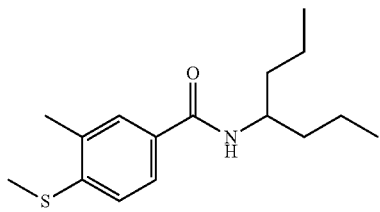

Prepared in a similar manner to example 4 using 3-methyl-4-(methylthio)benzoic acid (example 51a) and 4-hepthylamine. $^1$H NMR (500 MHz, CDCl$_3$): δ 0.93 (t, 6H); 1.37-1.46 (m, 6H); 1.54-1.56 (m, 2H); 2.35 (s, 3H); 2.49 (s, 3H); 4.17 (m, 1H); 5.73 (d, 1H); 7.14 (d, 1H); 7.52 (s, 1H); 7.58 (d, 1H). MS (280, M+H) m.p: 129-131° C.

a. 3-methyl-4-(methylthio)benzoic acid was prepared using the same procedure described in example 48a starting from 3-Amino-4-methylbenzoic acid. Yield 30%. $^1$H NMR (500 MHz, CDCl$_3$): δ 2.36 (s, 3H); 2.53 (s, 3H); 7.17 (d, 1H); 7.85 (s, 1H); 7.93 (d, 1H).

The compound had an $EC_{50}$ for activation of a hT1R1/hT1R3 umami receptor expressed in an HEK293 cell line of 0.12 µM.

Example 52

4-methoxy-3-methyl-N-(2-methylheptan-4-yl)benzamide

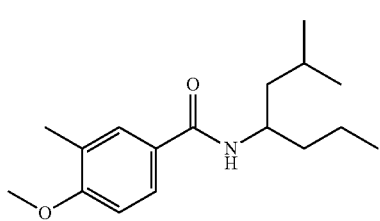

Prepared in a similar manner as described in example 4 using 4-methoxy-3-methylbenzoic acid and 2-methyl-4-heptanamine (example 2a). Yield: 45%. $^1$H NMR (500 MHz, CDCl$_3$): δ 0.93 (m, 9H); 1.39 (m, 5H); 1.53 (m, 1H); 1.67 (m, 1H); 2.24 (s, 3H); 3.86 (s, 3H); 4.23 (m, 1H); 5.64 (d, 1H); 6.82 (d, 1H); 7.54 (s, 1H); 7.61 (d, 1H). MS (278, M+H).

The compound had an $EC_{50}$ for activation of a hT1R1/hT1R3 umami receptor expressed in an HEK293 cell line of 0.1 µM.

Example 53

4-methoxy-3-methyl-N-(5-methylhexan-3-yl)benzamide

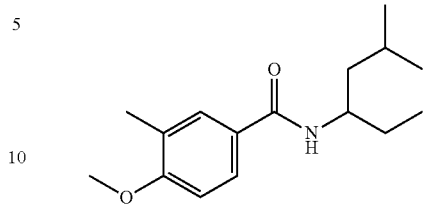

Prepared in a similar manner to example 4 using 4-methoxy-3-methylbenzoic acid and 5-methylhexan-3-amine (example 5a). $^1$H NMR (500 MHz, CDCl$_3$): δ 0.94 (m, 9H); 1.38 (m, 2H); 1.47 (m, 1H); 1.65 (m, 2H); 2.24 (s, 3H); 3.86 (s, 3H); 4.16 (m, 1H); 5.65 (d, 1H); 6.83 (d, 1H); 7.54 (s, 1H); 7.61 (d, 1H). MS (264, M+H).

The compound had an $EC_{50}$ for activation of a hT1R1/hT1R3 umami receptor expressed in an HEK293 cell line of 0.09 µM.

Example 54

4-methoxy-N-(1-(4-methoxyphenyl)butyl)-3-methyl-benzamide

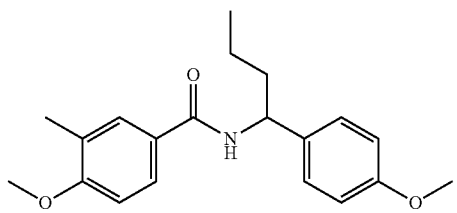

Prepared in a similar manner to example 4 using 3-methyl-4-methoxy-benzoic acid and 1-(4-methoxyphenyl)butan-1-amine (example 54a). Yield 52%. $^1$H NMR (500 MHz, CDCl$_3$): δ 0.94 (t, 3H); 1.31-1.41 (m, 2H); 1.82-1.92 (m, 2H); 2.22 (s, 3H); 3.79 (s, 3H); 3.86 (s, 3H); 5.11 (m, 1H); 6.14 (d, 1H); 6.81 (d, 1H); 6.88 (d, 2H). 7.28 (d, 2H); 7.53 (s, 1H); 7.61 (d, 1H). MS (328, M+H).

a. 1-(4-methoxyphenyl)butan-1-amine was prepared as described in example 2a from 1-(4-methoxyphenyl)butan-1-one. Yield 90%. MS (M+H, 180).

The compound had an $EC_{50}$ for activation of a hT1R1/hT1R3 umami receptor expressed in an HEK293 cell line of 3.14 µM.

Example 55

(R)-4-methoxy-3-methyl-N-(3-methyl-1-(3-methyl-1,2,4-oxadiazol-5-yl)butyl)benzamide

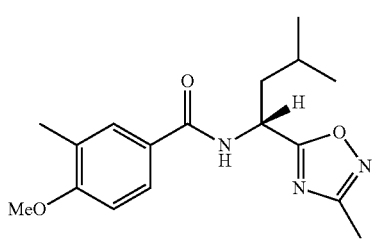

Prepared in a similar manner to example 4 using 4-methoxy-3-methylbenzoic acid and 3-methyl-1-(3-methyl-[1,2,4]oxadiazol-5-yl)-butylamine (Example 55a). MS (M+H, 318).

a. (R)-3-methyl-1-(3-methyl-1,2,4-oxadiazol-5-yl)butan-1-amine: Boc-D-Leu-OH (0.23 g, 1 mmol) was treated with N-hydroxyacetamidine (74 mg, 1 eq) and DIC (155 μL, 1 eq) in dioxane (2 mL) at room temperature overnight. Another portion of DIC (1 equiv) was added and the reaction mixture was heated at 110° C. for 4 hours. After removal of the solvent, the residue was treated with 50% TFA/DCM (2 mL) for 1 h and then the solvent was evaporated. The crude mixture was purified by preparative HPLC (C-18 column, MeOH—H$_2$O mobile phase and formic acid as modifier) to give 75 mg of the amine (45% yield). $^1$H NMR (500 MHz, CDCl$_3$): δ 0.95 (d, 3H), 0.99 (d, 3H); 1.70-1.78 (m, 1H), 1.92-1.98 (m, 2H), 2.39 (s, 3H), 3.50 (b, 2H, NH$_2$), 4.65 (t, 1H). MS (M+H, 170).

The compound had an EC$_{50}$ for activation of a hT1R1/hT1R3 umami receptor expressed in an HEK293 cell line of 5.4 μM.

Example 56

4-ethoxy-N-(heptan-4-yl)-3-methylbenzamide

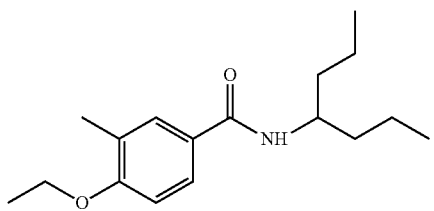

Prepared in a similar manner as example 4 using 4-ethoxy-3-methyl benzoic acid (example 56a) and 4-heptylamine. Yield: 75%. $^1$H NMR (500 MHz, CDCl$_3$): δ 0.93 (t, 6H); 1.37-1.45 (m, 6H); 1.53-1.59 (m, 2H); 2.24 (s, 3H); 4.07 (q, 2H); 4.15 (m, 1H); 5.67 (d, 1H); 6.80 (d, 1H); 7.54 (s, 1H); 7.58 (d, 1H). MS (278, M+H)

a. 4-ethoxy-3-methyl benzoic acid: 4-hydroxy-3-methyl benzoic acid (10 g) was dissolved in DMF (400 mL) followed by the addition of sodium carbonate (3 eq). Ethyl iodide (3 eq) was dissolved in DMF (50 mL) was added dropwise to the reaction mixture and the solution was stirred overnight. After the reaction was completed, the solvent was evaporated. The residue was dissolved in ethyl acetate and washed with water. The organic layer was isolated and evaporated. The residue was dissolved in 200 mL methanol/water (3:1). Lithium hydroxide (3 eq) was added and allowed to stir overnight. Upon the completion of hydrolysis, the solvent was removed and the product was crystallized using ethyl acetate/hexane mixture to give 8.2 g of 4-ethoxy-3-methyl benzoic acid. Yield: 70%, MS (M–H, 179.20).

The compound had an EC$_{50}$ for activation of a hT1R1/hT1R3 umami receptor expressed in an HEK293 cell line of 0.17 μM.

Example 57

4-ethoxy-N-(1-methoxypentan-2-yl)-3-methylbenzamide

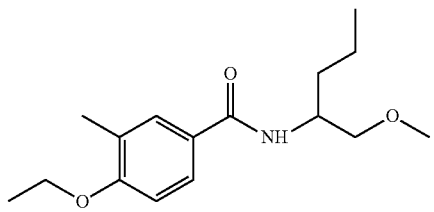

Prepared in a similar manner as example 4 using 4-ethoxy-3-methyl benzoic acid (example 56a) and 1-methoxypentan-2-amine (example 57a). Yield: 33%. MS (M+H, 280.1).

a. 1-methoxypentan-2-amine was prepared in a similar manner to example 9a from 2-(1-methoxypentan-2-yl)isoindoline-1,3-dione (example 57b). Yield 67%. $^1$H NMR (500 MHz, CDCl$_3$): δ 0.91 (t, 3H); 1.24-1.45 (m, 4H); 1.52 (s, 2H); 2.94 (m, 1H); 3.12 (t, 1H); 3.33 (m, 1H); 3.35 (s, 3H).

b. 2-(1-methoxypentan-2-yl)isoindoline-1,3-dione was prepared in a similar manner to example 9b from 2-(1-hydroxypentan-2-yl)isoindoline-1,3-dione (example 57c). Yield: 82%. $^1$H NMR (500 MHz, CDCl$_3$): δ 0.91 (t, 3H); 1.32 (m, 2H); 1.64 (m, 1H); 2.03 (m, 1H); 3.31 (s, 3H); 3.54 (m, 1H); 3.98 (t, 1H); 4.50 (m, 1H); 7.70 (m, 2H); 7.82 (m, 2H).

c. 2-(1-hydroxypentan-2-yl)isoindoline-1,3-dione was prepared in a similar manner to example 9c using isobenzofuran-1,3-dione and 2-aminopentan-1-ol. Yield 62%. $^1$H NMR (500 MHz, CDCl$_3$): δ 0.92 (t, 3H); 1.33 (m, 2H); 1.76 (m, 1H); 1.95 (m, 1H); 3.88 (m, 1H); 4.06 (m, 1H); 4.39 (m, 1H); 7.72 (m, 2H); 7.83 (m, 2H).

The compound had an EC$_{50}$ for activation of a hT1R1/hT1R3 umami receptor expressed in an HEK293 cell line of 0.69 μM.

Example 58

4-hydroxy-3-methyl-N-(1-propyl-butyl)-benzamide

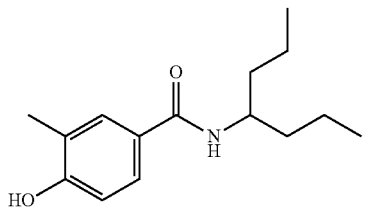

Prepared in a similar manner as described in example 4 using 4-hydroxy-3-methyl benzoic acid and 4-heptylamine. MS (M+H, 250.2).

The compound had an EC$_{50}$ for activation of a hT1R1/hT1R3 umami receptor expressed in an HEK293 cell line of 0.92 μM.

Example 59

N-(heptan-4-yl)-4-(2-methoxyethoxy)-3-methylbenzamide

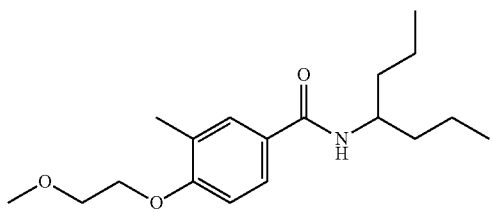

Potassium hydroxide (4 mmol) was dissolved in ethanol (5 mL) and heated at 80° C. 4-hydroxy-3-methyl-N-(1-propylbutyl)-benzamide (example 58) (1 mmol) was added into the solution followed by chloroethanol (3 mmol). The reaction was stirred overnight at 80° C. The reaction mixture was concentrated down and dissolved in 5% citric acid. the mixture was stirred for 1 hour. The aqueous mixture was extracted three times with ethyl acetate. The combined ethyl acetate was washed with water and dried down over sodium sulfate. The organic layer was concentrated down and purified by HPLC to yield 39% of N-(heptan-4-yl)-4-(2-methoxyethoxy)-3-methylbenzamide. MS (M+H, 308.25).

The compound had an $EC_{50}$ for activation of a hT1R1/hT1R3 umami receptor expressed in an HEK293 cell line of 0.21 µM.

Example 60

(R)-methyl 2-(3-fluoro-4-methoxybenzamido)-4-methylpentanoate

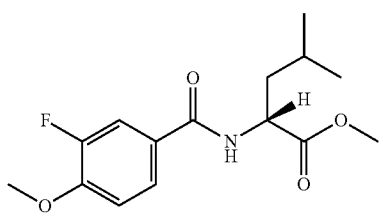

Prepared in a similar manner to example 4 using 3-fluoro-4-methoxybenzoic acid and D-leucine methyl ester. MS (M+H, 298).

The compound had an $EC_{50}$ for activation of a hT1R1/hT1R3 umami receptor expressed in an HEK293 cell line of 0.3 µM.

Example 61

3-chloro-4-methoxy-N-(pentan-3-yl)benzamide

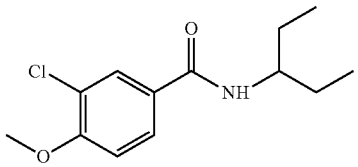

Prepared in a similar manner to example 4 using 3-pentylamine and 3-chloro-4-methoxy benzoic acid. Yield 40%. MS (M+H, 256.20).

The compound had an $EC_{50}$ for activation of a hT1R1/hT1R3 umami receptor expressed in an HEK293 cell line of 0.56 µM, and when present at 0.3 µM enhanced the effectiveness of monosodium glutamate with an $EC_{50}$ ratio of 6.28.

Example 62

(R)-methyl 2-(3-chloro-4-methoxybenzamido)-4-methylpentanoate

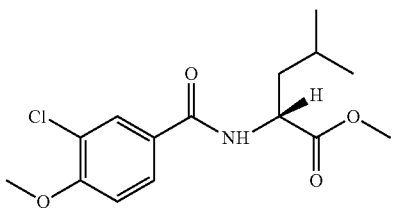

Prepared in a similar manner to example 4 using 3-chloro-4-methoxy benzoic acid and D-leucine methyl ester hydrochloride. MS (M+H, 314.10).

The compound had an $EC_{50}$ for activation of a hT1R1/hT1R3 umami receptor expressed in an HEK293 cell line of 0.08 µM, and when present at 0.01 µM enhanced the effectiveness of monosodium glutamate with an $EC_{50}$ ratio of 13.18.

Example 63

(R)-3-chloro-4-methoxy-N-(1-phenylethyl)benzamide

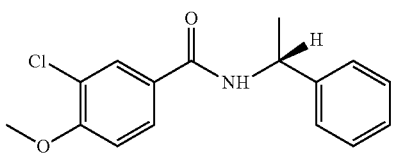

Prepare in a similar manner to example 4 using (R)-1-phenylethanamine and 3-chloro-4-methoxy benzoic acid. MS (M+H, 290.0).

The compound had an $EC_{50}$ for activation of a hT1R1/hT1R3 umami receptor expressed in an HEK293 cell line of 2.5 μM, and when present at 0.3 μM enhanced the effectiveness of monosodium glutamate with an $EC_{50}$ ratio of 2.7.

Example 64

4-Chloro-3-methyl-N-(1-propyl-butyl)-benzamide

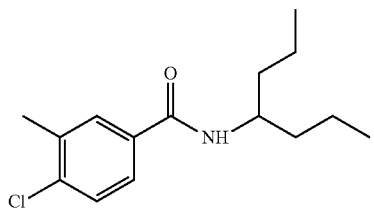

Prepared in a similar manner to example 4 using 4-chloro-3-methyl benzoic acid and heptan-4-amine. MS (M+H, 268).

The compound had an $EC_{50}$ for activation of a hT1R1/hT1R3 umami receptor expressed in an HEK293 cell line of 0.8 μM.

Example 65

3,4-Dimethoxy-N-(1-prop-1-butyl)-benzamide

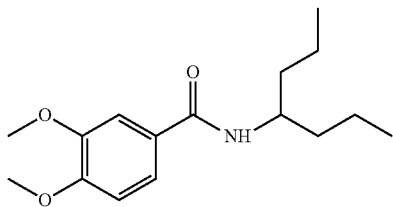

Prepared in a similar manner to example 4 using 3,4-dimethoxy benzoic acid and heptan-4-amine. MS (M+H, 279.37).

The compound had an $EC_{50}$ for activation of a hT1R1/hT1R3 umami receptor expressed in an HEK293 cell line of 0.36 μM.

Example 66

(R)-methyl 2-(4-fluoro-3-methylbenzamido)-4-methylpentanoate

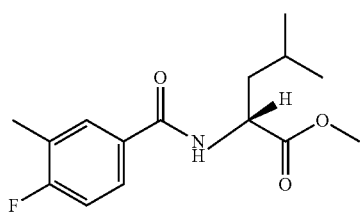

Prepared in a similar manner to example 4 using 4-fluoro-3-methylbenzoic acid and D-leucine methyl ester. MS (M+H, 282).

The compound had an $EC_{50}$ for activation of a hT1R1/hT1R3 umami receptor expressed in an HEK293 cell line of 0.32 μM.

Example 67

4-methoxy-3,5-dimethyl-N-(2-methylheptan-4-yl)benzamide

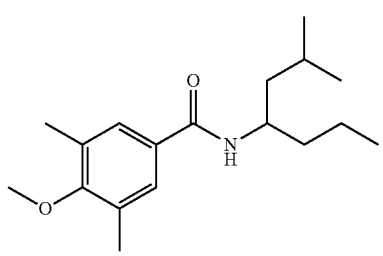

Prepared in a similar manner to example 4 using 4-methoxy-3,5-dimethylbenzoic acid and 2-methylheptan-4-amine (example 2a). MS (M+H, 292.2).

The compound had an $EC_{50}$ for activation of a hT1R1/hT1R3 umami receptor expressed in an HEK293 cell line of 0.85 μM.

Example 68

3,4-dimethyl-N-(2-methylhexan-3-yl)benzamide

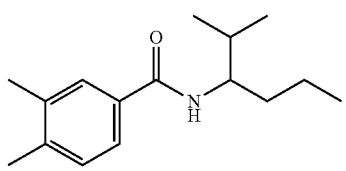

Prepared in a similar manner to example 4 using 3,4-dimethylbenzoic acid and hexan-3-amine (example 3a). $^1$H NMR (500 MHz, CDCl$_3$): δ 0.94 (m, 9H); 1.39 (m, 3H); 1.56 (m, 1H); 1.84 (m, 1H); 2.30 (s, 3H); 2.31 (s, 3H); 4.04 (m, 1H); 5.76 (d, 1H); 7.18 (d, 1H); 7.46 (d, 1H); 7.55 (s, 1H); MS (248, M+H).

The compound had an $EC_{50}$ for activation of a hT1R1/hT1R3 umami receptor expressed in an HEK293 cell line of 0.11 μM.

Example 69

3,4-dimethyl-N-(2-methylheptan-4-yl)benzamide

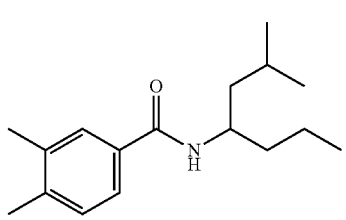

Prepared in a similar manner to example 4 using 3,4-dimethylbenzoic acid and 2-methylheptan-4-amine (example 2a). $^1$H NMR (500 MHz, CDCl$_3$): δ 0.94 (m, 9H); 1.40 (m, 5H); 1.53 (m, 1H); 1.68 (m, 1H); 2.29 (s, 3H); 2.30 (s, 3H); 4.24 (m, 1H); 5.69 (d, 1H); 7.17 (d, 1H); 7.46 (d, 1H); 7.54 (s, 1H). MS (262, M+H).

The compound had an EC$_{50}$ for activation of a hT1R1/hT1R3 umami receptor expressed in an HEK293 cell line of 0.13 μM.

Example 70

3,4-dimethyl-N-(5-methylhexan-3-yl)benzamide

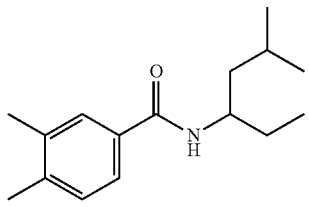

Prepared in a similar manner to example 4 using 3,4-dimethylbenzoic acid and 5-methylhexan-3-amine (example 5a). $^1$H NMR (500 MHz, CDCl$_3$): δ 0.94 (m, 9H); 1.38 (m, 2H); 1.46 (m, 1H); 1.65 (m, 2H); 2.29 (s, 3H); 2.30 (s, 3H); 4.18 (m, 1H); 5.70 (d, 1H); 7.17 (d, 1H); 7.46 (d, 1H); 7.55 (s, 1H). MS (248, M+H).

The compound had an EC$_{50}$ for activation of a hT1R1/hT1R3 umami receptor expressed in an HEK293 cell line of 0.17 μM.

Example 71

(R)—N-(1-methoxy-4-methylpentan-2-yl)-3,4-dimethylbenzamide

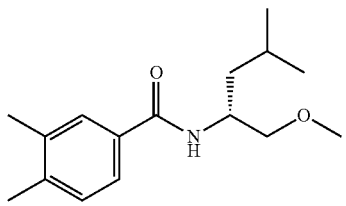

To a solution of (R)—N-(1-hydroxy-4-methylpentan-2-yl)-3,4-dimethylbenzamide (1.59 g, 6.39 mmol) (example 71a) in dry DMF (20 mL) was added powdered NaOH (281 mg, 7 mmol) an the solution was stirred at 0° C. for 2 hrs. Iodomethane (1 eq, 6.39 mmol) was added in DMF (10 ml) drop-wise over period of 1 hr. The temperature was kept at 0° C. and the mixture was stirred for 1 hr. The reaction was quenched by adding 300 ml of water. The aqueous layer was extracted with dichloromethane, dried over MgSO$_4$ and evaporated. The residue was purified by flash chromatography on silica-gel (toluene-ethyl acetate; 5-20% gradient) to give 1.23 g (R)—N-(1-methoxy-4-methylpentan-2-yl)-3,4-dimethylbenzamide (73%). $^1$H NMR (500 MHz, CDCl$_3$): δ 0.94-0.97 (t, 6H), 1.41-1.47 (M, 1H), 1.54-1.60 (m, 1H), 1.64-1.68 (m, 1H), 2.29 (d, 6H), 3.36 (s, 3H), 3.45-3.50 (m, 2H), 4.34-4.39 (m, 1H), 6.23-6.25 (d, 1H), 7.16-7.17 (d, 1H), 7.47-7.49 (dd, 1H), 7.56 (s, 1H). MS (M+H, 264.3)

a. (R)—N-(1-hydroxy-4-methylpentan-2-yl)-3,4-dimethylbenzamide was prepared in a similar manner as described in example 4 using 3,4-dimethylbenzoic acid and with (R)-aminoleucinol. Yield: 75%. MS (M+H, 250.3).

The compound had an EC$_{50}$ for activation of a hT1R1/hT1R3 umami receptor expressed in an HEK293 cell line of 0.2 μM.

Example 72

(R)—N-(1-(methoxymethoxy)-4-methylpentan-2-yl)-3,4-dimethylbenzamide

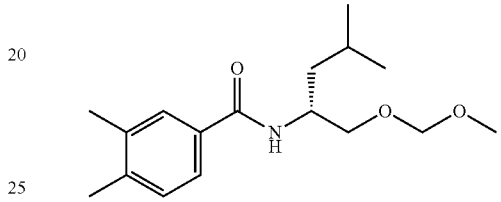

To a solution of (R)—N-(1-hydroxy-4-methylpentan-2-yl)-3,4-dimethylbenzamide (Example 71a) (0.24 mmol) dissolved in dry DMF (2 mL) was added at 0° C. powdered NaOH (0.36 mmol, 14.5 mg, 1.5 eq) and the mixture was stirred for 1 hr at 0° C. Then chloro-methoxy-methane (19.3 μl, 1 eq) was added and the reaction stirred at 0° C. for 1 hour. The reaction was quenched with water (30 mL) and the mixture was extracted with dichloromethane. The organic phase was dried over MgSO$_4$ and evaporated. The crude product was purified by preparative TLC (20% ethyl acetate/hexanes) to give 37.7 mg of (R)—N-(1-(methoxymethoxy)-4-methylpentan-2-yl)-3,4-dimethylbenzamide (53%). $^1$H NMR (500 MHz, CDCl$_3$): δ 0.98-1.00 (t, 6H), 1.49-1.53 (m, 1H), 1.58-1.64 (m, 1H), 1.69-1.73 (m, 2H), 2.32-2.33 (d, 6H), 3.38-3.39 (t, 3H), 3.64-3.72 (ddd, 2H), 4.41-4.44 (m, 1H), 4.65-4.69 (dd, 2H), 6.37-6.39 (d, 1H), 7.19-7.21 (d, 1H), 7.50-7.52 (dd, 1H), 7.60 (sb, 1H). MS (M+H, 294.3).

The compound had an EC$_{50}$ for activation of a hT1R1/hT1R3 umami receptor expressed in an HEK293 cell line of 1.06 μM.

Example 73

N-(1-Methoxymethyl-2-methyl-propyl)-3,4-dimethyl-benzamide

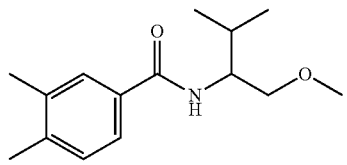

Prepared in a similar manner to example 71 using N-(1-hydroxy-3-methylbutan-2-yl)-3,4-dimethylbenzamide (example 73a) and methyl iodide. Yield 87%. $^1$H NMR (500 MHz, CDCl$_3$): δ 0.97-1.00 (dt, 6H), 1.96-2.00 (m, 1H), 2.29 (s, 3H), 2.30 (s, 3H), 3.35 (s, 3H), 3.42-3.45 (dd, 1H), 3.60-

3.62 (dd, 1H), 4.01-4.05 (m, 1H), 6.31-6.33 (d, 1H), 7.16-7.18 (d, 1H), 7.48-7.50 (dd, 1H), 7.56-7.57 (d, 1H). MS (M+H, 250).

a. N-(1-hydroxy-3-methylbutan-2-yl)-3,4-dimethylbenzamide was prepared in a similar manner to example 71a using 3,4-dimethoxybenzoic acid and 2-amino-3-methylbutan-1-ol. Yield 75%. MS (M+H, 236.2).

The compound had an $EC_{50}$ for activation of a hT1R1/hT1R3 umami receptor expressed in an HEK293 cell line of 0.87 μM.

Example 74

(R)-methyl 2-(2-methoxy-4-(methylthio)benzamido)-4-methylpentanoate

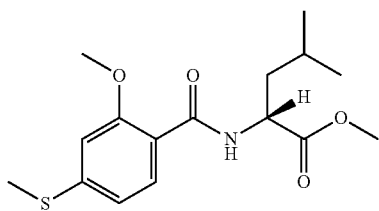

Prepared in a similar manner to example 4 using 2-methoxy-4-(methylthio)benzoic acid and D-leucine methyl ester. MS (M+H, 326).

The compound had an $EC_{50}$ for activation of a hT1R1/hT1R3 umami receptor expressed in an HEK293 cell line of 15.8 μM.

Example 75

N-(2-methylheptan-4-yl)benzo[d][1,3]dioxole-5-carboxamide

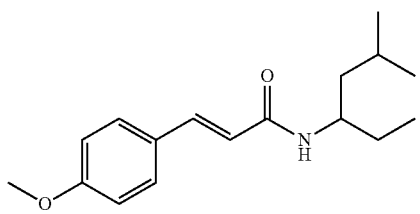

Prepared in a similar manner to example 4 using 3-(4-Methoxy-phenyl)-acrylic acid and 5-methylhexan-3-amine (example 5a). Yield: 59%. $^1$H NMR (500 MHz, CDCl$_3$): δ 0.93 (m, 9H); 1.33 (t, 2H); 1.43 (m, 1H); 1.58-1.67 (m, 2H); 3.83 (s, 3H); 4.11 (m, 1H); 5.19 (d, 1H); 6.25 (d, 1H); 6.88 (d, 2H); 7.44 (d, 2H); 7.58 (d, 1H). MS (276, M+H).

The compound had an $EC_{50}$ for activation of a hT1R1/hT1R3 umami receptor expressed in an HEK293 cell line of 0.24 μM.

Example 76

N-(1-Ethyl-propyl)-3-[4-(2-hydroxy-ethoxy)-phenyl]-acrylamide

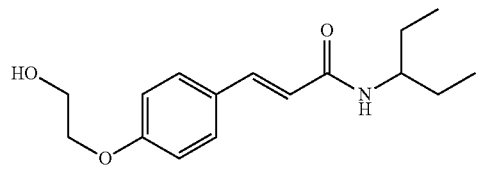

N-(1-Ethyl-propyl)-3-(4-hydroxy-phenyl)-acrylamide (example 76a) (0.44 mmol, 103 mg) was dissolved in absolute ethanol with KOH (0.7 mmol, 37 mg). The mixture was stirred at 80° C. for 1 hr. Then 2-chloro-ethanol (1.76 mmol, 118 μL) was added dropwise and the mixture was refluxed overnight. Following evaporation the crude product was dissolved in dichloromethane and washed with water and 5% citric acid. The organic phase was evaporated and the residue was purified by chromatography on silica gel to give 73 mg of desired product (60%). $^1$H NMR (500 MHz, CDCl$_3$): δ 0.92-0.95 (t, 6H), 1.25 (s, 1H), 1.40-1.46 (m, 2H), 1.59-1.64 (m, 2H), 3.93-3.94 (m, 1H), 3.95-3.98 (m, 2H), 4.09-4.11 (m, 2H), 5.28-5.30 (d, 1H), 6.26-6.29 (d, 1H), 6.88-6.90 (d, 2H), 7.43-7.45 (d, 2H), 7.56-7.59 (d, 1H). MS (M+H, 278.1).

a. N-(1-Ethyl-propyl)-3-(4-hydroxy-phenyl)-acrylamide was prepared in a similar manner as described in example 4 from 4-hydroxy-cinnamic acid and 3-pentylamine. MS (M+H, 234.10).

The compound had an $EC_{50}$ for activation of a hT1R1/hT1R3 umami receptor expressed in an HEK293 cell line of 5.8 μM.

Example 77

(E)-N-(heptan-4-yl)-3-(thiophen-2-yl)acrylamide

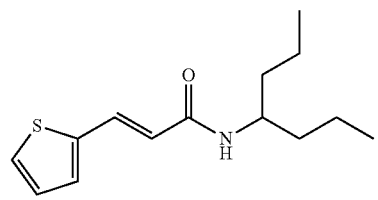

Prepared in a similar manner as described in example 4 from (E)-3-(thiophen-2-yl)acrylic acid and 4-hepthylamine. MS (M+H, 252).

The compound had an $EC_{50}$ for activation of a hT1R1/hT1R3 umami receptor expressed in an HEK293 cell line of 0.44 μM.

Example 78

(R,E)-methyl 4-methyl-2-oct-2-enamidopentanoate

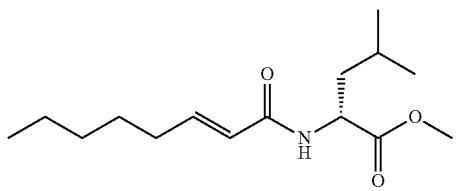

Prepared in a similar manner as described in example 4 from (E)-oct-2-enoic acid and D-leucine methyl ester. MS (M+H, 270).

The compound had an $EC_{50}$ for activation of a hT1R1/hT1R3 umami receptor expressed in an HEK293 cell line of 0.92 μM.

Example 79

3-(4-Methoxy-phenyl)-N-(3-methyl-1-propyl-butyl)-acrylamide

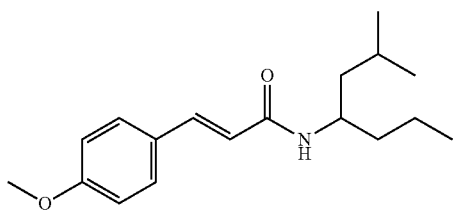

Prepared in a similar manner to example 4 using 3-(4-methoxy-phenyl)-acrylic acid and 3-methyl-1-propyl-butylamine (example 2a). Yield: 65%. $^1$H NMR (500 MHz, CDCl$_3$): δ 0.90-0.95 (m, 9H), 1.30-1.39 (m, 5H), 1.49-1.50 (m, 1H), 1.64-1.67 (m, 1H), 3.82 (s, 3H), 4.17-4.18 (m, 1H), 5.18-5.20 (d, 1H), 6.22-6.26 (d, 1H), 6.86-6.89 (d, 2H), 7.42-7.45 (d, 2H), 7.56-7.59 (d, 1H). MS (M+H, 290.1).

The compound had an $EC_{50}$ for activation of a hT1R1/hT1R3 umami receptor expressed in an HEK293 cell line of 1.84 μM.

Example 80

N-(1-Methoxymethyl-3-methyl-butyl)-3-(4-methoxy-phenyl)-acrylamide

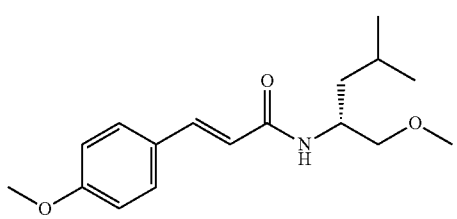

Prepared in a similar manner as described in example 71 from 3-(4-methoxyphenyl)-acrylic acid and D-leucinol. Yield: 41%. $^1$H NMR (500 MHz, CDCl$_3$): δ 0.93-0.96 (t, 6H), 1.38-1.42 (m, 1H), 1.48-1.54 (m, 1H), 1.63-1.66 (m, 1H), 3.36 (s, 3H), 3.41-3.46 (m, 2H), 3.82-3.83 (s, 3H), 4.29-4.31 (m, 1H), 5.69-5.71 (d, 1H), 6.24-6.27 (d, 1H), 6.87-6.89 (d, 2H), 7.43 (s, 1H), 7.44 (s, 1H), 7.56-7.59 (d, 1H). MS (M+H, 292.1).

The compound had an $EC_{50}$ for activation of a hT1R1/hT1R3 umami receptor expressed in an HEK293 cell line of 0.90 μM.

Example 81

N-(1-Benzyl-2-hydroxy-ethyl)-3-(4-methoxy-phenyl)-acrylamide

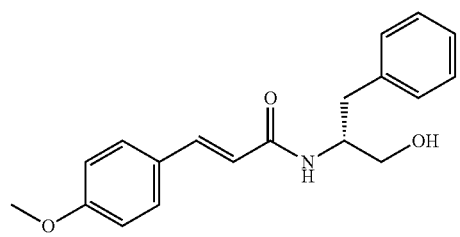

Prepared in a similar manner as described in example 4 from 3-(4-methoxyphenyl)-acrylic acid and D-phenylalaminol. MS (M+H, 312.3).

The compound had an $EC_{50}$ for activation of a hT1R1/hT1R3 umami receptor expressed in an HEK293 cell line of 1.1 μM.

Example 82

3-(4-Ethoxy-phenyl)-N-(1-ethyl-propyl)-acrylamide

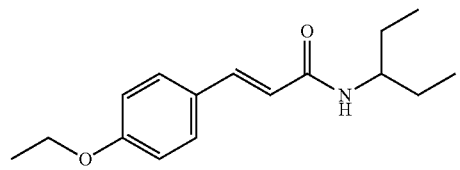

Prepared in a similar manner to example 4 using 3-(4-ethoxy-phenyl)-acrylic acid and 3-pentylamine. MS (M+H, 262.2).

The compound had an $EC_{50}$ for activation of a hT1R1/hT1R3 umami receptor expressed in an HEK293 cell line of 1.35 μM.

Example 83

4-Methyl-2-(3-thiophen-2-yl-acryloylamino)-pentanoic Acid Methyl Ester

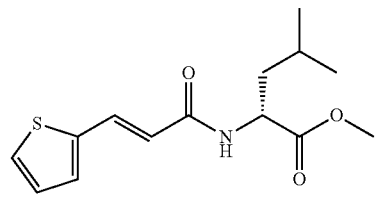

Prepared in a similar manner as described in example 4 from 3-thiophen-2-yl-acrylic acid and D-leucine methyl ester. MS (M+H, 282.2).

The compound had an $EC_{50}$ for activation of a hT1R1/hT1R3 umami receptor expressed in an HEK293 cell line of 0.59 μM.

Example 84

4-Methyl-pent-2-enoic Acid (1,2,3,4-tetrahydro-naphthalen-1-yl)-amide

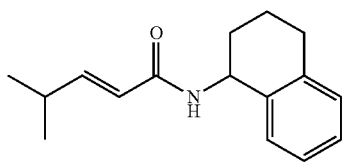

Prepared in a similar manner as described in example 4 from 4-methyl-pent-2-enoic acid and 1,2,3,4-tetrahydro-naphthalen-1-ylamine. MS (M+H, 244.2).

The compound had an $EC_{50}$ for activation of a hT1R1/hT1R3 umami receptor expressed in an HEK293 cell line of 1.5 μM.

Example 85

3-(2-Fluoro-phenyl)-N-(1-propyl-butyl)-acrylamide

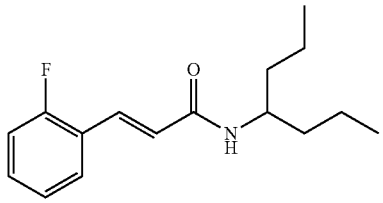

Prepared in a similar manner as described in example 4 from 3-(2-fluoro-phenyl)-acrylic acid and 4-heptylamine. MS (M+H, 264.2).

The compound had an $EC_{50}$ for activation of a hT1R1/hT1R3 umami receptor expressed in an HEK293 cell line of 0.16 μM.

Example 86

3-(2-Methoxy-phenyl)-N-(1-propyl-butyl)-acrylamide

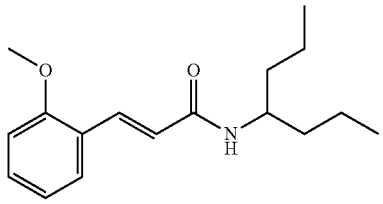

Prepared in a similar manner as described in example 4 from 3-(2-methoxyphenyl)-acrylic acid and 4-heptylamine. MS (M+H, 276.2).

The compound had an $EC_{50}$ for activation of a hT1R1/hT1R3 umami receptor expressed in an HEK293 cell line of 0.90 μM.

Example 87

3-(3,4-Dimethoxy-phenyl)-N-(1-propyl-butyl)-acrylamide

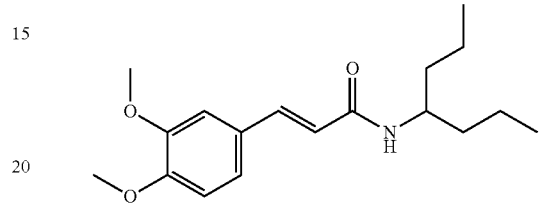

Prepared in a similar manner as described in example 4 from 3-(3,4-dimethoxyphenyl)-acrylic acid and 4-heptylamine. MS (M+H, 306.2).

The compound had an $EC_{50}$ for activation of a hT1R1/hT1R3 umami receptor expressed in an HEK293 cell line of 0.97 μM, and when present at 0.3 μM enhanced the effectiveness of monosodium glutamate with an $EC_{50}$ ratio of 2.4.

Example 89

3-(2-Methoxy-phenyl)-N-(2-methyl-cyclohexyl)-acrylamide

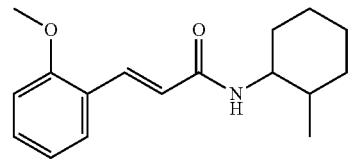

Prepared in a similar manner as described in example 4 from 3-(2-methoxyphenyl)-acrylic acid and 2-methyl-cyclohexylamine. MS (M+H, 274.2).

The compound had an $EC_{50}$ for activation of a hT1R1/hT1R3 umami receptor expressed in an HEK293 cell line of 3.4 μM Example 90

N-(heptan-4-yl)benzofuran-5-carboxamide

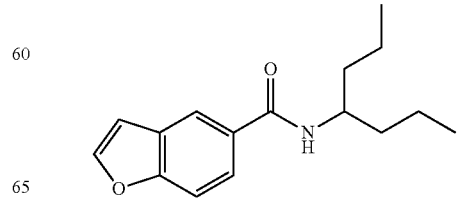

Prepared in a similar manner to example 4 using benzofuran-5-carboxylic acid and heptan-4-amine. Yield 41%. MS (M+H, 260.2).

The compound had an $EC_{50}$ for activation of a hT1R1/hT1R3 umami receptor expressed in an HEK293 cell line of 1.19 μM.

Example 91

N-(heptan-4-yl)-5,6-dimethylpicolinamide

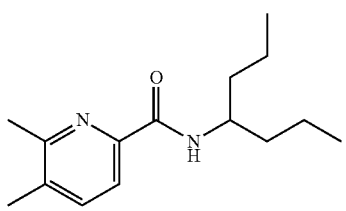

Prepared in a similar manner to example 4 using 5,6-Dimethylpicolinic acid (Example 91a) and 4-heptylamine. Yield: 49%. $^1$H NMR (500 MHz, CDCl$_3$): δ 0.91-0.94 (t, 6H), 1.38-1.48 (m, 4H), 1.49-1.61 (m, 4H), 2.32 (s, 3H), 2.52 (s, 3H), 4.11-4.13 (m, 1H), 7.52-7.53 (d, 1H), 7.93-7.94 (d, 1H). MS (M+H, 249.1).

a. 5,6-Dimethylpicolinic acid: 5,6-dimethylpicolinonitrile (example 91b) was refluxed in concentrated HCl (15 mL) overnight. The solvent was evaporated and the solid residue was co-evaporated several times with EtOH. Drying provided 453 mg of 5,6-Dimethylpicolinic acid (80%) as a white solid. MS (M+H, 152.1).

b. 5,6-dimethylpicolinonitrile: 2,3-lutidine (13.25 mmol) was refluxed overnight with 18 ml of glacial AcOH and 6 ml of hydrogen peroxide. The solvent was evaporated and the residue was co-evaporated two times with water, basified with Na$_2$CO$_3$ and extracted with chloroform. The organic layer was dried over Na$_2$SO$_4$ and evaporated to give 1.45 g of a crystalline product. The product (615 mg, 5 mmol) was reacted with trimethylsilane carbonitrile (5.5 mmol) in dichloromethane (10 mL) at room temperature for 5 min followed by addition of dimethylcarbamoyl chloride (5 mmol) and the solution was stirred at room temperature for 3 days. The reaction mixture was treated with 10% potassium carbonate (10 mL), the organic layer was separated and the aqueous layer was extracted 2 times with dichloromethane. The organic phase was dried over Na$_2$SO$_4$ and evaporated to give 495 mg of 5,6-dimethylpicolinonitrile (75%). $^1$H NMR (500 MHz, CDCl$_3$): δ 2.35 (s, 3H), 2.53 (s, 3H), 7.43-7.45 (d, 1H), 7.51-7.52 (d, 1H); [13]C: δ 19.71, 22.80, 117.87, 126.36, 130.60, 136.58, 137.66, 159.84). MS (M+H, 133.1).

The compound had an $EC_{50}$ for activation of a hT1R1/hT1R3 umami receptor expressed in an HEK293 cell line of 2.8 μM.

Example 92

4-(diethylamino)-N-(heptan-4-yl)benzamide

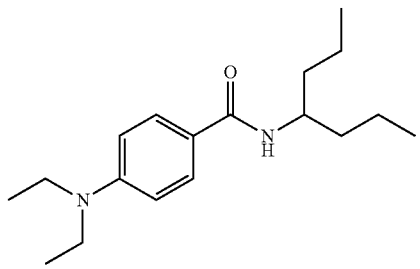

Prepared in a similar manner to example 4 using 4-diethylamino benzoic acid and 4-heptylamine. (31% %). $^1$H NMR (500 MHz, CDCl$_3$): δ 0.92 (t, 6H, J=7.17 Hz), 1.18 (t, 6H, J=7.04 Hz), 1.41 (m, 4H), 1.55 (m, 4H), 3.39 (m, 4H), 4.15 (m, 1H), 5.62 (m, 1H), 6.64 (d, 2H, J=10.26 Hz), 7.64 (d, 2H, J=10.26 Hz). MS (M+H, 291).

The compound had an $EC_{50}$ for activation of a hT1R1/hT1R3 umami receptor expressed in an HEK293 cell line of 7.6 μM.

Example 93

(R)-methyl 2-(2,6-dimethoxyisonicotinamido)-4-methylpentanoate

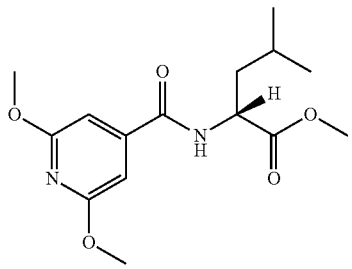

Prepared in a similar manner to example 4 using 2,6-Dimethoxy-isonicotinic acid and D-leucine methyl ester. $^1$H NMR (500 MHz, CDCl$_3$): δ 0.92 (d, 3H, J=7.27 Hz), 0.93 (d, 3H, J=7.26 Hz), 1.41-1.58 (m, 8H), 3.95 (s, 3H), 4.08 (s, 3H), 4.15 (m, 1H), 6.43 (d, 1H, J=8.32 Hz), 7.47 (m, broad, 1H), 8.41 (d, 1H, J=8.34 Hz). MS (M+H; 311).

The compound had an $EC_{50}$ for activation of a hT1R1/hT1R3 umami receptor expressed in an HEK293 cell line of 1.91 μM.

Example 94

N-(heptan-4-yl)-6-methoxynicotinamide

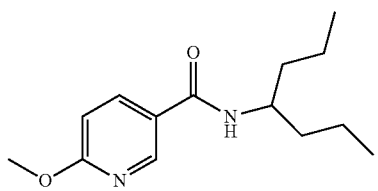

Prepared in a similar manner to example 4 using sodium 6-methoxynicotinate (example 94a) and 4-hepthylamine. Yield: 44%. MS (M+H, 251).

a. methyl 6-methoxynicotinate (2.097 g, 12.56 mmol) was dissolved in dioxane (30 mL). An aqueous solution of NaOH (1.0N, 25 mL) was added to the solution and the mixture was stirred at room temperature overnight. The solvent was removed under reduced pressure to provide 2.2 g of sodium 6-methoxynicotinate.

The compound had an $EC_{50}$ for activation of a hT1R1/hT1R3 umami receptor expressed in an HEK293 cell line of 2.66 μM.

Example 95

5,6-dimethylpyrazine-2-carboxylic Acid (1-propylbutyl)amide

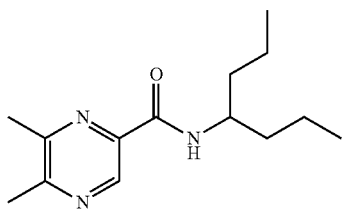

Prepared in a similar manner to example 4 using 5,6-dimethyl-pyrazine-2-carboxylic acid (example 95a) and 4-heptylamine. $^1$H NMR (500 MHz, CDCl$_3$): δ 0.91-0.94 (t, 6H), 1.35-1.42 (m, 4H), 1.48-1.51 (m, 2H), 1.55-1.60 (m, 2H), 2.57-2.60 (d, 6H), 4.13-4.16 (m, 1H), 7.52-7.53 (d, 1H), 9.09 (s, 1H); MS (M+H, 250).

a. 5,6-dimethyl-pyrazine-2-carboxylic acid: To a solution of 2,3-diaminopropionic acid (1.0 g, 9.6 mmol) in methanol (20 mL) was added butane-2,3-dione (728 μL; 11.5 mmol) and NaOH (1.4 g; 56.6 mmol). The mixture was refluxed for 2 h and then cooled to room temperature while air was bubbled through for 1 hour. The white precipitate was filtered and the gelatinous product was concentrated under vacuum. The crude product was taken up in dichloromethane, washed with 10% citric acid, dried over MgSO$_4$ and filtered. The solvent was removed under reduced pressure to give 5,6-dimethyl-pyrazine-2-carboxylic acid as a volatile solid. The compound was used as is in the next step.

The compound had an $EC_{50}$ for activation of a hT1R1/hT1R3 umami receptor expressed in an HEK293 cell line of 1.01 μM.

Example 96

2-chloro-N-(heptan-4-yl)-6-methylnicotinamide

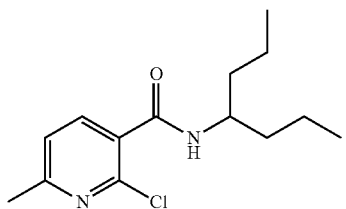

Prepared in a similar manner to example 4 using 2-chloro-6-methylnicotinic acid and 4-Heptylamine. MS (M+H, 269).

The compound had an $EC_{50}$ for activation of a hT1R1/hT1R3 umami receptor expressed in an HEK293 cell line of 3.9 μM.

Example 97

2-cyano-N-(heptan-4-yl)-4-methoxybenzamide

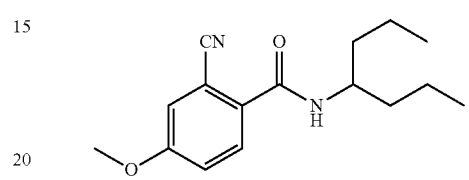

Prepared in a similar manner to example 4 using 2-cyano-4-methoxybenzoic acid and 4-Heptylamine. Yield: 73%. $^1$H NMR (CD$_3$OD): δ0.94 (t, 6H, J=7.3 Hz), 1.38 (m, 4H), 1.53 (m, 4H), 4.02 (s, 3H), 4.12 (m, 1H), 7.27 (d, 1H, J=9.40 Hz), 8.11 (d, 2H, J=2.21 Hz). MS (M+H, 275).

The compound had an $EC_{50}$ for activation of a hT1R1/hT1R3 umami receptor expressed in an HEK293 cell line of 1.39 μM, and when present at 1 μM enhanced the effectiveness of monosodium glutamate with an $EC_{50}$ ratio of 4.52.

Example 98

(R)-methyl 2-(2,3-dimethylfuran-5-carboxamido)-4-methylpentanoate

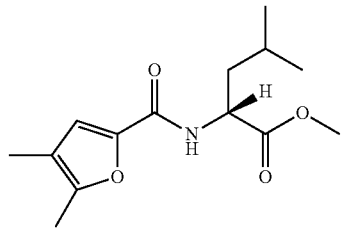

Prepared in a similar manner to example 4 using 4,5-dimethyl-furan-2-carboxylic acid and D-leucine methyl ester. Yield: 27%. $^1$H NMR (500 MHz, CDCl$_3$): δ 0.96 (t, 6H), 1.66 (m, 3H), 1.96 (s, 3H), 2.26 (s, 3H), 3.75 (s, 3H), 4.78 (m, 1H), 6.51 (d, 1H), 6.89 (s, 1H). MS (M+H, 268).

The compound had an $EC_{50}$ for activation of a hT1R1/hT1R3 umami receptor expressed in an HEK293 cell line of 0.59 μM.

Example 99

N-(heptan-4-yl)-1,3-dimethyl-1H-pyrazole-5-carboxamide

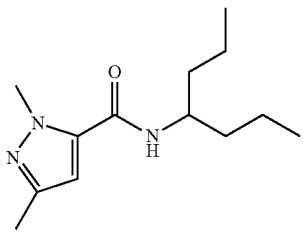

Prepared in a similar manner to example 4 using 1,3-dimethyl-1H-pyrazole-5-carboxylic acid and 4-heptylamine. $^1$H NMR (500 MHz, CDCl$_3$): δ 0.90 (t, 6H, J=7.2 Hz), 1.41 (m, 4H), 1.50 (m, 4H), 2.27 (s, 3H), 3.77 (s, 3H), 4.09 (m, 1H), 6.49 (d, 1H), 6.53 (s, 1H). MS (M+H, 238).

The compound had an EC$_{50}$ for activation of a hT1R1/hT1R3 umami receptor expressed in an HEK293 cell line of 7.8 μM.

Example 100

N-(heptan-4-yl)-2-methylthiazole-4-carboxamide

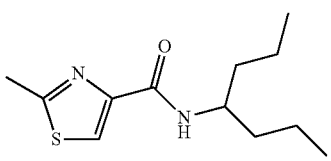

Prepared in a similar manner to example 4 using 1,3-dimethyl-1H-pyrazole-5-carboxylic acid and 4-heptylamine. MS (M+H, 241).

The compound had an EC$_{50}$ for activation of a hT1R1/hT1R3 umami receptor expressed in an HEK293 cell line of 7.2 μM.

Example 101

N-(heptan-4-yl)quinoline-6-carboxamide

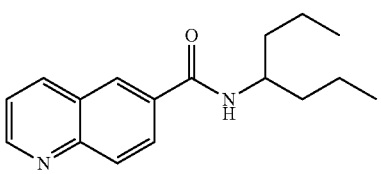

Prepared in a similar manner to example 4 using quinoline-6-carboxylic acid and 4-hepthylamine. $^1$H NMR (500 MHz, CDCl$_3$) δ 0.96 (t, J=7.2 Hz, 6H), 1.42-1.58 (m, 6H), 1.62-1.70 (m, 2H), 4.18-4.20 (m, 1H), 5.95 (d, J=9.0 Hz, 1H), 7.49 (br s, 1H), 8.04 (dd, J=8.5, 1.5 Hz, 1H), 8.17 (d, J=8.5 Hz, 1H), 8.27 (d, J=8.2 Hz, 1H), 8.30 (s, 1H), 8.99 (br s, 1H); MS (M+H, 271.2).

The compound had an EC$_{50}$ for activation of a hT1R1/hT1R3 umami receptor expressed in an HEK293 cell line of 3.2 μM.

Example 102

N-(heptan-4-yl)quinoline-3-carboxamide

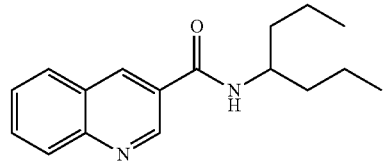

Prepared in a similar manner to example 4 using quinoline-3-carboxylic acid and hepthylamine: $^1$H NMR (500 MHz, CDCl$_3$) δ 0.96 (t, J=7.3 Hz, 6H), 1.40-1.58 (m, 6H), 1.60-1.67 (m, 2H), 4.20-4.30 (m, 1H), 6.01 (d, J=8.8 Hz, 1H), 7.61 (t, J=7.5, 1H), 7.80 (t, J=7.6 Hz, 1H), 7.90 (d, J=8.1 Hz, 1H), 8.15 (d, J=8.5 Hz, 1H), 8.57 (d, J=1.2 Hz, 1H), 9.26 (br s, 1H); MS (M+H, 271.2).

The compound had an EC$_{50}$ for activation of a hT1R1/hT1R3 umami receptor expressed in an HEK293 cell line of 15.8 μM.

Example 103

N-(heptan-4-yl)isoquinoline-1-carboxamide

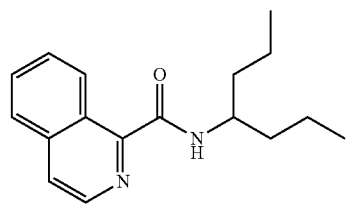

Prepared in a similar manner to example 4 using isoquinoline-1-carboxylic acid and heptamine: $^1$H NMR (500 MHz, CDCl$_3$) δ 0.98 (t, J=7.05 Hz, 6H), 1.42-1.56 (m, 6H), 1.58-1.66 (m, 2H), 4.20-4.32 (m, 1H), 5.83 (d, J=9.1 Hz, 1H), 7.36 (d, J=4.2, 1H), 7.60 (t, J=7.7 Hz, 1H), 7.75 (t, J=7.7 Hz, 1H), 8.11 (d, J=8.5 Hz, 1H), 8.18 (d, J=8.4 Hz, 1H), 8.88 (d, J=4.9, 1H); MS (APCI, M+): 271.2.

The compound had an EC$_{50}$ for activation of a hT1R1/hT1R3 umami receptor expressed in an HEK293 cell line of 14.2 μM.

Example 104

4-Methoxy-N-(1-methoxymethyl-3-methyl-butyl)-3-methyl-benzamide

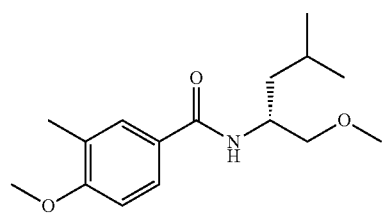

Prepared in a similar manner as described in example 71 from 4-methoxy-3-methylbenzoic acid and D-leucinol. Yield: 86%. $^1$H NMR (500 MHz, CDCl$_3$): δ 0.94-0.97 (t, 6H), 1.42-1.47 (m, 1H), 1.54-1.60 (m, 1H), 1.64-1.68 (m, 2H), 2.24 (s, 3H), 3.37 (s, 3H), 3.46-3.48 (m, 2H), 3.87 (s, 3H), 4.35-4.38 (m, 1H), 6.14-6.16 (d, 1H), 6.82-6.84 (d, 1H), 7.56 (d, 1H), 7.61-7.63 (dd, 1H). MS (M+H, 280.3).

The compound had an EC$_{50}$ for activation of a hT1R1/hT1R3 umami receptor expressed in an HEK293 cell line of 0.24 µM.

Example 105

N-(4-(trifluoromethoxy)benzyl)thiophene-2-carboxamide

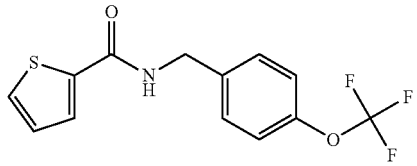

Prepared in a similar manner as described in example 4 from thiophene-2-carboxylic acid and (4-(trifluoromethoxy)phenyl)methanamine. MS (M+H, 303).

The compound had an EC$_{50}$ for activation of a hT1R1/hT1R3 umami receptor expressed in an HEK293 cell line of 2.4 µM.

Example 106

N-(2-(furan-2-ylmethylthio)ethyl)-4-methoxy-3-methylbenzamide

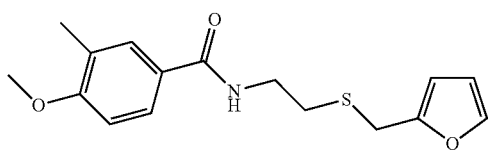

Prepared in a similar manner as described in example 4 from 4-methoxy-3-methylbenzoic acid and 2-(furan-2-ylmethylthio)ethanamine. Yield 58%. $^1$H NMR (500 MHz, CDCl$_3$) 2.23 (s, 3H), 2.76 (t, 2H, J=6.37 Hz), 3.59 (q, 2H, J=12.2 Hz), 3.76 (s, 2H), 3.86 (s, 3H), 6.22 (dd, 1H, J=3.49 Hz, J=2.67 Hz), 6.30 (dd, 1H, J=3.04 Hz, J=1.78 Hz), 6.46 (m, 1H, broad), 6.83 (d, 1H, J=8.51 Hz), 7.34 (dd, 1H, J=1.97 Hz, J=1 Hz), 7.56 (d, 1H, J=1.72 Hz), 7.61 (dd, 1H, J=8.53 Hz, J=2.25 Hz). MS (M+H, 306).

The compound had an EC$_{50}$ for activation of a hT1R1/hT1R3 umami receptor expressed in an HEK293 cell line of 5.6 µM.

Example 107

Thiophene-3-carboxylic acid 4-trifluoromethoxy-benzylamide

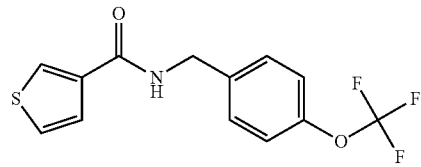

Prepared in a similar manner to example 4 using thiophene-3-carboxylic acid and 4-trifluoromethoxy-benzylamine. MS (M+H, 302.0).

The compound had an EC$_{50}$ for activation of a hT1R1/hT1R3 umami receptor expressed in an HEK293 cell line of 2.2 µM, and when present at 3 µM enhanced the effectiveness of monosodium glutamate with an EC$_{50}$ ratio of 8.5.

Example 108

3-Methyl-thiophene-2-carboxylic Acid 2,4-dimethoxy-benzylamide

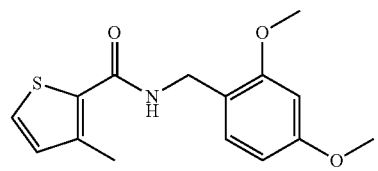

Prepared in a similar manner to example 4 using 3-methyl-thiophene-2-carboxylic acid and 2,4-dimethoxy-benzylamine. MS (M+H, 292.2).

The compound had an EC$_{50}$ for activation of a hT1R1/hT1R3 umami receptor expressed in an HEK293 cell line of 5.6 µM, and when present at 3 µM enhanced the effectiveness of monosodium glutamate with an EC$_{50}$ ratio of 5.8.

Example 109

5-Pyridin-2-yl-thiophene-2-carboxylic Acid 2,4-dimethoxy-benzylamide

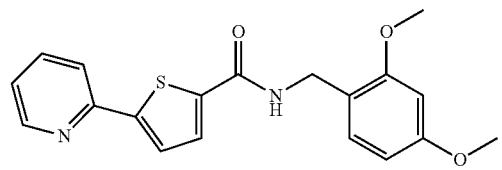

Prepared in a similar manner to example 4 using 5-pyridin-2-yl-thiophene-2-carboxylic acid and 2,4-dimethoxy-benzylamine. MS (M+H, 355.2).

The compound had an EC$_{50}$ for activation of a hT1R1/hT1R3 umami receptor expressed in an HEK293 cell line of

Example 110

2-Methyl-2H-pyrazole-3-carboxylic Acid 2,4-dimethoxy-benzylamide

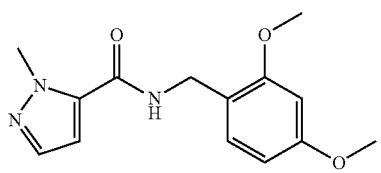

Prepared in a similar manner to example 4 using 2-methyl-2H-pyrazole-3-carboxylic acid and 2,4-dimethoxy-benzylamine. MS (M+H, 276.2).

The compound had an $EC_{50}$ for activation of a hT1R1/hT1R3 umami receptor expressed in an HEK293 cell line of 6 μM, and when present at 3 μM enhanced the effectiveness of monosodium glutamate with an $EC_{50}$ ratio of 7.9.

Example 111

4-Hydroxy-3-methyl-N-(1-methyl-3-phenyl-propyl)-benzamide

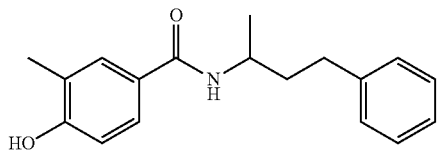

Prepared in a similar manner to example 4 using 4-hydroxy-3-methyl-benzoic acid and 1-methyl-3-phenyl-propylamine. MS (M+H, 284.2)

The compound had an $EC_{50}$ for activation of a hT1R1/hT1R3 umami receptor expressed in an HEK293 cell line of 2.7 μM, and when present at 0.3 μM enhanced the effectiveness of monosodium glutamate with an $EC_{50}$ ratio of 7.

Example 112

Benzo[1,3]dioxole-5-carboxylic Acid [2-(4-ethyl-phenyl)-ethyl]-amide

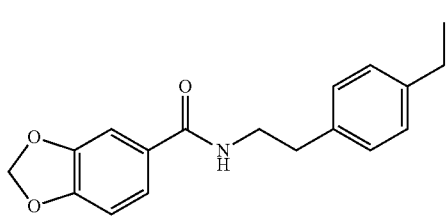

Prepared in a similar manner to example 4 using benzo[1,3]dioxole-5-carboxylic acid and 2-(4-ethyl-phenyl)-ethylamine. MS (M+H, 298.2).

The compound had an $EC_{50}$ for activation of a hT1R1/hT1R3 umami receptor expressed in an HEK293 cell line of 3.86 μM.

Example 113

4-Methoxy-3-methyl-N-(1-phenyl-butyl)-benzamide

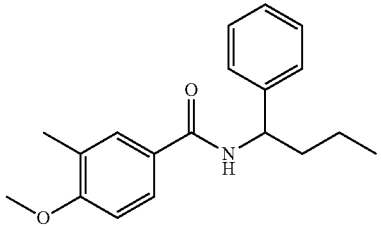

Prepared in a similar manner to example 4 using 4-methoxy-3-methyl-benzoic acid and 1-phenyl-butylamine. MS (M+H, 298.2).

The compound had an $EC_{50}$ for activation of a hT1R1/hT1R3 umami receptor expressed in an HEK293 cell line of 2.5 μM.

Example 114

4-Methoxy-3-methyl-N-(1-pyridin-2-yl-butyl)-benzamide

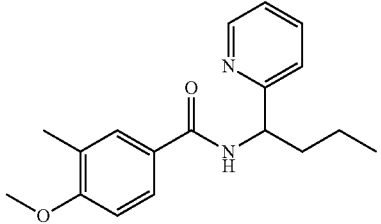

Prepared in a similar manner to example 4 using 4-methoxy-3-methyl-benzoic acid and 1-pyridin-2-yl-butylamine. $^1$H NMR (500 MHz, CDCl$_3$): δ 0.91-0.92 (t, 3H), 1.25-1.3 (m, 2H, 1.85-1.9 (m, 2H), 3.86 (s, 3H), 5.25-5.3 (m, 1H), 6.80-6.82 (d, 1H), 7.2-7.3 (m, 2H), 7.42-7.44 (d, 1H), 7.6-7.7 (m, 3H), 8.6 (d, 1H). MS (M+H, 299.1).

The compound had an $EC_{50}$ for activation of a hT1R1/hT1R3 umami receptor expressed in an HEK293 cell line of 1.54 μM.

Example 115

Benzo[1,3]dioxole-5-carboxylic Acid [1-(4-methoxy-phenyl)-butyl]-amide

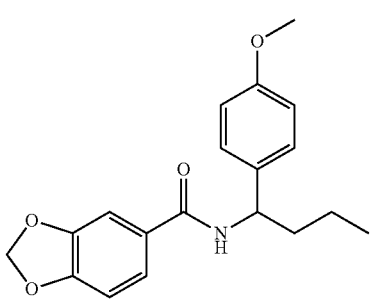

Prepared in a similar manner to example 4 using benzo[1,3]dioxole-5-carboxylic acid and 1-(4-methoxy-phenyl)-butylamine. $^1$H NMR (500 MHz, CDCl$_3$): δ 0.93-0.95 (t, 3H), 1.30-1.39 (m, 2H), 1.80-1.90 (m, 2H), 3.79 (s, 3H), 5.08-5.09 (dd, 1H), 6.00 (s, 2H), 6.10-6.12 (d, 1H), 6.79-6.80 (d, 1H), 6.87 (s, 1H), 6.88 (s, 1H), 7.25-7.28 (m, 4H). MS (M+H, 328.1).

The compound had an EC$_{50}$ for activation of a hT1R1/hT1R3 umami receptor expressed in an HEK293 cell line of 4.12 μM.

Example 116

4-Ethoxy-N-[1-(4-methoxy-phenyl)-butyl]-3-methyl-benzamide

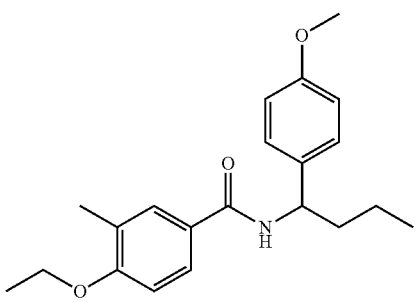

Prepared in a similar manner to example 4 using 4-ethoxy-3-methyl-benzoic acid and 1-(4-methoxy-phenyl)-butylamine. $^1$H NMR (500 MHz, CDCl$_3$): δ 0.93-0.96 (t, 3H), 1.31-1.41 (m, 2H), 1.41-1.45 (t, 3H), 1.82-1.92 (m, 2H), 2.28 (s, 3H), 3.79 (s, 3H), 4.04-4.08 (q, 2H), 5.10-5.12 (d, 1H), 6.12-6.14 (d, 1H), 6.78-6.80 (d, 1H), 6.87 (s, 1H), 6.88 (s, 1H), 7.26-7.29 (m, 2H), 7.52-7.53 (d, 1H), 7.57-7.59 (d, 1H). MS (M+H, 342.1).

The compound had an EC$_{50}$ for activation of a hT1R1/hT1R3 umami receptor expressed in an HEK293 cell line of 3.9 μM.

Example 117

4-Methoxy-N-[1-(R)-(4-methoxy-phenyl)-ethyl]-3-methyl-benzamide

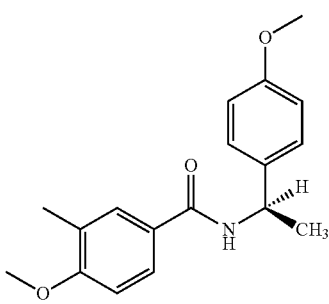

Prepared in a similar manner to example 4 using 4-methoxy-3-methyl-benzoic acid and 1-(R)-(4-methoxy-phenyl)-ethylamine. MS (M+H, 300.1).

The compound had an EC$_{50}$ for activation of a hT1R1/hT1R3 umami receptor expressed in an HEK293 cell line of 2.8 μM.

Example 118

Benzo[1,3]dioxole-5-carboxylic Acid indan-1-ylamide

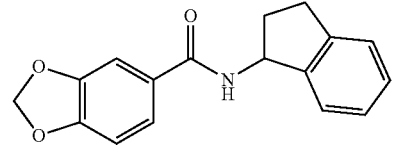

Prepared in a similar manner to example 4 using benzo[1,3]dioxole-5-carboxylic acid and indan-1-ylamine. MS (M+H, 282.2).

The compound had an EC$_{50}$ for activation of a hT1R1/hT1R3 umami receptor expressed in an HEK293 cell line of 1.2 μM, and when present at 0.3 μM enhanced the effectiveness of monosodium glutamate with an EC$_{50}$ ratio of 5.33.

Example 119

4-methoxy-3-methyl-N-(pentan-3-yl)benzamide

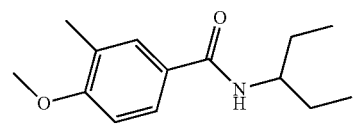

Prepared in a similar manner as described in example 4 from 4-methoxy-3-methylbenzoic acid and pentan-3-amine. MS (M+H, 236)

The compound had an EC$_{50}$ for activation of a hT1R1/hT1R3 umami receptor expressed in an HEK293 cell line of 0.4 μM.

Example 120

3-methyl-N-(p-tolylethyl)furan-2-carboxamide

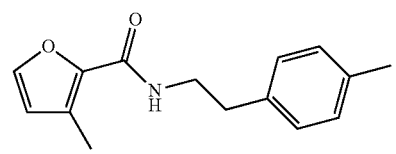

Prepared in a similar manner as described in example 4 from 3-methylfuran-2-carboxylic acid and 2-p-tolylethanamine. MS (M+H, 244).

The compound had an EC$_{50}$ for activation of a hT1R1/hT1R3 umami receptor expressed in an HEK293 cell line of 6 μM, and when present at 1 μM enhanced the effectiveness of monosodium glutamate with an EC$_{50}$ ratio of 3.3.

Example 121

N-(2,4-dimethoxybenzyl)-2-(1H-pyrrol-1-yl)benzamide

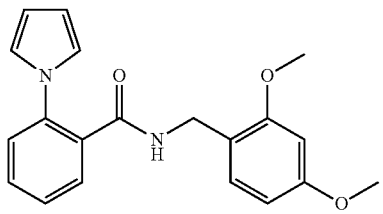

Prepared in a similar manner to example 4 using 1-(2-(1H-pyrrol-1-yl)phenyl)ethanone and 2,4-dimethoxy-benzylamine. MS (M+H, 337.2).

The compound had an $EC_{50}$ for activation of a hT1R1/hT1R3 umami receptor expressed in an HEK293 cell line of 1.66 μM, and when present at 1 μM enhanced the effectiveness of monosodium glutamate with an $EC_{50}$ ratio of 11.

Additional "amide" compounds that were synthesized and experimentally tested and found to have a relatively high level of effectiveness as an activator of a hT1R1/hT1R3 umami receptor expressed in an HEK293 cell line. The results of that testing are shown below in Table A.

TABLE A

| | Umami Amides | | | |
|---|---|---|---|---|
| Compound No. | Compound | Umami $EC_{50}$ (uM) | $EC_{50}$ ratio (vs. MSG) | @ (uM) |
| A1 | 3,6-Dichloro-N-(4-ethoxy-phenyl)-2-methoxy-benzamide | 0.22 | 2.74 | 1 |
| A2 | 4-(3,6-Dichloro-2-methoxy-benzoylamino)-benzoic acid methyl ester | 0.93 | 6.98 | 0.01 |
| A3 c | 2,5-dichloro-N-(4-ethoxyphenyl)benzamide | 1.08 | 6.14 | 0.03 |
| A4 | 2-[(Benzo[b]thiophene-2-carbonyl)-amino]-4-methyl-pentanoic acid methyl ester | 0.4 | | |

TABLE A-continued

Umami Amides

| Compound No. | Compound | Umami EC$_{50}$ (uM) | Ec$_{50}$ ratio (vs. MSG) | @ (uM) |
|---|---|---|---|---|
| A5 | 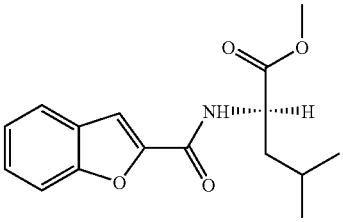<br>2-[(Benzofuran-2-carbonyl)-amino]-4-methyl-pentanoic acid methyl ester | 0.31 | | |
| A6 | 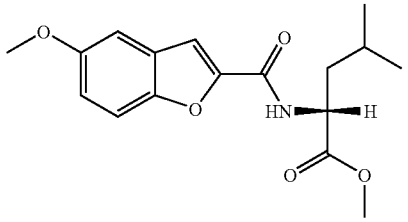<br>2-[(5-Methoxy-benzofuran-2-carbonyl)-amino]-4-methyl-pentanoic acid methyl ester | 0.32 | 2.86 | 1 |
| A7 | 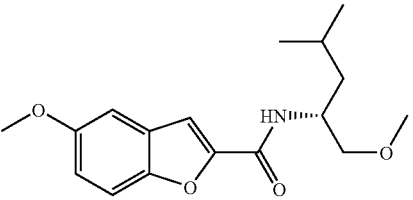<br>(R)-5-methoxy-N-(1-methoxy-4-methylpentan-2-yl)benzofuran-2-carboxamide | 0.46 | | |
| A8 | 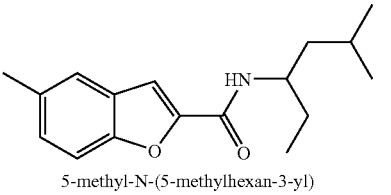<br>5-methyl-N-(5-methylhexan-3-yl)benzofuran-2-carboxamide | 0.5 | | |
| A9 | 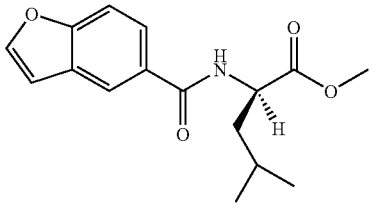<br>2-[(Benzofuran-5-carbonyl)-amino]-4-methyl-pentanoic acid methyl ester(R)-methyl 2-(benzofuran-5-carboxamido)-4-methylpentanoate | 0.71 | | |

TABLE A-continued

Umami Amides

| Compound No. | Compound | Umami $EC_{50}$ (uM) | $Ec_{50}$ ratio (vs. MSG) | @ (uM) |
|---|---|---|---|---|
| A10 | 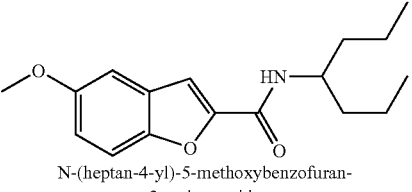<br>N-(heptan-4-yl)-5-methoxybenzofuran-2-carboxamide | 0.91 | 4.51 | 1 |
| A11 | 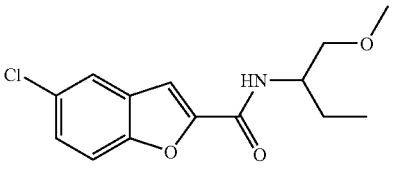<br>5-chloro-N-(1-methoxybutan-2-yl)benzofuran-2-carboxamide | 1.05 | 6.5 | 0.3 |
| A12 | 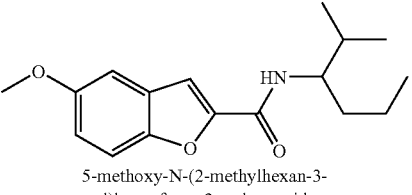<br>5-methoxy-N-(2-methylhexan-3-yl)benzofuran-2-carboxamide | 1.13 | | |
| A13 | 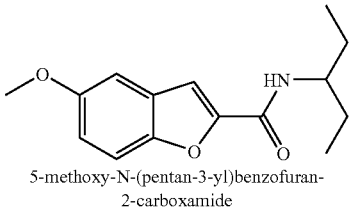<br>5-methoxy-N-(pentan-3-yl)benzofuran-2-carboxamide | 1.14 | 4.46 | 1 |
| A14 | 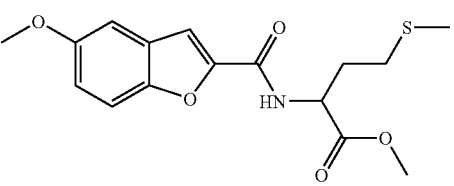<br>2-[(5-Methoxy-benzofuran-2-carbonyl)-amino]-4-methylsulfanyl-butyric acid methyl ester methyl 2-(5-methoxybenzofuran-2-carboxamido)-4-(methylthio)butanoate | 1.14 | | |
| A15 | 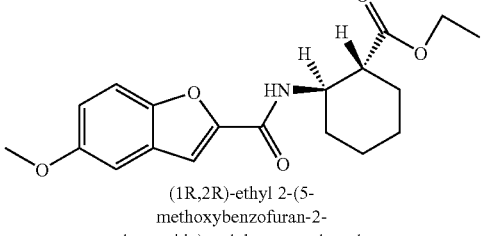<br>(1R,2R)-ethyl 2-(5-methoxybenzofuran-2-carboxamido)cyclohexanecarboxylate | 1.14 | | |

TABLE A-continued

Umami Amides

| Compound No. | Compound | Umami EC$_{50}$ (uM) | Ec$_{50}$ ratio (vs. MSG) | @ (uM) |
|---|---|---|---|---|
| A16 | 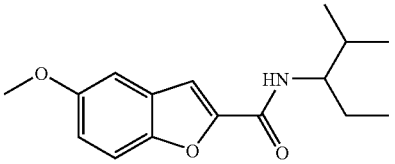<br>5-methoxy-N-(2-methylpentan-3-yl)benzofuran-2-carboxamide | 1.18 | | |
| A17 | 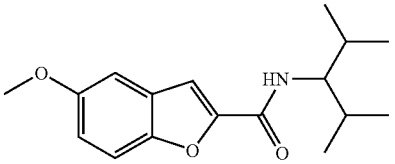<br>N-(2,4-dimethylpentan-3-yl)-5-methoxybenzofuran-2-carboxamide | 1.2 | | |
| A18 | 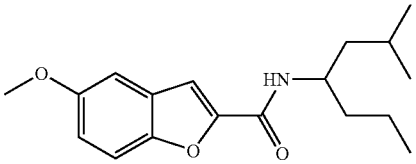<br>5-methoxy-N-(2-methylheptan-4-yl)benzofuran-2-carboxamide | 1.27 | | |
| A19 | 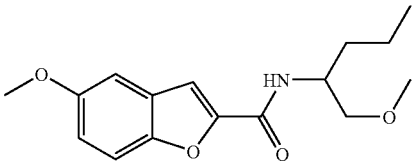<br>5-methoxy-N-(1-methoxypentan-2-yl)benzofuran-2-carboxamide | 1.3 | | |
| A20 | 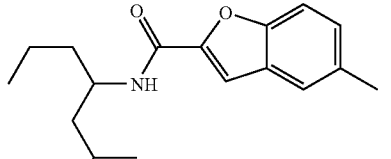<br>5-methyl-N-(2-methylheptan-4-yl)benzofuran-2-carboxamide | 1.32 | | |
| A21 | 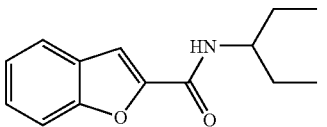<br>N-(pentan-3-yl)benzofuran-2-carboxamide | 1.52 | 3.74 | 1 |

TABLE A-continued

| Umami Amides | | | | |
|---|---|---|---|---|
| Compound No. | Compound | Umami EC$_{50}$ (uM) | Ec$_{50}$ ratio (vs. MSG) | @ (uM) |
| A22 | 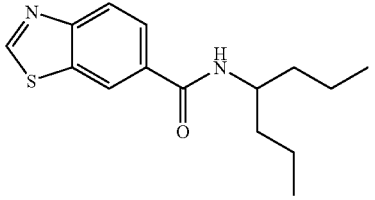<br>Benzothiazole-6-carboxylic acid (1-propyl-butyl)-amide | 1.58 | | |
| A23 | 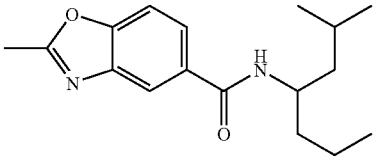<br>2-methyl-N-(2-methylheptan-4-yl)benzo[d]oxazole-5-carboxamide | 0.38 | | |
| A24 | 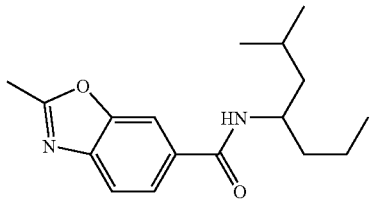<br>2-methyl-N-(2-methylheptan-4-yl)benzo[d]oxazole-6-carboxamide | 1.12 | | |
| A25 | 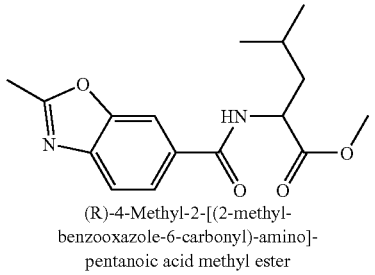<br>(R)-4-Methyl-2-[(2-methyl-benzooxazole-6-carbonyl)-amino]-pentanoic acid methyl ester | 1.48 | | |
| A26 | 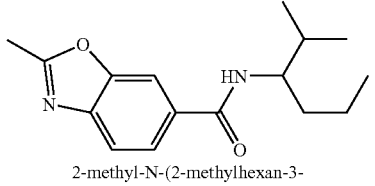<br>2-methyl-N-(2-methylhexan-3-yl)benzo[d]oxazole-6-carboxamide | 1.6 | | |
| A27 | 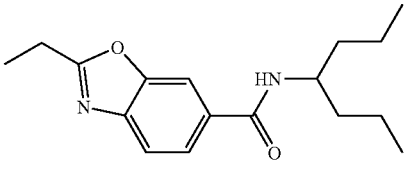<br>2-ethyl-N-(heptan-4-yl)benzo[d]oxazole-6-carboxamide | 1.61 | | |

TABLE A-continued

Umami Amides

| Compound No. | Compound | Umami EC$_{50}$ (uM) | Ec$_{50}$ ratio (vs. MSG) | @ (uM) |
|---|---|---|---|---|
| A28 | 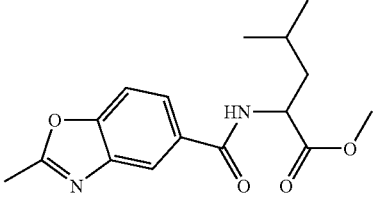<br>(R)-4-Methyl-2-[(2-methyl-benzooxazole-5-carbonyl)-amino]-pentanoic acid methyl ester | 1.69 | | |
| A29 | 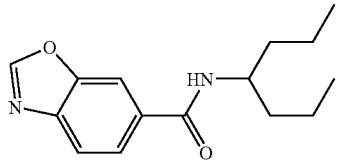<br>N-(heptan-4-yl)benzo[d]oxazole-6-carboxamide | 1.91 | | |
| A30 | 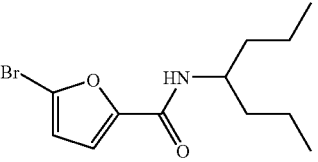<br>5-bromo-N-(heptan-4-yl)furan-2-carboxamide | 0.49 | 12.6 | 1 |
| A31 | 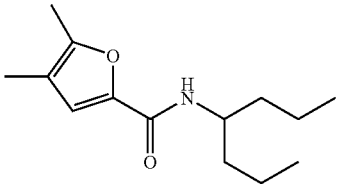<br>N-(heptan-4-yl)-4,5-dimethylfuran-2-carboxamide | 0.62 | 10.04 | 1 |
| A32 | 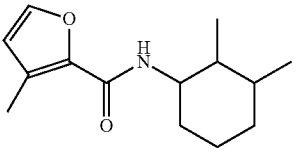<br>N-(2,3-dimethylcyclohexyl)-3-methylfuran-2-carboxamide | 1.15 | | |
| A33 | 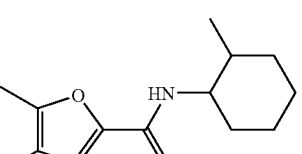<br>4,5-dimethyl-N-(2-methylcyclohexyl)furan-2-carboxamide | 1.33 | | |

TABLE A-continued

Umami Amides

| Compound No. | Compound | Umami EC$_{50}$ (uM) | Ec$_{50}$ ratio (vs. MSG) | @ (uM) |
|---|---|---|---|---|
| A34 | (R)-methyl 2-(1H-indole-2-carboxamido)-4-methylpentanoate | 0.53 | | |
| A35 | N-(heptan-4-yl)-1H-indole-6-carboxamide | 0.82 | 8.81 | 1 |
| A36 | (R)-methyl 2-(1H-indole-5-carboxamido)-4-methylpentanoate | 1.01 | | |
| A37 | (R)-methyl 4-methyl-2-(quinoline-6-carboxamido)pentanoate | 1.5 | | |
| A38 | 5-Methyl-thiophene-2-carboxylic acid (1-propyl-butyl)-amide | 1.22 | 6.54 | 1 |
| A39 | 5-Methyl-thiophene-2-carboxylic acid (1,2,3,4-tetrahydro-naphthalen-1-yl)-amide | 1.31 | 2.3 | 1 |

TABLE A-continued

Umami Amides

| Compound No. | Compound | Umami EC$_{50}$ (uM) | Ec$_{50}$ ratio (vs. MSG) | @ (uM) |
|---|---|---|---|---|
| A40 | (R)-methyl 2-(2-naphthamido)-4-methylpentanoate | 0.37 | | |
| A41 | N-(nonan-5-yl)benzo[d][1,3]dioxole-5-carboxamide | 0.7 | 2.14 | 3 |
| A42 | (2R,3R)-methyl 2-(benzo[d][1,3]dioxole-5-carboxamido)-3-methylpentanoate | 0.35 | | |
| A43 | 2-[(Benzo[1,3]dioxole-5-carbonyl)-amino]-hexanoic acid methyl ester | 0.49 | | |
| A44 | (R)-2-[(Benzo[1,3]dioxole-5-carbonyl)-amino]-hexanoic acid methyl ester | 0.61 | | |

TABLE A-continued

Umami Amides

| Compound No. | Compound | Umami EC$_{50}$ (uM) | Ec$_{50}$ ratio (vs. MSG) | @ (uM) |
|---|---|---|---|---|
| A45 | 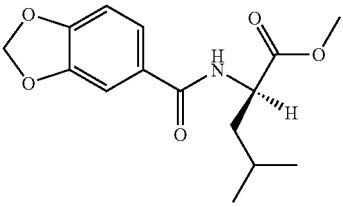<br>(R)-ethyl 2-(benzo[d][1,3]dioxole-5-carboxamido)-4-methylpentanoate | 0.88 | | |
| A46 | 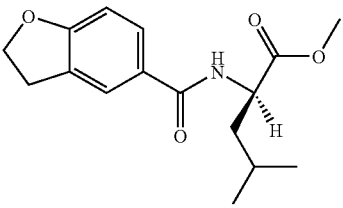<br>(R)-methyl 2-(2,3-dihydrobenzofuran-5-carboxamido)-4-methylpentanoate | 1.32 | | |
| A47 | 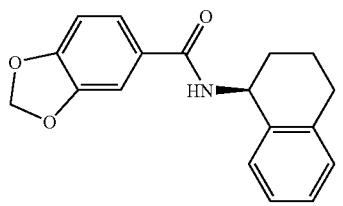<br>(S)-N-(1,2,3,4-tetrahydronaphthalen-1-yl)benzo[d][1,3]dioxole-5-carboxamide | 1.33 | 6.42 | 0.1 |
| A48 | 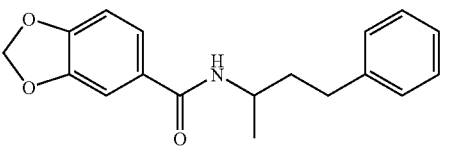<br>N-(4-phenylbutan-2-yl)benzo[d][1,3]dioxole-5-carboxamide | 1.51 | 9.27 | 1 |
| A49 | 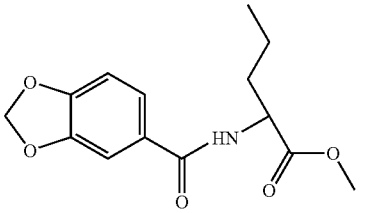<br>2-[(Benzo[1,3]dioxole-5-carbonyl)-amino]-pentanoic acid methyl ester | 1.54 | 9.53 | 1 |
| A50 | 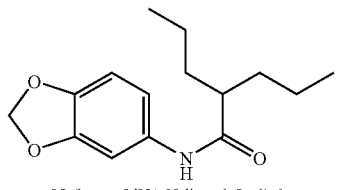<br>N-(benzo[d][1,3]dioxol-5-yl)-2-propylpentanamide | 1.57 | | |

TABLE A-continued

Umami Amides

| Compound No. | Compound | Umami EC$_{50}$ (uM) | Ec$_{50}$ ratio (vs. MSG) | @ (uM) |
|---|---|---|---|---|
| A51 | 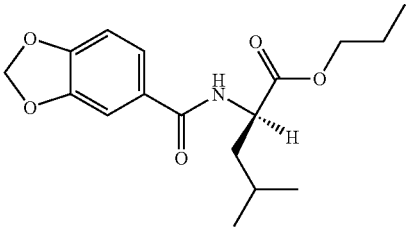<br>(R)-propyl 2-(benzo[d][1,3]dioxole-5-carboxamido)-4-methylpentanoate | 1.58 | | |
| A52 | 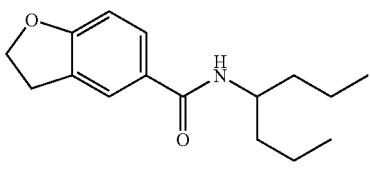<br>N-(heptan-4-yl)-2,3-dihydrobenzofuran-5-carboxamide | 1.65 | | |
| A53 | 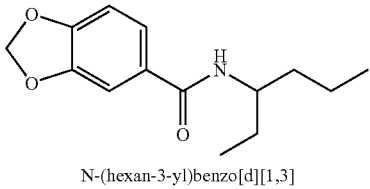<br>N-(hexan-3-yl)benzo[d][1,3]dioxole-5-carboxamide | 1.83 | | |
| A54 | 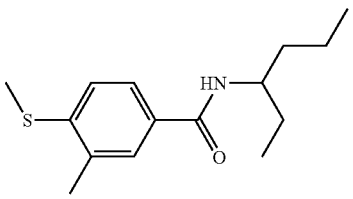<br>N-(hexan-3-yl)-3-methyl-4-(methylthio)benzamide | 0.12 | | |
| A55 | 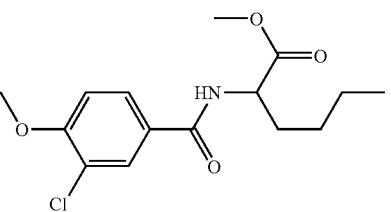<br>methyl 2-(3-chloro-4-methoxybenzamido)hexanoate | 0.12 | | |
| A56 | 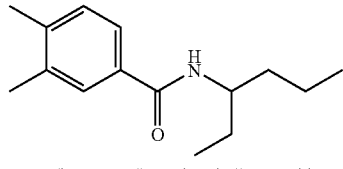<br>N-(hexan-3-yl)-3,4-imethylbenzamide | 0.14 | | |

TABLE A-continued

Umami Amides

| Compound No. | Compound | Umami EC$_{50}$ (uM) | Ec$_{50}$ ratio (vs. MSG) | @ (uM) |
|---|---|---|---|---|
| A57 | 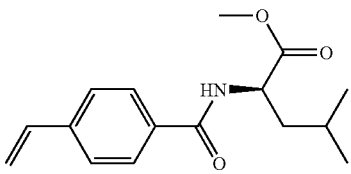<br>(R)-methyl 4-methyl-2-(4-vinylbenzamido)pentanoate | 0.18 | | |
| A58 | 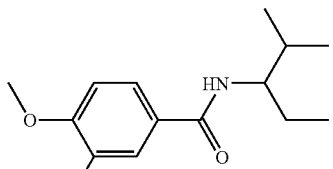<br>4-methoxy-3-methyl-N-(2-methylpentan-3-yl)benzamide | 0.2 | | |
| A59 | 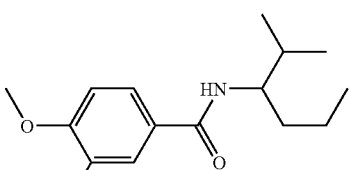<br>4-methoxy-3-methyl-N-(2-methylhexan-3-yl)benzamide | 0.2 | | |
| A60 | 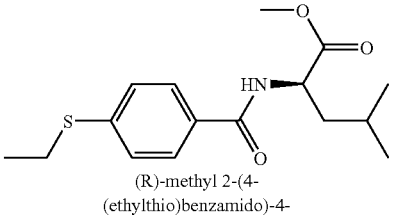<br>(R)-methyl 2-(4-(ethylthio)benzamido)-4-methylpentanoate | 0.2 | | |
| A61 | 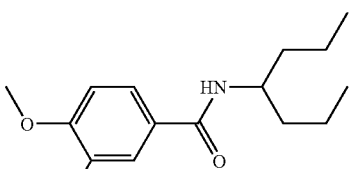<br>N-(heptan-4-yl)-4-methoxy-3-methylbenzamide | 0.22 | | |
| A62 | 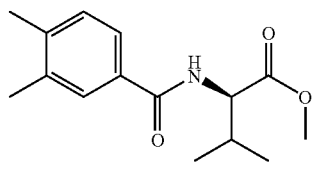<br>(R)-methyl 2-(3,4-dimethylbenzamido)-3-methylbutanoate | 0.25 | | |

TABLE A-continued

Umami Amides

| Compound No. | Compound | Umami EC$_{50}$ (uM) | Ec$_{50}$ ratio (vs. MSG) | @ (uM) |
|---|---|---|---|---|
| A63 | (R)-methyl 2-(4-methoxy-3-methylbenzamido)-4-methylpentanoate | 0.25 | | |
| A64 | 4-ethoxy-3-methyl-N-(pentan-3-yl)benzamide | 0.26 | | |
| A65 | (R)-N-(1-methoxy-4-methylpentan-2-yl)-3-methyl-4-(methylthio)benzamide | 0.29 | | |
| A66 | N-(2,4-dimethoxybenzyl)-3-(1H-pyrrol-1-yl)isonicotinamide | 0.29 | | |
| A67 | methyl 2-(3-chloro-4-methoxybenzamido)pentanoate | 0.29 | 10.75 | 1 |
| A68 | 4-ethoxy-N-(heptan-4-yl)benzamide | 0.32 | 2.62 | 0.3 |

TABLE A-continued

Umami Amides

| Compound No. | Compound | Umami EC$_{50}$ (uM) | Ec$_{50}$ ratio (vs. MSG) | @ (uM) |
|---|---|---|---|---|
| A69 | 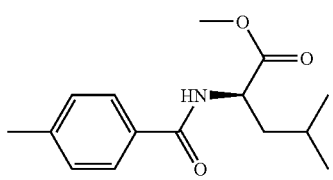<br>(R)-methyl 4-methyl-2-(4-methylbenzamido)pentanoate | 0.32 | | |
| A70 | 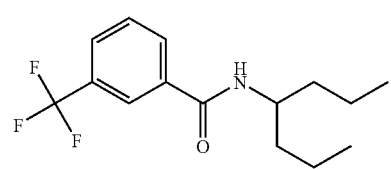<br>N-(heptan-4-yl)-3-(trifluoromethyl)benzamide | 0.33 | | |
| A71 | 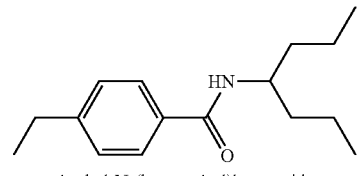<br>4-ethyl-N-(heptan-4-yl)benzamide | 0.34 | | |
| A72 | 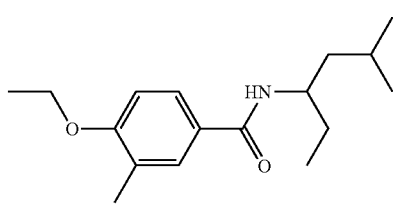<br>4-ethoxy-3-methyl-N-(5-methylhexan-3-yl)benzamide | 0.34 | | |
| A73 | 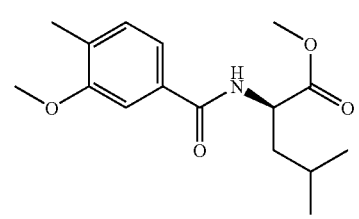<br>(R)-methyl 2-(3-methoxy-4-methylbenzamido)-4-methylpentanoate | 0.34 | | |
| A74 | 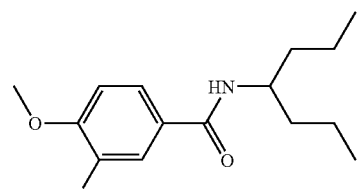<br>3-fluoro-N-(heptan-4-yl)-4-methoxybenzamide | 0.35 | 4.98 | 0.3 |

TABLE A-continued
Umami Amides
| Compound No. | Compound | Umami EC$_{50}$ (uM) | Ec$_{50}$ ratio (vs. MSG) | @ (uM) |
|---|---|---|---|---|
| A75 | 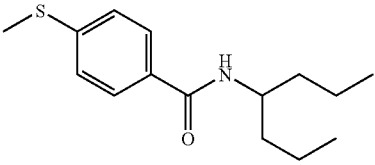<br>N-(heptan-4-yl)-4-(methylthio)benzamide | 0.39 | | |
| A76 | 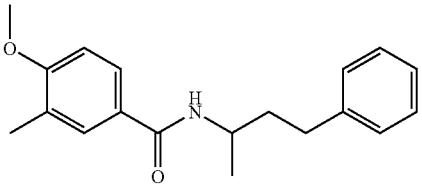<br>4-methoxy-3-methyl-N-(4-phenylbutan-2-yl)benzamide | 0.4 | | |
| A77 | 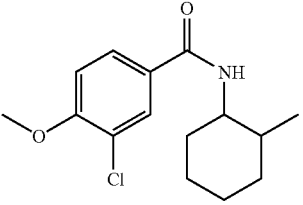<br>3-chloro-4-methoxy-N-(2-methylcyclohexyl)benzamide | 0.44 | | |
| A78 | 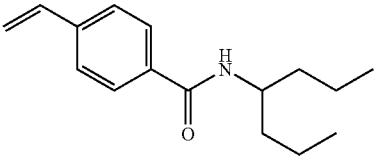<br>c<br>N-(heptan-4-yl)-4-vinylbenzamide | 0.46 | 10.22 | 0.3 |
| A79 | 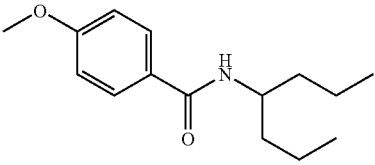<br>N-(heptan-4-yl)-4-methoxybenzamide | 0.46 | | |
| A80 | 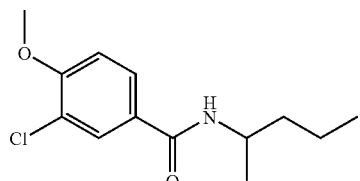<br>3-chloro-4-methoxy-N-(pentan-2-yl)benzamide | 0.47 | 5.12 | 0.1 |

133 134

TABLE A-continued

Umami Amides

| Compound No. | Compound | Umami EC$_{50}$ (uM) | Ec$_{50}$ ratio (vs. MSG) | @ (uM) |
|---|---|---|---|---|
| A81 | 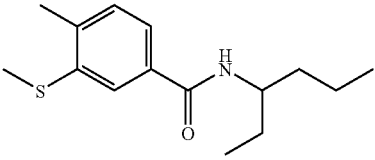<br>N-(hexan-3-yl)-4-methyl-3-(methylthio)benzamide | 0.5 | | |
| A82 | 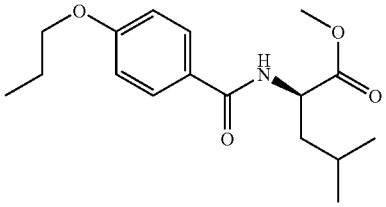<br>(R)-methyl 4-methyl-2-(4-propoxybenzamido)pentanoate | 0.51 | | |
| A83 | 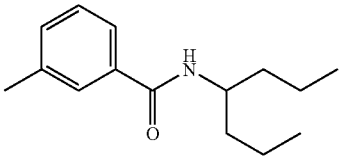<br>N-(heptan-4-yl)-3-methylbenzamide | 0.52 | | |
| A84 | 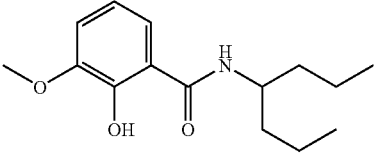<br>N-(heptan-4-yl)-2-hydroxy-3-methoxybenzamide | 0.53 | | |
| A85 | 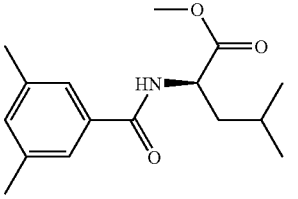<br>(R)-methyl 2-(3,5-dimethylbenzamido)-4-methylpentanoate | 0.53 | | |
| A86 | 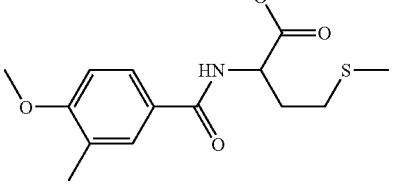<br>methyl 2-(4-methoxy-3-methylbenzamido)-4-(methylthio)butanoate | 0.53 | | |

TABLE A-continued

Umami Amides

| Compound No. | Compound | Umami EC$_{50}$ (uM) | Ec$_{50}$ ratio (vs. MSG) | @ (uM) |
|---|---|---|---|---|
| A87 | 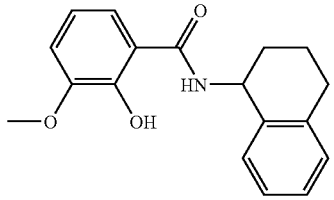<br>2-hydroxy-3-methoxy-N-(1,2,3,4-tetrahydronaphthalen-1-yl)benzamide | 0.54 | 3.8 | 1 |
| A88 | 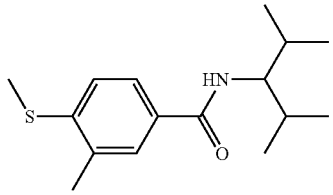<br>N-(2,4-dimethylpentan-3-yl)-3-methyl-4-(methylthio)benzamide | 0.55 | | |
| A89 | 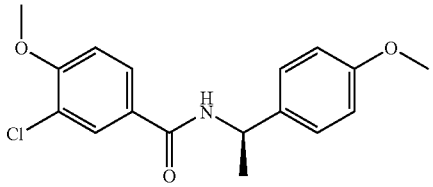<br>(R)-3-chloro-4-methoxy-N-(1-(4-methoxyphenyl)ethyl)benzamide | 0.6 | 2.85 | 1 |
| A90 | 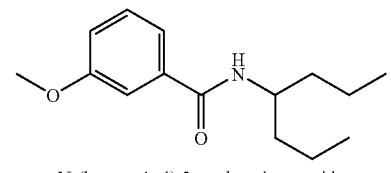<br>N-(heptan-4-yl)-3-methoxybenzamide | 0.61 | | |
| A91 | 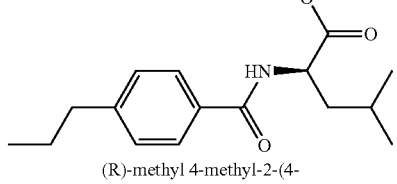<br>(R)-methyl 4-methyl-2-(4-propylbenzamido)pentanoate | 0.62 | | |
| A92 | 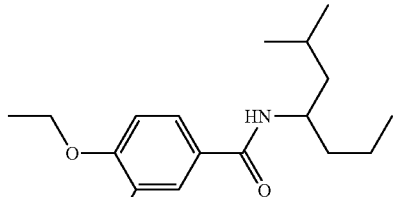<br>4-ethoxy-3-methyl-N-(2-methylheptan-4-yl)benzamide | 0.65 | | |

TABLE A-continued

Umami Amides

| Compound No. | Compound | Umami EC$_{50}$ (uM) | Ec$_{50}$ ratio (vs. MSG) | @ (uM) |
|---|---|---|---|---|
| A93 | 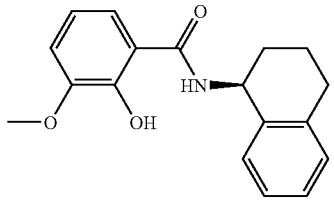<br>(S)-2-hydroxy-3-methoxy-N-(1,2,3,4-tetrahydronaphthalen-1-yl)benzamide | 0.7 | 5.7 | 1 |
| A94 | 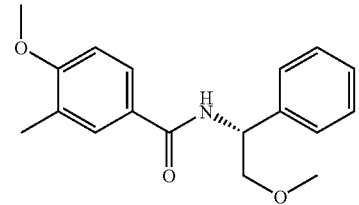<br>(R)-4-methoxy-N-(2-methoxy-1-phenylethyl)-3-methylbenzamide | 0.72 | | |
| A95 | 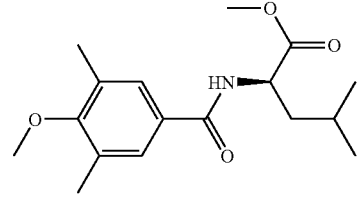<br>(R)-methyl 2-(4-methoxy-3,5-dimethylbenzamido)-4-methylpentanoate | 0.74 | | |
| A96 | 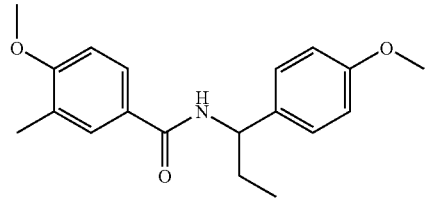<br>4-methoxy-N-(1-(4-methoxyphenyl)propyl)-3-methylbenzamide | 0.76 | | |
| A97 | 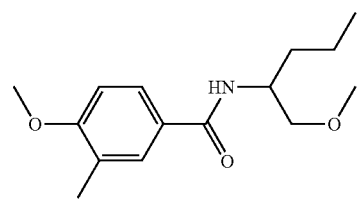<br>4-methoxy-N-(1-methoxypentan-2-yl)-3-methylbenzamide | 0.85 | | |

TABLE A-continued

Umami Amides

| Compound No. | Compound | Umami EC$_{50}$ (uM) | Ec$_{50}$ ratio (vs. MSG) | @ (uM) |
|---|---|---|---|---|
| A98 | 3-chloro-N-(1-hydroxy-4-methylpentan-2-yl)-4-methoxybenzamide | 0.88 | | |
| A99 | (R)-methyl 4-methyl-2-(3-methylbenzamido)pentanoate | 0.89 | | |
| A100 | 3-chloro-4-methoxy-N-(1-p-tolylethyl)benzamide | 1.1 | | |
| A101 | N-(heptan-4-yl)-2-hydroxy-4-methoxybenzamide | 1.16 | 7.62 | 1 |
| A102 | 4-hydroxy-3-methyl-N-(1,2,3,4-tetrahydronaphthalen-1-yl)benzamide | 1.32 | 9.49 | 1 |

TABLE A-continued
Umami Amides
| Compound No. | Compound | Umami EC$_{50}$ (uM) | Ec$_{50}$ ratio (vs. MSG) | @ (uM) |
|---|---|---|---|---|
| A103 | 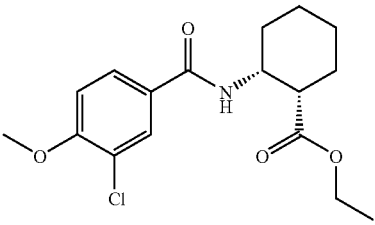<br>(1S,2R)-ethyl 2-(3-chloro-4-methoxybenzamido)cyclohexanecarboxylate | 1.36 | | |
| A104 | 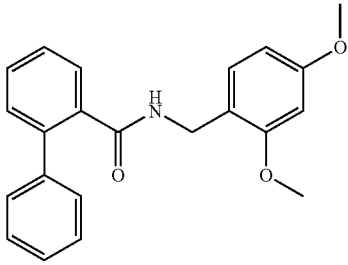<br>Biphenyl-2-carboxylic acid 2,4-dimethoxy-benzylamide | 1.37 | | |
| A105 | 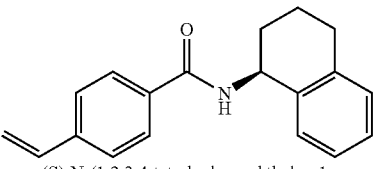<br>(S)-N-(1,2,3,4-tetrahydronaphthalen-1-yl)-4-vinylbenzamide | 1.38 | 2.79 | 1 |
| A106 | 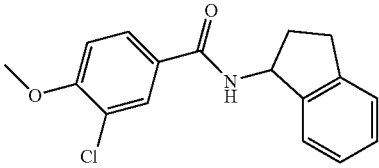<br>3-chloro-N-(2,3-dihydro-1H-inden-1-yl)-4-methoxybenzamide | 1.39 | 4.01 | 0.3 |

Numerous amide compounds of Formula (I) that fall within the subgenus of "oxalamide" compounds described elsewhere herein were also synthesized and experimentally tested for effectiveness as activator of a hT1R1/hT1R3 umami receptor expressed in an HEK293 cell line

Example 122

General Procedure A for the Preparation of an Oxalamide Synthesis of N-(2-Methoxy-benzyl)-N'-(2-pyridin-2-yl-ethyl)-oxalamide

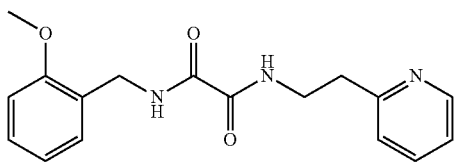

2-Methoxybenzyl amine (5 mmol) was mixed with triethylamine (2 equiv.) in anhydrous Dioxane. Ethyl oxalyl chloride (1 equiv.) was added and the mixture was shaken at room temperature for 0.5-2 hours. Then 2-(2-pyridinyl)ethyl amine (1 equiv.) was added and the suspension was heated at 80° C. overnight. The solution was concentrated and the residue was dissolved in ethyl acetate and washed with water. The organic layer was dried by sodium sulfate and solvent was evaporated to give the crude product, which was purified by flash column chromatography to afford the title compound: yield 70%, m.p. 118-119° C.; m/e=314 [M+1]; $^1$H NMR (CDCl$_3$): δ 3.02 (t, 2H), 3.76 (dt, 2H), 3.86 (s, 3H), 4.47 (d, 2H), 6.80-6.90 (m, 2H), 7.14-7.18 (m, 2H), 7.20-7.30 (m, 2H), 7.55-7.62 (m, 1H), 7.75-7.83 (m, 1H), 8.05-8.12 (m, 1H), 8.55-8.63 (m, 1H).

The compound had an EC$_{50}$ for activation of a hT1R1/hT1R3 umami receptor expressed in an HEK293 cell line of 0.34 μM, and when present at 0.3 μM enhanced the effectiveness of monosodium glutamate with an EC$_{50}$ ratio of 18.85.

Example 123

N-(2,4-Dimethoxy-benzyl)-N'-(2-pyridin-2-yl-ethyl)-oxalamide

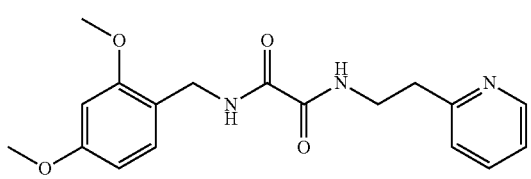

Prepared in a similar manner to example 122 using 2,4-dimethoxybenzyl amine, ethyl oxalyl chloride and 2-(2-pyridinyl)ethyl amine. Yield 72%, m.p. 123-124° C.; m/e=344 [M+1]; $^1$H NMR (CDCl$_3$): δ 3.02 (t, 2H); 3.73 (dd, 2H); 3.78 (s, 3H); 3.82 (s, 3H); 4.38 (d, 2H) 6.40 (dd, 1H); 6.44 (d, 1H); 7.14 (m, 3H); 7.59 (m, 1H); 7.82 (t, 1H); 8.11 (t, 1H); 8.56 (d, 1H); $^{13}$C NMR: δ 36.9, 38.9, 39.4, 55.6, 55.6, 98.8, 104.1, 117.8, 121.9, 123.5, 130.7, 136.8, 149.6, 158.8, 158.8, 159.6, 160.1, 161.0.

The compound had an EC$_{50}$ for activation of a hT1R1/hT1R3 umami receptor expressed in an HEK293 cell line of 0.09 μM, and when present at 0.3 μM enhanced the effectiveness of monosodium glutamate with an EC$_{50}$ ratio of 6.51.

Example 124

N-(3-Methyl-thiophen-2-ylmethyl)-N'-(2-pyridin-2-yl-ethyl)-oxalamide

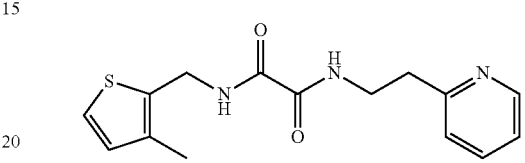

Prepared in a similar manner to example 122 using (3-methyl-thiophen-2-yl)-methylamine, ethyl oxalyl chloride and 2-(2-pyridinyl)ethyl amine. Yield 40%; m.p. 122-124° C.; m/e=304 [M+1]; $^1$H NMR (DMSO-d$_6$): δ 2.19 (s, 3H), 2.92-2.95 (t, 2H), 3.48-3.52 (dd, 2H), 4.37-4.38 (d, 2H), 6.79-6.80 (d, 1H), 7.20-7.27 (m, 3H), 7.67-7.71 (dt, 1H), 8.48-8.49 (d, 1H), 8.87-8.89 (t, 1H), 9.25-9.28 (t, 1H).

The compound had an EC$_{50}$ for activation of a hT1R1/hT1R3 umami receptor expressed in an HEK293 cell line of 0.37 μM.

Example 125

General Procedure B for the Synthesis of an Oxalamide N-(4-methyl-benzyl)-N'-(2-pyridin-2-yl-ethyl)-oxalamide

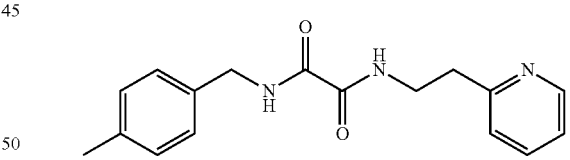

4-Methylbenzyl amine (1 mmol) was allowed to react with ethyl oxalyl chloride (1 equiv.) in the presence of triethyl amine (2 equiv.) in acetonitrile at room temperature for 0.5-1 hour. Then 2-(2-pyridinyl)ethyl amine (1 equiv.) was added and the suspension was heated at 160° C. in a microwave reactor for 5 minutes. The reaction mixture was subject to preparative HPLC to give the pure title oxalamide: yield 60%; m.p. 152-154° C.; m/e=298 [M+1]; $^1$H NMR (CDCl$_3$): δ 2.33 (s, 3H), 3.10 (t, 2H), 3.75 (dt, 2H), 4.43 (d, 2H), 7.10-7015 (m, 4H), 7.18-7.22 (m, 2H), 7.65-7.73 (m, 2H), 8.12 (b, 1H), 8.60 (d, 1H).

The compound had an EC$_{50}$ for activation of a hT1R1/hT1R3 umami receptor expressed in an HEK293 cell line of 0.41 μM.

Example 126

N-(2-Methyl-4-methoxybenzyl)-N'-(2-pyridin-2-yl-ethyl)-oxalamide

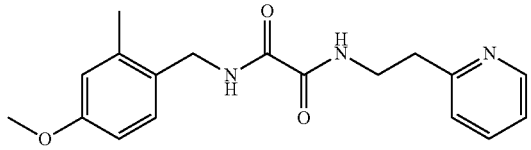

Prepared in a similar manner to example 122 using 2-methyl-4-methoxybenzyl amine, ethyl oxalyl chloride and 2-(2-pyridinyl)ethyl amine. Yield 51%; m.p. 133-134° C.; m/e=328 [M+1]; $^1$H NMR (CDCl$_3$): δ 2.29 (s, 3H); 3.04 (t, 2H); 3.74-3.77 (m, 2H); 3.78 (s, 3H); 4.40 (d, 2H); 6.69-6.73 (m, 2H); 7.13-7.18 (m, 3H); 7.51 (t, 1H); 7.60-7.63 (m, 1H); 8.17 (t, 1H); 8.58 (d, 1H).

The compound had an EC$_{50}$ for activation of a hT1R1/hT1R3 umami receptor expressed in an HEK293 cell line of 0.11 μM.

Example 127

N-(2,4-Dimethoxy-benzyl)-N'-(3-pyridin-2-yl-propyl)-oxalamide

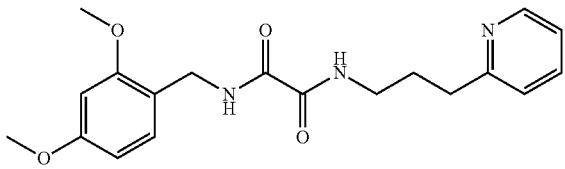

Prepared in a similar manner to example 125 using 2,4-dimethoxybenzyl amine, ethyl oxalyl chloride and 3-(2-pyridinyl)propyl amine. Yield 60%; m/e=358 [M+1]; $^1$H NMR (CDCl$_3$): δ 1.99-2.04 (m, 2H); 2.84 (t, 2H); 3.36 (dd, 2H); 3.79 (s, 3H); 3.82 (s, 3H) 4.60 (d, 2H); 6.41-6.45 (m, 2H); 7.10-7.17 (m, 3H); 7.57-7.60 (m, 1H); 7.81 (t, 1H); 7.89 (t, 1H); 8.54 (d, 1H).

The compound had an EC$_{50}$ for activation of a hT1R1/hT1R3 umami receptor expressed in an HEK293 cell line of 1.84 μM.

Example 128

N-(4-Methoxybenzyl)-N'-(2-pyridin-2-yl-ethyl)-oxalamide

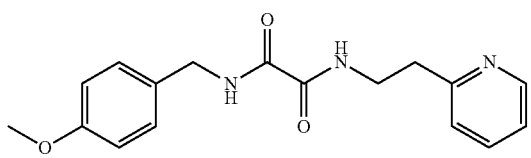

Prepared in a similar manner to example 125 using 4-methoxybenzyl amine, ethyl oxalyl chloride and 2-(2-pyridinyl) ethyl amine. Yield 50%; m.p. 156-158° C.; $^1$H NMR: 3.05 (t, 3H), 3.72-3.77 (m, 2H), 3.79 (s, 3H), 4.40 (d, 2H), 6.86 (d, 2H), 7.16-7.22 (m, 4H), 7.65-7.69 (m, 3H), 8.15 (b, 1H), 8.62 (d, 1H).

The compound had an EC$_{50}$ for activation of a hT1R1/hT1R3 umami receptor expressed in an HEK293 cell line of 0.75 μM.

Example 129

N-(2,4-Dimethoxybenzyl)-N'-(2-(3-methylpyridin-2-yl)ethyl)oxalamide

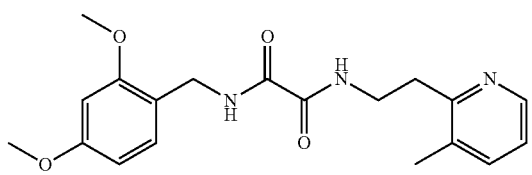

Prepared in a similar manner to example 125 using 2,4-dimethoxybenzyl amine, ethyl oxalyl chloride and 2-(3-methylpyridin-2-yl)ethyl amine (example 129a). Yield 10%; m/e=358 [M+1]; $^1$H NMR (CDCl$_3$): δ 2.28 (s, 3H), 3.01 (t, 2H), 3.75-3.82 (m, 2H), 3.79 (s, 3H), 3.82 (s, 3H), 4.39 (d, 2H), 6.41 (dd, 1H), 6.44 (d, 1H), 7.10 (t, 1H), 7.15 (d, 1H), 7.45 (d, 1H), 7.81 (bs, 1H), 8.28 (bs, 1H), 8.40 (d, 1H).

a. 2-(3-Methylpyridin-2-yl)ethyl amine: To a solution of 2-(3-methylpyridine-2-yl)acetonitrile (example 129b) (95 mg, 0.72 mmol) in THF (0.5 mL) was added 1 M BH$_3$.THF (2.2 mL, 2.2 mmol) dropwise at room temperature. The resulting mixture was heated in a microwave reactor at 130° C. for 7 min. Then, 6 N aqueous HCl (1 mL) was added dropwise at room temperature. The resulting mixture was heated in a microwave reactor at 120° C. for 4 min. The reaction mixture was washed with Et$_2$O (3×3 mL), then cooled to 0° C. and 10 N aqueous NaOH (0.8 mL) was added. The aqueous solution was saturated with K$_2$CO$_3$. The product was extracted with CHCl$_3$ (6×5 mL). The organic extracts were dried (1:1 K$_2$CO$_3$/Na$_2$SO$_4$), filtered, concentrated in vacuo to afford an oil (85 mg, 86%), which was used directly in Example 8. m/e=137 [M+1].

b. 2-(3-Methylpyridine-2-yl)acetonitrile: To a solution of n-BuLi (2.5 N in hexanes, 7.92 mL, 19.8 mmol) at −78° C. under N$_2$ was added dry THF (75 mL), followed immediately by a solution of dry MeCN (1.15 mL, 21.78 mmol) in anhydrous THF (30 mL) over a 5-min period. The resulting reaction mixture was stirred continuously at −78° C. for 1 h. Then 2-bromo-3-methylpyridine (516 mg, 3 mmol) was added. The resulting reaction mixture was stirred at −78° C. for 1 h, then warmed to room temperature, and quenched with water. The organic solvent was evaporated in vacuo, dissolved in CH$_2$Cl$_2$. The organic layer was washed with brine, dried (MgSO$_4$), concentrated, purified via column chromatography (20% EtOAc in hexanes) to afford the product quantitatively: m/e=133 [M+1].

The compound had an EC$_{50}$ for activation of a hT1R1/hT1R3 umami receptor expressed in an HEK293 cell line of 1.64 μM.

Example 130

N-(2,5-Dimethyl-furan-3-ylmethyl)-N'-(2-pyridin-2-yl-ethyl)-oxalamide

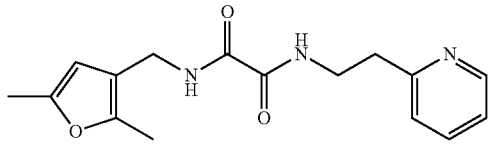

Prepared in a similar manner to example 122 using 2,5-dimethyl-furan-3-ylmethylamine, ethyl oxalyl chloride and 2-(2-pyridinyl)ethyl amine. Yield 51%; m.p. 112-115° C.; m/e=302 [M+1]; $^1$H NMR (DMSO-d$_6$): δ 2.14 (s, 3H), 2.18 (s, 3H), 2.91-2.94 (t, 2H), 3.47-3.51 (dd, 2H), 3.98-3.99 (d, 2H), 5.89 (s, 1H), 7.20-7.25 (m, 2H), 7.68-7.71 (dt, 1H), 8.48-8.49 (d, 1H), 8.81-8.84 (t, 1H), 8.97-9.00 (t, 1H).

The compound had an EC$_{50}$ for activation of a hT1R1/hT1R3 umami receptor expressed in an HEK293 cell line of 1.01 μM.

Example 131

N-(1,5-Dimethyl-1H-pyrrol-2-ylmethyl)-N'-(2-pyridin-2-yl-ethyl)-oxalamide

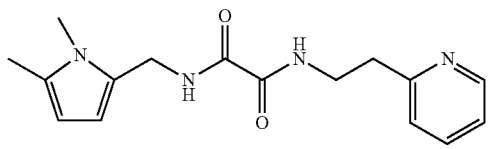

Prepared in a similar manner to example 122 using 1,5-dimethyl-1H-pyrrol-2-ylmethyl amine, ethyl oxalyl chloride and 2-(2-pyridinyl)ethyl amine. Yield 25%; m.p. 147-149° C.; m/e=301 [M+1]; $^1$H NMR (DMSO-d$_6$): δ 2.11 (s, 3H), 2.92-2.95 (t, 2H), 3.38 (s, 3H), 3.48-3.52 (q, 2H), 4.24-4.25 (d, 2H), 5.64-5.65 (d, 1H), 5.79-5.65 (d, 1H), 7.20-7.25 (m, 2H), 7.68-7.71 (dt, 1H), 8.48-8.49 (d, 1H), 8.82-8.86 (m, 2H).

The compound had an EC$_{50}$ for activation of a hT1R1/hT1R3 umami receptor expressed in an HEK293 cell line of 2.3 μM.

Example 132

N-(2-methoxy-4-methylbenzyl)-N'-(2-(pyridin-2-yl)ethyl)oxalamide

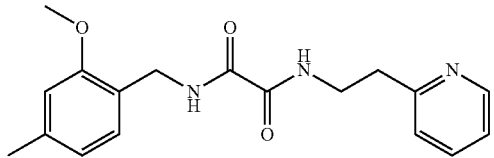

Prepared in a similar manner to example 125 using (2-methoxy-4-methylphenyl)methanamine (example 132a), ethyl oxalyl chloride, and 2-(2-pyridinyl)ethyl amine, yield 20%. m.p: 128-131° C.; m/e=328 [M+1]; $^1$H NMR (CDCl$_3$): 2.33 (s, 3H); 3.02 (t, 2H); 3.73 (m, 2H); 3.84 (s, 3H); 4.42 (d, 2H); 6.70 (m, 2H); 7.14 (m, 3H); 7.60 (m, 1H); 7.86 (s, 1H); 8.09 (s, 1H); 8.56 (d, 1H).

a. (2-methoxy-4-methylphenyl)methanamine: To a solution of 2-methoxy-4-methylbenzamide (example 132b) (200 mg, 1.21 mmol) in THF (0.5 mL) was added 1 M BH$_3$-THF (2.4 ml, 2.42 mmol) slowly at room temperature. The resulting mixture was heated in a microwave reactor at 130° C. for 7 min. Then 6 N aqueous HCl (1 mL) was added dropwise at room temperature. The resulting mixture was heated in a microwave reactor at 120° C. for 4 min. The reaction mixture was washed with Et$_2$O (3×3 mL), then cooled to 0° C. and 10 N aqueous NaOH (0.8 mL) was added. The aqueous solution was saturated with K$_2$CO$_3$. The product was extracted with CHCl$_3$ (6×5 mL). The organic extracts were dried (1:1 K$_2$CO$_3$/Na$_2$SO$_4$), filtered, concentrated in vacuo to afford 180 mg of (2-methoxy-4-methylphenyl)methanamine which was used directly in Example 11.

b. 2-methoxy-4-methylbenzamide: 2-methoxy-4-methylbenzoic acid (500 mg, 3.01 mmol) was mixed with 1-ethyl-3-(3-dimethylaminopropyl)carbodiimide hydrochloride (577 mg, 3.01 mmol) and 1-hydroxybenzotriazole (407 mg, 3.01 mmol) in 25 ml of dichloromethane at r.t. and stirred for 5 min. 2M ammonia solution in methanol (4.5 ml, 9.03 mmol) was added, the reaction mixture was stirred at r.t. for about 5 hr. then it was diluted with dichloromethane, washed with 1N HCl, sat. NaHCO$_3$, water and brine, dried over MgSO$_4$, filtered and evaporated to give 440 mg of 2-methoxy-4-methylbenzamide, yield 88%.

The compound had an EC$_{50}$ for activation of a hT1R1/hT1R3 umami receptor expressed in an HEK293 cell line of 0.04 uM

Example 133

N-(2,4-dimethylbenzyl)-N'-(2-(pyridin-2-yl)ethyl)oxalamide

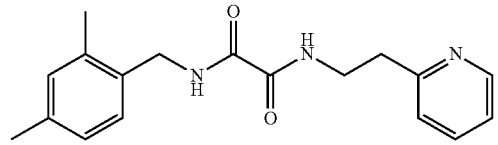

Prepared in a similar manner to example 125 using (2,4-dimethylphenyl)methanamine (example 133a), ethyl oxalyl chloride, and 2-(2-pyridinyl)ethyl amine, yield 60%; m.p. 148-149° C.; m/e=312 [M+1]; $^1$H NMR (CDCl$_3$): 2.28 (s, 3H); 2.30 (s, 3H); 3.05 (t, 2H); 3.76 (dd, 2H); 4.43 (d, 2H); 6.99 (m, 2H); 7.11 (d, 1H); 7.17 (m, 2H); 7.54 (s, 1H); 7.62 (m, 1H); 8.17 (s, 1H); 8.58 (d, 1H).

a. (2,4-Dimethylphenyl)methanamine: Lithium aluminum hydride 1M solution in THF (15.2 ml, 15.2 mmol) was placed in a pre-dried flask under argon at 0° C.; a solution of 2,4-dimethylbenzonitrile (1.0 g, 7.6 mmol) in 15 ml of anhydrous ether was added drop wisely. After the addition, the reaction mixture was warmed up slowly to r.t. and stirred for 3 hr. then it was cooled to 0° C., anhydrous sodium sulfate was added, and 1 ml of water was added drop wisely. The mixture was diluted with ethyl acetate, the insoluble matter was filtered out, the filtrate was washed with water and brine, dried over MgSO$_4$, filtered and evaporated to give 1.03 g of pure (2,4-dimethylphenyl)methanamine in quantitative yield without purification.

The compound had an EC$_{50}$ for activation of a hT1R1/hT1R3 umami receptor expressed in an HEK293 cell line of 0.07 uM.

Example 134

N-(4-ethoxy-2-methoxybenzyl)-N'-(2-(pyridin-2-yl)ethyl)oxalamide

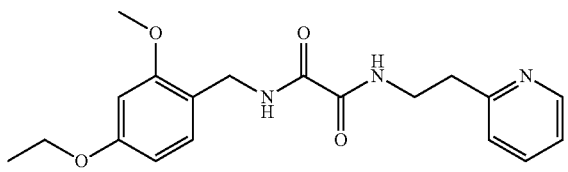

Prepared in a similar manner to example 125 using (4-ethoxy-2-methoxyphenyl)methanamine (example 134a), ethyl oxalyl chloride, and 2-(2-pyridinyl)ethyl amine; yield 10%; m.p. 117-118° C.; m/e=358 [M+1]; $^1$H NMR (CDCl$_3$): 1.40 (t, 3H); 3.03 (t, 2H); 3.74 (dd, 2H); 3.82 (s, 3H); 4.01 (dd, 2H); 4.39 (d, 2H); 6.39 (d, 1H); 6.44 (s, 1H); 7.15 (m, 3H), 7.61 (m, 1H); 7.81 (s, 1H); 8.10 (s, 1H); 8.56 (d, 1H).

a. (4-ethoxy-2-methoxyphenyl)methanamine: To a solution of 4-ethoxy-2-methoxybenzaldehyde (example 134b) (880 mg, 4.88 mmol) in 50 ml of anhydrous methanol, were added ammonium acetate (7.5 g, 97.60 mmol) and sodium cyanoborohydride (613 mg, 9.76 mmol). The reaction mixture was stirred at r.t. for about 4 hr. then it was concentrated on a rotary evaporator, the residue was diluted with water and basified with 15% aqueous NaOH, extracted with ethyl acetate, washed with water and brine, dried over MgSO$_4$, filtered and the solvent was evaporated, the residue was column chromatographed on silica gel (DCM/MeOH 9:1) to afford 150 mg of product; yield 17% (The method was not optimized).

b. 4-Ethoxy-2-methoxybenzaldehyde: To a solution of 4-hydroxy-2-methoxybenzaldehyde (1.0 g, 6.57 mmol) in 10 ml of acetone, was added potassium carbonate (0.91 g, 6.57 mmol) and iodoethane (1.6 ml, 19.71 mmol), the reaction mixture was stirred at r.t. overnight. Acetone was removed on a rotary evaporator; the residue was diluted with water and ethyl acetate; extracted with ethyl acetate, washed with brine, dried over MgSO$_4$, filtered and evaporated to give crude product, which was column chromatographed on silica gel (ethyl acetate/hexane=1:4) to give 943 mg of product; yield 80%.

The compound had an EC$_{50}$ for activation of a hT1R1/hT1R3 umami receptor expressed in an HEK293 cell line of 0.1 uM

Example 135

N-(4-Methoxy-3-methylbenzyl)-N'-(2-(pyridin-2-yl)ethyl)oxalamide

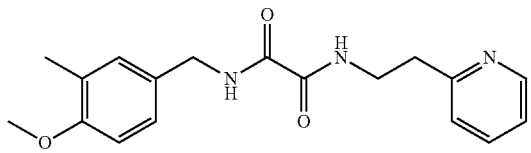

Prepared in a similar manner to example 125 using (4-methoxy-3-methylphenyl)-methanamine (example 135a), ethyl oxalyl chloride, and 2-(2-pyridinyl)ethyl amine, yield 12%; m.p. 145-147° C.; m/e=328 [M+1]; $^1$H NMR (CDCl$_3$): 2.19 (s, 3H); 3.04 (t, 2H); 3.76 (dd, 2H); 3.81 (s, 3H); 4.37 (d, 2H); 6.76 (d, 1H); 7.06 (m, 2H); 7.16 (m, 2H); 7.61 (m, 1H); 7.66 (s, 1H); 8.18 (s, 1H); 8.58 (d, 1H).

a. 4-Methoxy-3-methylphenyl)methanamine: Prepared in a similar manner to example 134a using 4-methoxy-3-methylbenzaldehyde, ammonium acetate, and sodium cyanoborohydride in MeOH; yield 22% (110 mg).

The compound had an EC$_{50}$ for activation of a hT1R1/hT1R3 umami receptor expressed in an HEK293 cell line of 1.04 uM.

Example 136

N-(2-chlorobenzyl)-N'-(2-(pyridin-2-yl)ethyl)oxalamide

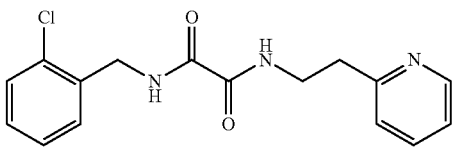

Prepared in a similar manner to example 125 using (2-chlorophenyl)methanamine, ethyl oxalyl chloride, and 2-(2-pyridinyl)ethyl amine; yield 45%; m/e=318 [M+1].

The compound had an EC$_{50}$ for activation of a hT1R1/hT1R3 umami receptor expressed in an HEK293 cell line of 0.01 uM

Example 137

N-((2,3-dihydrobenzo[b][1,4]dioxin-5-yl)methyl)-N'-(2-(pyridin-2-yl)ethyl) oxalamide

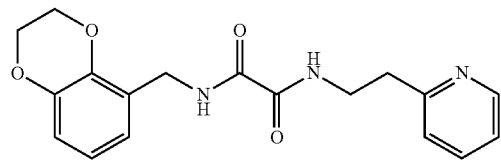

Prepared in a similar manner to example 122 using (2,3-dihydrobenzo[b][1,4]dioxin-5-yl)methanamine, ethyl oxalyl chloride, and 2-(2-pyridinyl)ethyl amine; yield 50%; m/e=342 [M+1].

The compound had an EC$_{50}$ for activation of a hT1R1/hT1R3 umami receptor expressed in an HEK293 cell line of 0.3 uM.

Example 138

N-(benzo[d][1,3]dioxol-5-ylmethyl)-N'-(2-(pyridin-2-yl)ethyl)oxalamide

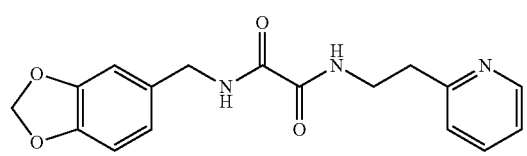

Prepared in a similar manner to example 125 using benzo[d][1,3]dioxol-5-ylmethanamine, ethyl oxalyl chloride, and 2-(2-pyridinyl)ethyl amine; yield 35%; m/e=328 [M+1].

The compound had an $EC_{50}$ for activation of a hT1R1/hT1R3 umami receptor expressed in an HEK293 cell line of 0.5 uM.

Example 139

N-(4-Ethylbenzyl)-N'-(2-(pyridin-2-yl)ethyl)oxalamide

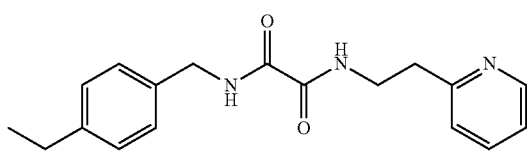

Prepared in a similar manner to example 125 using 4-ethylbenzylamine, ethyl oxalyl chloride, and 2-(2-pyridinyl)ethyl amine; yield 38%; m/e=312 [M+1].

The compound had an $EC_{50}$ for activation of a hT1R1/hT1R3 umami receptor expressed in an HEK293 cell line of 0.79 uM.

Example 140

N-(Benzofuran-5-ylmethyl)-N'-(2-(pyridin-2-yl)ethyl)oxalamide

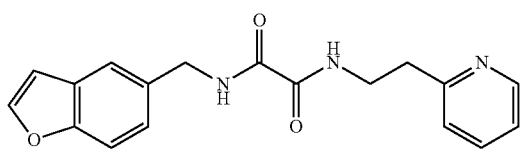

Prepared in a similar manner to example 125 using benzofuran-5-ylmethylamine, ethyl oxalyl chloride, and 2-(2-pyridinyl)ethyl amine; yield 64%; m/e=324 [M+1].

The compound had an $EC_{50}$ for activation of a hT1R1/hT1R3 umami receptor expressed in an HEK293 cell line of 1.78 uM.

Example 141

N-((4-Methoxycarbonylphenyl)methyl)-N'-(2-(pyridin-2-yl)ethyl)oxalamide

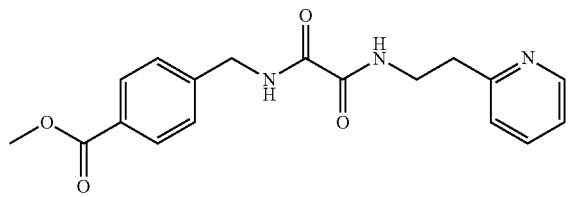

Prepared in a similar manner to example 122 using 4-methoxycarbonylphenyl methylamine, ethyl oxalyl chloride, and 2-(2-pyridinyl)ethyl amine; yield 52%; m/e=342 [M+1].

The compound had an $EC_{50}$ for activation of a hT1R1/hT1R3 umami receptor expressed in an HEK293 cell line of 3.63 uM.

Example 142

N-((2-Carbamoylphenyl)methyl)-N'-(2-(pyridin-2-yl)ethyl)oxalamide

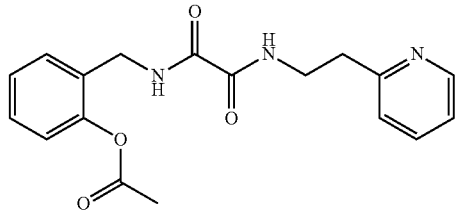

Prepared in a similar manner to example 122 using 2-carbamoylphenyl methylamine, ethyl oxalyl chloride, and 2-(2-pyridinyl)ethyl amine; yield 48%; m/e=342 [M+1].

The compound had an $EC_{50}$ for activation of a hT1R1/hT1R3 umami receptor expressed in an HEK293 cell line of 8.5 uM.

Example 143

N-(2,4-Dimethoxybenzyl)-N'-(1-(pyridin-2-yl)propan-2-yl)oxalamide

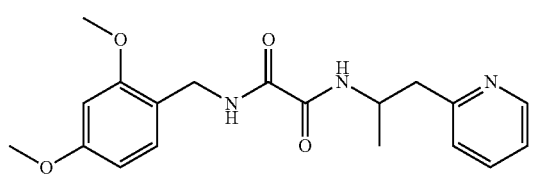

Prepared in a similar manner to example 125 using 2,4-dimethoxybenzylamine, ethyl oxalyl chloride, and 1-(pyridin-2-yl)propan-2-yl amine (example 143a); yield 34%; m/e=357 [M+1].

a. 1-(Pyridin-2-yl)propan-2-yl amine: Prepared in a similar manner to example 129a using 2-(pyridine-2-yl)propanenitrile (example 143b); crude product was used directly in example 143; yield 53%; m/e=137 [M+1].

b. 2-(pyridine-2-yl)propanenitrile: 5 mmol of 2-(pyridine-2-yl)acetonitrile was dissolved in 8 ml anhydrous THF and placed in an ice bath. Potassium t-butoxide (1 equiv) was added and reaction was stirred for 30 minutes. Methyl iodide (1 equiv) was dissolved in 5 mL anhydrous THF and added slowly over 30 minutes. Reaction was stirred overnight at room temperature. Solvent was evaporated and crude mixture was dissolved in ethyl acetate and washed with water. Ethyl acetate layer was evaporated and product was purified by preparative TLC (30% Ethyl acetate/Hexane); yield 71%; m/e=133 [M+1].

Example 144

N-(2,4-Dimethoxybenzyl)-N'-(2-(pyridin-2-yl)propyl)oxalamide

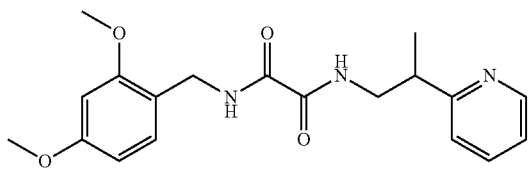

Prepared in a similar manner to example 125 using 2,4-dimethoxybenzylamine, ethyl oxalyl chloride, and 2-(pyridin-2-yl)propylamine (example 144a); yield 35%; m/e=357 [M+1].

a. 2-(pyridin-2-yl)propylamine: 10 mmol of 2-methylpyridine was dissolved in anhydrous THF and kept under inert condition at 0° C. Butyl lithium (1.2 equiv) was added dropwise and stirred for additional 15 minutes at 0° C. while letting temperature to go back to room temperature. After stirring at room temperature for 1 hour, the reaction mixture was cooled again to 0° C. and acetonitrile (2 equiv) was added dropwise. Reaction was stirred overnight at room temperature. After cooling the reaction to 0° C., 30 mL of methanol was added into the reaction mixture. Sodium borohydride (3 equiv) was added in portion slowly at 0° C. Reaction was stirred for another hour letting temperature to rise to room temperature. The reaction mixture was diluted with water and extracted exhaustively with ethyl acetate. The combined extracts were washed with water, brine and dried down over sodium sulfate. Solution was concentrated down and dissolved in ether. Product was extracted with 3 N aqueous HCl, and the acidic extract was washed with ether and made basic with NaOH. Product was extracted exhaustively with ether. The combined ether extracts was washed with water and dried down over sodium sulfate. Solvent was evaporated down to yield sufficiently pure product; yield 47%; m/e=137 [M+1].

The compound had an $EC_{50}$ for activation of a hT1R1/hT1R3 umami receptor expressed in an HEK293 cell line of 1.07 uM

Example 145

N-(2-Methoxybenzyl)-N'-(2-(pyridin-2-yl)ethyl)oxalamide

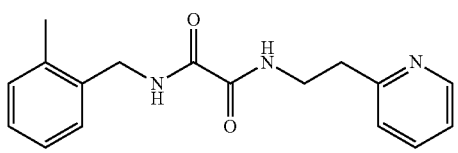

Prepared in a similar manner to example 125 using 2-methylbenzylamine, ethyl oxalyl chloride, and 2-(pyridin-2-yl)ethylamine; m/e=298 [M+1]; $^1$H NMR (CDCl$_3$) δ 2.32 (s, 3H), 3.11 (t, 2H), 3.78 (dt, 2H), 4.46 (d, 2H), 7.15-7.26 (m, 6H), 7.50-7.55 (m, 1H), 7.62-7.67 (m, 1H), 8.12-8.15 (m, 1H), 8.60 (d, 1H).

The compound had an $EC_{50}$ for activation of a hT1R1/hT1R3 umami receptor expressed in an HEK293 cell line of 0.59 uM.

Example 146

N-(2,3-Dimethoxybenzyl)-N'-(2-(pyridin-2-yl)ethyl)oxalamide

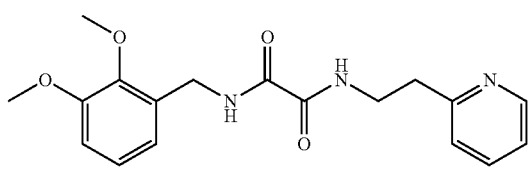

Prepared in a similar manner to example 125 using 2,3-dimethoxybenzylamine, ethyl oxalyl chloride, and 2-(pyridin-2-yl)ethylamine; m/e=343 [M+1].

The compound had an $EC_{50}$ for activation of a hT1R1/hT1R3 umami receptor expressed in an HEK293 cell line of 0.69 uM.

Example 147

N-(2-(Methylthio)benzyl)-N'-(2-(pyridin-2-yl)ethyl)oxalamide

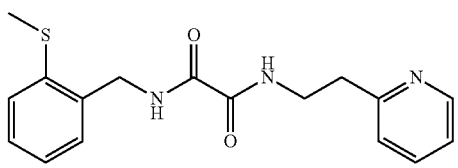

Prepared in a similar manner to example 125 using 2-methylthiobenzylamine, ethyl oxalyl chloride, and 2-(pyridin-2-yl)ethylamine; m/e=330 [M+1]; $^1$H NMR (CDCl$_3$) δ 2.49 (s, 3H), 3.08 (t, 2H), 3.77 (dt, 2H), 4.55 (d, 2H), 7.11-7.14 (m, 1H), 7.15-7.20 (m, 2H), 7.22-7.27 (m, 3H), 7.62 (t, 1H), 7.78-7.83 (m, 1H), 8.08-8.11 (m, 1H), 8.56 (d, 1H).

The compound had an $EC_{50}$ for activation of a hT1R1/hT1R3 umami receptor expressed in an HEK293 cell line of 0.96 uM.

Example 148

N-(2-Hydroxybenzyl)-N'-(2-(pyridin-2-yl)ethyl)oxalamide

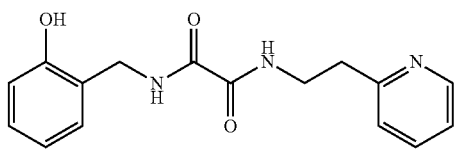

Prepared in a similar manner to example 125 using 2-hydroxybenzylamine, ethyl oxalyl chloride, and 2-(pyridin-2-yl)ethylamine; m/e=300 [M+1].

The compound had an $EC_{50}$ for activation of a hT1R1/hT1R3 umami receptor expressed in an HEK293 cell line of 3.11 uM.

Example 149

N-(Benzo[d][1,3]-dioxol-4-ylmethyl)-N'-(2-(pyridin-2-yl)ethyl)oxalamide

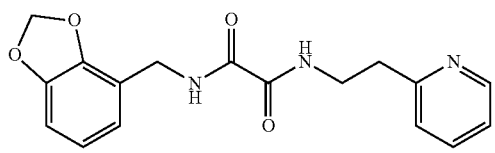

Prepared in a similar manner to example 125 using benzo[d][1,3]dioxol-4-ylmethyl amine (example 149a), ethyl oxalyl chloride, and 2-(pyridin-2-yl)ethyl amine; yield 12%; m/e=328 [M+1]; $^1$H NMR (CDCl$_3$): δ 3.12 (m, 2H), 3.77-3.80 (m, 2H), 4.46-4.47 (d, 2H), 5.98 (s, 2H), 6.74-6.79 (m, 3H), 7.24 (m, 1H), 7.7-7.8 (m, 3H), 8.10-8.15 (m, 1H), 8.58-8.59 (m, 1H).

a. Benzo[d][1,3]dioxol-4-ylmethyl amine: Prepared in a similar manner to example 134a from benzo[d][1,3]dioxole-4-carbaldehyde and ammonium acetate. The crude material contained app. 20% of the product (m/e=152.2 [M+1]) and was used directly in example 149.

The compound had an $EC_{50}$ for activation of a hT1R1/hT1R3 umami receptor expressed in an HEK293 cell line of 0.17 uM.

Example 150

N-(Benzo[b]thiophen-2-ylmethyl)-N'-(2-(pyridin-2-yl)ethyl)oxalamide

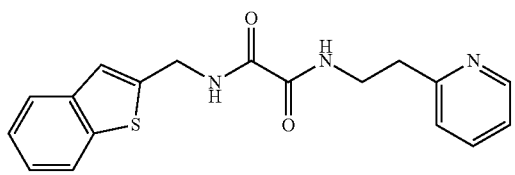

Prepared in a similar manner to example 125 using benzo[b]thiophen-2-ylmethanamine, ethyl oxalyl chloride, and 2-(pyridin-2-yl)ethyl amine; yield 32%; m/e=240 [M+1]; $^1$H NMR (DMSO-d$_6$): δ 2.92-2.95 (t, 2H), 3.48-3.53 (m, 2H), 4.55-4.56 (d, 2H), 7.20-7.25 (m, 2H), 7.38-7.41 (m, 2H), 7.50 (s, 1H), 7.66-7.70 (m, 1H), 7.95-7.99 (m, 2H), 8.47-8.49 (d, 1H), 8.88-8.90 (t, 1H), 9.29-9.31 (t, 1H).

The compound had an $EC_{50}$ for activation of a hT1R1/hT1R3 umami receptor expressed in an HEK293 cell line of 0.74 uM.

Example 151

N-(Benzo[d]thiazol-2-ylmethyl)-N'-(2-(pyridin-2-yl)ethyl)oxalamide

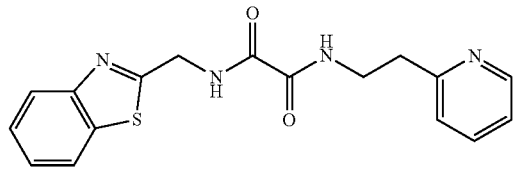

Prepared in a similar manner to example 125 using benzo[d]thiazol-2-ylmethanamine, ethyl oxalyl chloride, and 2-(pyridin-2-yl)ethyl amine; yield 33%; m/e=341 [M+1]; $^1$H NMR (DMSO-d$_6$): δ 2.95-2.98 (t, 2H), 3.52-3.57 (m, 2H), 4.72-4.73 (d, 2H), 7.22-7.24 (m, 1H), 7.25-7.27 (d, 1H), 7.40-7.44 (t, 1H), 7.48-7.51 (t, 1H), 7.69-7.72 (dt, 1H), 7.95-7.96 (d, 1H), 8.05-8.07 (d, 1H), 8.49-8.50 (d, 1H), 8.96-8.98 (t, 1H), 9.67-9.70 (t, 1H).

The compound had an $EC_{50}$ for activation of a hT1R1/hT1R3 umami receptor expressed in an HEK293 cell line of 4.4 uM.

Example 152

N-((5-Methylfuran-2-yl)methyl)-N2-(2-(pyridin-2-yl)ethyl)oxalamide

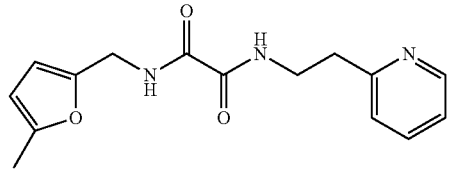

Prepared in a similar manner to example 125 using (5-methylfuran-2-yl)methanamine, ethyl oxalyl chloride, and 2-(pyridin-2-yl)ethyl amine; yield 38%; m/e=288 [M+1]; $^1$H NMR (DMSO-d$_6$): δ 2.20 (s, 3H), 2.92-2.95 (t, 2H), 3.48-3.52 (m, 2H), 4.23-4.24 (d, 2H), 5.96-5.97 (d, 1H), 6.06-6.07 (d, 1H), 7.20-7.25 (m, 2H), 7.68-7.71 (t, 1H), 8.48-8.49 (d, 1H), 8.85-8.87 (t, 1H), 9.04-9.07 (t, 1H).

The compound had an $EC_{50}$ for activation of a hT1R1/hT1R3 umami receptor expressed in an HEK293 cell line of 4.9 uM

Example 153

N-((2-Methylfuran-3-yl)methyl)-N'-(2-(pyridin-2-yl)ethyl)oxalamide

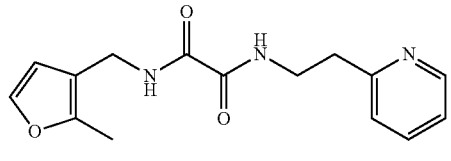

Prepared in a similar manner to example 125 using (2-methylfuran-3-yl)methanamine (example 153a), ethyl oxalyl chloride, and 2-(pyridin-2-yl)ethyl amine; yield 50%; m/e=288 [M+1]; $^1$H NMR (DMSO-d$_6$): δ 2.23 (s, 3H), 2.91-2.94 (t, 2H), 3.48-3.52 (q, 2H), 4.05-4.06 (d, 2H), 6.30-6.31

(d, 1H), 7.20-7.25 (m, 2H), 7.38-7.39 (d, 1H), 7.67-7.71 (dt, 1H), 8.48-8.49 (d, 1H), 8.83-8.86 (t, 1H), 9.04-9.07 (t, 1H).

a. (2-Methylfuran-3-yl)methanamine: A solution of 10 mmol (1.256 ml) of methyl 2-methylfuran-3-carboxylate and 38.9 mmol (2.1 g) of NaOMe in 20 ml of formamide was stirred at 100° C. for 30 min. The reaction mixture was poured into ice-water (20 ml) and extracted with ethyl acetate (3×). The extract was dried over MgSO4 and concentrated to give 1.05 g (83%) of 2-methylfuran-3-carboxamide as oil (m/e=126.2 [M+1]). The amide was dissolved in dry THF (10 ml) and drop-wise added to 15 ml of 1M LiAlH$_4$ with 15 ml THF at 0° C. under argon. Then the mixture was stirred for 5 hrs at 60° C. Following cooling, 50% aqueous THF (30 ml) was added to the mixture at 5-10° C. The resulting precipitate was removed by filtration and the filtered solution was dried and concentrated to give an oily product (0.93 g, 84%).

The compound had an $EC_{50}$ for activation of a hT1R1/hT1R3 umami receptor expressed in an HEK293 cell line of 1.82 uM Example 154

N-(2,4-Dimethoxybenzyl)-N'-(2-(4-methylpyridin-2-yl)ethyl)oxalamide

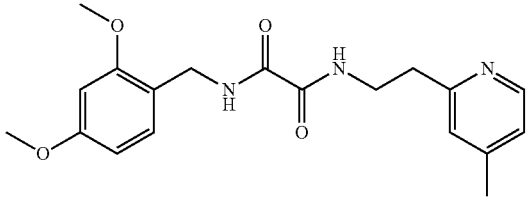

Prepared in a similar manner to Example 122 using 2,4-dimethoxybenzylamine, ethyl oxalyl chloride, and 2-(4-methylpyridin-2-yl)ethyl amine (example 154a); yield 11%; m/e=358 [M+1]; m.p. 144-145° C.; $^1$H NMR (CDCl$_3$): δ 2.31 (s, 3H), 2.97 (t, 2H), 3.71 (q, 2H), 3.79 (s, 3H), 3.83 (s, 3H), 4.39 (d, 2H), 6.40 (dd, 1H), 6.44 (d, 1H), 6.97 (s, 1H), 6.98 (d, 1H), 7.15 (d, 1H), 7.81 (brs, 1H), 8.08 (brs, 1H), 8.41 (d, 1H).

a. 2-(4-Methylpyridin-2-yl)ethyl amine: Prepared in a similar manner to example 129 using 2-(4-methylpyridin-2-yl)acetonitrile (example 154b); yield 83%; m/e=137 [M+1].

b. 2-(4-Methylpyridin-2-yl)acetonitrile: Prepared in a similar manner to example 129b using 2-bromo-4-methylpyridine, acetonitrile and n-BuLi; yield 88%; m/e=133 [M+1].

The compound had an $EC_{50}$ for activation of a hT1R1/hT1R3 umami receptor expressed in an HEK293 cell line of 1.64 uM Example 155

N-(2,4-Dimethoxybenzyl)-N'-(2-(5-methylpyridin-2-yl)ethyl)oxalamide

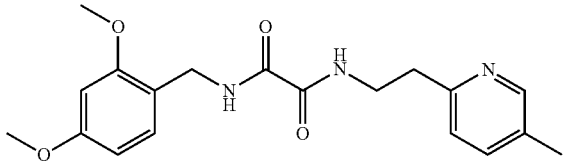

Prepared in a similar manner to Example 122 using 2,4-dimethoxybenzylamine, ethyl oxalyl chloride, and 2-(5-methylpyridin-2-yl)ethyl amine (example 155a); yield 9%; m/e=358 [M+1]; m.p. 124-125° C.; $^1$H NMR (CDCl$_3$): δ 2.30 (s, 3H), 2.97 (t, 2H), 3.70 (q, 2H), 3.79 (s, 3H), 3.82 (s, 3H), 4.38 (d, 2H), 6.40 (dd, 1H), 6.44 (d, 1H), 7.03 (d, 1H), 7.14 (d, 1H), 7.40 (dd, 1H), 7.81 (br s, 1H), 8.08 (br s, 1H), 8.38 (d, 1H).

a. 2-(5-Methylpyridin-2-yl)ethyl amine: Prepared in a similar manner to 129a using 2-(5-methylpyridin-2-yl)acetonitrile (155b); yield 40%; m/e=137 [M+1].

b. 2-(5-Methylpyridin-2-yl)acetonitrile: Prepared in a similar manner to 129b using 2-bromo-5-methylpyridine, acetonitrile and n-BuLi; yield 68%; m/e=133 [M+1].

The compound had an $EC_{50}$ for activation of a hT1R1/hT1R3 umami receptor expressed in an HEK293 cell line of 0.07 uM Example 156

N-(2,4-Dimethoxybenzyl)-N'-(2-(thiophen-2-yl)ethyl)oxalamide

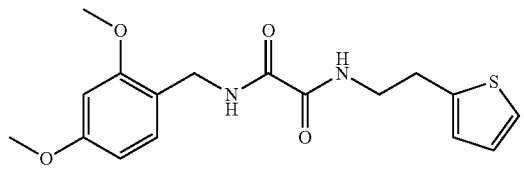

Prepared in a similar manner to Example 122 using 2,4-dimethoxybenzylamine, ethyl oxalyl chloride and 2-(thiophen-2-yl)ethyl amine; yield 72%; m/e=349 [M+1]; m.p. 146-147° C.; $^1$H NMR (CDCl$_3$): δ 3.06 (t, 2H), 3.58 (q, 2H), 3.80 (s, 3H), 3.83 (s, 3H), 4.40 (d, 2H), 6.41 (dd, 1H), 6.45 (d, 1H), 6.84 (dd, 1H), 6.93 (dd, 1H), 7.15 (d, 1H), 7.16 (d, 1H), 7.61 (br s, 1H), 7.81 (br s, 1H).

The compound had an $EC_{50}$ for activation of a hT1R1/hT1R3 umami receptor expressed in an HEK293 cell line of 4.87 uM Example 157

$N^1$-(2-methoxy-4-methylbenzyl)-$N^2$-(2-(5-methylpyridin-2-yl)ethyl)oxalamide

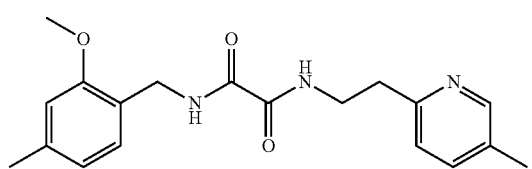

Prepared in a similar manner to Example 125 using 2-methoxy-4-methylbenzylamine (example 132a), ethyl oxalyl chloride and 2-(4-methylpyridin-2-yl)ethylamine (example 155a). Yield 20%; m.p. 116-117° C.; $^1$H NMR (CDCl$_3$): δ 2.31 (s, 3H), 2.34 (s, 3H), 3.00 (t, 2H), 3.71 (q, 2H), 3.84 (s, 3H), 4.42 (d, 2H), 6.69 (s, 1H), 6.71 (d, 1H), 7.05 (d, 1H), 7.11 (d, 1H), 7.43 (d, 1H), 7.84 (br s, 1H), 8.04 (br s, 1H), 8.39 (s, 1H); MS (M+H, 342).

The compound had an $EC_{50}$ for activation of a hT1R1/hT1R3 umami receptor expressed in an HEK293 cell line of 0.03 uM Additional "oxalamide" compounds were synthesized and experimentally tested and found to have a relatively high level of effectiveness as an activator of a hT1R1/hT1R3 umami receptor expressed in an HEK293 cell line. The results of that testing are shown below in Table B.

TABLE B
Umami Oxalamides
| Compound No. | Compound | Umami EC$_{50}$ (uM) | Ec$_{50}$ ratio (vs. MSG) |
|---|---|---|---|
| B1 | 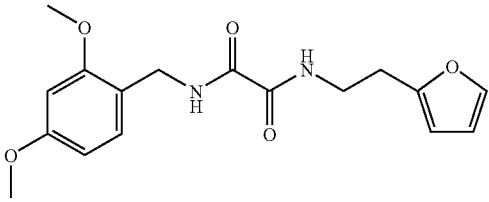N1-(2,4-dimethoxybenzyl)-N2-(2-(furan-2-yl)ethyl)oxalamide | 0.18 | |
| B2 | 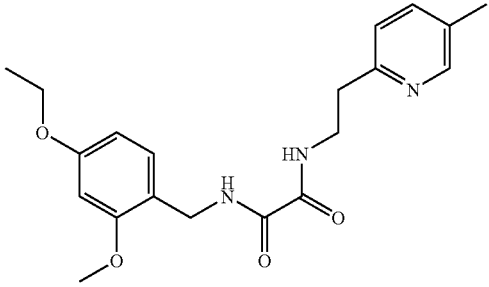N1-(4-ethoxy-2-methoxybenzyl)-N2-(2-(5-methylpyridin-2-yl)ethyl)oxalamide | 0.19 | |
| B3 | 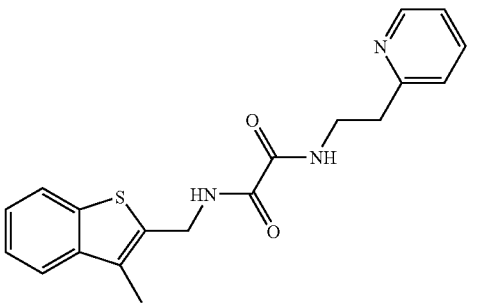N-(3-Methyl-benzo[b]thiophen-2-ylmethyl)-N'-(2-pyridin-2-yl-ethyl)-oxalamide | 0.81 | |
| B4 | 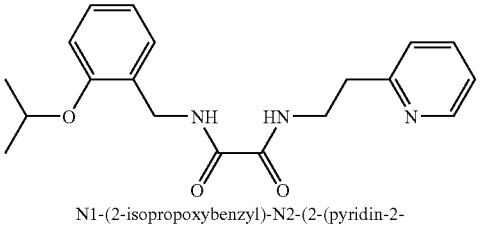N1-(2-isopropoxybenzyl)-N2-(2-(pyridin-2-yl)ethyl)oxalamide | 1.22 | |

Numerous amide compounds of Formula (I) that fall within the subgenus of "urea" compounds described elsewhere herein were also synthesized and experimentally tested for effectiveness as activator of a hT1R1/hT1R3 umami receptor expressed in an HEK293 cell line.

Example 158

1-(4-chlorophenyl)-3-(heptan-4-yl)urea

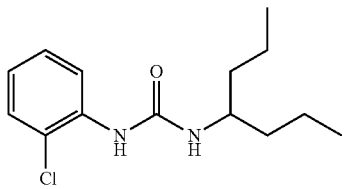

To a solution of heptan-4-amine (0.18 mL, 1 mmol) in CH$_2$Cl$_2$ (5 mL) was added 1-chloro-2-isocyanatobenzene (0.12 mL, 1 mmol) at room temperature. The reaction mixture was stirred for 2 h. A white solid was precipitated out. The reaction mixture was filtered. The solid was washed with CH$_2$Cl$_2$ to afford 1-(4-chlorophenyl)-3-(heptan-4-yl)urea (180 mg, 67%) as a white solid. mp: 135-136° C. $^1$H NMR (500 MHz, CDCl$_3$): δ 0.93 (t, 6H), 1.45 (m, 6H), 1.53 (m, 2H), 3.80 (br s, 1H), 4.33 (d, 1H), 6.00 (s, 1H), 6.95 (td, 1H), 7.23 (dt, 1H), 7.33 (dd, 1H), 8.13 (dd, 1H). MS (M+H, 269).

The compound had an EC$_{50}$ for activation of a hT1R1/hT1R3 umami receptor expressed in an HEK293 cell line of 0.37 μM, and when present at 1 μM enhanced the effectiveness of monosodium glutamate with an EC$_{50}$ ratio of 4.95.

Example 159

1-(2,4-dimethoxyphenyl)-3-(heptan-4-yl)urea

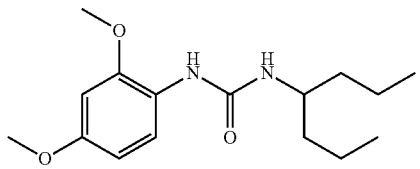

Prepared in a similar manner to example 158 using heptan-4-amine and 1-isocyanato-2,4-dimethoxybenzene. Yield: 88%. mp: 172-173° C. $^1$H NMR (500 MHz, CDCl$_3$): δ 0.93 (t, 6H), 1.45 (m, 8H), 3.82 (s, 3H), 3.83 (m, 1H), 3.84 (s, 1H), 4.32 (br s, 1H), 6.34 (br s, 1H), 6.49 (d, 1H), 6.50 (s, 1H), 7.71 (d, 1H). MS (M+H, 295).

The compound had an EC$_{50}$ for activation of a hT1R1/hT1R3 umami receptor expressed in an HEK293 cell line of 0.98 μM, and when present at 0.3 μM enhanced the effectiveness of monosodium glutamate with an EC$_{50}$ ratio of 7.61.

Example 160

1-(4-ethoxyphenyl)-3-(2-(pyridine-2-yl)ethyl)urea

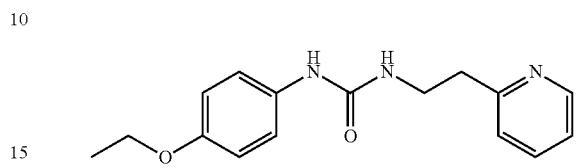

Prepared in a similar manner to example 158 using 2-(pyridine-2-yl)ethanamine and 1-ethoxy-4-isocyanatobenzene. Yield: 95%. mp: 163-164° C. $^1$H NMR (500 MHz, CDCl$_3$): δ 1.43 (t, 3H), 3.03 (t, 2H), 3.68 (t, 2H), 4.03 (q, 2H), 5.69 (br s, 1H), 6.45 (br s, 1H), 6.84 (m, 2H), 7.14 (m, 3H), 7.20 (d, 1H), 7.64 (dt, 1H), 8.43 (dd, 1H). MS (M+H, 286).

The compound had an EC$_{50}$ for activation of a hT1R1/hT1R3 umami receptor expressed in an HEK293 cell line of 4.1 μM, and when present at 1 μM enhanced the effectiveness of monosodium glutamate with an EC$_{50}$ ratio of 4.2.

Example 161

1-(4-isopropylphenyl)-3-(2-(pyridine-2-yl)ethyl)urea

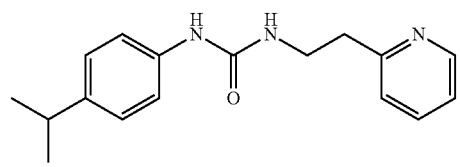

Prepared in a similar manner to example 158 using 2-(pyridine-2-yl)ethanamine and 1-isocyanato-4-isopropylbenzene. Purified via column chromatography (1% MeOH in CH$_2$Cl$_2$ to 3% MeOH in CH$_2$Cl$_2$) to afford 1-(4-isopropylphenyl)-3-(2-(pyridine-2-yl)ethyl)urea (130 mg, 50%) as a white solid. mp: 72-73° C. $^1$H NMR (500 MHz, CDCl$_3$): δ 1.25 (d, 6H), 2.89 (m, 1H), 3.06 (t, 2H), 3.70 (t, 2H), 5.80 (br s, 1H), 6.55 (br s, 1H), 7.19 (m, 5H), 7.24 (d, 1H), 7.68 (dt, 1H), 8.46 (d, 1H). MS (M+H, 284).

The compound had an EC$_{50}$ for activation of a hT1R1/hT1R3 umami receptor expressed in an HEK293 cell line of 0.98 μM.

Additional "urea" compounds were synthesized and experimentally tested and found to have a relatively high level of effectiveness as an activator of a hT1R1/hT1R3 umami receptor expressed in an HEK293 cell line. The results of that testing are shown below in Table C.

TABLE C

Umami Ureas

| Compound No. | IUPAC Name | Umami EC$_{50}$ uM | Ec50 ratio (vs MSG) | Con. (uM) |
|---|---|---|---|---|
| C1 | 1-(2-chlorophenyl)-3-(heptan-4-yl)urea | 0.37 | 4.95 | 1 |
| C2 | 1-(2,4-dichlorophenyl)-3-(1-phenylpropyl)urea | 0.49 | 4.52 | 1 |
| C3 | 1-(2-chlorophenyl)-3-(2-methylcyclohexyl)urea | 0.52 | 3.24 | 3 |
| C4 | 1-(2-fluorophenyl)-3-(heptan-4-yl)urea | 0.79 | 12.15 | 3 |
| C5 | 1-(2-chlorophenyl)-3-(1-cyclohexylethyl)urea | 0.84 | 9.08 | 1 |
| C6 | 1-(4-isopropylphenyl)-3-(2-(pyridin-2-yl)ethyl)urea | 0.98 | | |

TABLE C-continued
Umami Ureas
| Compound No. | IUPAC Name | Umami EC$_{50}$ uM | Ec50 ratio (vs MSG) | Con. (uM) |
|---|---|---|---|---|
| C7 | 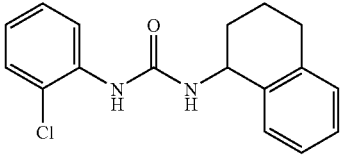<br>1-(2-chlorophenyl)-3-(1,2,3,4-tetrahydronaphthalen-1-yl)urea | 0.99 | 3.68 | 1 |
| C8 | 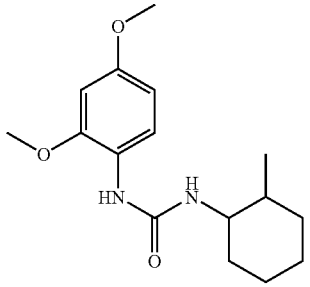<br>1-(2,4-dimethoxyphenyl)-3-(2-methylcyclohexyl)urea | 1.41 | 2.62 | 0.3 |
| C9 | 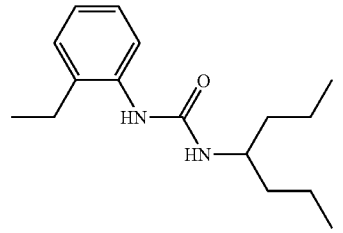<br>1-(2-ethylphenyl)-3-(heptan-4-yl)urea | 1.42 | | |
| C10 | 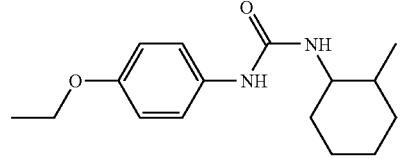<br>1-(4-ethoxyphenyl)-3-(2-methylcyclohexyl)urea | 1.51 | 2.1 | 0.3 |
| C11 | 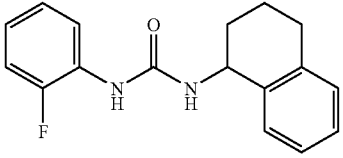<br>1-(2-fluorophenyl)-3-(1,2,3,4-tetrahydronaphthalen-1-yl)urea | 1.65 | 4.49 | 1 |
| C12 | 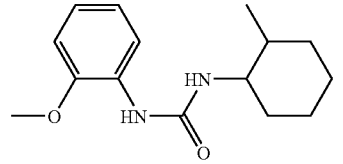<br>1-(2-methoxyphenyl)-3-(2-methylcyclohexyl)urea | 1.67 | | |

TABLE C-continued

Umami Ureas

| Compound No. | IUPAC Name | Umami EC$_{50}$ uM | Ec50 ratio (vs MSG) | Con. (uM) |
|---|---|---|---|---|
| C13 | 1-(2,4-dimethoxyphenyl)-3-(pentan-3-yl)urea 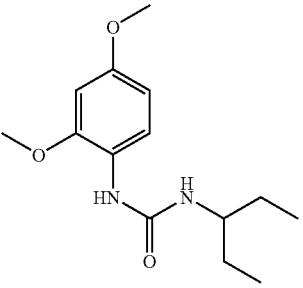 | 1.72 | 11.87 | 1 |

Numerous amide compounds of Formula (I) that fall within the subgenus of "acrylamide" compounds described elsewhere herein were also synthesized and experimentally tested for effectiveness as activator of a hT1R1/hT1R3 umami receptor expressed in an HEK293 cell line. The results of that testing are shown below in Table D.

TABLE D

Umami Acrylamides

| Compound No. | Compound | Umami EC$_{50}$ (uM) | Ec$_{50}$ ratio (vs. MSG) | @ (uM) |
|---|---|---|---|---|
| D1 | (E)-N-(2,4-dimethylpentan-3-yl)-3-(4-methoxyphenyl)acrylamide 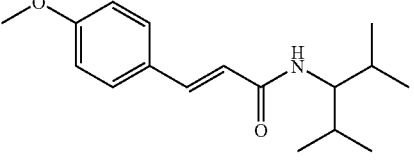 | 0.29 | 3.46 | 1 |
| D2 | (R,E)-methyl 2-(3-(4-methoxyphenyl)acrylamido)-4-methylpentanoate 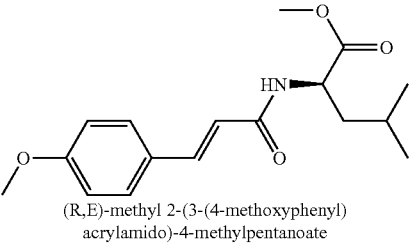 | 0.32 | | |
| D3 | (E)-methyl 2-(3-(4-methoxyphenyl)acrylamido)hexanoate 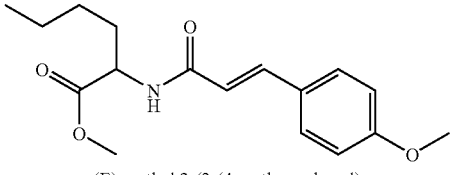 | 0.63 | | |
| D4 | N-(1-Methyl-3-phenyl-propyl)-3-thiophen-2-yl-acrylamide 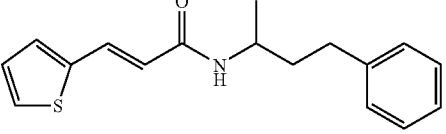 | 0.69 | 9.73 | 1 |

TABLE D-continued

Umami Acrylamides

| Compound No. | Compound | Umami EC$_{50}$ (uM) | Ec$_{50}$ ratio (vs. MSG) | @ (uM) |
|---|---|---|---|---|
| D5 | 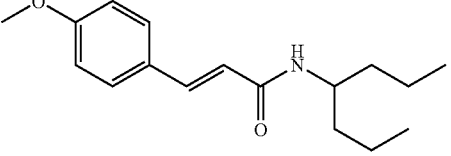<br>(E)-N-(heptan-4-yl)-3-(4-methoxyphenyl)acrylamide | 0.72 | 3.48 | 0.3 |
| D6 | 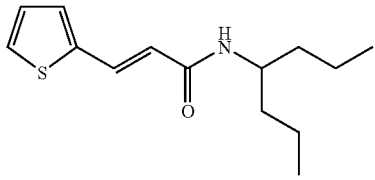<br>N-(1-Propyl-butyl)-3-thiophen-2-yl-acrylamide | 0.75 | 6.3 | 1 |
| D7 | 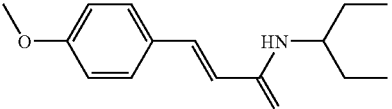<br>(E)-3-(4-methoxyphenyl)-N-(pentan-3-yl)acrylamide | 0.82 | 9.62 | 1 |
| D8 | 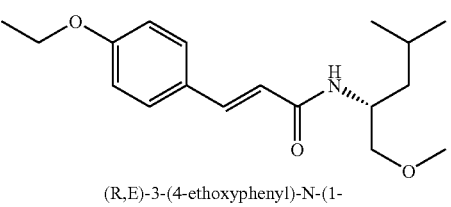<br>(R,E)-3-(4-ethoxyphenyl)-N-(1-methoxy-4-methylpentan-2-yl)acrylamide | 0.94 | | |
| D9 | 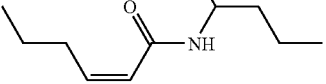<br>(Z)-N-(heptan-4-yl)hex-2-enamide | 0.98 | | |
| D10 | 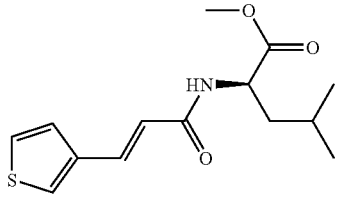<br>(R,E)-methyl 4-methyl-2-(3-(thiophen-3-yl)acrylamido)pentanoate | 1.09 | | |
| D11 | 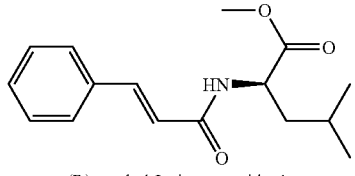<br>(R)-methyl 2-cinnamamido-4-methylpentanoate | 1.17 | | |

TABLE D-continued

Umami Acrylamides

| Compound No. | Compound | Umami EC$_{50}$ (uM) | Ec$_{50}$ ratio (vs. MSG) | @ (uM) |
|---|---|---|---|---|
| D12 | 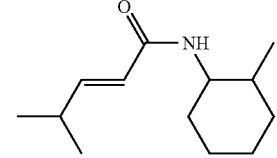(E)-4-methyl-N-(2-methylcyclohexyl)pent-2-enamide | 1.28 | | |
| D13 | 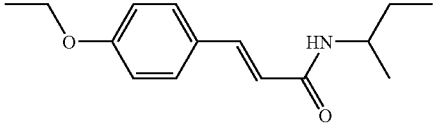(E)-N-sec-butyl-3-(4-ethoxyphenyl)acrylamide | 1.31 | 2.7 | 0.3 |
| D14 | 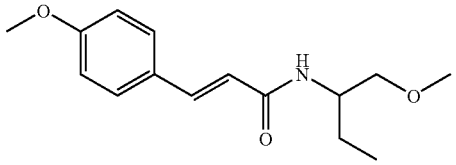(E)-N-(1-methoxybutan-2-yl)-3-(4-methoxyphenyl)acrylamide | 1.43 | 8.48 | 1 |
| D15 | 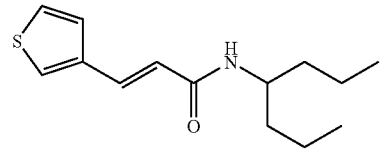(E)-N-(heptan-4-yl)-3-(thiophen-3-yl)acrylamide | 1.54 | 2.22 | 0.3 |
| D16 | 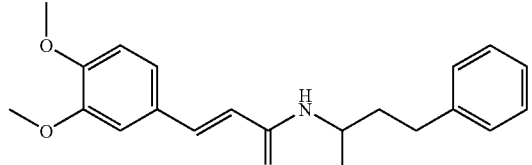(E)-3-(3,4-dimethoxyphenyl)-N-(4-phenylbutan-2-yl)acrylamide | 1.56 | 3.13 | 1 |

Umami/Savory Flavor Experiments Using Human Panelists:

General Panelist Selection: Basic screening of sensory taste testers: Potential panelists were tested for their abilities to rank and rate intensities of solutions representing the five basic tastes. Panelists ranked and rated intensity of five different concentrations of each of the five following compounds: sucrose (sweet), sodium chloride (salty), citric acid (sour), caffeine (bitter), and monosodium glutamate (savory). In order to be selected for participation in testing, panelists needed to correctly rank and rate samples for intensity, with a reasonable number of errors Preliminary Taste Tests: The panelists selected in the above procedure were deemed qualified for performing Preliminary Taste Testing procedures. The preliminary taste tests are used to evaluate new compounds for intensity of basic tastes and off-tastes. A small group of panelists (n=5) taste approximately 5 concentrations of the compound (range typically between 1-100 μM, in half-log cycles, e.g., 1, 3, 10, 30, and 100 μM) in water and in a solution of 12 mM MSG to evaluate enhancement. Panelists rate the five basic tastes (sweet, salty, sour, bitter, and savory) as well as off-tastes (such as chemical, metallic, sulfur) on a labeled magnitude scale. Samples are served in 10 mL portions at room temperature. The purpose of the test is to determine the highest concentration at which there is no objectionable off-taste, and determine if obvious savory taste or enhancement of savory taste exists at any of the concentrations tested.

If the compound is effective and does not have objectionable off-tastes, it is tested with a trained (expert panel) in a larger study.

Trained Panelist Selection: A trained expert panel was used to further evaluate compounds that had been tested with the preliminary taste test.

Panelists for the trained panel were selected from the larger group of qualifying taste panelists. Panelists were further trained on savory taste by ranking and rating experiments using MSG and IMP combinations. Panelists completed a series of ranking, rating, and difference from reference tests with savory solutions. In ranking and rating experiments, panelists evaluated easy MSG concentrations (0, 6, 18, 36 mM) and more difficult MSG concentrations (3, 6, 12, 18 mM MSG) in water.

Compound testing with Trained Panel: Compounds tested by the trained panel were evaluated in difference from reference experiments. Panelists were given a reference sample (12 mM MSG+100 μM IMP) and asked to rate samples on a scale of −5 to +5 in terms of difference in savory taste from the reference (score: −5=much less savory taste than the reference; 0=same savory taste as the reference; +5=much more savory taste than the reference). Test samples were solutions with varying amounts of MSG, IMP, and the compound. Typically, each session compares the reference sample to numerous test samples Tests typically included various samples with varying concentrations of MSG and IMP, as well as one blind sample of the reference itself, to evaluate panel accuracy. Results of the taste tests are describe in table 3 and shows that compounds of the invention have been found to provide savory taste or enhancement of the savory taste at 3 μM+

MSG when compared to 100 μM IMP+MSG. Compounds were tested against the reference in samples with and without 12 mM MSG. All samples were presented in 10 ml volumes at room temperature. Two sessions were completed for each compound tested to evaluate panel reproducibility.

Taste Test in Product Prototype: could be done similarly as described above.

TABLE 3

Savory Taste Test Results

| Compound No. | Chemical Name | Taste Data |
|---|---|---|
| Example 1 | N-(heptan-4-yl)benzo[d][1,3]dioxole-5-carboxamide | 12 mM MSG + 3 μM cpd as strong as 12 mM MSG + 100 μM IMP |
| Example 6 | (R)-methyl 2-(benzo[d][1,3]dioxole-6-carboxamido)-4-methylpentanoate | 12 mM MSG + 10 μM cpd as strong as 12 mM MSG + 100 μM IMP |
| Example 71 | (R)—N-(1-methoxy-4-methylpentan-2-yl)-3,4-dimethylbenzamide | 12 mM MSG + 3 μM cpd as strong as 12 mM MSG + 100 μM IMP |
| Example 98 | (R)-methyl-2-(2,3-dimethylfuran-5-carboxamido)-4-methylpentanoate | 12 mM MSG + 10 μM cpd as strong as 12 mM MSG + 100 μM IMP |
| Example 104 | 4-Methoxy-N-(1-methoxymethyl-3-methyl-butyl)-3-methyl-benzamide | 12 mM MSG + 3 μM cpd as strong as 12 mM MSG + 100 μM IMP |
| Example 123 | N-(2,4-Dimethoxy-benzyl)-N'-(2-pyridin-2-yl-ethyl)-oxalamide | 12 mM MSG + 1 μM cpd as strong as 12 mM MSG + 100 μM IMP |
| Example 157 | $N^1$-(2-methoxy-4-methylbenzyl)-$N^2$-(2-(5-methylpyridin-2-yl)ethyl)oxalamide | 12 mM MSG + 0.3 μM cpd as strong as 12 mM MSG + 100 μM IMP |

Sweet Amide Examples

Numerous amide compounds of Formula (I) were synthesized and experimentally tested for effectiveness as activator of a hT1R2/hT1R3 "sweet" receptor expressed in an HEK293 cell line. Examples of the synthesis and biological effectiveness testing in terms of Sweet $EC_{50}$ measurements for such sweet compounds are listed below. Moreover, many of the "sweet" amides of Formula (I) were also screened for activity in the umami $EC_{50}$ and $EC_{50}$ ratio assays, and as illustrated below, some of the amide compounds of Formula (I) have significant activity and potential to simultaneously serve as savory and sweet taste enhancers for use in comestible and medicinal products and compositions.

Example 162

2,3,5,6-tetrafluoro-4-methyl-N-(2-methylcyclohexyl)benzamide

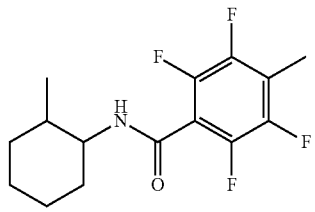

2,3,5,6-tetrafluoro-p-toluic acid (4.00 g, 19.22 mmol), HOBt (5.19 g, 38.44 mmol) and EDCI (4.42 g 23.06 mmol) were mixed in 200 ml of anhydrous DCM and 30 ml of anhydrous DMF. The mixture was cooled to 0° C. and allowed to stir under Ar for 15 minutes. To the mixture was added 2-methylcyclohexanamine (3.05 mL, 23.06 mmol) and the reaction mixture was allowed to slowly warm to ambient temperature and stirred overnight. The reaction mixture was diluted with DCM, washed with 1N HCl, water, aqueous NaHCO₃, water and brine, drying over MgSO₄, filtration and removal of solvent in vacuo, afforded the crude product as a pale yellow solid Recrystallization (EtOH/H₂O) and drying in vacuo gave 5.23 g of the title compound as a white solid (mixture of 2 diasteromers, 90%). $^1$H NMR (CDCl₃) δ 0.95, 1.01 (d, J=7.0, 6.6 Hz, 3H) 1.1-2.1 (m, 9H), 2.29 (m, 3H), 3.70, 4.29 (m, 1H), 5.65, 5.92 (m, 1H). MS (304.1, M+H). m.p. 202-204° C.

The compound had an $EC_{50}$ for activation of a hT1R2/hT1R3 sweet receptor expressed in an HEK293 cell line of 0.39 μM.

Example 163

(S)-2,3,5,6-tetrafluoro-4-methyl-N-(3-methylbutan-2-yl)benzamide

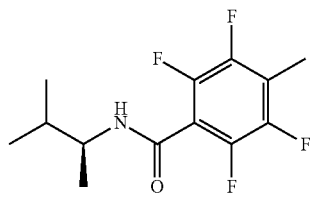

Prepared in a similar manner to Example 162 using (S)-3-methylbutan-2-amine and 2,3,5,6-tetrafluoro-p-toluic acid acid (93%). $^1$H NMR (CDCl₃) δ 0.98 (d, J=6.9 Hz, 6H) 1.18 (d, J=6.8 Hz, 3H), 2.29 (m, 3H), 4.09 (m, 1H), 5.72 (bs, 1H). MS (304.1, M+H) m.p. 146-147° C.

The compound had an $EC_{50}$ for activation of a hT1R2/hT1R3 sweet receptor expressed in an HEK293 cell line of 0.6 μM.

Example 164

N-cycloheptyl-2,3,5,6-tetrafluoro-4-methylbenzamide

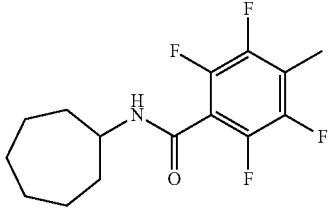

Prepared in a similar manner to Example 162 using cycloheptylamine and 2,3,5,6-tetrafluoro-p-toluic acid (94%). $^1$H NMR (CDCl$_3$) δ 1.53 (m, 6H), 1.57 (m, 4H), 2.03 (m, 2H) 2.28 (m, 3H), 4.17 (m, 1H), 5.85 (bs, 1H). MS (304.1, M+H) m.p. 164-165° C.

The compound had an EC$_{50}$ for activation of a hT1R2/hT1R3 sweet receptor expressed in an HEK293 cell line of 1.85 µM.

Example 165

N-(2,4-dimethylpentan-3-yl)-2,3,5,6-tetrafluoro-4-methylbenzamide

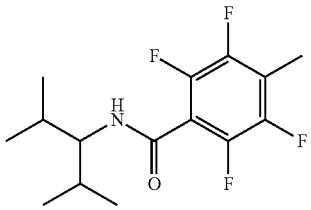

Prepared in a similar manner to Example 162 using 2,4-dimethylpentan-3-amine and 2,3,5,6-tetrafluoro-p-toluic acid (90%). $^1$H NMR (CDCl$_3$) δ 0.91 (d, J=6.7 Hz, 6H), 1.00 (d, J=6.8 Hz, 6H), 1.85 (m, 2H), 2.29 (m, 3H), 3.82 (m, 1H), 5.52 (bd, 1H). MS (306.1, M+H) m.p. 184-187° C.

The compound had an EC$_{50}$ for activation of a hT1R2/hT1R3 sweet receptor expressed in an HEK293 cell line of 0.81 µM.

Example 166

N-(5,7-dimethyl-1,2,3,4-tetrahydronaphthalen-1-yl)-3-methylisoxazole-4-carboxamide

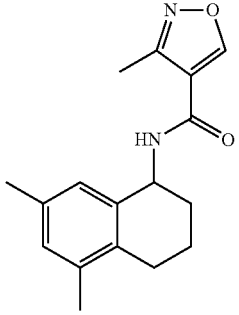

To a solution of 3-methylisoxazole-4-carboxylic acid (83 mg, 0.0.67 mmol), HOBt (100 mg, 0.74 mmol) and EDCI/HCl (142 mg, 0.74 mmol) in DMF (4 mL), was added 5,7-dimethyl-1,2,3,4-tetrahydronaphthyl-1-amine (example 166a) (130 mg, 0.74 mmol). The reaction mixture was stirred for 24 h at rt, at which time the solvent was removed under reduced pressure and the residue was purified by flash-column chromatography (10:1 Hex:EtOAc) to afford 134 mg of N-(5,7-dimethyl-1,2,3,4-tetrahydronaphthalen-1-yl)-3-methylisoxazole-4-carboxamide (70%) as a white foamy solid. $^1$H NMR (500 MHz, DMSO-d$_6$): δ 1.74 (m, 2H), 1.86 (m, 2H), 2.16 (s, 3H), 2.19 (s, 3H), 2.43 (s, 3H), 2.55 (m, 2H), 5.10 (m, 1H), 6.86 (s, 1H), 6.89 (s, 1H), 8.60 (d, 1H, J=8.40 Hz), 9.27 (s, 1H). $^{13}$C NMR (125 MHz, DMSO-d$_6$): δ 10.6, 19.1, 19.6, 20.6, 25.8, 29.4, 46.9, 115.4, 126.4, 129.1, 132.6, 134.1, 135.8, 136.6, 158.5, 159.6, 159.9. MS (M+H, 285). Mp 57-58° C.

a. 5,7-dimethyl-1,2,3,4-tetrahydronaphthalen-1-amine: A catalytic amount of Raney nickel (slurry in water) was washed with dry MeOH under argon in a round bottom flask. To a solution of the washed Raney Ni in methanolic ammonia (25 mL, 7N), was added 5,7-dimethyl-3,4-dihydronaphthalen-1(2H)-one oxime (example 166b) (420 mg, 2.22 mmol), and the mixture was stirred under a balloon of H$_2$ for 20 hr. Upon completion, the reaction was filtered through celite, the filtrate was concentrated in vacuo, diluted with EtOAC, washed with water and brine, dried over MgSO$_4$, filtered and the solvent was removed under reduced pressure to afford 360 mg of 5,7-dimethyl-1,2,3,4-tetrahydronaphthalen-1-amine (93%). $^1$H NMR (500 MHz, CDCl$_3$): δ 1.66-1.83 (m, 4H), 1.96 (m, 2H), 2.19 (s, 3H), 2.28 (s, 3H), 2.55 (m, 1H), 2.66 (m, 1H), 3.97 (m, 1H), 6.88 (s, 1H), 7.09 (s, 1H).

b. Preparation of 5,7-dimethyl-3,4-dihydronaphthalen-1(2H)-one oxime: To a mixture of 5,7-dimethyl-3,4-dihydronaphthalen-1(2H)-one (2.0 g, 11.48 mmol) and hydroxylamine hydrochloride (1.6 g, 19.73 mmol) in 10 ml of water at 70° C., were added MeOH (14 mL), THF (3 mL) and a solution of sodium acetate (2.53 g, 30.83 mmol, in 7 mL of H$_2$O). Stirring was continued for 85 min at 70° C., at which time a precipitate was formed and 10 ml of water were added. The resulting mixture was stirred at room temperature for 2 hr. Upon completion, the product was collected by filtration to afford 2.12 g of 5,7-dimethyl-3,4-dihydronaphthalen-1(2H)-one oxime (98%). MS (M+H, 190).

The compound had an EC$_{50}$ for activation of a hT1R2/hT1R3 sweet receptor expressed in an HEK293 cell line of 0.76 µM.

Example 167

3-chloro-2-hydroxy-N-(5-methoxy-1,2,3,4-tetrahydronaphthalen-1-yl) benzamide

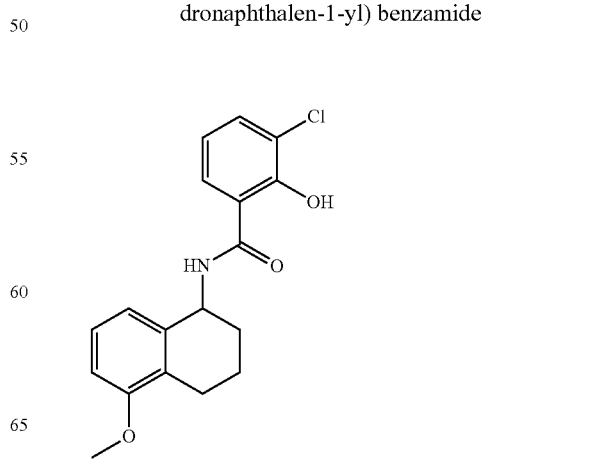

Prepared in similar manner to Example 166 using 5-methoxy-1,2,3,4-tetrahydronaphthalen-1-amine (Example 167a). Yield 40%. $^1$H NMR (500 MHz, DMSO-$d_6$): δ 1.73 (m, 1H), 1.83 (m, 1H), 1.96 (m, 2H), 2.61 (m, 2H), 3.78 (s, 3H), 5.27 (m, 1H), 6.78 (d, 1H, J=7.82 Hz), 6.86 (m, 2H), 7.14 (t, 1H, J=7.98 Hz), 7.60 (dd, 1H, J=7.88, 1.30 Hz), 7.94 (dd, 1H, J=8.03, 1.39 Hz), 9.30 (d, 1H, J=8.06 Hz), 13.80 (s, 1H). $^{13}$C NMR (125 MHz, DMSO-$d_6$): δ 19.5, 22.7, 28.9, 47.4, 55.3, 108.6, 115.8, 118.7, 119.8, 121.1, 125.9, 126.2, 126.4, 133.8, 137.3, 156.7, 156.8, 168.7. MS (M+H, 332). Mp 175-176° C.

a. 5-methoxy-1,2,3,4-tetrahydronaphthalen-1-amine: Prepared in a similar manner to example 166a using 5-methoxy-3,4-dihydronaphthalen-1(2H)-one. Yield 94%. $^1$H NMR (500 MHz, CDCl$_3$): δ 1.63-1.79 (m, 4H), 1.94 (m, 2H), 2.60 (m, 1H), 2.71 (m, 1H), 3.82 (s, 3H), 3.97 (m, 1H), 6.71 (d, 1H), 7.02 (d, 1H), 7.17 (t, 1H).

The compound had an EC$_{50}$ for activation of a hT1R2/hT1R3 sweet receptor expressed in an HEK293 cell line of 0.21 μM.

Example 168

2,6-dimethyl-N-(2-methylcyclohexyl)benzamide

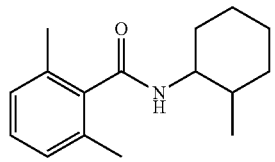

Prepared in a similar manner to Example 162 using 2,6-dimethylbenzoic acid and 2-methylcyclohexylamine. Yield: 59%. $^1$H NMR (500 MHz, CDCl$_3$): δ 0.88-0.94 (3H, dd), 1.14-1.89 (9H, m), 2.21-2.22 (6H, d), 3.39-3.45 (1H, m), 7.02-7.03 (2H, d), 7.12-7.15 (1H, t), 8.11-8.13 (1H, d). MS (M+H, 246.2).

The compound had an EC$_{50}$ for activation of a hT1R2/hT1R3 sweet receptor expressed in an HEK293 cell line of 1.88 μM.

Example 169

4-methoxy-2,6-dimethyl-N-(2-methylcyclohexyl)benzamide

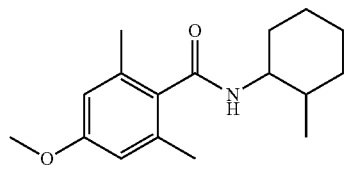

Prepared in a similar manner to Example 166 using 4-methoxy-2,6-dimethylbenzoic acid (example 169a) and 2-methylcyclohexylamine. $^1$H NMR (500 MHz, CDCl$_3$): δ 0.86-0.92 (3H, dd), 1.00-1.85 (m, 9H), 2.18-2.19 (6H, d), 3.33-3.45 (1H, m), 3.71-3.72 (3H, d), 6.59 (2H, s), 7.98-8.05 (1H, m). MS (276.2, M+H)

a. 4-methoxy-2,6-dimethylbenzoic acid: 2-Bromo-5-methoxy-1,3-dimethylbenzene (example 169b) (3.38 g, 15.79 mmol) was without further purification dissolved in 100 ml of dry THF. The mixture was cooled to −78° C. and under argon n-butyllithium (1.6 M solution in hexanes, 9.9 ml, 15.8 mmol) was added drop wise over 15 min and the mixture was stirred for 15 more min at −78° C. Than small pieces of dry ice were added and the mixture was stirred 20 min at −78° C. Then the cooling was removed and the mixture was stirred as long as evolution of carbon dioxide continued. Then the mixture was poured over ice (100 ml) and acidified using 6N HCl. The organic layer was separated and water phase was extracted with EtOAc. Organic extracts were combined, washed with brine, water, dried over MgSO$_4$ and concentrated under vacuum. The product 4-methoxy-2,6-dimethylbenzoic acid was obtained as a white solid (2.7 g, 95%). (M+H, 181).

b. 2-Bromo-5-methoxy-1,3-dimethylbenzene: 20 mmol of 1-methoxy-3,5-dimethylbenzene (2.82 ml) was dissolved in 100 ml of dry acetonitrile followed by 22 mmol (3.56 g) of N-bromosuccinimide. The mixture was stirred at room temperature overnight. Then the solvent vas evaporated under reduced pressure and a solid was filtered off and washed with hexanes providing 2-bromo-5-methoxy-1,3-dimethylbenzene (3.9 g, 92%) as white solid. $^1$H NMR (500 MHz, CDCl$_3$): δ 2.41 (6H, s), 3.78 (3H, s), 6.67 (2H, s).

The compound had an EC$_{50}$ for activation of a hT1R2/hT1R3 sweet receptor expressed in an HEK293 cell line of 2.1 μM.

Example 170

(R)—N-(1,2,3,4-tetrahydronaphthalen-1-yl)furan-3-carboxamide

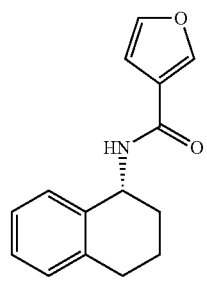

To a solution of furan-3-carboxylic acid (100 mg, 0.68 mmol), HOBt (240 mg, 1.78 mmol) and EDCI.HCl (196 mg, 1.03 mmol) in CH$_2$Cl$_2$ (8 mL) and DMF (1.5 mL) at 0° C., was added (R)-1,2,3,4-tetrahydronaphthalen-1-amine (160 μL, 1.06 mmol). The reaction was stirred at rt for 24 h, after which CH$_2$Cl$_2$ was added. The resulting solution was washed with saturated NaHCO$_3$, H$_2$O, brine, dried over MgSO$_4$ and concentrated in vacuo. Recrystallization from EtOH/H$_2$O afforded (R)—N-(1,2,3,4-tetrahydronaphthalen-1-yl)-2,5-dihydrofuran-3-carboxamide. $^1$H NMR (500 MHz, CDCl$_3$): δ 1.89 (m, 3H), 2.12 (m, 1H), 2.84 (m, 2H), 5.35 (m, 1H), 5.96 (br d, 1H, J=7.75 Hz), 6.59 (dd, 1H, J=1.90, 0.86 Hz), 7.13 (m, 1H), 7.19 (m, 2H), 7.32 (m, 1H), 7.43 (t, 1H, J=1.73 Hz), 7.93 (m, 1H). MS (M+H, 242).

The compound had an EC$_{50}$ for activation of a hT1R2/hT1R3 sweet receptor expressed in an HEK293 cell line of 6.6 μM.

Example 171

(R)-5-methyl-N-(1,2,3,4-tetrahydronaphthalen-1-yl)isoxazole-4-carboxamide

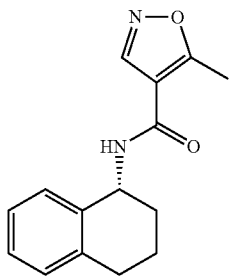

Prepared in a similar manner to Example 170 using 5-methylisoxazole-4-carboxylic acid. Purified by preparative TLC (5:1 Hex:EtOAc). $^1$H NMR (500 MHz, CDCl$_3$): δ 1.80 (m, 3H), 2.12 (m, 1H), 2.74 (s, 3H), 2.85 (m, 2H), 5.35 (m, 1H), 5.89 (br d, 1H, J=7.75 Hz), 7.10 (m, 1H), 7.18 (m, 2H), 7.32 (m, 1H), 8.26 (s, 1H). MS (M+H, 257).

The compound had an EC$_{50}$ for activation of a hT1R2/hT1R3 sweet receptor expressed in an HEK293 cell line of 8.1 μM.

Example 172

N-(4-chloro-2-methylphenyl)isoindoline-2-carboxamide

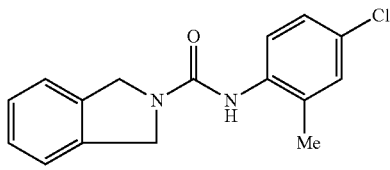

To a solution of isoindoline (238 mg, 2.0 mmol) in dry 1,4-dioxane (10 mL) was added 4-chloro-2-methylphenyl isocyanate (335 mg, 2.0 mmol) under argon at room temperature. The reaction mixture was then stirred at RT overnight. The solvent was evaporated under reduced pressure, and the residue was purified by recrystallization from ethanol to give the title compound (540 mg, 94%) as a white solid. $^1$H NMR (500 MHz, DMSO-d$_6$): δ 2.24 (s, 2H), 4.76 (s, 4H), 7.20 (dd, J=2.5, 8.5 Hz, 1H), 7.27 (d, J=2.5 Hz, 1H), 7.30-7.32 (m, 2H), 7.34-7.37 (m, 2H), 7.42 (d, J=8.5 Hz, 1H), 7.84 (s, 1H); $^{13}$C NMR (DMSO-d$_6$): δ 17.7, 51.9, 122.8, 125.6, 126.8, 127.3, 128.1, 129.5, 134.7, 136.8, 154.2; MS (MH$^+$, 287); EA calc'd for C$_{16}$H$_{15}$ClN$_2$O: C, 67.02; H, 5.27; N, 9.77. Found C, 66.82; H, 5.41; N, 9.92.

The compound had an EC$_{50}$ for activation of a hT1R2/hT1R3 sweet receptor expressed in an HEK293 cell line of 0.89 μM.

Example 173

N-(4-methoxy-2-methylphenyl)isoindoline-2-carboxamide

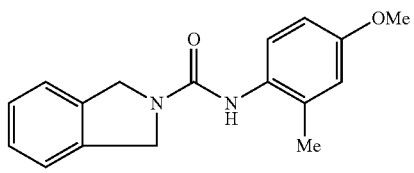

To a solution of isoindoline (576 mg, 4.0 mmol) in dry 1,4-dioxane (20 mL) was added 4-methoxy-2-methylphenyl isocyanate (815 mg, 5.0 mmol) under argon at room temperature. The reaction mixture was then stirred at RT overnight. The solvent was evaporated under reduced pressure, and the residue was purified by chromatography on silica gel (EtOAc/hexanes: 1:1) to give the title compound (1.18 g, 84%) as a white solid. $^1$H NMR (500 MHz, DMSO-d$_6$): δ 2.19 (s, 3H), 3.72 (s, 3H), 4.73 (s, 4H), 6.72 (dd, J=2.5 Hz, 8.5 Hz, 1H), 6.78 (d, J=2.5 Hz, 1H), 7.17 (d, J=8.5 Hz, 1H), 7.30-7.32 (m, 2H), 7.34-7.36 (m, 2H), 7.74 (s, 1H), $^{13}$C NMR (DMSO-d$_6$): δ 18.2, 51.9, 55.1, 110.9, 115.1, 122.8, 127.2, 127.8, 130.6, 135.1, 137.0, 154.9, 156.5; MS (MH$^+$, 283); EA calc'd for C$_{17}$H$_{18}$N$_2$O$_2$: C, 72.32; H, 6.43; N, 9.92. Found C, 72.16; H, 6.82; N, 9.98.

The compound had an EC$_{50}$ for activation of a hT1R2/hT1R3 sweet receptor expressed in an HEK293 cell line of 4.5 μM.

Example 174

N-(3,4-methylenedioxyphenyl)isoindoline-2-carboxamide

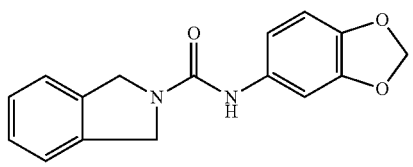

To a solution of 3,4-(methylenedioxy)aniline (150 mg, 1.09 mmol) in dry DCM (4 mL) was added dropwise phenyl chloroformate (0.138 ml, 1.09 mmol) and triethylamine (0.153 ml, 1.09 mmol). After the reaction mixture was stirred at r.t for 8 hr., isoindoline (0.123 ml, 1.09 mmol) and triethylamine (0.153 ml, 1.09 mmol) were added, and the reaction mixture was stirred overnight. The solvent was then removed under reduced pressure, and the residue was purified by chromatographed on silica gel (EtOAC/Hexane: 1:3) to give the title compound (185 mg, 60%) as a white solid: m.p: 165-166° C. $^1$H NMR (CDCl$_3$, 500 MHz): 4.82 (s, 4H); 5.93 (s, 2H); 6.20 (s, 1H); 6.73 (s, 2H); 7.17 (s, 1H); 7.30 (m, 4H). MS (MH$^+$, 283).

The compound had an $EC_{50}$ for activation of a hT1R2/hT1R3 sweet receptor expressed in an HEK293 cell line of 1.05 μM.

Example 175

3-Methyl-isoxazole-4-carboxylic Acid (1,2,3,4-tetrahydro-naphthalen-1-yl)-amide

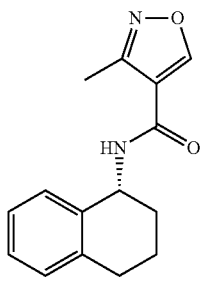

To a solution of 3-Methyl-isoxazole-4-carboxylic acid (0.52 g, 4.06 mmol) in DCM (15 mL) and DMF (2 mL), was added HOBt (1.1 g, 8.14 mmol) and EDCI (0.896 g 4.67 mmol). The clear yellow solution was cooled to 0 C and allowed to stir under Ar for 15 minutes. To the solution was added (R)-1-Amino-1,2,3,4-tetrahydronaphthalene (0.73 mL, 5.04 mmol and the reaction mixture was allowed to slowly warm to ambient temperature and was stirred for overnight. Dilution with DCM (50 mL) was followed by aqueous extraction ($NaHCO_3$ water, brine (50 mL), drying over $MgSO_4$, filtration and removal of solvent in vacuo. Silica gel chromatography (0-25% Hexane:EtOAc) afforded the title compound (650 mg; 62.5%) as a sticky solid. $^1$H NMR ($CDCl_3$) δ 1.88 (m, 3H), 2.12 (m, 1H), 2.51 (s, 3H), 2.81 (m, 2H), 5.32 (m, 1H), 5.99 (bd, 1H), 7.13 (m, 1H), 7.20 (m, 2H) 7.20 (m, 2H); $^{13}$C NMR ($CDCl_3$) δ 11.22, 20.15, 29.41, 30.35, 47.93, 116.73, 126.72, 127.88, 128.88, 129.65, 136.25, 138.00, 158.45, 160.28. ESIMS: 257 (M+H) EA calc'd for $C_{15}H_{16}N_2O_2$: C, 70.29; H, 6.29; N, 10.93. found C, 70.61; H, 6.11; N, 11.09.

The compound had an $EC_{50}$ for activation of a hT1R2/hT1R3 sweet receptor expressed in an HEK293 cell line of 5.8 μM.

Numerous amide compounds of Formula (D) were also synthesized and experimentally tested for effectiveness as activator of a hT1R2/hT1R3 "sweet" receptor expressed in an HEK293 cell line.

The results of that testing are shown below in Table E.

TABLE E

| | Sweet Enhancer Amides | | | |
|---|---|---|---|---|
| Compound No. | Compound | Sweet $EC_{50}$ uM | Umami $EC_{50}$ uM | Umami $EC_{50}$ ratio |
| E1 | 3-chloro-2-hydroxy-N-(2-methyl-1,2,3,4-tetrahydronaphthalen-1-yl)benzamide | 0.19 | | |
| E2 | (R)-3-chloro-2-hydroxy-N-(1,2,3,4-tetrahydronaphthalen-1-yl)benzamide | 0.65 | | |
| E3 | 3-chloro-2-hydroxy-N-(5-hydroxy-1,2,3,4-tetrahydronaphthalen-1-yl)benzamide | 1.03 | | |

TABLE E-continued

Sweet Enhancer Amides

| Compound No. | Compound | Sweet EC$_{50}$ uM | Umami EC$_{50}$ uM | Umami EC$_{50}$ ratio |
|---|---|---|---|---|
| E4 | 3-chloro-2-hydroxy-N-(4-methyl-1,2,3,4-tetrahydronaphthalen-1-yl)benzamide | 1.61 | | |
| E5 | 3-chloro-2-hydroxy-N-(6-methoxy-1,2,3,4-tetrahydronaphthalen-1-yl)benzamide | 1.61 | | |
| E6 | 3-methyl-N-(2-methyl-1,2,3,4-tetrahydronaphthalen-1-yl)isoxazole-4-carboxamide | 1.48 | | |
| E7 | 3-chloro-2-hydroxy-N-(1,2,3,4-tetrahydronaphthalen-1-yl)benzamide | 1.81 | 4.04 | |
| E8 | 2,3-dihydroxy-N-(2-methyl-1,2,3,4-tetrahydronaphthalen-1-yl)benzamide | 1.98 | | |
| E9 | 2-hydroxy-N-(2-methyl-1,2,3,4-tetrahydronaphthalen-1-yl)benzamide | 2.36 | | |

TABLE E-continued

Sweet Enhancer Amides

| Compound No. | Compound | Sweet EC$_{50}$ uM | Umami EC$_{50}$ uM | Umami EC$_{50}$ ratio |
|---|---|---|---|---|
| E10 | 2,3-dihydroxy-N-(5-methoxy-1,2,3,4-tetrahydronaphthalen-1-yl)benzamide | 2.44 | | |
| E11 | 3-methyl-N-(4-methyl-1,2,3,4-tetrahydronaphthalen-1-yl)isoxazole-4-carboxamide | 2.46 | | |
| E12 | N-(5-methoxy-1,2,3,4-tetrahydronaphthalen-1-yl)-3-methylisoxazole-4-carboxamide | 2.85 | | |
| E13 | (S)-3-chloro-2-methyl-N-(1,2,3,4-tetrahydronaphthalen-1-yl)benzamide | 2.91 | | |
| E14 | (S)-2,6-dimethyl-N-(1,2,3,4-tetrahydronaphthalen-1-yl)benzamide | 2.91 | | |
| E15 | 2,6-dichloro-N-(1,2,3,4-tetrahydronaphthalen-1-yl)benzamide | 3.02 | | |

TABLE E-continued

Sweet Enhancer Amides

| Compound No. | Compound | Sweet EC$_{50}$ uM | Umami EC$_{50}$ uM | Umami EC$_{50}$ ratio |
|---|---|---|---|---|
| E16 | 3,6-dichloro-2-methoxy-N-(1,2,3,4-tetrahydronaphthalen-1-yl)benzamide | 3.04 | | |
| E17 | (R)-2,3-dihydroxy-N-(1,2,3,4-tetrahydronaphthalen-1-yl)benzamide | 3.13 | | |
| E18 | 2,5-dihydroxy-N-(5-methoxy-1,2,3,4-tetrahydronaphthalen-1-yl)benzamide | 3.38 | | |
| E19 | (S)-3-fluoro-2-methyl-N-(1,2,3,4-tetrahydronaphthalen-1-yl)benzamide | 3.57 | | |
| E20 | (S)-3-chloro-2,6-dimethoxy-N-(1,2,3,4-tetrahydronaphthalen-1-yl)benzamide | 4.13 | | |
| E21 | (R)-5-bromo-N-(1,2,3,4-tetrahydronaphthalen-1-yl)nicotinamide | 4.19 | | |

TABLE E-continued

Sweet Enhancer Amides

| Compound No. | Compound | Sweet EC$_{50}$ uM | Umami EC$_{50}$ uM | Umami EC$_{50}$ ratio |
|---|---|---|---|---|
| E22 | (R)-3-chloro-N-(1,2,3,4-tetrahydronaphthalen-1-yl)benzamide | 4.52 | | |
| E23 | (R)-3-fluoro-N-(1,2,3,4-tetrahydronaphthalen-1-yl)benzamide | 4.86 | | |
| E24 | (R)-2,5-dihydroxy-N-(1,2,3,4-tetrahydronaphthalen-1-yl)benzamide | 6.04 | | |
| E25 | (R)-3-methyl-N-(1,2,3,4-tetrahydronaphthalen-1-yl)isoxazole-4-carboxamide | 7.79 | | |
| E26 | (R)-5-methyl-N-(1,2,3,4-tetrahydronaphthalen-1-yl)isoxazole-4-carboxamide | 8.09 | | |
| E27 | 2,3,5,6-tetrafluoro-4-methyl-N-(3-methylbutan-2-yl)benzamide | 0.14 | | |

TABLE E-continued

Sweet Enhancer Amides

| Compound No. | Compound | Sweet EC$_{50}$ uM | Umami EC$_{50}$ uM | Umami EC$_{50}$ ratio |
|---|---|---|---|---|
| E28 | 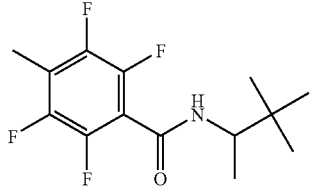<br>N-(3,3-dimethylbutan-2-yl)-2,3,5,6-tetrafluoro-4-methylbenzamide | 0.21 | | |
| E29 | 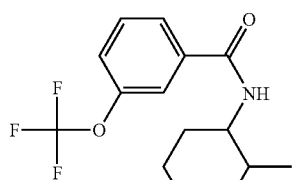<br>N-(2-methylcyclohexyl)-3-(trifluoromethoxy)benzamide | 0.42 | | |
| E30 | 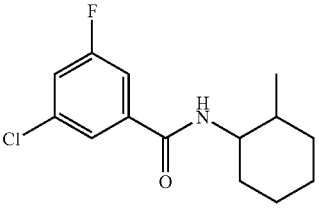<br>3-chloro-5-fluoro-N-(2-methylcyclohexyl)benzamide | 0.45 | | |
| E31 | 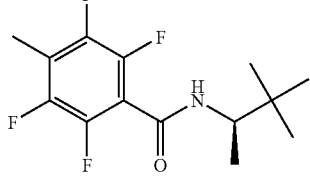<br>(R)-N-(3,3-dimethylbutan-2-yl)-2,3,5,6-tetrafluoro-4-methylbenzamide | 0.49 | | |
| E32 | 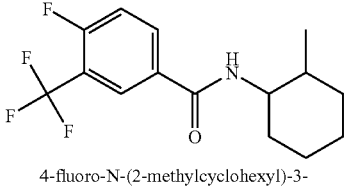<br>4-fluoro-N-(2-methylcyclohexyl)-3-(trifluoromethyl)benzamide | 0.51 | | |
| E33 | 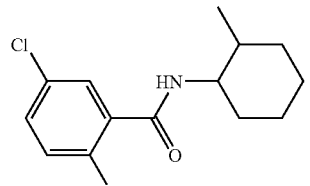<br>2,5-dichloro-N-(2-methylcyclohexyl)benzamide | 0.63 | | |

TABLE E-continued

Sweet Enhancer Amides

| Compound No. | Compound | Sweet EC$_{50}$ uM | Umami EC$_{50}$ uM | Umami EC$_{50}$ ratio |
|---|---|---|---|---|
| E34 | 2,3,5,6-tetrafluoro-N-(hexan-2-yl)-4-methylbenzamide | 0.71 | | |
| E35 | 3,5-dichloro-2,6-dimethoxy-N-(2-methylcyclohexyl)benzamide | 0.71 | | |
| E36 | 2,4,6-trimethyl-N-(2-methylcyclohexyl)benzamide | 0.72 | | |
| E37 | 3,6-dichloro-2-methoxy-N-(2-methylcyclohexyl)benzamide | 0.77 | | |
| E38 | (S)-N-(3,3-dimethylbutan-2-yl)-2,3,5,6-tetrafluoro-4-methylbenzamide | 0.9 | | |
| E39 | 2,6-dichloro-N-(2-methylcyclohexyl)benzamide | 0.91 | | |

TABLE E-continued

Sweet Enhancer Amides

| Compound No. | Compound | Sweet EC$_{50}$ uM | Umami EC$_{50}$ uM | Umami EC$_{50}$ ratio |
|---|---|---|---|---|
| E40 | 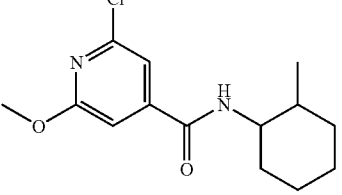<br>2-chloro-6-methoxy-N-(2-methylcyclohexyl)isonicotinamide | 0.95 | | 9.77 |
| E41 | 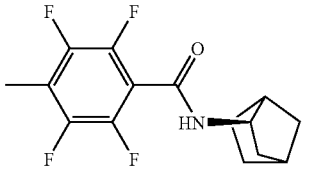<br>N-((2R)-bicyclo[2.2.1]heptan-2-yl)-2,3,5,6-tetrafluoro-4-methylbenzamide | 1.02 | | |
| E42 | 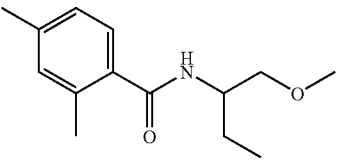<br>N-(1-methoxybutan-2-yl)-2,4-dimethylbenzamide | 1.06 | | |
| E43 | 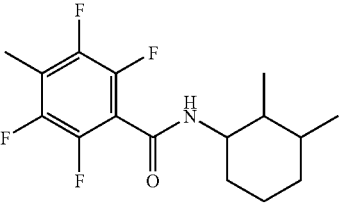<br>N-(2,3-dimethylcyclohexyl)-2,3,5,6-tetrafluoro-4-methylbenzamide | 1.08 | | |
| E44 | 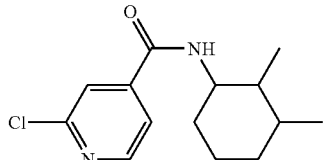<br>2-chloro-N-(2,3-dimethylcyclohexyl)isonicotinamide | 1.08 | | |
| E45 | 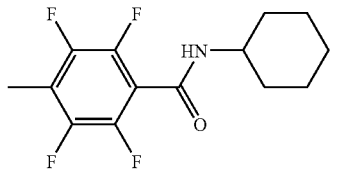<br>N-cyclohexyl-2,3,5,6-tetrafluoro-4-methylbenzamide | 1.13 | | |

TABLE E-continued

Sweet Enhancer Amides

| Compound No. | Compound | Sweet EC50 uM | Umami EC50 uM | Umami EC50 ratio |
|---|---|---|---|---|
| E46 | 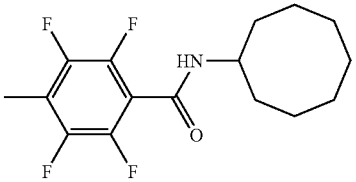<br>N-cyclooctyl-2,3,5,6-tetrafluoro-4-methylbenzamide | 1.25 | | |
| E47 | 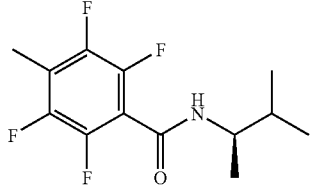<br>(R)-2,3,5,6-tetrafluoro-4-methyl-N-(3-methylbutan-2-yl)benzamide | 1.25 | | |
| E48 | 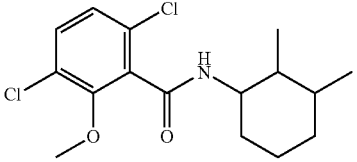<br>3,6-dichloro-N-(2,3-dimethylcyclohexyl)-2-methoxybenzamide | 1.29 | | |
| E49 | 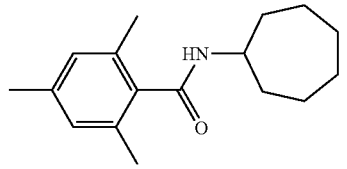<br>N-cycloheptyl-2,4,6-trimethylbenzamide | 1.39 | | |
| E50 | 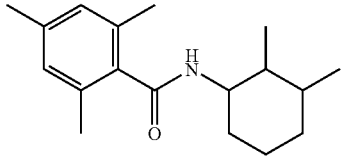<br>N-(2,3-dimethylcyclohexyl)-2,4,6-trimethylbenzamide | 1.41 | | |
| E51 | 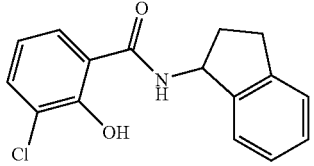<br>3-chloro-N-(2,3-dihydro-1H-inden-1-yl)-2-hydroxybenzamide | 1.49 | | |

TABLE E-continued

Sweet Enhancer Amides

| Compound No. | Compound | Sweet EC$_{50}$ uM | Umami EC$_{50}$ uM | Umami EC$_{50}$ ratio |
|---|---|---|---|---|
| E52 | 2-methyl-N-(2-methylcyclohexyl)-1-naphthamide | 1.52 | | |
| E53 | 3-chloro-4-fluoro-N-(2-methylcyclohexyl)benzamide | 1.7 | | |
| E54 | 3,4-dichloro-N-(2-methylcyclohexyl)benzamide | 1.83 | 10.66 | |
| E55 | 5-bromo-N-(2,3-dimethylcyclohexyl)nicotinamide | 1.89 | | |
| E56 | 2-chloro-N-(2-methylcyclohexyl)isonicotinamide | 1.92 | 2.08 | |
| E57 | 2-chloro-3-methyl-N-(2-methylcyclohexyl)benzamide | 1.95 | | |

TABLE E-continued

Sweet Enhancer Amides

| Compound No. | Compound | Sweet EC$_{50}$ uM | Umami EC$_{50}$ uM | Umami EC$_{50}$ ratio |
|---|---|---|---|---|
| E58 | N-cyclopentyl-2,3,5,6-tetrafluoro-4-methylbenzamide | 2.23 | | |
| E59 | N-(2-methylcyclohexyl)-3-(trifluoromethyl)benzamide | 2.34 | | 2.07 |
| E60 | 4-fluoro-N-(4-methylcyclohexyl)-3-(trifluoromethyl)benzamide | 2.37 | | |
| E61 | 2-fluoro-N-(2-methylcyclohexyl)-3-(trifluoromethyl)benzamide | 2.4 | | |
| E62 | 5-bromo-N-(2-methylcyclohexyl)nicotinamide | 2.42 | | |
| E63 | 2,3-dimethyl-N-(2-methylcyclohexyl)benzamide | 2.6 | | |
| E64 | 2,6-dichloro-N-(2,3-dimethylcyclohexyl)benzamide | 2.77 | | |

TABLE E-continued

Sweet Enhancer Amides

| Compound No. | Compound | Sweet EC$_{50}$ uM | Umami EC$_{50}$ uM | Umami EC$_{50}$ ratio |
|---|---|---|---|---|
| E65 | 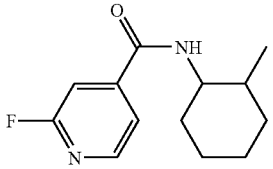<br>2-fluoro-N-(2-methylcyclohexyl)isonicotinamide | 2.83 | | |
| E66 | 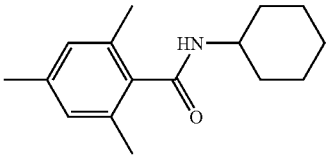<br>N-cyclohexyl-2,4,6-trimethylbenzamide | 2.86 | | |
| E67 | 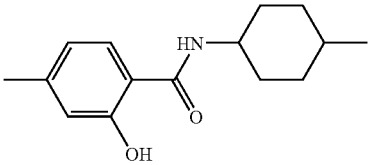<br>2-hydroxy-4-methyl-N-(4-methylcyclohexyl)benzamide | 2.98 | | |
| E68 | 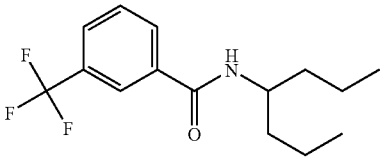<br>N-(heptan-4-yl)-3-(trifluoromethyl)benzamide | 3.03 | 0.33 | |
| E69 | 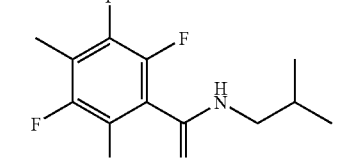<br>2,3,5,6-tetrafluoro-N-isobutyl-4-methylbenzamide | 3.19 | | |
| E70 | 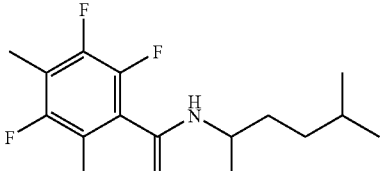<br>2,3,5,6-tetrafluoro-4-methyl-N-(5-methylhexan-2-yl)benzamide | 3.2 | | |
| E71 | 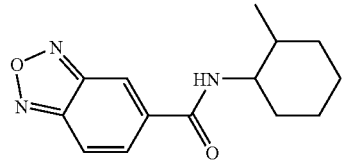<br>N-(2-methylcyclohexyl)benzo[c][1,2,5]oxadiazole-5-carboxamide | 3.33 | | |

TABLE E-continued

Sweet Enhancer Amides

| Compound No. | Compound | Sweet EC$_{50}$ uM | Umami EC$_{50}$ uM | Umami EC$_{50}$ ratio |
|---|---|---|---|---|
| E72 | 2-hydroxy-3-methoxy-N-(4-methylcyclohexyl)benzamide | 3.35 | | |
| E73 | Thiophene-2-carboxylic acid (1,3,3-trimethyl-bicyclo[2.2.1]hept-2-yl)-amide | 3.36 | | |
| E74 | N-(2,3-dimethylcyclohexyl)-2-(perfluorophenyl)acetamide | 3.62 | | |
| E75 | 2,3-dichloro-N-(pentan-3-yl)benzamide | 3.78 | | |
| E76 | 2,3-dichloro-N-(2,3-dimethylcyclohexyl)benzamide | 3.99 | | |
| E77 | N-(2,3-dimethylcyclohexyl)-2,5-difluorobenzamide | 4.11 | | |
| E78 | 4,5-Dichloro-isothiazole-3-carboxylic acid (2-methyl-cyclohexyl)-amide | 4.24 | 8.51 | |

TABLE E-continued

Sweet Enhancer Amides

| Compound No. | Compound | Sweet EC$_{50}$ uM | Umami EC$_{50}$ uM | Umami EC$_{50}$ ratio |
|---|---|---|---|---|
| E79 | 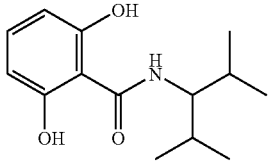<br>N-(2,4-dimethylpentan-3-yl)-2,6-dihydroxybenzamide | 4.28 | | |
| E80 | 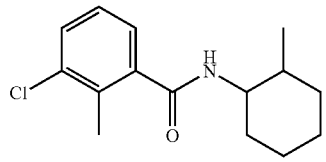<br>3-chloro-2-methyl-N-(2-methylcyclohexyl)benzamide | 4.29 | | |
| E81 | 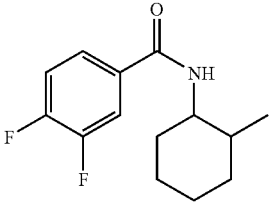<br>3,4-difluoro-N-(2-methylcyclohexyl)benzamide | 4.37 | | 6.98 |
| E82 | 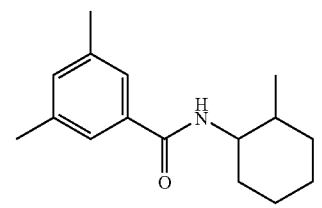<br>3,5-dimethyl-N-(2-methylcyclohexyl)benzamide | 4.48 | | |
| E83 | 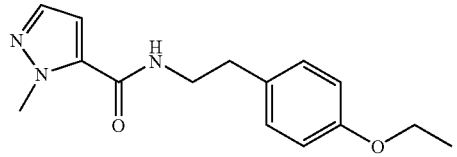<br>N-(4-ethoxyphenethyl)-1-methyl-1H-pyrazole-5-carboxamide | 4.68 | | |
| E84 | 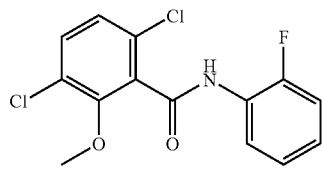<br>3,6-dichloro-N-(2-fluorophenyl)-2-methoxybenzamide | 0.83 | | 16.51 |

TABLE E-continued

Sweet Enhancer Amides

| Compound No. | Compound | Sweet EC$_{50}$ uM | Umami EC$_{50}$ uM | Umami EC$_{50}$ ratio |
|---|---|---|---|---|
| E85 | N-(2-Chloro-4,6-dimethoxy-phenyl)-3-trifluoromethyl-benzamide | 1.42 | | |
| E86 | 3,5-dichloro-N-(2,4-dimethylphenyl)-4-methoxybenzamide | 1.48 | | |
| E87 | 3-Chloro-4-fluoro-N-(5-trifluoromethyl-[1,3,4]thiadiazol-2-yl)-benzamide | 1.55 | | |
| E88 | 3,5-dichloro-4-methoxy-N-o-tolylbenzamide | 1.84 | | |
| E89 | 5-Chloro-N-(2,4-difluoro-phenyl)-2-hydroxy-benzamide | 2.56 | | |
| E90 | 2,4-Dichloro-N-(2-cyano-3-fluoro-phenyl)-benzamide | 2.71 | | |

TABLE E-continued

Sweet Enhancer Amides

| Compound No. | Compound | Sweet EC$_{50}$ uM | Umami EC$_{50}$ uM | Umami EC$_{50}$ ratio |
|---|---|---|---|---|
| E91 | 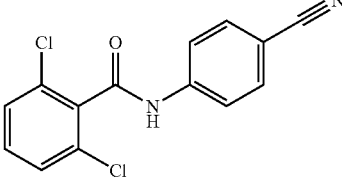<br>2,6-Dichloro-N-(4-cyano-phenyl)-benzamide | 2.74 | | |
| E92 | 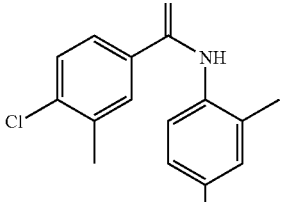<br>4-chloro-N-(2,4-dimethylphenyl)-3-methylbenzamide | 2.74 | | |
| E93 | 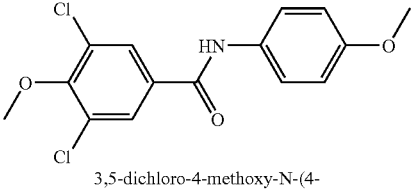<br>3,5-dichloro-4-methoxy-N-(4-methoxyphenyl)benzamide | 3.24 | | |
| E94 | 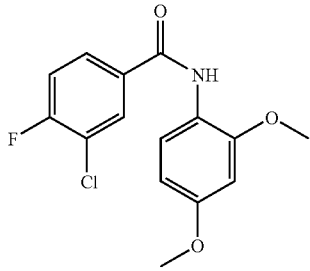<br>3-chloro-N-(2,4-dimethoxyphenyl)-4-fluorobenzamide | 3.56 | | |
| E95 | 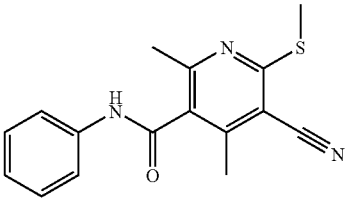<br>5-Cyano-2,4-dimethyl-6-methylsulfanyl-N-phenyl-nicotinamide | 3.58 | | |
| E96 | 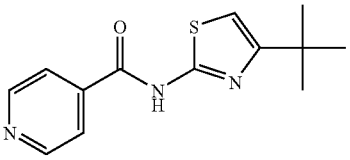<br>N-(4-tert-Butyl-thiazol-2-yl)-isonicotinamide | 3.73 | | |

TABLE E-continued

Sweet Enhancer Amides

| Compound No. | Compound | Sweet EC$_{50}$ uM | Umami EC$_{50}$ uM | Umami EC$_{50}$ ratio |
|---|---|---|---|---|
| E97 | 3,6-Dichloro-N-(2,4-dimethyl-phenyl)-2-methoxy-benzamide | 4.25 | | |
| E98 | N-(3-ethylphenyl)-2-methoxy-6-methylbenzamide | 4.63 | | |
| E99 | N-(4-bromo-2,6-dimethylphenyl)isoindoline-2-carboxamide | 0.93 | | |
| E100 | N-(2-methyl-4-nitrophenyl)isoindoline-2-carboxamide | 1.3 | | |
| E101 | N-(2,4-difluorophenyl)isoindoline-2-carboxamide | 1.37 | | |
| E102 | N-(2-methyl-3-nitrophenyl)isoindoline-2-carboxamide | 2.01 | | |
| E103 | N-(2,3,4-trifluorophenyl)isoindoline-2-carboxamide | 2.58 | | |

TABLE E-continued

Sweet Enhancer Amides

| Compound No. | Compound | Sweet EC$_{50}$ uM | Umami EC$_{50}$ uM | Umami EC$_{50}$ ratio |
|---|---|---|---|---|
| E104 | 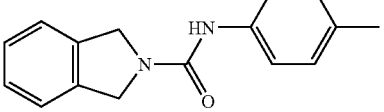<br>N-p-tolylisoindoline-2-carboxamide | 3.05 | | |
| E105 | 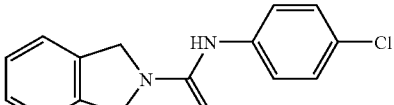<br>N-(4-chlorophenyl)isoindoline-2-carboxamide | 3.4 | | |
| E106 | 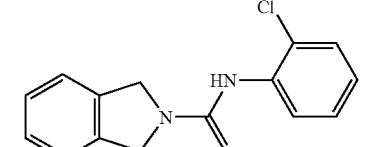<br>N-(2-chlorophenyl)isoindoline-2-carboxamide | 3.85 | | |
| E107 | 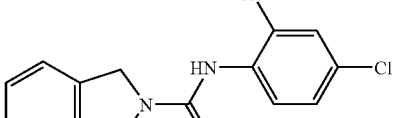<br>N-(2,4-dichlorophenyl)isoindoline-2-carboxamide | 4.15 | | |
| E108 | 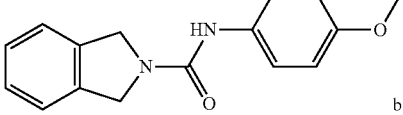<br>N-(4-methoxyphenyl)isoindoline-2-carboxamide | 4.99 b | | |
| E109 | 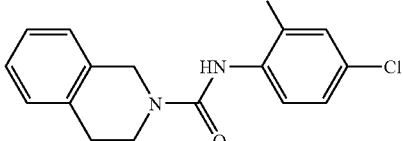<br>N-(2,4-dichlorophenyl)-3,4-dihydroisoquinoline-2(1H)-carboxamide | 2.34 | | |
| E110 | 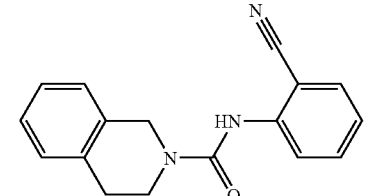<br>N-(2-cyanophenyl)-3,4-dihydroisoquinoline-2(1H)-carboxamide | 2.5 | | |

TABLE E-continued

Sweet Enhancer Amides

| Compound No. | Compound | Sweet EC$_{50}$ uM | Umami EC$_{50}$ uM | Umami EC$_{50}$ ratio |
|---|---|---|---|---|
| E111 | N-p-tolyl-3,4-dihydroisoquinoline-2(1H)-carboxamide | 4.27 | | |
| E112 | N-(3-chloro-2-methylphenyl)-3,4-dihydroisoquinoline-2(1H)-carboxamide | 4.33 | | |
| E113 | N-(2,4-dimethoxyphenyl)-3,4-dihydroisoquinoline-2(1H)-carboxamide | 4.44 | | |

Sweet Flavor and Sweet Flavor Enhancement Measurement Using Human Panelists

Purpose: To investigate the intensity of various tastes and off-tastes of an experimental compound. To determine the maximum concentration of the experimental compound that does not elicit an undesirable characteristic or off-taste.

Overview: Various concentrations of the experimental compound (normally aqueous solutions containing 1, 3, 10, and 30 uM concentrations of the experimental compound; and optionally 50 uM and/or 100 uM concentrations) are individually tasted by trained human subjects and rated for intensity of several taste attributes. The experimental compound may also be tasted when dissolved in a "key tastant" solution.

Procedure: An appropriate quantity of the experimental compound is dissolved in water typically also containing 0.1% ethanol, which is utilized to aid initial dispersion of the compound in the aqeuous stock solution. When appropriate, the experimental compound may also be dissolved in aqueous solutions of a "key tastant" (for example, 4% sucrose, 6% sucrose, 6% fructose/glucose, or 7% fructose/glucose, at pH 7.1 or 2.8).

Five human Subjects are used for preliminary taste tests. The Subjects have a demonstrated ability to taste the desired taste attributes, and are trained to use a Labeled Magnitude Scale (LMS) from 0 (Barely Detectible Sweetness) to 100 (Strongest Imaginable Sweetness). Subjects refrain from eating or drinking (except water) for at least 1 hour prior to the test. Subjects eat a cracker and rinse with water four times to clean the mouth before taste tests.

The aqueous solutions are dispensed in 10 ml volumes into 1 oz. sample cups and served to the Subjects at room temperature. Samples of the experimental compound dissolved in an appropriate key tastant (e.g., 4% sucrose, 6% fructose, or 6% fructose/glucose, typically at pH 7.1) at various concentrations of the experimental compound may also be served to the Subjects. Subjects also receive a reference sample of the key tastant (e.g., sucrose, fructose, or fructose/glucose, typically at pH 7.1) at different concentrations for comparison.

Subjects taste the solutions, starting with the lowest concentration, and rate intensity of the following attributes on the Labeled Magnitude Scale (LMS) for sweetness, saltiness, sourness, bitterness, savory (umami), and other (off-taste). Subjects rinse three times with water between tastings. If a particular concentration elicits an undesirable characteristic or off-taste, subsequent tastings of higher concentrations are eliminated. After a break, Subjects taste a solution of the key tastant (e.g., 4% sucrose, 6% fructose, or 6% fructose/glucose, typically at pH 7.1) without the experimental compound. Then solutions of the key tastant plus experimental compound are tasted in increasing order of concentration. The key tastant solution can be retasted for comparison with key tastant+experimental compound solutions if necessary. Discussion among panelists is permitted.

The maximum concentration of an experimental compound that does not elicit an objectionable characteristic or off-taste is the highest concentration that a particular compound will be tested at in subsequent sensory experiments. To confirm preliminary test results, the test may be repeated with another small group of panelists.

The preliminary profiling test is always the first test performed on a new experimental compound. Depending on the results of the preliminary profiling test, additional more quantitative tests may be performed to further characterize the experimental compound.

"Difference from Reference" Human Taste Test Procedures

Purpose: To determine how the intensity of a test sample of an experimental compound differs from that of a reference sample in terms of sweetness. This type of study requires a larger panel (typically 15-20 Subjects) in order to obtain statistically significant data.

Overview: A group of 10 or more panelists taste pairs of solutions where one sample is the "Reference" (which typically does not include an experimental compound and is an approved substance or Generally Recognized As Safe (GRAS) substance, i.e., a sweetener) and one sample is the "Test" (which may or may not include an experimental compound). Subjects rate the difference in intensity of the test sample compared to the reference sample for the key attribute on a scale of −5 (much less sweet than the reference) to +5 (much more sweet than the reference). A score of 0 indicates the test sample is equally as sweet as the reference.

Procedure:

Ten or more Subjects are used for the "Difference from Reference" tests. Subjects have been previously familiarized with the key attribute taste and are trained to use the −5 to +5 scale. Subjects refrain from eating or drinking (except water) for at least 1 hour prior to the test. Subjects eat a cracker and rinse with water four times to clean the mouth.

Test solutions can include the experimental compound in water, the experimental compound plus a key tastant (e.g., 4% sucrose, 6% sucrose, 6% fructose, 6% fructose/glucose, or 7% fructose/glucose, at pH 7.1 or 2.8), and a range of key tastant only solutions as references.

Samples of the key tastant without the experimental compound are used to determine if the panel is rating accurately; i.e., the reference is tested against itself (blind) to determine how accurate the panel is rating on a given test day. The solutions are dispensed in 10 ml volumes into 1 oz. sample cups and served to the Subjects at room temperature.

Subjects first taste the reference sample then immediately taste the test sample and rate the difference in intensity of the key attribute on the Difference from Reference scale (−5 to +5). All samples are expectorated. Subjects may retaste the samples but can only use the volume of sample given. Subjects must rinse at least twice with water between pairs of samples. Eating a cracker between sample pairs may be required depending on the samples tasted.

The scores for each test are averaged across Subjects and standard error is calculated. Panel accuracy can be determined using the score from the blind reference test. ANOVA and multiple comparison tests (such as Tukey's Honestly Significant Difference test) can be used to determine differences among pairs, provided the reference sample is the same among all tests. If the identical test pair is tested in another session, a Student's t-test (paired, two-tailed; alpha=0.05) can be used to determine if there is any difference in the ratings between sessions.

A number of different reference sweeteners have been utilized for the measurement of sweet taste enhancement. For example, for testing (R)-3-methyl-N-(1,2,3,4-tetrahydronaphthalen-1-yl)isoxazole-4-carboxamide, a reference sample consisting of 4% sucrose was used, which has a greater than the threshold level sweetness (i.e., 2% sucrose), and a sweetness in the region of sweet taste perception where human subjects are most sensitive to small changes in sweet taste perception. For the testing of 2,3,5,6-tetrafluoro-4-methyl-N-(2-methylcyclohexyl)benzamide, a 50:50 mix of fructose:glucose was used to better model high fructose corn syrup solutions commonly utilized in the beverage industry. A 6% fructose/glucose mixture was demonstrated to be approximately equal in sweet taste perception as 6% sucrose, which is within the range where panelists are sensitive to small changes in sweet taste perception. After initial studies in 6% fructose/glucose at pH 7.1, studies shift to evaluating the performance of the compound in a product prototype more similar to a cola beverage, i.e. higher concentrations of sweetener and lower pH.

The results of some human taste tests of the sweet amide compounds of the invention in aqueous compositions intended to model the composition of a carbonated beverage are shown below in Table F

TABLE F

Sweet Taste Test Results

| Compound No. | Contents of Solution | pH | Perceived Equivalent Sweet Solution |
|---|---|---|---|
| 174 | 50 uM Compound 174 + 4% sucrose | * | 6% sucrose |
| 171 | 30 uM Compound 171 + 6% fructose/glucose | * | Greater than 6% but less than 8% fructose/glucose |
| 170 | 30 uM Compound 170 + 6% fructose/glucose | pH 7.1 | Greater than 6% but less than 8% fructose/glucose |
| 162 | 10 uM Compound 162 + 6% fructose/glucose | pH 7.1 | Greater than or equal to 8% fructose/glucose |
| 162 | 10 uM Compound 162 + 7% fructose/glucose | pH 2.8 | Greater than or equal to 9% fructose/glucose |
| 168 | 30 uM Compound 168 + 6% fructose/glucose | pH 7.1 | Equal to 8% fructose/glucose |
| 163 | 10 uM Compound 163 + 6% fructose/glucose | pH 7.1 | Greater than 6% but less than 8% fructose/glucose |

* The pH of these aqeous solutions was not measured or controlled.

Example 176

Soup Preparation Using an Ethanol Stock Solution

A compound of the invention is diluted using 200 proof ethanol to 1000× the desired concentration in soup. The compound can be sonicated and heated (if stable) to ensure complete solubility in ethanol. The soup from bouillon base is made by adding 6 g of vegetable bouillon base in 500 mL of hot water in a glass or stoneware bowl. The water is heated to 80° C. The concentration of MSG in the dissolved bouillon is 2.2 g/L and there is no IMP added. After the bouillon base is dissolved, the ethanol stock solution is added to the soup base. For 500 mL of soup, 0.5 mL of the 1000× ethanol stock is added for a final ethanol concentration of 0.1%. If the ethanol interferes with the taste of the soup, a higher concentration of ethanol stock solution can be prepared provided the compound is soluble.

Example 177

Chip Preparation

A salt mixture of a compound of the invention is made by mixing with salt such that a 1.4% of the salt mixture added w/w to chips would result in the desired concentration of the compound. For 1 ppm final of the compound on chips, 7 mg of the compound is mixed with 10 g of salt. The compound is ground using a mortar and pestle with the salt and the compound and salt are mixed well. The chips are broken into uniform small pieces by using a blender. For each 98.6 g of chips, 1.4 g of the salt mixture is weighed out. The chip pieces are first heated in a microwave for 50 seconds or until warm. The pieces are spread out on a large piece of aluminum foil. The salt mixture is spread evenly over the chips. The chips are then placed in a plastic bag making sure that all the salt is place in the bag as well. The salt mixture and chips are then shaken to ensure that the salt is spread evenly over the chips.

Example 178

Cookie Preparation

A compound of the invention is diluted using 200 proof ethanol to 1000× the desired concentration in the final product. The compound can be sonicated and heated (if stable) to ensure complete solubility in ethanol. The solution containing the compound of the invention is then mixed with other liquid ingredients (i.e., water, liquid egg, and flavorings) until well blended. The mixture is blended with a dry emulsifier such as lecithin and further blended with shortening. The shortening is blended with dry components (i.e., flour, sugar, salt, cocoa) which have been well mixed. Dough is portioned out onto a baking sheet, and baked at desired temperature until done.

Example 179

Juice Preparation

A compound of the invention is diluted using 200 proof ethanol to 1000× the desired concentration in juice. The compound is further blended with the alcohol component of natural and/or artificial flavors to make a "key". The flavor key is blended with a portion of juice concentrate to assure homogeneity. The remainder of the juice concentrate is diluted with water and mixed. Sweeteners, such as HFCS (High Fructose Corn Syrup), aspartame, or sucralose, are mixed in and blended. The flavor/compound portion is added as a final step, and blended.

Example 180

Spicy Tomato Juice or Bloody Mary Mix

A compound of the invention is added as a dry ingredient to the spice blend and blended thoroughly. Spice blend is dispersed into a portion of the tomato paste, blended, and that blended paste is further blended into the remaining paste. The paste is then diluted with water. It may be processed at high temperature for a short time.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

We claim:
1. An oxalamide compound having the formula

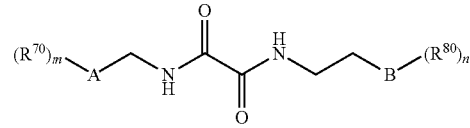

wherein
A is a substituted aryl or heteroaryl ring comprising five to ten ring carbon atoms;
B is a five-membered or six-membered heteroaryl;
m is 1, 2 or 3 and n is 0, 1, 2 or 3;
each $R^{70}$ and $R^{80}$ is independently selected from the group consisting of, hydroxy, fluoro, chloro, $NH_2$, $NHCH_3$, $N(CH_3)_2$, $COOCH_3$, $SCH_3$, SEt, methyl, ethyl, isopropyl, vinyl, trifluoromethyl, methoxy, ethoxy, isopropoxy, and trifluoromethoxy, or two of $R^{70}$ together form a methylenedioxy ring; or a comestibly acceptable salt thereof.

2. The oxalamide compound of claim 1 wherein B is a pyridyl ring.

3. The oxalamide compound of claim 1 wherein the pyridyl-$R^{80}$ radical has the structure

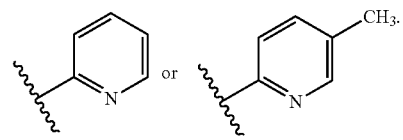

4. The oxalamide compound of claim 1 wherein A is a phenyl ring.

5. The oxalamide compound of claim 4 wherein B is a pyridyl ring.

6. The oxalamide compound of claim 4 wherein the pyridyl-$R^{80}$ radical has the structure

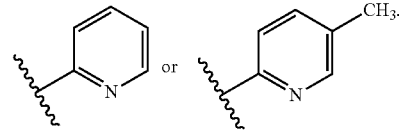

7. The oxalamide compound of claim 1, which is selected from the group consisting of
N1-(2-methoxy-4-methylbenzyl)-N2-(2-(5-methylpyridin-2-yl)ethyl) oxalamide,
N1-(2-methoxy-4-methylbenzyl)-N2-(2-(pyridin-2-yl)ethyl) oxalamide,
N1-(2,4-dimethoxybenzyl)-N2-(2-(5-methylpyridin-2-yl)ethyl) oxalamide,
N1-(2,4-dimethylbenzyl)-N2-(2-(pyridin-2-yl)ethyl) oxalamide,
N1-(2,4-dimethoxybenzyl)-N2-(2-(pyridin-2-yl)ethyl) oxalamide, and
N1-(2,3-dimethoxybenzyl)-N2-(2-pyridin-2-yl-ethyl)-oxalamide;
or a comestibly acceptable salt thereof.

* * * * *